United States Patent
Ko et al.

(10) Patent No.: US 6,780,857 B2
(45) Date of Patent: Aug. 24, 2004

(54) N-UREIDOALKYL-PIPERIDINES AS MODULATORS OF CHEMOKINE RECEPTOR ACTIVITY

(75) Inventors: Soo S. Ko, Hockessin, DE (US); George V. DeLucca, Wilmington, DE (US); John V. Duncia, Hockessin, DE (US); Joseph B. Santella, III, Springfield, PA (US); Dean A. Wacker, Chadds Ford, PA (US); Ui Tae Kim, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 30 days.

(21) Appl. No.: 10/279,231

(22) Filed: Oct. 24, 2002

(65) Prior Publication Data

US 2004/0006107 A1 Jan. 8, 2004

Related U.S. Application Data

(62) Division of application No. 09/465,287, filed on Dec. 17, 1999, now Pat. No. 6,492,400.
(60) Provisional application No. 60/112,717, filed on Dec. 18, 1998, and provisional application No. 60/161,184, filed on Oct. 22, 1999.

(51) Int. Cl.$^7$ ...................... A61K 31/33; A61K 31/40; C07D 207/00
(52) U.S. Cl. ...................... 514/183; 514/408; 514/422; 548/400; 548/566; 548/570
(58) Field of Search ...................... 514/408, 422; 548/400, 566, 570

(56) References Cited

U.S. PATENT DOCUMENTS

| | | | |
|---|---|---|---|
| 3,461,120 A | 8/1969 | Zenitz et al. | 260/240 |
| 5,547,966 A | 8/1996 | Atwal et al. | 514/352 |
| 5,668,151 A | 9/1997 | Poindexter et al. | 514/318 |
| 5,688,955 A | 11/1997 | Kruse et al. | 546/276.4 |
| 6,331,541 B1 | 12/2001 | Ko et al. | 514/237.2 |
| 6,331,545 B1 | 12/2001 | Ko et al. | 514/253.01 |
| 6,441,001 B1 | 8/2002 | Watson et al. | 514/331 |
| 6,444,686 B1 | 9/2002 | Ko et al. | 514/318 |
| 6,486,180 B1 | 11/2002 | Ko et al. | 514/331 |

FOREIGN PATENT DOCUMENTS

| | | |
|---|---|---|
| DE | 940980 | 5/1964 |
| DE | 1169943 | 5/1964 |
| EP | 0350309 | 11/1992 |
| EP | 0747357 | 12/1996 |
| EP | 0903349 | 3/1999 |
| WO | 9422826 | * 10/1994 |
| WO | 9427991 | 12/1994 |
| WO | 9519344 | 7/1995 |
| WO | 9626196 | 8/1996 |
| WO | 9717954 | 5/1997 |
| WO | 9722597 | 6/1997 |
| WO | 9727752 | 8/1997 |
| WO | 9805292 | 2/1998 |
| WO | 9825604 | * 6/1998 |
| WO | 9831364 | 7/1998 |
| WO | 9825617 | 8/1998 |
| WO | 9904794 | 2/1999 |
| WO | 9967204 | 12/1999 |

OTHER PUBLICATIONS

Granata et al, PubMed Abstract 12876405, also cited as Int.Arch.Allergy Immunol. 131/3, 153–63(2003).*
Liu et al, PubMed Abstract 12447698, also cited as Oncogene, 21/54,8347–50(2002).*
Barnes PJ.,PubMed ABSTRACT 11807165, Also Cited As Annu.Rev. Pharmacol. Toxicol.,42,81–98(2002).*
Nair et al, PubMed Abstract 12462994, also cited as Biol. Res.35/3–4,421–31(2002).*
Barnes PJ.,PubMed Abstract 10887299, also cited as J. Allergy Clin.Immunol..,1,5–16(2000).*
Gangur et al.,PubMed Abstract 10875484, also cited as Ann. Allergy Asthma Immunol. 84/6,569–79(2000).*
Gabuzda et al.,PubMed Abstract 10871762, also cited as J. Neurovirol.,1,S24–32(2000).*
Chem.Abstr. 132:49803, Delorme et al. 'Preparation of 1–N–substituted aminomethyl–4(or 3–)guanidinomethyl-benzene useful in management of pain' PCT/WO 9967204, see entire document.
Chem.Abstr. 128:34783, Kruse et al. 'Kappa agonist compounds (acylpiperazines and analogs) and pharmaceuticals formulations thereof' US 5,688,955 see entire document.
Chem.Abstr. 112:235186, Alker et al. 'Preparation of 1–aralkyl–3–(aralkoxy)piperidines as muscarinic areceptor antagonists' EP 350309, see entire document.
Chem.Abstr. 123:133809, Kim et al. 'Migration and proliferation of guinea pig and human airway epithelial cells in response to tachykinins' Am.J.Physiol, 1995, vol. 269, (1 Pt. 1), pp. L119–L126, see entire article.
Chem.Abstr. 129:107602, Kraneveld et al. Airway hyperresponsiveness; first eosinophils and then neuropeptides; Int.J.Immunopharmacol. 1998, vol. 19(9/10), pp. 517–527, see entire article.

* cited by examiner

Primary Examiner—Mukund J. Shah
Assistant Examiner—Sudhaker B. Patel
(74) Attorney, Agent, or Firm—Mary K. VanAtten

(57) ABSTRACT

The present application describes modulators of CCR3 of formula (I):

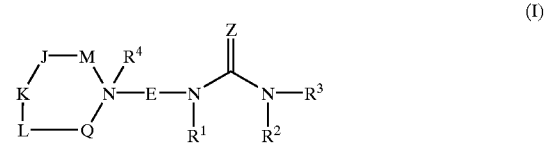

(I)

or pharmaceutically acceptable salt forms thereof, useful for the prevention of asthma and other allergic diseases.

27 Claims, No Drawings

N-UREIDOALKYL-PIPERIDINES AS MODULATORS OF CHEMOKINE RECEPTOR ACTIVITY

This application is a divisional of application Ser. No. 09/465,287, filed Dec. 17, 1999 now U.S. Pat. No. 6,492,400, which claims the benefit of provisional application 60/112,717 filed Dec. 18, 1998, and provisional application 60/161,184 filed Oct. 22, 1999, the contents of each of the above are hereby incorporated by reference.

FIELD OF THE INVENTION

This invention relates generally to modulators of chemokine receptor activity, pharmaceutical compositions containing the same, and methods of using the same as agents for treatment and prevention of inflammatory diseases such as asthma and allergic diseases, as well as autoimmune pathologies such as rheumatoid arthritis and atherosclerosis.

BACKGROUND OF THE INVENTION

Chemokines are chemotactic cytokines, of molecular weight 6–15 kDa, that are released by a wide variety of cells to attract and activate, among other cell types, macrophages, T and B lymphocytes, eosinophils, basophils and neutrophils (reviewed in Luster, New Eng. J Med., 338, 436–445 (1998) and Rollins, Blood, 90, 909–928 (1997)). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (−1, −2, and −3) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven-transmembrane-domain proteins (reviewed in Horuk, Trends Pharm. Sci., 15, 159–165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] (Ben-Barruch, et al., Cell, 72, 415–425 (1993), Luster, New Eng. J. Med., 338, 436–445 (1998)); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., Proc. Natl. Acad. Sci. USA, 91, 2752–2756 (1994), Luster, New Eng. J. Med., 338, 436–445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491–16494 (1995), Luster, New Eng. J. Med., 338, 436–445 (1998)); CCR-4 (or "CKR-4" or "CC-CKR-4") [TARC, MIP-1α, RANTES, MCP-1] (Power et al., J. Biol. Chem., 270, 19495–19500 (1995), Luster, New Eng. J. Med., 338, 436–445 (1998)); CCR-5 (or "CKR-5" OR "CC-CKR-5") [MIP-1α, RANTES, MIP-1β] (Sanson, et al., Biochemistry, 35, 3362–3367 (1996)); CCR-6 (or "CKR-6" or "CC-CKR-6") [LARC] (Baba et al., J. Biol. Chem., 272, 14893–14898 (1997)); CCR-7 (or "CKR-7" or "CC-CKR-7") [ELC] (Yoshie et al., J. Leukoc. Biol. 62, 634–644 (1997)); CCR-8 (or "CKR-8" or "CC-CKR-8") [I-309, TARC, MIP-1β] (Napolitano et al., J. Immunol., 157, 2759–2763 (1996), Bernardini et al., Eur. J. Immunol., 28, 582–588 (1998)); and CCR-10 (or "CKR-10" or "CC-CKR-10") [MCP-1, MCP-3] (Bonini et al, DNA and Cell Biol., 16, 1249–1256 (1997)).

In addition to the mammalian chemokine receptors, mammalian cytomegaloviruses, herpesviruses and poxviruses have been shown to express, in infected cells, proteins with the binding properties of chemokine receptors (reviewed by Wells and Schwartz, Curr. Opin. Biotech., 8, 741–748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of CCR3 expressing cells by HIV or in preventing the manipulation of immune cellular responses by viruses such as cytomegaloviruses.

A substantial body of art has accumulated over the past several decades with respect to substituted piperidines and pyrrolidines. These compounds have implicated in the treatment of a variety of disorders.

WO 98/25604 describes spiro-substituted azacycles which are useful as modulators of chemokine receptors:

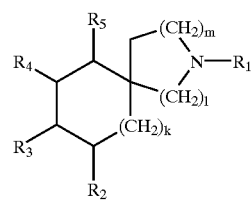

wherein $R_1$ is $C_{1-6}$ alkyl, optionally substituted with functional groups such as —NR$^6$CONHR$^7$, wherein R$^6$ and R$^7$ may be phenyl further substituted with hydroxy, alkyl, cyano, halo and haloalkyl. Such spiro compounds are not considered part of the present invention.

WO 95/13069 is directed to certain piperidine, pyrrolidine, and hexahydro-1H-azepine compounds of general formula:

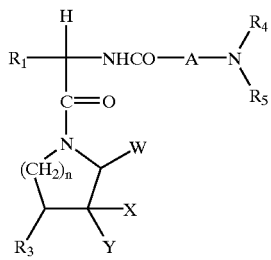

wherein A may be substituted alkyl or Z-substituted alkyl, with $Z=NR_{6a}$ or O. Compounds of this type are claimed to promote the release of growth hormone in humans and animals.

WO 93/06108 discloses pyrrolobenzoxazine derivatives as 5-hydroxytryptamine (5-HT) agonists and antagonists:

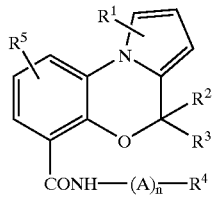

wherein A is lower alkylene and $R^4$ may be phenyl optionally substituted with halogen.

U.S. Pat. No. 5,668,151 discloses Neuropeptide Y (NPY) antagonists comprising 1,4-dihydropyridines with a piperidinyl or tetrahydropyridinyl-containing moiety attached to the 3-position of the 4-phenyl ring:

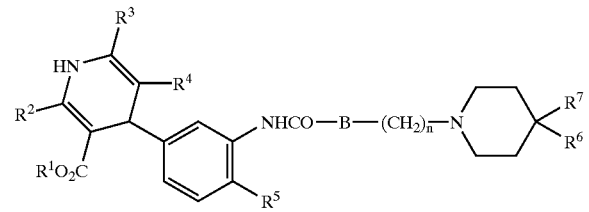

wherein B may be NH, $NR^1$, O, or a bond, and $R^7$ may be substituted phenyl, benzyl, phenethyl and the like.

These reference compounds are readily distinguished structurally by either the nature of the urea functionality, the attachment chain, or the possible substitution of the present invention. The prior art does not disclose nor suggest the unique combination of structural fragments which embody these novel piperidines and pyrrolidines as having activity toward the chemokine receptors.

SUMMARY OF THE INVENTION

Accordingly, one object of the present invention is to provide novel agonists or antagonists of CCR-3, or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory diseases and allergic disorders comprising administering to a host in need of such treatment a therapeutically effective amount of at least one of the compounds of the present invention or a pharmaceutically acceptable salt or prodrug form thereof.

It is another object of the present invention to provide novel N-ureidoalkyl-piperidines for use in therapy.

It is another object of the present invention to provide the use of novel N-ureidoalkyl-piperidines for the manufacture of a medicament for the treatment of allergic disorders.

In another embodiment, the present invention provides novel N-ureidoalkyl-piperidines for use in therapy.

In another embodiment, the present invention provides the use of novel N-ureidoalkyl-piperidines for the manufacture of a medicament for the treatment of allergic disorders.

These and other objects, which will become apparent during the following detailed description, have been achieved by the inventors' discovery that compounds of formula (I):

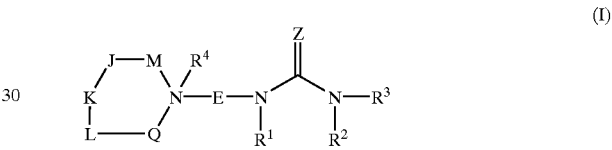

or stereoisomers or pharmaceutically acceptable salts thereof, wherein E, Z, M, J, K, L, Q, $R^1$, $R^2$, $R^3$, and $R^4$ are defined below, are effective modulators of chemokine activity.

DETAILED DESCRIPTION OF PREFERRED EMBODIMENTS

[1] In one embodiment, the present invention provides novel compounds of formula (I):

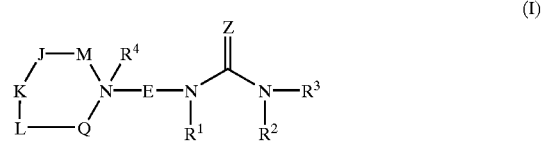

or stereoisomers or pharmaceutically acceptable salts thereof, wherein:

M is absent or selected from $CH_2$, $CHR^5$, $CHR^{13}$, $CR^{13}R^{13}$, and $CR^5R^{13}$;

Q is selected from $CH_2$, $CHR^5$, $CHR^{13}$, $CR^{13}R^{13}$, and $CR^5R^{13}$;

J, K, and L are independently selected from $CH_2$, $CHR^5$, $CHR^6$, $CR^6R^6$ and $CR^5R^6$;

with the provisos:
1) at least one of M, J, K, L, or Q contains an $R^5$; and
2) when M is absent, J is selected from $CH_2$, $CHR^5$, $CHR^{13}$, and $CR^5R^{13}$;

Z is selected from O and S;
E is selected from:

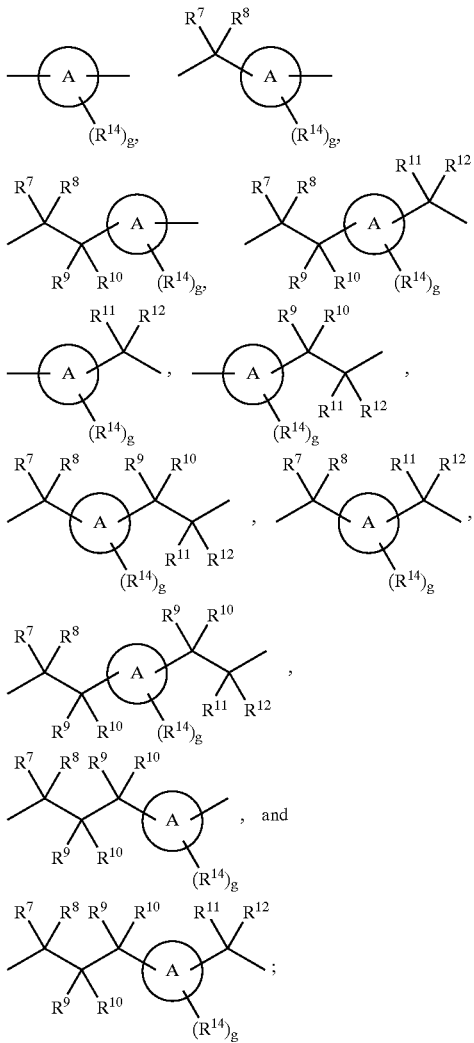

ring A is phenyl or naphthyl;

$R^1$ and $R^2$ are independently selected from H, $C_{1-6}$ alkyl, $C_{2-8}$ alkenyl, $C_{2-8}$ alkynyl, $(CH_2)_rC_{3-6}$ cycloalkyl, and a $(CH_2)_r$—$C_{3-10}$ carbocyclic residue substituted with 0–5 $R^a$;

$R^a$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^bR^b$, $(CH_2)_rOH$, $(CH_2)_rOR^c$, $(CH_2)_rSH$, $(CH_2)_rSR^c$, $(CH_2)_rC(O)R^b$, $(CH_2)_rC(O)NR^bR^b$, $(CH_2)_rNR^bC(O)R^b$, $(CH_2)_rC(O)OR^b$, $(CH_2)_rOC(O)R^c$, $(CH_2)_rCH(=NR^b)NR^bR^b$, $(CH_2)_rNHC(=NR^b)NR^bR^b$, $(CH_2)_rS(O)_pR^c$, $(CH_2)_rS(O)_2NR^bR^b$, $(CH_2)_rNR^bS(O)_2R^c$, and $(CH_2)_r$phenyl;

$R^b$, at each occurrence, is selected from H, $C_{1-6}$ alkyl, $C_{3-6}$ cycloalkyl, and phenyl;

$R^c$, at each occurrence, is selected from $C_{1-6}$ alkyl, $C_{3-6}$ cycloalkyl, and phenyl;

alternatively, $R^2$ and $R^3$ join to form a 5, 6, or 7-membered ring substituted with 0–3 $R^a$;

$R^3$ is selected from a $(CR^{3'}R^{3''})_r$—$C_{3-8}$ carbocyclic residue substituted with 1 $R^{15'}$ and 0–4 $R^{15}$; a $(CR^{3'}R^{3''})_r$—$C_{9-10}$ carbocyclic residue substituted with 0–4 $R^{15}$; and a $(CR^{3'}R^{3''})_r$-5–10 membered heterocyclic system containing 1–4 heteroatoms selected from N, O, and S, substituted with 0–3 $R^{15}$;

$R^{3'}$ and $R^{3''}$, at each occurrence, are selected from H, $C_{1-6}$ alkyl, $(CH_2)_rC_{3-6}$ cycloalkyl, and phenyl;

$R^4$ is absent, taken with the nitrogen to which it is attached to form an N-oxide, or selected from $C_{1-6}$ alkyl, $C_{2-8}$ alkenyl, $C_{2-8}$ alkynyl, $(CH_2)_rC_{3-6}$ cycloalkyl, $(CH_2)_qC(O)R^{4b}$, $(CH_2)_qC(O)NR^{4a}R^{4a'}$, $(CH_2)_qC(O)OR^{4b}$, and a $(CH_2)_r$—$C_{3-10}$ carbocyclic residue substituted with 0–3 $R^{4c}$;

$R^{4a}$ and $R^{4a'}$, at each occurrence, are selected from H, $C_{1-6}$ alkyl, $(CH_2)_rC_{3-6}$ cycloalkyl, and phenyl;

$R^{4b}$, at each occurrence, is selected from $C_{1-6}$ alkyl, $C_{2-8}$ alkenyl, $(CH_2)_rC_{3-6}$ cycloalkyl, $C_{2-8}$ alkynyl, and phenyl;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_r SC_{1-5}$ alkyl, $(CH_2)_rNR^{4a}R^{4a'}$, and $(CH_2)_r$ phenyl;

alternatively, $R^4$ joins with $R^7$, $R^9$, $R^{11}$, or $R^{14}$ to form a 5, 6 or 7 membered piperidinium spirocycle or pyrrolidinium spirocycle substituted with 0–3 $R^a$;

$R^5$ is selected from a $(CR^{5'}R^{5''})_r$—$C_{3-10}$ carbocyclic residue substituted with 0–5 $R^{16}$ and a $(CR^{5'}R^{5''})_r$-5–10 membered heterocyclic system containing 1–4 heteroatoms selected from N, O, and S, substituted with 0–3 $R^{16}$;

$R^{5'}$ and $R^{5''}$, at each occurrence, are selected from H, $C_{1-6}$ alkyl, $(CH_2)_rC_{3-6}$ cycloalkyl, and phenyl;

$R^6$, at each occurrence, is selected from $C_{1-6}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rNR^{6a}R^{6a'}$, $(CH_2)_rOH$, $(CH_2)_rOR^{6b}$, $(CH_2)_rSH$, $(CH_2)_rSR^{6b}$, $(CH_2)_rC(O)OH$, $(CH_2)_rC(O)R^{6b}$, $(CH_2)_rC(O)NR^{6a}R^{6a'}$, $(CH_2)_rNR^{6d}C(O)R^{6a}$, $(CH_2)_rC(O)OR^{6b}$, $(CH_2)_rOC(O)R^{6b}$, $(CH_2)_rS(O)_pR^{6b}$, $(CH_2)_rS(O)_2NR^{6a}R^{6a'}$, $(CH_2)_rNR^{6d}S(O)_2R^{6b}$, and $(CH_2)_r$phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is selected from H, $C_{1-6}$ alkyl, and $C_{3-6}$ cycloalkyl;

with the proviso that when any of J, K, or L is $CR^6R^6$ and $R^6$ is halogen, cyano, nitro, or bonded to the carbon to which it is attached through a heteroatom, the other $R^6$ is not halogen, cyano, or bonded to the carbon to which it is attached through a heteroatom;

$R^7$, is selected from H, $C_{1-6}$ alkyl, $C_{2-8}$ alkenyl, $C_{2-8}$ alkynyl, $(CH_2)_qOH$, $(CH_2)_qSH$, $(CH_2)_qOR^{7d}$, $(CH_2)_q SR^{7d}$, $(CH_2)_qNR^{7a}R^{7a'}$, $(CH_2)_rC(O)OH$, $(CH_2)_rC(O)R^{7b}$, $(CH_2)_rC(O)NR^{7a}R^{7a'}$, $(CH_2)_qNR^{7a}C(O)R^{7a}$, $(CH_2)_qNR^{7a}C(O)H$, $(CH_2)_rC(O)OR^{7b}$, $(CH_2)_qOC(O)R^{7b}$, $(CH_2)_qS(O)_pR^{7b}$, $(CH_2)_qS(O)_2NR^{7a}R^{7a'}$, $(CH_2)_qNR^{7a}S(O)_2R^{7b}$, $C_{1-6}$ haloalkyl, a $(CH_2)_r$—$C_{3-10}$ carbocyclic residue substituted with 0–3 $R^{7c}$, and a $(CH_2)_r$-5–10 membered heterocyclic system containing 1–4 heteroatoms selected from N, O, and S, substituted with 0–2 $R^{7c}$;

$R^{7a}$ and $R^{7a'}$, at each occurrence, are selected from H, $C_{1-6}$ alkyl, $C_{2-8}$ alkenyl, $C_{2-8}$ alkynyl, $(CH_2)_rC_{3-6}$ cycloalkyl, a $(CH_2)_r$—$C_{3-10}$ carbocyclic residue substituted with 0–5 $R^{7e}$, and a $(CH_2)_r$-5–10 membered heterocyclic system containing 1–4 heteroatoms selected from N, O, and S, substituted with 0–3 $R^{7e}$;

$R^{7b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–2 $R^{7e}$, and a $(CH_2)_r$-5–6 membered heterocyclic system containing 1–4 heteroatoms selected from N, O, and S, substituted with 0–3 $R^{7e}$;

$R^{7c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{7f}R^{7f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{7b}$, $(CH_2)_rC(O)NR^{7f}R^{7f}$, $(CH_2)_rNR^{7f}C(O)R^{7a}$, $(CH_2)_rC(O)OC_{1-4}$ alkyl, $(CH_2)_rOC(O)R^{7b}$, $(CH_2)_rC(=NR^{7f})NR^{7f}R^{7f}$, $(CH_2)_rS(O)_pR^{7b}$, $(CH_2)_rNHC(=NR^{7f})NR^{7f}R^{7f}$, $(CH_2)_rS(O)_2NR^{7f}R^{7f}$, $(CH_2)_rNR^{7f}S(O)_2R^{7b}$, and $(CH_2)_r$phenyl substituted with 0–3 $R^{7e}$;

$R^{7d}$, at each occurrence, is selected from $C_{1-6}$ alkyl substituted with 0–3 $R^{7e}$, alkenyl, alkynyl, and a $C_{3-10}$ carbocyclic residue substituted with 0–3 $R^{7c}$;

$R^{7e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

$R^{7f}$, at each occurrence, is selected from H, $C_{1-6}$ alkyl, and $C_{3-6}$ cycloalkyl;

$R^8$ is selected from H, $C_{1-6}$ alkyl, $C_{3-6}$ cycloalkyl, and $(CH_2)_r$phenyl substituted with 0–3 $R^{8a}$;

$R^{8a}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

alternatively, $R^7$ and $R^8$ join to form $C_{3-7}$ cycloalkyl, or $=NR^{8b}$;

$R^{8b}$ is selected from H, $C_{1-6}$ alkyl, $C_{3-6}$ cycloalkyl, OH, CN, and $(CH_2)_r$-phenyl;

$R^9$, is selected from H, $C_{1-6}$ alkyl, $C_{2-8}$ alkenyl, $C_{2-8}$ alkynyl, F, Cl, Br, I, $NO_2$, CN, $(CH_2)_rOH$, $(CH_2)_rSH$, $(CH_2)_rOR^{9d}$, $(CH_2)_rSR^{9d}$, $(CH_2)_rNR^{9a}R^{9a'}$, $(CH_2)_rC(O)OH$, $(CH_2)_rC(O)R^{9b}$, $(CH_2)_rC(O)NR^{9a}R^{9a'}$, $(CH_2)_rNR^{9a}C(O)R^{9a}$, $(CH_2)_rNR^{9a}C(O)H$, $(CH_2)_rNR^{9a}C(O)NHR^{9a}$, $(CH_2)_rC(O)OR^{9b}$, $(CH_2)_rOC(O)R^{9b}$, $(CH_2)_rOC(O)NHR^{9a}$, $(CH_2)_rS(O)_pR^{9b}$, $(CH_2)_rS(O)_2NR^{9a}R^{9a'}$, $(CH_2)_rNR^{9a}S(O)_2R^{9b}$, $C_{1-6}$ haloalkyl, a $(CH_2)_r$—$C_{3-10}$ carbocyclic residue substituted with 0–5 $R^{9c}$, and a $(CH_2)_r$-5–10 membered heterocyclic system containing 1–4 heteroatoms selected from N, O, and S, substituted with 0–3 $R^{9c}$;

$R^{9a}$ and $R^{9a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{9e}$, and a $(CH_2)_r$-5–10 membered heterocyclic system containing 1–4 heteroatoms selected from N, O, and S, substituted with 0–3 $R^{9e}$;

$R^{9b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–2 $R^{9e}$, and a $(CH_2)_r$-5–6 membered heterocyclic system containing 1–4 heteroatoms selected from N, O, and S, substituted with 0–3 $R^{9e}$;

$R^{9c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{9f}R^{9f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{9b}$, $(CH_2)_rC(O)NR^{9f}R^{9f}$, $(CH_2)_rNR^{9f}C(O)R^{9a}$, $(CH_2)_rC(O)OC_{1-4}$ alkyl, $(CH_2)_rOC(O)R^{9b}$, $(CH_2)_rC(=NR^{9f})NR^{9f}R^{9f}$, $(CH_2)_rS(O)_pR^{9b}$, $(CH_2)_rNHC(=NR^{9f})NR^{9f}R^{9f}$, $(CH_2)_rS(O)_2NR^{9f}R^{9f}$, $(CH_2)_rNR^{9f}S(O)_2R^{9b}$, and $(CH_2)_r$phenyl substituted with 0–3 $R^{9e}$;

$R^{9d}$, at each occurrence, is selected from $C_{1-6}$ alkyl, $C_{2-6}$ alkenyl, $C_{2-6}$ alkynyl, a $C_{3-10}$ carbocyclic residue substituted with 0–3 $R^{9c}$, and a 5–6 membered heterocyclic system containing 1–4 heteroatoms selected from the group consisting of N, O, and S substituted with 0–3 $R^{9c}$;

$R^{9e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{9f}R^{9f}$, and $(CH_2)_r$phenyl;

$R^{9f}$, at each occurrence, is selected from H, $C_{1-6}$ alkyl, and $C_{3-6}$ cycloalkyl;

$R^{10}$, is selected from H, $C_{1-6}$ alkyl, $C_{2-8}$ alkenyl, $C_{2-8}$ alkynyl, F, Cl, Br, I, $NO_2$, CN, $(CH_2)_rOH$, $(CH_2)_rOR^{10d}$, $(CH_2)_rSR^{10d}$, $(CH_2)_rNR^{10a}R^{10a'}$, $(CH_2)_rC(O)OH$, $(CH_2)_rC(O)R^{10b}$, $(CH_2)_rC(O)NR^{10a}R^{10a'}$, $(CH_2)_rNR^{10a}C(O)R^{10a}$, $(CH_2)_rNR^{10a}C(O)H$, $(CH_2)_rC(O)OR^{10b}$, $(CH_2)_rOC(O)R^{10b}$, $(CH_2)_rS(O)_pR^{10b}$, $(CH_2)_rS(O)_2NR^{10a}R^{10a'}$, $(CH_2)_rNR^{10a}S(O)_2R^{10b}$, $C_{1-6}$ haloalkyl, a $(CH_2)_r$—$C_{3-10}$ carbocyclic residue substituted with 0–5 $R^{10c}$, and a $(CH_2)_r$-5–10 membered heterocyclic system containing 1–4 heteroatoms selected from N, O, and S, substituted with 0–3 $R^{10c}$;

$R^{10a}$ and $R^{10a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{10e}$, and a $(CH_2)_r$-5–10 membered heterocyclic system containing 1–4 heteroatoms selected from N, O, and S, substituted with 0–3 $R^{10e}$;

$R^{10b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–2 $R^{10e}$, and a $(CH_2)_r$-5–6 membered heterocyclic system containing 1–4 heteroatoms selected from N, O, and S, substituted with 0–3 $R^{10e}$;

$R^{10c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{10f}R^{10f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{10b}$, $(CH_2)_rC(O)NR^{10f}R^{10f}$, $(CH_2)_rNR^{10f}C(O)R^{10a}$, $(CH_2)_rC(O)OC_{1-4}$ alkyl, $(CH_2)_rOC(O)R^{10b}$, $(CH_2)_rC(=NR^{10f})NR^{10f}R^{10f}$, $(CH_2)_rS(O)_pR^{10b}$, $(CH_2)_rNHC(=NR^{10f})NR^{10f}R^{10f}$, $(CH_2)_rS(O)_2NR^{10f}R^{10f}$, $(CH_2)_rNR^{10f}S(O)_2R^{10b}$, and $(CH_2)_r$phenyl substituted with 0–3 $R^{10e}$;

$R^{10d}$, at each occurrence, is selected from $C_{1-6}$ alkyl, $C_{2-6}$ alkenyl, $C_{2-6}$ alkynyl, a $C_{3-10}$ carbocyclic residue substituted with 0–3 $R^{10c}$, and a 5–6 membered heterocyclic system containing 1–4 heteroatoms selected from the group consisting of N, O, and S substituted with 0–3 $R^{10c}$;

$R^{10e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{10f}R^{10f}$, and $(CH_2)_r$ phenyl;

$R^{10f}$, at each occurrence, is selected from H, $C_{1-5}$ alkyl, and $C_{3-6}$ cycloalkyl;

alternatively, $R^9$ and $R^{10}$ join to form $C_{3-7}$ cycloalkyl, 5–6-membered cyclic ketal or =O;

with the proviso that when $R^{10}$ is halogen, cyano, nitro, or bonded to the carbon to which it is attached through a heteroatom, $R^9$ is not halogen, cyano, or bonded to the carbon to which it is attached through a heteroatom;

$R^{11}$, is selected from H, $C_{1-6}$ alkyl, $C_{2-8}$ alkenyl, $C_{2-8}$ alkynyl, $(CH_2)_qOH$, $(CH_2)_qSH$, $(CH_2)_qOR^{11d}$, $(CH_2)_q SR^{11d}$, $(CH_2)_qNR^{11a}R^{11a'}$, $(CH_2)_rC(O)OH$, $(CH_2)_rC(O)R^{11b}$, $(CH_2)_qC(O)NR^{11a}R^{11a'}$, $(CH_2)_qNR^{11a}C(O)R^{11a}$, $(CH_2)_qNR^{11a}C(O)NHR^{11a}$, $(CH_2)_rC(O)OR^{11b}$, $(CH_2)_qOC(O)R^{11b}$, $(CH_2)_qS(O)_pR^{11b}$, $(CH_2)_qS(O)_2NR^{11a}R^{11a'}$, $(CH_2)_qNR^{11a}S(O)_2R^{11b}$, $C_{1-6}$ haloalkyl, a $(CH_2)_r$—$C_{3-10}$ carbocyclic residue substituted with 0–5 $R^{11c}$, and a $(CH_2)_r$-5–10 membered heterocyclic system containing 1–4 heteroatoms selected from N, O, and S, substituted with 0–3 $R^{11c}$;

$R^{11a}$ and $R^{11a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{11e}$, and a $(CH_2)_r$-5–10 membered heterocyclic system containing 1–4 heteroatoms selected from N, O, and S, substituted with 0–3 $R^{11e}$;

$R^{11b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–2 $R^{11e}$, and a $(CH_2)_r$-5–6 membered heterocyclic system containing 1–4 heteroatoms selected from N, O, and S, substituted with 0–3 $R^{11e}$;

$R^{11c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{11f}R^{11f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{11b}$, $(CH_2)_rC(O)NR^{11f}R^{11f}$, $(CH_2)_rNR^{11f}C(O)R^{11a}$, $(CH_2)_rC(O)OC_{1-4}$ alkyl, $(CH_2)_rOC(O)R^{11b}$, $(CH_2)_rC(=NR^{11f})NR^{11f}R^{11f}$, $(CH_2)_rNHC(=NR^{11f})NR^{11f}R^{11f}$, $(CH_2)_rS(O)_pR^{11b}$, $(CH_2)_rS(O)_2NR^{11f}R^{11f}$, $(CH_2)_rNR^{11f}S(O)_2R^{11b}$, and $(CH_2)_r$phenyl substituted with 0–3 $R^{11e}$;

$R^{11d}$, at each occurrence, is selected from $C_{1-6}$ alkyl substituted with 0–3 $R^{11e}$, $C_{2-6}$ alkenyl, $C_{2-6}$ alkynyl, and a $C_{3-10}$ carbocyclic residue substituted with 0–3 $R^{11c}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{11f}R^{11f}$, and $(CH_2)_r$phenyl; $R^{11f}$, at each occurrence, is selected from H, $C_{1-6}$ alkyl, and $C_{3-6}$ cycloalkyl;

$R^{12}$ is selected from H, $C_{1-6}$ alkyl, $(CH_2)_qOH$, $(CH_2)_rC_{3-6}$ cycloalkyl, and $(CH_2)_r$phenyl substituted with 0–3 $R^{12a}$;

$R^{12a}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r SC_{1-5}$ alkyl, $(CH_2)_rNR^{9f}R^{9f}$, and $(CH_2)_r$phenyl;

alternatively, $R^{11}$ and $R^{12}$ join to form $C_{3-7}$ cycloalkyl;

$R^{13}$, at each occurrence, is selected from $C_{1-6}$ alkyl, $C_{2-8}$ alkenyl, $C_{2-8}$ alkynyl, $C_{3-6}$ cycloalkyl, $(CF_2)_wCF_3$, $(CH_2)_rNR^{13a}R^{13a'}$, $(CH_2)_rOH$, $(CH_2)_rOR^{13b}$, $(CH_2)_r SH$, $(CH_2)_rSR^{13b}$, $(CH_2)_wC(O)OH$, $(CH_2)_wC(O)R^{13b}$, $(CH_2)_wC(O)NR^{13a}R^{13a'}$, $(CH_2)_rNR^{13d}C(O)R^{13a}$, $(CH_2)_wC(O)OR^{13b}$, $(CH_2)_wOC(O)R^{13b}$, $(CH_2)_wS(O)_pR^{13b}$, $(CH_2)_wS(O)_2NR^{13a}R^{13a'}$, $(CH_2)_rNR^{13d}S(O)_2R^{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_r OC_{1-5}$ alkyl, $(CH_2)_rOH$, $(CH_2)_rSC_{1-5}$ alkyl, and $(CH_2)_r NR^{13d}R^{13d}$;

$R^{13d}$, at each occurrence, is selected from H, $C_{1-6}$ alkyl, and $C_{3-6}$ cycloalkyl;

$R^{14}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{14a}R^{14a'}$, $(CHR')_rOH$, $(CHR')_r O(CHR')_rR^{14d}$, $(CHR')_rSH$, $(CHR')_rC(O)H$, $(CHR')_rS(CHR')_rR^{14d}$, $(CHR')_rC(O)$ OH, $(CHR')_rC(O)$ $(CHR')_rR^{14b}$, $(CHR')_rC(O)NR^{14a}R^{14a'}$, $(CHR')_rNR^{14f}C(O)(CHR')_rR^{14b}$, $(CHR')_rC(O)O(CHR')_rR^{14d}$, $(CHR')_rOC(O)(CHR')_rR^{14b}$, $(CHR')_rC(=NR^{14f})NR^{14a}R^{14a'}$, $(CHR')_rNHC(=NR^{14f})NR^{14f}R^{14f}$, $(CHR')_rS(O)_p(CHR')_rR^{14b}$, $(CHR')_rS(O)_2NR^{14a}R^{14a'}$, $(CHR')_rNR^{14f}S(O)_2(CHR')_rR^{14b}$, $C_{1-6}$ haloalkyl, $C_{2-8}$ alkenyl substituted with 0–3 R', $C_{2-8}$ alkynyl substituted with 0–3 R', $(CHR')_r$phenyl substituted with 0–3 $R^{14e}$, and a $(CH_2)_r$-5–10 membered heterocyclic system containing 1–4 heteroatoms selected from N, O, and S, substituted with 0–2 $R^{15e}$, or two $R^{14}$ substituents on adjacent atoms on ring A form to join a 5–6 membered heterocyclic system containing 1–3 heteroatoms selected from N, O, and S substituted with 0–2 $R^{15e}$;

alternatively, $R^{14}$ joins with $R^4$ to form a 5, 6 or 7 membered piperidinium spirocycle or pyrrolidinium spirocycle fused to ring A, the spirocycle substituted with 0–3 $R^a$;

R', at each occurrence, is selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with $R^{14e}$;

$R^{14a}$ and $R^{14a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{14e}$, and a $(CH_2)_r$-5–10 membered heterocyclic system containing 1–4 heteroatoms selected from N, O, and S, substituted with 0–2 $R^{14e}$;

$R^{14b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{14e}$, and $(CH_2)_r$-5–6 membered heterocyclic system containing 1–4 heteroatoms selected from N, O, and S, substituted with 0–2 $R^{14e}$;

$R^{14d}$, at each occurrence, is selected from $C_{2-8}$ alkenyl, $C_{2-8}$ alkynyl, $C_{1-6}$ alkyl substituted with 0–3 $R^{14e}$, a $(CH_2)_r$—$C_{3-10}$ carbocyclic residue substituted with 0–3 $R^{14e}$, and a $(CH_2)_r$5–6 membered heterocyclic system containing 1–4 heteroatoms selected from N, O, and S, substituted with 0–3 $R^{14e}$;

$R^{14e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{14f}R^{14f}$, and $(CH_2)_r$ phenyl;

$R^{14f}$, at each occurrence, is selected from H, $C_{1-6}$ alkyl, $C_{3-6}$ cycloalkyl, and phenyl;

$R^{15}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{15a}R^{15a'}$, $(CHR')_rOH$, $(CHR')_r O(CHR')_rR^{15d}$, $(CHR')_rSH$, $(CHR')_rC(O)H$, $(CHR')_rS(CHR')_rR^{15d}$, $(CHR')_rC(O)OH$, $(CHR')_rC(O)$ $(CHR')_r R^{15b}$, $(CHR')_rC(O)NR^{15a}R^{15a'}$, $(CHR')_rNR^{15f}C(O)(CHR')_rR^{15b}$, $(CHR')_rC(O)O(CHR')_rR^{15d}$, $(CHR')_rOC (O) (CHR')$_r$R$^{15b}$, ((CHR')$_r$C(=NR$^{15f}$)NR$^{15a}$R$^{15a'}$, (CHR')$_r$NHC(=NR$^{15f}$)NR$^{15f}$R$^{15f}$, (CHR')$_r$S(O)$_p$(CHR')$_r$R$^{15b}$, (CHR')$_r$S(O)$_2$NR$^{15a}$R$^{15a'}$, (CHR')$_r$NR$^{15f}$S(O)$_2$(CHR')$_r$R$^{15b}$, C$_{1-6}$ haloalkyl, C$_{2-8}$ alkenyl substituted with 0–3 R', C$_{2-8}$ alkynyl substituted with 0–3 R', (CHR')$_r$phenyl substituted with 0–3 R$^{15e}$, and a (CH$_2$)$_r$-5–10 membered heterocyclic system containing 1–4 heteroatoms selected from N, O, and S, substituted with 0–2 R$^{15e}$;

R$^{15'}$, at each occurrence, is selected from C$_{2-8}$ alkenyl, C$_{2-8}$ alkynyl, (CH$_2$)$_r$C$_{3-6}$ cycloalkyl, (CHR')$_r$NR$^{15a}$R$^{15a'}$, (CHR')$_r$O(CHR')$_r$R$^{15d}$, (CHR')$_r$SH, (CHR')$_{3-5}$C(O)H, (CHR')$_r$S(CHR')$_r$R$^{15d}$, (CHR')$_q$C(O)OH, (CHR')$_q$C(O) (CHR')$_q$R$^{15b}$, (CHR')$_r$C(O)NR$^{15a}$R$^{15a'}$, (CHR')$_r$NR$^{15f}$C(O) (CHR')$_r$R$^{15b}$, (CHR')$_r$C(O)O(CHR')$_r$R$^{15d}$, (CHR')$_r$OC(O) (CHR')$_r$R$^{15b}$, (CHR')$_r$C(=NR$^{15f}$)NR$^{15a}$R$^{15a'}$, (CHR')$_r$NHC(=NR$^{15f}$)NR$^{15f}$R$^{15f}$, (CHR')$_r$S(O)$_p$(CHR')$_r$R$^{15b}$, (CHR')$_r$S(O)$_2$NR$^{15a}$R$^{15a'}$, (CHR')$_r$NR$^{15f}$S(O)$_2$(CHR')$_r$R$^{15b}$, C$_{2-8}$ alkenyl substituted with 0–3 R', C$_{2-8}$ alkynyl substituted with 0–3 R', (CHR')$_r$phenyl substituted with 0–3 R$^{15e}$, and a (CH$_2$)$_r$-5–10 membered heterocyclic system containing 1–4 heteroatoms selected from N, O, and S, substituted with 0–2 R$^{15e}$;

R$^{15a}$ and R$^{15a'}$, at each occurrence, are selected from H, C$_{1-6}$ alkyl, C$_{2-8}$ alkenyl, C$_{2-8}$ alkynyl, a (CH$_2$)$_r$—C$_{3-10}$ carbocyclic residue substituted with 0–5 R$^{15e}$, and a (CH$_2$)$_r$-5–10 membered heterocyclic system containing 1–4 heteroatoms selected from N, O, and S, substituted with 0–2 R$^{15e}$;

R$^{15b}$, at each occurrence, is selected from C$_{1-6}$ alkyl, C$_{2-8}$ alkenyl, C$_{2-8}$ alkynyl, a (CH$_2$)$_r$—C$_{3-6}$ carbocyclic residue substituted with 0–3 R$^{15e}$, and (CH$_2$)$_r$-5–6 membered heterocyclic system containing 1–4 heteroatoms selected from N, O, and S, substituted with 0–2 R$^{15e}$;

R$^{15d}$, at each occurrence, is selected from C$_{2-8}$ alkenyl, C$_{2-8}$ alkynyl, C$_{1-6}$ alkyl substituted with 0–3 R$^{15e}$, a (CH$_2$)$_r$—C$_{3-10}$ carbocyclic residue substituted with 0–3 R$^{15e}$, and a (CH$_2$)$_r$-5–6 membered heterocyclic system containing 1–4 heteroatoms selected from N, O, and S, substituted with 0–3 R$^{15e}$;

R$^{15e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{15f}$R$^{15f}$, and (CH$_2$)$_r$ phenyl;

R$^{15f}$, at each occurrence, is selected from H, C$_{1-6}$ alkyl, C$_{3-6}$ cycloalkyl, and phenyl;

R$^{16}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CHR')$_r$NR$^{16a}$R$^{16a'}$, (CHR')$_r$OH, (CHR')$_r$O(CHR')$_r$R$^{16d}$, (CHR')$_r$SH, (CHR')$_r$C(O)H, (CHR')$_r$S(CHR')$_r$R$^{16d}$, (CHR')$_r$C(O)OH, (CHR')$_r$C(O)(CHR')$_r$R$^{16b}$, (CHR')$_r$C(O)NR$^{16a}$R$^{16a'}$, (CHR')$_r$NR$^{16f}$C(O)(CHR')$_r$R$^{16b}$, (CHR')$_r$C(O)O(CHR')$_r$R$^{16d}$, (CHR')$_r$OC(O)(CHR')$_r$R$^{16b}$, (CHR')$_r$C(=NR$^{16f}$)NR$^{16a}$R$^{16a'}$, (CHR')$_r$NHC(=NR$^{16f}$)NR$^{16f}$R$^{16f}$, (CHR')$_r$S(O)$_p$(CHR')$_r$R$^{16b}$, (CHR')$_r$S(O)$_2$NR$^{16a}$R$^{16a'}$, (CHR')$_r$NR$^{16f}$S(O)$_2$(CHR')$_r$R$^{16b}$, C$_{1-6}$ haloalkyl, C$_{2-8}$ alkenyl substituted with 0–3 R', C$_{2-8}$ alkynyl substituted with 0–3 R', and (CHR')$_r$phenyl substituted with 0–3 R$^{16e}$;

R$^{16a}$ and R$^{16a'}$, at each occurrence, are selected from H, C$_{1-6}$ alkyl, C$_{2-8}$ alkenyl, C$_{2-8}$ alkynyl, a (CH$_2$)$_r$—C$_{3-10}$ carbocyclic residue substituted with 0–5 R$^{16e}$, and a (CH$_2$)$_r$-5–10 membered heterocyclic system containing 1–4 heteroatoms selected from N, O, and S, substituted with 0–2 R$^{16e}$;

R$^{16b}$, at each occurrence, is selected from C$_{1-6}$ alkyl, C$_{2-8}$ alkenyl, C$_{2-8}$ alkynyl, a (CH$_2$)$_r$C$_{3-6}$ carbocyclic residue substituted with 0–3 R$^{16e}$, and a (CH$_2$)$_r$-5–6 membered heterocyclic system containing 1–4 heteroatoms selected from N, O, and S, substituted with 0–2 R$^{16e}$;

R$^{16d}$, at each occurrence, is selected from C$_{2-8}$ alkenyl, C$_{2-8}$ alkynyl, C$_{1-6}$ alkyl substituted with 0–3 R$^{16e}$, a (CH$_2$)$_r$—C$_{3-10}$ carbocyclic residue substituted with 0–3 R$^{16e}$, and a (CH$_2$)$_r$-5–6 membered heterocyclic system containing 1–4 heteroatoms selected from N, O, and S, substituted with 0–3 R$^{16e}$;

R$^{16e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{16f}$R$^{16f}$, and (CH$_2$)$_r$ phenyl;

R$^{16f}$, at each occurrence, is selected from H, C$_{1-6}$ alkyl, and C$_{3-6}$ cycloalkyl, and phenyl;

g is selected from 0, 1, 2, 3, and 4;
t is selected from 1 and 2;
w is selected from 0 and 1;
r is selected from 0, 1, 2, 3, 4, and 5;
q is selected from 1, 2, 3, 4, and 5; and
p is selected from 0, 1, 2, and 3.

[2] In a preferred embodiment, the present invention provides novel compounds of formula (I), wherein:
Z is selected from O and S;
E is selected from:

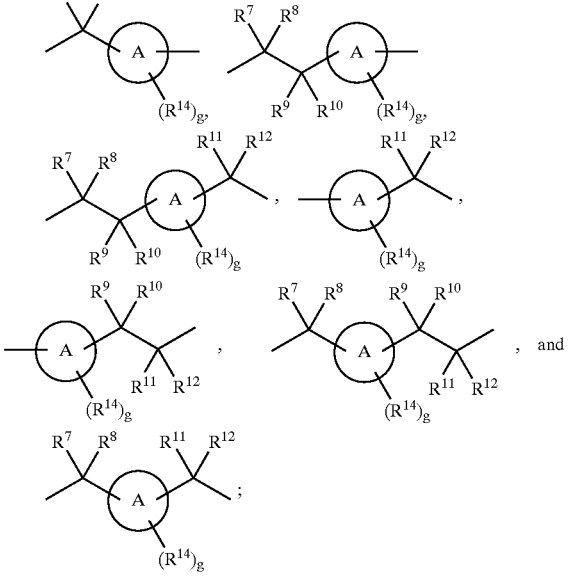

R$^4$ is absent, taken with the nitrogen to which it is attached to form an N-oxide, or selected from C$_{1-8}$ alkyl, (CH$_2$)$_r$C$_{3-6}$ cycloalkyl, and (CH$_2$)$_r$-phenyl substituted with 0–3 R$^{4c}$;

R$^{4c}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$ SC$_{1-5}$ alkyl, (CH$_2$)$_r$NR$^{4a}$R$^{4a'}$, and (CH$_2$)$_r$ phenyl;

alternatively, R$^4$ joins with R$^7$ R$^9$, or R$^{14}$ to form a 5, 6 or 7 membered piperidinium spirocycle substituted with 0–3 R$^a$;

R$^1$ and R$^2$ are independently selected from H and C$_{1-4}$ alkyl;

$R^6$, at each occurrence, is selected from $C_{1-4}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rOH$, $(CH_2)_rOR^{6b}$, $(CH_2)_rC(O)R^{6b}$, $(CH_2)_rC(O)NR^{6a}R^{6a'}$, $(CH_2)_rNR^{6d}C(O)R^{6a}$, and $(CH_2)_r$ phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is selected from H, $C_{1-6}$ alkyl, and $C_{3-6}$ cycloalkyl;

$R^7$, is selected from H, $C_{1-3}$ alkyl, $(CH_2)_qC_{3-6}$ cycloalkyl, $(CH_2)_qOH$, $(CH_2)_qOR^{7d}$, $(CH_2)_qNR^{7a}R^{7a'}$, $(CH_2)_rC(O)R^{7b}$, $(CH_2)_rC(O)NR^{7a}R^{7a'}$, $(CH_2)_qNR^{7a}C(O)R^{7a}$, $C_{1-6}$ haloalkyl, $(CH_2)_r$phenyl with 0–2 $R^{7c}$;

$R^{7a}$ and $R^{7a'}$, at each occurrence, are selected from H, $C_{1-6}$ alkyl, $(CH_2)_rC_{3-6}$ cycloalkyl, a $(CH_2)_r$phenyl substituted with 0–3 $R^{7e}$;

$R^{7b}$, at each occurrence, is selected from $C_{1-6}$ alkyl, $C_{2-8}$ alkenyl, $C_{2-8}$ alkynyl, $(CH_2)_rC_{3-6}$ cycloalkyl, $(CH_2)_r$ phenyl substituted with 0–3 $R^{7e}$;

$R^{7c}$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{7f}R^{7f}$, $(CH_2)_rOH$, $(CH_2)_rOC_{1-4}$ alkyl, $(CH_2)_rC(O)R^{7b}$, $(CH_2)_rC(O)NR^{7f}R^{7f}$, $(CH_2)_rNR^{7f}C(O)R^{7a}$, $(CH_2)_rS(O)_pR^{7b}$, $(CH_2)_r$ $S(O)_2NR^{7f}R^{7f}$, $(CH_2)_rNR^{7f}S(O)_2R^{7b}$, and $(CH_2)_r$ phenyl substituted with 0–2 $R^{7e}$;

$R^{7d}$, at each occurrence, is selected from $C_{1-6}$ alkyl, $(CH_2)_rC_{3-6}$ cycloalkyl, $(CH_2)_r$phenyl substituted with 0–3 $R^{7e}$;

$R^{7e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

$R^{7f}$, at each occurrence, is selected from H, $C_{1-5}$ alkyl, and $C_{3-6}$ cycloalkyl;

$R^8$ is H or joins with $R^7$ to form $C_{3-7}$ cycloalkyl or $=NR^{8b}$;

$R^{11}$, is selected from H, $C_{1-6}$ alkyl, $(CH_2)_rC_{3-6}$ cycloalkyl, $(CH_2)_qOH$, $(CH_2)_qOR^{11d}$, $(CH_2)_qNR^{11a}R^{11a'}$, $(CH_2)_rC(O)R^{11b}$, $(CH_2)_rC(O)NR^{11a}R^{11a'}$, $(CH_2)_qNR^{11a}C(O)R^{11a}$, $C_{1-6}$ haloalkyl, $(CH_2)_r$phenyl with 0–2 $R^{11c}$, $(CH_2)_r$-5–10 membered heterocyclic system containing 1–4 heteroatoms selected from N, O, and S, substituted with 0–3 $R^{15}$;

$R^{11a}$ and $R^{11a'}$, at each occurrence, are selected from H, $C_{1-6}$ alkyl, $(CH_2)_rC_{3-6}$ cycloalkyl, a $(CH_2)_r$phenyl substituted with 0–3 $R^{11e}$;

$R^{11b}$, at each occurrence, is selected from $C_{1-6}$ alkyl, $C_{2-8}$ alkenyl, $C_{2-8}$ alkynyl, $(CH_2)_rC_{3-6}$ cycloalkyl, $(CH_2)_r$ phenyl substituted with 0–3 $R^{11e}$;

$R^{11c}$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{11f}R^{11f}$, $(CH_2)_rOH$, $(CH_2)_rOC_{1-4}$ alkyl, $(CH_2)_rC(O)R^{11b}$, $(CH_2)_rC(O)NR^{11f}R^{11f}$, $(CH_2)_rNR^{11f}C(O)R^{11a}$, $(CH_2)_rS(O)_pR^{11b}$, $(CH_2)_rS(O)_2NR^{11f}R^{11f}$, $(CH_2)_rNR^{11f}S(O)_2R^{11b}$, and $(CH_2)_r$phenyl substituted with 0–2 $R^{11e}$;

$R^{11d}$, at each occurrence, is selected from $C_{1-6}$ alkyl, $(CH_2)_rC_{3-6}$ cycloalkyl, $(CH_2)_r$phenyl substituted with 0–3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{11f}R^{11f}$, and $(CH_2)_r$phenyl;

$R^{11f}$, at each occurrence, is selected from H, $C_{1-5}$ alkyl and $C_{3-6}$ cycloalkyl;

$R^{12}$ is H or joins with $R^{11}$ to form $C_{3-7}$ cycloalkyl;

$R^{13}$, at each occurrence, is selected from $C_{1-4}$ alkyl, $C_{3-6}$ cycloalkyl, $(CH_2)NR^{13a}R^{13a'}$, $(CH_2)OH$, $(CH_2)OR^{13b}$, $(CH_2)_wC(O)R^{13b}$, $(CH_2)_wC(O)NR^{13a}R^{13a'}$, $(CH_2)NR^{13d}C(O)R^{13a}$, $(CH_2)_wS(O)_2NR^{13a}R^{13a'}$, $(CH_2)NR^{13d}S(O)_2R^{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, and $(CH_2)_rNR^{13d}R^{13d}$;

$R^{13d}$, at each occurrence, is selected from H, $C_{1-6}$ alkyl, and $C_{3-6}$ cycloalkyl;

q is selected from 1, 2, and 3; and r is selected from 0, 1, 2, and 3.

[3] In a more preferred embodiment, the present invention provides novel compounds of formula (I), wherein:

ring A is selected from:

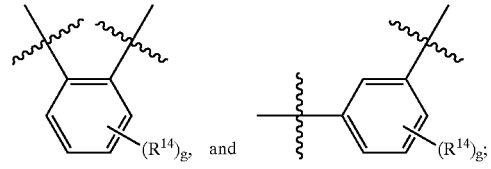

$R^3$ is selected from a $(CR^{3'}H)_r$—$C_{3-8}$ carbocyclic residue substituted with 1 $R^{15'}$ and 0–4 $R^{15}$, wherein the $C_{3-8}$ carbocyclic residue is selected from phenyl, $C_{3-6}$ cycloalkyl; a $(CR^{3'}H)_r$—$C_{9-10}$ carbocyclic residue substituted with 0–4 $R^{15}$, wherein the $C_{9-10}$ carbocyclic residue is selected from naphthyl and adamantyl; and a $(CR^{3'}H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^5$ is selected from $(CR^{5'}H)_r$-phenyl substituted with 0–5 $R^{16}$; and a $(CR^{5'}H)_r$-heterocyclic system substituted with 0–3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl.

[4] In an even more preferred embodiment, the present invention provides novel compounds of formula (I-i), wherein the compound of formula (I-i) is:

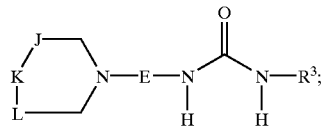

(I-i)

with the proviso that at least one of J, K, or L contains an $R^5$;

$R^{16}$, at each occurrence, is selected from $C_{1-8}$ alkyl, $(CH_2)_rC_{3-6}$ cycloalkyl, $CF_3$, Cl, Br, I, F, $(CH_2)_rNR^{16a}R^{16a'}$, $NO_2$, CN, OH, $(CH_2)_rOR^{16d}$, $(CH_2)_rC(O)R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_rNR^{16f}S(O)_2R^{16b}$, and $(CH_2)_r$phenyl substituted with 0–3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl;

$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

[5] In an another even more preferred embodiment, the present invention provides novel compounds of formula (I-ii), wherein (I-ii) is:

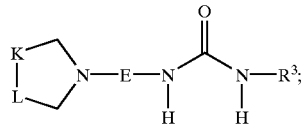

(I-ii)

with the proviso that at least one of K or L contains an $R^5$;

$R^{16}$, at each occurrence, is selected from $C_{1-8}$ alkyl, $(CH_2)_rC_{3-6}$ cycloalkyl, $CF_3$, Cl, Br, I, F, $(CH_2)_rNR^{16a}R^{16a'}$, $NO_2$, CN, OH, $(CH_2)_rOR^{16d}$, $(CH_2)_rC(O)R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_rNR^{16f}S(O)_2R^{16b}$, and $(CH_2)_r$phenyl substituted with 0–3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl;

$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

[6] In a preferred embodiment, the present invention provides novel compounds of formula (I-i), wherein:

$R^5$ is $CH_2$phenyl substituted with 0–3 $R^{16}$;

$R^9$, is selected from H, $C_{1-6}$ alkyl, $(CH_2)_rC_{3-6}$ cycloalkyl, F, Cl, CN, $(CH_2)_rOH$, $(CH_2)_rOR^{9d}$, $(CH_2)_rNR^{9a}R^{9a'}$, $(CH_2)_rOC(O)NHR^{9a}$, $(CH_2)_r$phenyl substituted with 0–5 $R^{9e}$, and a heterocyclic system substituted with 0–2 $R^{9e}$, wherein the heterocyclic system is selected from pyridyl, thiophenyl, furanyl, oxazolyl, and thiazolyl;

$R^{9a}$ and $R^{9a'}$, at each occurrence, are selected from H, $C_{1-6}$ alkyl, $C_{3-6}$ cycloalkyl, and $(CH_2)_r$phenyl substituted with 0–3 $R^{9e}$;

$R^{9d}$, at each occurrence, is selected from $C_{1-6}$ alkyl and phenyl;

$R^{9e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{10}$ is selected from H, $C_{1-5}$ alkyl, OH, and $CH_2OH$;

alternatively, $R^9$ and $R^{10}$ join to form $C_{3-7}$ cycloalkyl, 5–6-membered cyclic ketal or =O;

with the proviso that when $R^{10}$ is halogen, cyano, nitro, or bonded to the carbon to which it is attached through a heteroatom, $R^9$ is not halogen, cyano, or bonded to the carbon to which it is attached through a heteroatom;

$R^{11}$ is selected from H, $C_{1-8}$ alkyl, $(CH_2)_r$phenyl substituted with 0–5 $R^{11e}$, and a $(CH_2)_r$-heterocyclic system substituted with 0–2 $R^{11e}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl; and $R^{11e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{12}$ is H;

alternatively, $R^{11}$ and $R^{12}$ join to form $C_{3-7}$ cycloalkyl;

$R^{14}$, at each occurrence, is selected from $C_{1-8}$ alkyl, $(CH_2)_rC_{3-6}$ cycloalkyl, $CF_3$, Cl, Br, I, F, $(CH_2)_rNR^{14a}R^{14a'}$, $NO_2$, CN, OH, $(CH_2)_rOR^{14d}$, $(CH_2)_rC(O)R^{14b}$, $(CH_2)_rC(O)NR^{14a}R^{14a'}$, $(CH_2)_rNR^{14f}C(O)R^{14b}$, $(CH_2)_rS(O)_pR^{14b}$, $(CH_2)_rS(O)_2NR^{14a}R^{14a'}$, $(CH_2)_rNR^{14f}S(O)_2R^{14b}$, $(CH_2)_r$phenyl substituted with 0–3 $R^{14e}$;

$R^{14a}$ and $R^{14a'}$, at each occurrence, are selected from H, $C_{1-6}$ alkyl, $C_{3-6}$ cycloalkyl, and $(CH_2)_r$phenyl substituted with 0–3 $R^{14e}$, and a $(CH_2)_r$-5–6 membered heterocyclic system containing 1–4 heteroatoms selected from N, O, and S, substituted with 0–2 $R^{15e}$;

$R^{14b}$, at each occurrence, is selected from H, $C_{1-6}$ alkyl, $C_{3-6}$ cycloalkyl, and $(CH_2)_r$phenyl substituted with 0–3 $R^{14e}$;

$R^{14d}$, at each occurrence, is selected from $C_{1-6}$ alkyl and phenyl;

$R^{14e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{14f}$, at each occurrence, is selected from H, and $C_{1-5}$ alkyl; and r is selected from 0, 1, and 2.

[7] In a preferred embodiment, the present invention provides novel compounds of formula (I-ii), wherein:

$R^5$ is $CH_2$phenyl substituted with 0–3 $R^{16}$;

$R^9$, is selected from H, $C_{1-6}$ alkyl, $(CH_2)_rC_{3-6}$ cycloalkyl, F, Cl, CN, $(CH_2)_rOH$, $(CH_2)_rOR^{9d}$, $(CH_2)_rNR^{9a}R^{9a'}$, $(CH_2)_rOC(O)NHR^{9a}$, $(CH_2)_r$phenyl substituted with 0–5 $R^{9e}$, and a heterocyclic system substituted with 0–2 $R^{9e}$, wherein the heterocyclic system is selected from pyridyl, thiophenyl, furanyl, oxazolyl, and thiazolyl;

$R^{9a}$ and $R^{9a'}$, at each occurrence, are selected from H, $C_{1-6}$ alkyl, $C_{3-6}$ cycloalkyl, and $(CH_2)_r$phenyl substituted with 0–3 $R^{9e}$;

$R^{9d}$, at each occurrence, is selected from $C_{1-6}$ alkyl and phenyl;

$R^{9e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{10}$ is selected from H, $C_{1-8}$ alkyl, OH, and $CH_2OH$;

alternatively, $R^9$ and $R^{10}$ join to form $C_{3-7}$ cycloalkyl, 5–6-membered cyclic ketal or =O;

with the proviso that when $R^{10}$ is halogen, cyano, nitro, or bonded to the carbon to which it is attached through a heteroatom, $R^9$ is not halogen, cyano, or bonded to the carbon to which it is attached through a heteroatom;

$R^{11}$ is selected from H, $C_{1-8}$ alkyl, $(CH_2)_r$phenyl substituted with 0–5 $R^{11e}$, and a $(CH_2)_r$-heterocyclic system substituted with 0–2 $R^{11e}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{11e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{12}$ is H;

alternatively, $R^{11}$ and $R^{12}$ join to form $C_{3-7}$ cycloalkyl;

$R^{14}$, at each occurrence, is selected from $C_{1-8}$ alkyl, $(CH_2)_rC_{3-6}$ cycloalkyl, $CF_3$, Cl, Br, I, F, $(CH_2)_rNR^{14a}R^{14a'}$, $NO_2$, CN, OH, $(CH_2)_rOR^{14d}$, $(CH_2)_rC(O)R^{14b}$, $(CH_2)_rC(O)NR^{14a}R^{14a'}$, $(CH_2)_rNR^{14f}C(O)R^{14b}$, $(CH_2)_rS(O)_pR^{14b}$, $(CH_2)_rS(O)_2NR^{14a}R^{14a'}$, $(CH_2)_rNR^{14f}S(O)_2R^{14b}$, $(CH_2)_r$phenyl substituted with 0–3 $R^{14e}$, and a $(CH_2)_r$-5–6 membered heterocyclic system containing 1–4 heteroatoms selected from N, O, and S, substituted with 0–2 $R^{15e}$, or two $R^{14}$ substituents on adjacent atoms on ring A form to join a 5–6 membered heterocyclic system containing 1–3 heteroatoms selected from N, O, and S substituted with 0–2 $R^{15e}$;

$R^{14a}$ and $R^{14a'}$, at each occurrence, are selected from H, $C_{1-6}$ alkyl, $C_{3-6}$ cycloalkyl, and $(CH_2)_r$phenyl substituted with 0–3 $R^{14e}$;

$R^{14b}$, at each occurrence, is selected from H, $C_{1-6}$ alkyl, $C_{3-6}$ cycloalkyl, and $(CH_2)_r$phenyl substituted with 0–3 $R^{14e}$;

$R^{14d}$, at each occurrence, is selected from $C_{1-6}$ alkyl and phenyl;

$R^{14e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{14f}$, at each occurrence, is selected from H, and $C_{1-5}$ alkyl; and r is selected from 0, 1, and 2.

[8] In a more preferred embodiment, the present invention provides novel compounds of formula (I-i), wherein:

J is selected from $CH_2$ and $CHR^5$;

L is selected from $CH_2$ and $CHR^5$;

$R^3$ is selected from a $C_{3-8}$ carbocyclic residue substituted with 1 $R^{15'}$ and 0–3 $R^{15}$, wherein the $C_{3-8}$ carbocyclic residue is selected from cyclopropyl, cyclopentyl, cyclohexyl, and phenyl; a $C_{9-10}$ carbocyclic residue substituted with 0–3 $R^{15}$, wherein the $C_{9-10}$ carbocyclic residue is selected from naphthyl and adamantyl; and a $(CR^3H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{15}$, at each occurrence, is selected from $C_{1-8}$ alkyl, $(CH_2)_rC_{3-6}$ cycloalkyl, $CF_3$, Cl, Br, I, F, $(CH_2)_rNR^{15a}R^{15a'}$, $NO_2$, CN, OH, $(CH_2)_rOR^{15d}$, $(CH_2)_rC(O)R^{15b}$, $(CH_2)_rC(O)NR^{15a}R^{15a'}$, $(CH_2)_rNR^{15f}C(O)R^{15b}$, $(CH_2)_rS(O)_pR^{15b}$, $(CH_2)_rS(O)_2NR^{15a}R^{15a'}$, $(CH_2)_rNR^{15f}S(O)_2R^{15b}$, $(CH_2)_r$phenyl substituted with 0–3 $R^{15e}$, and a $(CH_2)_r$-5–6 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{3-6}$ cycloalkyl, and $(CH_2)_r$phenyl substituted with 0–3 $R^{15e}$;

$R^{15b}$, at each occurrence, is selected from H, $C_{1-6}$ alkyl, $C_{3-6}$ cycloalkyl, and $(CH_2)_r$phenyl substituted with 0–3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H, and $C_{1-5}$ alkyl.

[9] In a more preferred embodiment, the present invention provides novel compounds of formula (I-ii), wherein:

L is selected from $CH_2$ and $CHR^5$;

$R^3$ is selected from a $C_{3-8}$ carbocyclic residue substituted with 1 $R^{15'}$ and 0–3 $R^{15}$, wherein the $C_{3-8}$ carbocyclic residue is selected from cyclopropyl, cyclopentyl, cyclohexyl, and phenyl; a $C_{9-10}$ carbocyclic residue substituted with 0–3 $R^{15}$, wherein the $C_{9-10}$ carbocyclic residue is selected from naphthyl and adamantyl; and a $(CR^3H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{15}$, at each occurrence, is selected from $C_{1-8}$ alkyl, $(CH_2)_rC_{3-6}$ cycloalkyl, $CF_3$, Cl, Br, I, F, $(CH_2)_rNR^{15a}R^{15a'}$, $NO_2$, CN, OH, $(CH_2)_rOR^{15d}$, $(CH_2)_rC(O)R^{15b}$, $(CH_2)_rC(O)NR^{15a}R^{15a'}$, $(CH_2)_rNR^{15f}C(O)R^{15b}$, $(CH_2)_rS(O)_pR^{15b}$, $(CH_2)_rS(O)_2NR^{15a}R^{15a'}$, $(CH_2)_rNR^{15f}S(O)_2R^{15b}$, and $(CH_2)_r$phenyl substituted with 0–3 $R^{15e}$, and a $(CH_2)_r$-5–6 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{3-6}$ cycloalkyl, and $(CH_2)_r$phenyl substituted with 0–3 $R^{15e}$;

$R^{15b}$, at each occurrence, is selected from H, $C_{1-6}$ alkyl, $C_{3-6}$ cycloalkyl, and $(CH_2)_r$phenyl substituted with 0–3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H and $C_{1-5}$ alkyl.

[10] In a further even more preferred embodiment, the present invention provides novel compounds of formula (I) and pharmaceutically acceptable salt forms thereof, wherein the compound of formula (I) is selected from:

N-[1-(phenylmethyl)-4-piperidinyl]-N'-[2-[[4-(phenylmethyl)-1-piperidinyl]methyl]phenyl]urea, N-(2,5-difluorophenyl)-N'-[2-[[4-(phenylmethyl)-1-piperidinyl]methyl]phenyl]urea, N-(2,5-difluorophenyl)-N'-[[3-[[4-(phenylmethyl)-1-piperidinyl]methyl]methyl]urea, N-(2,5-difluorophenyl)-N'-[2-[[4-(phenylmethyl)-1-piperidinyl]acetyl]phenyl]urea, N-(2,5-difluorophenyl)-N'-[2-[[1-hydroxy-2-[4-(phenylmethyl)-piperidinyl]ethyl]phenyl]urea, N-[3-[imino-[4-(phenylmethyl)-1-piperidinyl]methyl]phenyl]-N'-phenylurea, N-[1-(phenylmethyl)-4-piperidinyl]-N'-[3-[[4-(phenylmethyl)-1-piperidinyl]methyl]phenyl]urea, N-[2-(4-fluorophenyl)ethyl]-N'-[2-[[4-(phenylmethyl)-1-piperidinyl]methyl]phenyl]urea, N-[3-hydroxypropyl]-N'-[2-[[4-(phenylmethyl)-1-piperidinyl] methyl]phenyl]urea, N-[2-[[4-(phenylmethyl)-1-piperidinyl]methyl]phenyl]-N'-[2-(1-piperidinyl)ethyl]urea, N-[2-(dimethylamino)ethyl]-N'-[2-[[4-(phenylmethyl)-1-piperidinyl]methyl]phenyl]urea, 4-(phenylmethyl)-N-[2-[[4-(phenylmethyl)-1-piperidinyl]methyl]phenyl]-1-piperazinecarboxamide, 4-(phenylmethyl)-N-[2-[[4-(phenylmethyl)-1-piperidinyl]methyl]phenyl]-1-piperidinecarboxamide, N-(1,3-benzodioxol-5-ylmethyl)-N'-[2-[[4-(phenylmethyl)-1-piperidinyl]methyl]phenyl]urea, N-[2,2-(diphenyl)ethyl]-N'-[2-[[4-(phenylmethyl)-1-piperidinyl]methyl]phenyl]urea, 4-(4-chlorophenyl)-4-hydroxy-N-[2-[[4-(phenylmethyl)-1-piperidinyl]methyl]phenyl]-1-piperidinecarboxamide, 4-phenyl-4-hydroxy-N-[2-[[4-(phenylmethyl)-1-piperidinyl]methyl]phenyl]-1-piperidinecarboxamide, 4-phenyl-N-[2-[[4-(phenylmethyl)-1-piperidinyl]methyl]phenyl]-1-piperidinecarboxamide, N-1H-indazol-5-yl-N'-[2-[[4-(phenylmethyl)-1-piperidinyl]methyl]phenyl]urea, N-1H-indazol-6-yl-N'-[2-[[4-(phenylmethyl)-1-piperidinyl]methyl] phenyl]urea, N-[phenylmethyl]-N'-[2-[[4-(phenylmethyl)-1-piperidinyl]methyl]phenyl] urea, N-1,3-benzodioxol-5-yl-N'-[2-[[4-(phenylmethyl)-1-piperidinyl]methyl]phenyl]urea, N-[1-(phenylmethyl)-4-piperidinyl]-N'-[6-[[4-(phenylmethyl)-1-piperidinyl]methyl]-1,3-benzodioxol-5-yl]urea, N-[2-(4-fluorophenyl)ethyl]-N'-[6-[[4-(phenylmethyl)-1-piperidinyl]methyl]-1,3-benzodioxol-5-yl]urea, 4-((2-phenyl)ethyl)-N-[6-[[4-(phenylmethyl)-1-piperidinyl]methyl]-1,3-benzodioxol-5-yl]-1-piperazinecarboxamide, N-1H-indazol-5-yl-N'-[6-[[4-(phenylmethyl)-1-piperidinyl]methyl]-1,3-benzodioxol-5-yl]urea, N-1H-indazol-6-yl-N'-[6-[[4-(phenylmethyl)-1-piperidinyl]methyl]-1,3-benzodioxol-5-yl]urea, N-benzothiazol-6-yl-N'-[6-[[4-(phenylmethyl)-1-piperidinyl]methyl]-1,3-benzodioxol-5-yl]urea, N-[2-(4-fluorophenyl)ethyl]-N'-[4-hydroxy-2-[[4-(phenylmethyl)-1-piperidinyl]methyl]phenyl]urea, N-[4-hydroxy-2-[[4-(phenylmethyl)-1-piperidinyl]methyl]phenyl]-N'-[1-(phenylmethyl)-4-piperidinyl]urea, N-[3-phenylpropyl]-N'-[6-[[4-(phenylmethyl)-1-piperidinyl]methyl]-1,3-benzodioxol-5-yl]urea, N-1H-indazol-5-yl-N'-[3-[[4-(phenylmethyl)-1-piperidinyl]methyl]phenyl]urea, N-[2-(4-fluorophenyl)ethyl]-N'-[3-[[4-(phenylmethyl)-1-piperidinyl]methyl]phenyl]urea, N-(2,5-difluorophenyl)-N'-[2-[4-(phenylmethyl)-1-piperidinyl]phenyl]urea, N-phenyl-N'-[2-[[4-(phenylmethyl)-1-piperidinyl]methyl] phenyl]urea, N-(4-methoxyphenyl)-N'-[2-[[4-(phenylmethyl)-1-piperidinyl]methyl]phenyl]urea, N-(3-methoxyphenyl)-N'-[2-[[4-(phenylmethyl)-1-piperidinyl]methyl]phenyl]urea, N'-(3-cyanophenyl)-N-[3-[[4-(phenylmethyl)-1-piperidinyl]methyl]phenyl]urea, N'-(3-cyanophenyl)-N-[4-[[4-(phenylmethyl)-1-piperidinyl]methyl]phenyl]urea, N-[2-phenylethyl]-N'-[4-[[4-(phenylmethyl)-1-piperidinyl]methyl]phenyl]urea, Ethyl-3-[[[[2-[4-(phenylmethyl)-1-piperidinyl]methyl]phenyl]amino]carbonyl]amino]benzoate, N'-(3-cyanophenyl)-N-[2-[[4-(phenylmethyl)-1-piperidinyl]methyl]phenyl]urea, N-phenyl-N'-[2-[[4-(4-fluorophenyl)methyl-1-piperidinyl]methyl]phenyl]urea, N'-(phenyl)-N-(phenylmethyl)-N-[2-[[4-(phenylmethyl)-1-piperidinyl]methyl]phenyl]urea, N'-(3-cyanophenyl)-N-(phenylmethyl)-N-[2-[[4-(phenylmethyl)-1-piperidinyl]methyl]phenyl]urea, N-[2-phenylethyl]-N'-[2-[[4-(phenylmethyl)-piperidinyl]methyl]phenyl]urea, N-(3-cyanophenyl)-N'-[6-[[4-(phenylmethyl)-1-piperidinyl]methyl]-1,3-benzodioxol-5-yl]urea, Ethyl-3-[[[[6-[[4-(phenylmethyl)-1-piperidinyl]methyl]-1,3-benzodioxol-5-yl]amino]carbonyl]amino]benzoate, Ethyl-4-[[[[6-[[4-(phenylmethyl)-1-piperidinyl]methyl]-1,3-benzodioxol-5-yl]amino]carbonyl]amino]benzoate, N-[4-hydroxy-2-[[4-(phenylmethyl)-1-piperidinyl]methyl]phenyl]-N'-[phenyl]urea, N-[3-cyanophenyl]-N'-[4-hydroxy-2-[[4-(phenylmethyl)-1-piperidinyl]methyl]phenyl]urea, N-[4-[(methylsulfonyl)oxy]-2-[[4-(phenylmethyl)-1-piperidinyl]methyl]phenyl]-N'-[3-methoxyphenyl]urea, N-[4-[(methylsulfonyl)oxy]-2-[[4-(phenylmethyl)-1-piperidinyl]methyl]phenyl]-N'-(2-phenylcyclopropyl) urea, Methyl-3-[[[(3-cyanophenyl)amino]carbonyl]amino]-4-[[4-(phenylmethyl)-1-piperidinyl]methyl]benzoate, Methyl-3-[[[(3-methoxyphenyl)amino]carbonyl]amino]-4-[[4-(phenylmethyl)-1-piperidinyl]methyl]benzoate, N-[4-[(methylsulfonyl)oxy]-2-[[4-(phenylmethyl)-1-piperidinyl]methyl]phenyl]-N'-[3-cyanophenyl]urea, N-[5-hydroxymethyl-2-[[4-(phenylmethyl)-1-piperidinyl]methyl]phenyl]-N'-[3-methoxyphenyl]urea, N-(3-cyanophenyl)-N'-[5-(hydroxymethyl)-2-[[4-(phenylmethyl)-1-piperidinyl]methyl]phenyl]urea,
Methyl-4-[[[(3-cyanophenyl)amino]carbonyl]amino]-3-[[4-[(4-fluorophenyl)methyl]-1-piperidinyl]methyl]benzoate,
Methyl-3-[[[(3-cyanophenyl)amino]carbonyl]amino]-2-[[4-[(4-fluorophenyl)methyl]-1-piperidinyl]methyl]-benzoate,
3-[[[(3-cyanophenyl)amino]carbonyl]amino]-2-[[4-[(4-fluorophenyl)methyl]-1-piperidinyl]methyl]-N-methylbenzamide
3-[[[(3-cyanophenyl)amino]carbonyl]amino]-2-[[4-[(4-fluorophenyl)methyl]-1-piperidinyl]methyl]benzamide,
Methyl-3-[[[3-(1-hydroxyethyl)phenyl)amino]carbonyl]amino]-2-[[4-[(4-fluorophenyl)methyl]-1-piperidinyl]methyl]-benzoate,
3-[[[(phenyl)amino]carbonyl]amino]-2-[[4-[(4-fluoro phenyl)methyl]-1-piperidinyl]methyl]benzoic acid,
Methyl-3-[[[(3-acetylphenyl)amino]carbonyl]amino]-2-[[4-[(4-fluorophenyl)methyl]-1-piperidinyl]methyl]-benzoate hydrochloride
Methyl-4-[[[phenylamino]carbonyl]amino]-3-[[4-[(4-fluorophenyl)methyl]-1-piperidinyl]methyl]benzoate,
Methyl-3-[[[(phenyl)amino]carbonyl]amino]-2-[[4-[(4-fluorophenyl)methyl]-1-piperidinyl]methyl]-benzoate,
3-[[[(phenyl)amino]carbonyl]amino]-2-[[4-[(4-fluoro phenyl)methyl]-1-piperidinyl]methyl]-N-methylbenzamide,
3-[[[(phenyl)amino]carbonyl]amino]-2-[[4-[(4-fluorophenyl)methyl]-1-piperidinyl]methyl]benzamide,
Methyl-4-[[[(3-methoxyphenyl)amino]carbonyl]amino]-3-[[4-[(4-fluorophenyl)methyl]-1-piperidinyl]methyl]benzoate,
Methyl-3-[[[(3-methoxyphenyl)amino]carbonyl]amino]-2-[[4-[(4-fluoro henyl)methyl]-1-piperidinyl]methyl]-benzoate,
3-[[[(3-methoxyphenyl)amino]carbonyl]amino]-2-[[4-[(4-fluorophenyl)methyl]-1-piperidinyl]methyl]-N-methylbenzamide,
Methyl-3-[[[(3-acetylphenyl)amino]carbonyl]amino]-2-[[4-[(4-fluorophenyl)methyl]-1-piperidinyl]methyl]-benzoate,
3-[[[(3-acetylphenyl)amino]carbonyl]amino]-2-[[4-[(4-fluorophenyl)methyl]-1-piperidinyl]methyl]-N-methylbenzamide
3-[[[(3-acetylphenyl)amino]carbonyl]amino]-2-[[4-[(4-fluorophenyl)methyl]-1-piperidinyl]methyl]benzamide,
N-[4-hydroxymethyl-2-[[4-(4-fluorophenylmethyl)-1-piperidinyl]methyl]phenyl]-N'-[3-cyanophenyl]urea,
N-(3-cyanophenyl)-N'-[2-[[4-[(4-fluorophenyl)methyl]-1-piperidinyl]methyl]-1-naphthalenyl]urea,
N-[2-[[4-[(4-fluorophenyl)methyl]-1-piperidinyl]methyl]-1-naphthalenyl]-N'-(3-methoxyphenyl)urea,
4-[[[(3-cyanophenyl)amino]carbonyl]amino]-3-[[4-[(4-fluorophenyl)methyl]-1-piperidinyl]methyl]-N-phenylbenzamide,
3-[[[(3-cyanophenyl)amino]carbonyl]amino]-2-[[4-[(4-fluorophenyl)methyl]-1-piperidinyl]methyl]-N-phenylbenzamide,
3-[[[(3-acetylphenyl)amino]carbonyl]amino]-2-[[4-[(4-fluorophenyl)methyl]-1-piperidinyl]methyl]-N-phenylbenzamide,
N-[4-hydroxymethyl-2-[[4-(4-fluorophenylmethyl)-1-piperidinyl]methyl]phenyl]-N'-[3-methoxyphenyl]urea,
4-[[[(3-cyanophenyl)amino]carbonyl]amino]-3-[[4-[(4-fluoro phenyl)methyl]-1-piperidinyl]methyl]-N-methylbenzamide,
3-[[[(3-cyanophenyl)amino]carbonyl]amino]-2-[[4-[(4-fluoro phenyl)methyl]-1-piperidinyl]methyl]-N-methylbenzamide hydrochloride
3-[[[(3-acetylphenyl)amino]carbonyl]amino]-2-[[4-[(4-fluoro phenyl)methyl]-1-piperidinyl]methyl]-N-methylbenzamide hydrochloride
3-[[[(3-acetylphenyl)amino]carbonyl]amino]-2-[[4-[(4-fluorophenyl)methyl]-1-piperidinyl]methyl]-N-[2-(N,N-dimethylamino)ethyl]benzamide
3-[[[(3-cyanophenyl)amino]carbonyl]amino]-2-[[4-[(4-fluorophenyl)methyl]-1-piperidinyl]methyl]-N-[2-(N,N-dimethylamino)ethyl]benzamide
3-[[[(3-acetylphenyl)amino]carbonyl]amino]-2-[[4-[(4-fluoro phenyl)methyl]-1-piperidinyl]methyl]-N-[cyclopropyl]benzamide
3-[[[(3-cyanophenyl)amino]carbonyl]amino]-2-[[4-[(4-fluoro phenyl)methyl]-1-piperidinyl]methyl]-N-[cyclopropyl]benzamide
3-[[[(3-methoxyphenyl)amino]carbonyl]amino]-2-[[4-[(4-fluoro phenyl)methyl]-1-piperidinyl]methyl]-N,N-dimethylbenzamide
3-[[[(3-acetylphenyl)amino]carbonyl]amino]-2-[[4-[(4-fluoro phenyl)methyl]-1-piperidinyl]methyl]-N,N-dimethylbenzamide
3-[[[(3-acetylphenyl)amino]carbonyl]amino]-2-[[4-[(4-fluorophenyl)methyl]-1-piperidinyl]methyl]-N(pyridin-2-yl)benzamide
3-[[[(3-methoxyphenyl)amino]carbonyl]amino]-2-[[4-[(4-fluorophenyl)methyl]-1-piperidinyl]methyl]-N(pyridin-2-yl)benzamide,
N-(2,5-difluorophenyl)-N'-[[2-[[4-(phenylmethyl)-1-piperidinyl]methyl]phenyl]methyl]urea,
N-(3-cyanophenyl)-N'-[[2-[[4-(phenylmethyl)-1-piperidinyl]methyl]phenyl]methyl]urea,
Ethyl-3-[[[[2-[[4-(phenylmethyl)-1-piperidinyl]methyl]phenyl]amino]carbonyl]amino]benzoate,
N-(3-methoxyphenyl)-N'-[[2-[[4-(phenylmethyl)-1-piperidinyl]methyl]phenyl]methyl]urea,
N-(4-methoxyphenyl)-N'-[[2-[[4-(phenylmethyl)-1-piperidinyl]methyl]phenyl]methyl]urea,
N-(3-methoxyrophenyl)-N'-[2-[[1-hydroxy-2-[4-(phenylmethyl)-1-piperidinyl]ethyl]phenyl]urea,
N-(3-cyanophenyl)-N'-[2-[[1-hydroxy-2-[4-(phenylmethyl)-1-piperidinyl]ethyl]phenyl]urea,
Ethyl-3-[[[[2-[1-hydroxy-2-[4-(phenylmethyl)-1-piperidinyl]ethyl]phenyl]amino]carbonyl]amino]benzoate,
N-(phenyl)-N'-[2-[[1-hydroxy-2-[4-(phenylmethyl)-1-piperidinyl]ethyl]phenyl]urea,
N-(phenyl)-N'-[3-(hydroxymethyl)-2-[[4-(4-fluorophenylmethyl)-1-piperidinyl]methyl]phenyl]urea,
N-[2-1-hydroxyimino)-2-[4-(phenylmethyl)-1-piperidinyl]ethyl]phenyl]-N'-phenylurea,
N-(phenyl)-N'-[3-[[4-(phenylmethyl)-1-piperidinyl]acetyl]phenyl]urea,
N-(phenyl)-N'-[3-[[1-hydroxy-2-[4-phenylmethyl)-1-piperidinyl]ethyl]phenyl]urea,
N-(phenyl)-N'-[2-[[1-hydroxy-2-[4-(4-fluorophenyl)methyl)-1-piperidinyl]ethyl]phenyl]urea,
N-(3-methoxyphenyl)-N'-[2-[[1-hydroxy-2-[4-(4-fluorophenyl)methyl)-1-piperidinyl]ethyl]phenyl]urea,
N-(3-cyanophenyl)-N'-[2-[[1-hydroxy-2-[4-(4-fluorophenyl)methyl)-1-piperidinyl]ethyl]phenyl]urea,
N-(3-cyanophenyl)-N'-[6-[1-hydroxy-2-[4-(4-fluorophenyl)methyl)-1-piperidinyl]ethyl]-1,3-benzodioxol-5-yl]urea,
N-(3-cyanophenyl)-N'-[2-[[2-4-phenylmethyl)-1-piperidinyl]ethyl]phenyl]urea,
N-(3-cyanophenyl)-N'-[2-[[2-4-(4-fluorophenyl)methyl)-1-piperidinyl]ethyl]phenyl]urea,
N-(3-methoxyphenyl)-N'-[2-[[2-[4-phenylmethyl)-1-piperidinyl]ethyl]phenyl]urea, N-(3-methoxyphenyl)-N'-[2-[[2-[4-(4-fluorophenyl)methyl]-1-piperidinyl]ethyl]phenyl]urea, N-(3-acetylphenyl)-N'-[2-[[2-[4-(4-fluorophenyl)methyl)-1-piperidinyl]ethyl]phenyl]urea, N-(4-fluorophenyl)-N'-[2-[[2-[4-(4-fluorophenyl)methyl)-1-piperidinyl]ethyl]phenyl]urea, N-(1-adamantyl)-N'-[2-[[2-[4-(4-fluorophenyl)methyl)-1-piperidinyl]ethyl]phenyl]urea, 1-[[6-[[[(3-cyanophenyl)amino]carbonyl]amino]-1,3-benzodioxol-5-yl]methyl]-1-methyl-4-(phenylmethyl)piperidinium iodide, 1-[[3-hydroxy-6-[[[(3-cyanophenyl)amino]carbonyl]amino]-phenyl]methyl]-1-methyl-4-(phenylmethyl)piperidinium chloride, 1-[[3-[(tetrahydropyran-2-yl)oxy]6-[[[(3-cyanophenyl)amino]carbonyl]amino]-phenyl]methyl]-1-methyl-4-(phenylmethyl)piperidinium iodide, N-(3-methoxyphenyl)-N'-[2-[[3-(phenylmethyl)-1-piperidinyl]methyl]phenyl]urea, N-(4-methoxyphenyl)-N'-[4-[[3-(phenylmethyl)-1-piperidinyl]methyl]phenyl]urea, Methyl-3-[[[(phenyl)amino]carbonyl]amino]-2-[[[3-phenylmethyl]-1-piperidinyl]methyl]-benzoate Methyl-3-[[[(3-cyanophenyl)amino]carbonyl]amino]-2-[[[3-phenylmethyl]-1-piperidinyl]methyl]-benzoate Methyl-3-[[[(3-methoxyphenyl)amino]carbonyl]amino]-2-[[[3-phenylmethyl]-1-piperidinyl]methyl]-benzoate Methyl-3-[[[(3-acetylphenyl)amino]carbonyl]amino]-2-[[[3-phenylmethyl]-1-piperidinyl]methyl]-benzoate Methyl-3-[[[(3-cyanophenyl)amino]carbonyl]amino]-2-[[[3-phenylmethyl]-1-piperidinyl]methyl]-benzoate Hydrochloride N-(3-methoxyphenyl)-N'-[2-[[1-hydroxy-2-[3-(phenylmethyl)-1-piperidinyl]ethyl]phenyl]urea, and N-(3-methoxyphenyl)-N'-[2-[[2-(3-phenylmethyl)-1-piperidinyl]ethyl]phenyl]urea.

[11] In another embodiment, the present invention provides a pharmaceutical composition, comprising a pharmaceutically acceptable carrier and a therapeutically effective amount of a compound of the present invention.

[12] In another embodiment, the present invention provides a method for modulation of chemokine receptor activity comprising administering to a patient in need thereof a therapeutically effective amount of the compounds of the present invention.

[13] In another embodiment, the present invention provides a method for treating or preventing inflammatory diseases, comprising administering to a patient in need thereof a therapeutically effective amount of a compound of the present invention.

[14] In another embodiment, the present invention provides a method for treating or preventing asthma, comprising administering to a patient in need thereof a therapeutically effective amount of a compound of the present invention.

[15] In another embodiment, the present invention provides a novel method for the modulation of the chemokine receptor CCR-3 comprising the administration of an effective amount of compounds of formula (I):

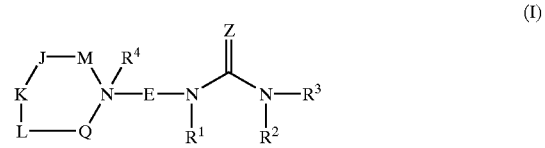

or stereoisomers or pharmaceutically acceptable salts thereof, wherein:

M is absent or selected from $CH_2$, $CHR^5$, $CHR^{13}$, $CR^{13}R^{13}$, and $CR^5R^{13}$;

Q is selected from $CH_2$, $CHR^5$, $CHR^{13}$, $CR^{13}R^{13}$, and $CR^5R^{13}$;

J, K, and L are independently selected from $CH_2$, $CHR^5$, $CHR^6$, $CR^6R^6$ and $CR^5R^6$;

with the proviso:
1) at least one of M, J, K, L, or Q contains an $R^5$; and
2) when M is absent, J is selected from $CH_2$, $CHR^5$, $CHR^{13}$, and $CR^5R^{13}$;

Z is selected from O and S;

E is selected from:

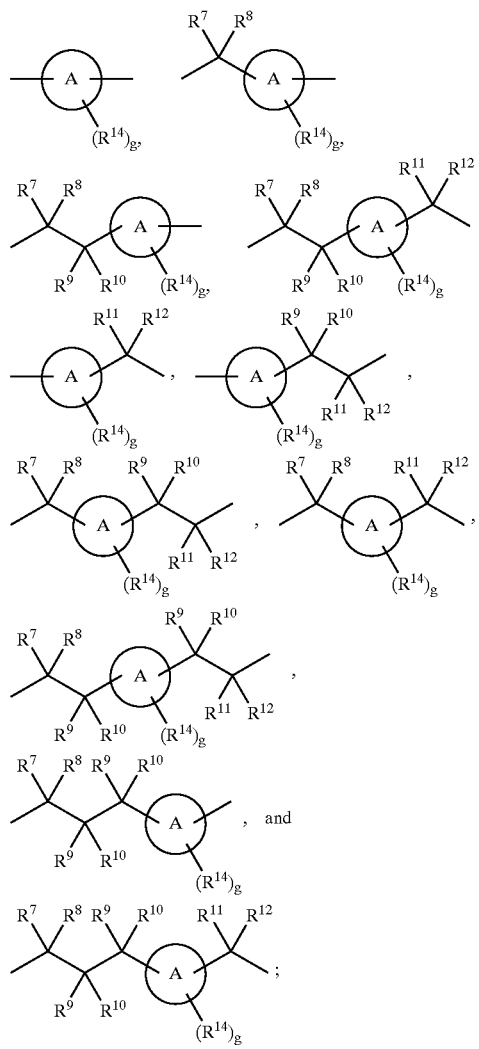

ring A is phenyl or naphthyl;

$R^1$ and $R^2$ are independently selected from H, $C_{1-6}$ alkyl, $C_{2-8}$ alkenyl, $C_{2-8}$ alkynyl, $(CH_2)_rC_{3-6}$ cycloalkyl, and a $(CH_2)_r$—$C_{3-10}$ carbocyclic residue substituted with 0–5 $R^a$;

$R^a$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^bR^b$, $(CH_2)_rOH$, $(CH_2)_rOR^c$, $(CH_2)_rSH$, $(CH_2)_rSR^c$, $(CH_2)_rC(O)R^b$, $(CH_2)_rC(O)NR^bR^b$, $(CH_2)_rNR^bC(O)R^b$, $(CH_2)_rC(O)OR^b$, $(CH_2)_rOC(O)R^c$, $(CH_2)_rCH(=NR^b)NR^bR^b$, $(CH_2)_rNHC(=NR^b)NR^bR^b$, $(CH_2)_rS(O)_pR^c$, $(CH_2)_rS(O)_2NR^bR^b$, $(CH_2)_rNR^bS(O)_2R^c$, and $(CH_2)_r$phenyl;

$R^b$, at each occurrence, is selected from H, $C_{1-6}$ alkyl, $C_{3-6}$ cycloalkyl, and phenyl;

$R^c$, at each occurrence, is selected from $C_{1-6}$ alkyl, $C_{3-6}$ cycloalkyl, and phenyl;

alternatively, $R^2$ and $R^3$ join to form a 5, 6, or 7-membered ring substituted with 0–3 $R^a$;

$R^3$ is selected from a $(CR^{3'}R^{3''})_t$—$C_{3-10}$ carbocyclic residue substituted with 0–5 $R^{15}$, and a $(CR^{3'}R^{3''})_t$-5–10 membered heterocyclic system containing 1–4 heteroatoms selected from N, O, and S, substituted with 0–3 $R^{15}$;

$R^{3'}$ and $R^{3''}$, at each occurrence, are selected from H, $C_{1-6}$ alkyl, $(CH_2)_rC_{3-6}$ cycloalkyl, and phenyl;

$R^4$ is absent, taken with the nitrogen to which it is attached to form an N-oxide, or selected from $C_{1-6}$ alkyl, $C_{2-8}$ alkenyl, $C_{2-8}$ alkynyl, $(CH_2)_rC_{3-6}$ cycloalkyl, $(CH_2)_qC(O)R^{4b}$, $(CH_2)_qC(O)NR^{4a}R^{4a'}$, $(CH_2)_qC(O)OR^{4b}$, and a $(CH_2)_r$—$C_{3-10}$ carbocyclic residue substituted with 0–3 $R^{4c}$;

$R^{4a}$ and $R^{4a'}$, at each occurrence, are selected from H, $C_{1-6}$ alkyl, $(CH_2)_rC_{3-6}$ cycloalkyl, and phenyl;

$R^{4b}$, at each occurrence, is selected from $C_{1-6}$ alkyl, $C_{2-8}$ alkenyl, $(CH_2)_rC_{3-6}$ cycloalkyl, $C_{2-8}$ alkynyl, and phenyl;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, $(CH_2)_rNR^{4a}R^{4a'}$, and $(CH_2)_r$phenyl;

alternatively, $R^4$ joins with $R^7$, $R^9$, $R^{11}$ or $R^{14}$ to form a 5, 6 or 7 membered piperidinium spirocycle or pyrrolidinium spirocycle substituted with 0–3 $R^a$;

$R^5$ is selected from a $(CR^{5'}R^{5''})_t$—$C_{3-10}$ carbocyclic residue substituted with 0–5 $R^{16}$ and a $(CR^{5'}R^{5''})_t$-5–10 membered heterocyclic system containing 1–4 heteroatoms selected from N, O, and S, substituted with 0–3 $R^{16}$;

$R^{5'}$ and $R^{5''}$, at each occurrence, are selected from H, $C_{1-6}$ alkyl, $(CH_2)_rC_{3-6}$ cycloalkyl, and phenyl;

$R^6$, at each occurrence, is selected from $C_{1-6}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rNR^{6a}R^{6a'}$, $(CH_2)_rOH$, $(CH_2)_rOR^{6b}$, $(CH_2)_rSH$, $(CH_2)_rSR^{6b}$, $(CH_2)_rC(O)OH$, $(CH_2)_rC(O)R^{6b}$, $(CH_2)_rC(O)NR^{6a}R^{6a'}$, $(CH_2)_rNR^{6d}C(O)R^{6a}$, $(CH_2)_rC(O)OR^{6b}$, $(CH_2)_rOC(O)R^{6b}$, $(CH_2)_rS(O)_pR^{6b}$, $(CH_2)_rS(O)_2NR^{6a}R^{6a'}$, $(CH_2)_rNR^{6d}S(O)_2R^{6b}$, and $(CH_2)_r$phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_r OC_{1-4}$ alkyl, $(CH_2)_rOH$, $(CH_2)_rSC_{1-5}$ alkyl, and $(CH_2)_r NR^{6d}R^{6d}$;

$R^{6d}$, at each occurrence, is selected from H, $C_{1-6}$ alkyl, and $C_{3-6}$ cycloalkyl;

with the proviso that when any of J, K, or L is $CR^6R^6$ and $R^6$ is halogen, cyano, nitro, or bonded to the carbon to which it is attached through a heteroatom, the other $R^6$ is not halogen, cyano, or bonded to the carbon to which it is attached through a heteroatom;

$R^7$, is selected from H, $C_{1-6}$ alkyl, $C_{2-8}$ alkenyl, $C_{2-8}$ alkynyl, $(CH_2)_qOH$, $(CH_2)_qSH$, $(CH_2)_qOR^{7d}$, $(CH_2)_qSR^{7d}$, $(CH_2)_qNR^{7a}R^{7a'}$, $(CH_2)_rC(O)OH$, $(CH_2)_rC(O)R^{7b}$, $(CH_2)_qC(O)NR^{7a}R^{7a'}$, $(CH_2)_qNR^{7a}C(O)R^{7a}$, $(CH_2)_qNR^{7a}C(O)H$, $(CH_2)_rC(O)OR^{7b}$, $(CH_2)_qOC(O)R^{7b}$, $(CH_2)_qS(O)_pR^{7b}$, $(CH_2)_qS(O)_2NR^{7a}R^{7a'}$, $(CH_2)_qNR^{7a}S(O)_2R^{7b}$, $C_{1-6}$ haloalkyl, a $(CH_2)_r$—$C_{3-10}$ carbocyclic residue substituted with 0–3 $R^{7c}$, and a $(CH_2)_r$-5–10 membered heterocyclic system containing 1–4 heteroatoms selected from N, O, and S, substituted with 0–2 $R^{7c}$;

$R^{7a}$ and $R^{7a'}$, at each occurrence, are selected from H, $C_{1-6}$ alkyl, $C_{2-8}$ alkenyl, $C_{2-8}$ alkynyl, $(CH_2)_rC_{3-6}$ cycloalkyl, a $(CH_2)_r$—$C_{3-10}$ carbocyclic residue substituted with 0–5 $R^{7e}$, and a $(CH_2)_r$-5–10 membered heterocyclic system containing 1–4 heteroatoms selected from N, O, and S, substituted with 0–3 $R^{7e}$;

$R^{7b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–2 $R^{7e}$, and a $(CH_2)_r$-5–6 membered heterocyclic system containing 1–4 heteroatoms selected from N, O, and S, substituted with 0–3 $R^{7e}$;

$R^{7c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{7f}R^{7f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{7b}$, $(CH_2)_rC(O)NR^{7f}R^{7f}$, $(CH_2)_rNR^{7f}C(O)R^{7a}$, $(CH_2)_rC(O)OC_{1-4}$ alkyl, $(CH_2)_rOC(O)R^{7b}$, $(CH_2)_rC(=NR^{7f})NR^{7f}R^{7f}$, $(CH_2)_rS(O)_pR^{7b}$, $(CH_2)_r NHC(=NR^{7f})NR^{7f}R^{7f}$, $(CH_2)_rS(O)_2NR^{7f}R^{7f}$, $(CH_2)_r NR^{7f}S(O)_2R^{7b}$, and $(CH_2)_r$phenyl substituted with 0–3 $R^{7e}$;

$R^{7d}$, at each occurrence, is selected from $C_{1-6}$ alkyl substituted with 0–3 $R^{7e}$, alkenyl, alkynyl, and a $C_{3-10}$ carbocyclic residue substituted with 0–3 $R^{7c}$;

$R^{7e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r SC_{1-5}$ alkyl, $(CH_2)_rNR^{7f}R^{7f}$, and $(CH_2)_r$phenyl;

$R^{7f}$, at each occurrence, is selected from H, $C_{1-6}$ alkyl, and $C_{3-6}$ cycloalkyl;

$R^8$ is selected from H, $C_{1-6}$ alkyl, $C_{3-6}$ cycloalkyl, and $(CH_2)_r$phenyl substituted with 0–3 $R^{8a}$;

$R^{8a}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r SC_{1-5}$ alkyl, $(CH_2)_rNR^{7f}R^{7f}$, and $(CH_2)_r$phenyl;

alternatively, $R^7$ and $R^8$ join to form $C_{3-7}$ cycloalkyl, or $=NR^{8b}$;

$R^{8b}$ is selected from H, $C_{1-6}$ alkyl, $C_{3-6}$ cycloalkyl, OH, CN, and $(CH_2)_r$-phenyl;

$R^9$, is selected from H, $C_{1-6}$ alkyl, $C_{2-8}$ alkenyl, $C_{2-8}$ alkynyl, F, Cl, Br, I, $NO_2$, CN, $(CH_2)_rOH$, $(CH_2)_rSH$, $(CH_2)_rOR^{9d}$, $(CH_2)_rSR^{9d}$, $(CH_2)_rNR^{9a}R^{9a'}$, $(CH_2)_rC$ (O)OH, $(CH_2)_rC(O)R^{9b}$, $(CH_2)_rC(O)NR^{9a}R^{9a'}$, $(CH_2)_r$ $NR^{9a}C(O)R^{9a}$, $(CH_2)_rNR^{9a}C(O)H$, $(CH_2)_rNR^{9a}C(O)$ $NHR^{9a}$, $(CH_2)_rC(O)OR^{9b}$, $(CH_2)_rOC(O)R^{9b}$, $(CH_2)_r$ $OC(O)NHR^{9a}$, $(CH_2)_rS(O)_pR^{9b}$, $(CH_2)_rS(O)_2$ $NR^{9a}R^{9a'}$, $(CH_2)_rNR^{9a}S(O)_2R^{9b}$, $C_{1-6}$ haloalkyl, a $(CH_2)_r$—$C_{3-10}$ carbocyclic residue substituted with 0–5 $R^{9c}$, and a $(CH_2)_r$-5–10 membered heterocyclic system containing 1–4 heteroatoms selected from N, O, and S, substituted with 0–3 $R^{9c}$;

$R^{9a}$ and $R^{9a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{9e}$, and a $(CH_2)_r$-5–10 membered heterocyclic system containing 1–4 heteroatoms selected from N, O, and S, substituted with 0–3 $R^{9e}$;

$R^{9b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–2 $R^{9e}$, and a $(CH_2)_r$-5–6 membered heterocyclic system containing 1–4 heteroatoms selected from N, O, and S, substituted with 0–3 $R^{9e}$;

$R^{9c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{9f}R^{9f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{9b}$, $(CH_2)_rC(O)NR^{9f}R^{9f}$, $(CH_2)_rNR^{9f}C$ $(O)R^{9a}$, $(CH_2)_rC(O)OC_{1-4}$ alkyl, $(CH_2)_rOC(O)R^{9b}$, $(CH_2)_rC(=NR^{9f})NR^{9f}R^{9f}$, $(CH_2)_rS(O)_pR^{9b}$, $(CH_2)_r$ $NHC(=NR^{9f})NR^{9f}R^{9f}$, $(CH_2)_rS(O)_2NR^{9f}R^{9f}$, $(CH_2)_r$ $NR^{9f}S(O)_2R^{9b}$, and $(CH_2)_r$phenyl substituted with 0–3 $R^{9e}$;

$R^{9d}$, at each occurrence, is selected from $C_{1-6}$ alkyl, $C_{2-6}$ alkenyl, $C_{2-6}$ alkynyl, a $C_{3-10}$ carbocyclic residue substituted with 0–3 $R^{9c}$, and a 5–6 membered heterocyclic system containing 1–4 heteroatoms selected from the group consisting of N, O, and S substituted with 0–3 $R^{9c}$;

$R^{9e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{9f}R^{9f}$, and $(CH_2)_r$phenyl;

$R^{9f}$, at each occurrence, is selected from H, $C_{1-6}$ alkyl, and $C_{3-6}$ cycloalkyl;

$R^{10}$, is selected from H, $C_{1-6}$ alkyl, $C_{2-8}$ alkenyl, $C_{2-8}$ alkynyl, F, Cl, Br, I, $NO_2$, CN, $(CH_2)_rOH$, $(CH_2)_r$ $OR^{10d}$, $(CH_2)_rSR^{10d}$, $(CH_2)_rNR^{10a}R^{10a'}$, $(CH_2)_rC(O)$ OH, $(CH_2)_rC(O)R^{10b}$, $(CH_2)_rC(O)NR^{10a}R^{10a'}$, $(CH_2)_r$ $NR^{10a}C(O)R^{10a}$, $(CH_2)_rNR^{10a}C(O)H$, $(CH_2)_rC(O)$ $OR^{10b}$, $(CH_2)_rOC(O)R^{10b}$, $(CH_2)_rS(O)_pR^{10b}$, $(CH_2)_rS$ $(O)_2NR^{10a}R^{10a'}$, $(CH_2)_rNR^{10a}S(O)_2R^{10b}$, $C_{1-6}$ haloalkyl, a $(CH_2)_r$—$C_{3-10}$ carbocyclic residue substituted with 0–5 $R^{10c}$, and a $(CH_2)_r$-5–10 membered heterocyclic system containing 1–4 heteroatoms selected from N, O, and S, substituted with 0–3 $R^{10c}$;

$R^{10a}$ and $R^{10a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{10e}$, and a $(CH_2)_r$-5–10 membered heterocyclic system containing 1–4 heteroatoms selected from N, O, and S, substituted with 0–3 $R^{10e}$;

$R^{10b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–2 $R^{10e}$, and a $(CH_2)_r$-5–6 membered heterocyclic system containing 1–4 heteroatoms selected from N, O, and S, substituted with 0–3 $R^{10e}$;

$R^{10c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{10f}R^{10f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{10b}$, $(CH_2)_rC(O)NR^{10f}R^{10f}$, $(CH_2)_r$ $NR^{10f}C(O)R^{10a}$, $(CH_2)_rC(O)OC_{1-4}$ alkyl, $(CH_2)_rOC$ $(O)R^{10b}$, $(CH_2)_rC(=NR^{10f})NR^{10f}R^{10f}$, $(CH_2)_rS(O)_p$ $R^{10b}$, $(CH_2)_rNHC(=NR^{10f})NR^{10f}R^{10f}$, $(CH_2)_rS(O)_2$ $NR^{10f}R^{10f}$, $(CH_2)_rNR^{10f}S(O)_2R^{10b}$, and $(CH_2)_r$phenyl substituted with 0–3 $R^{10e}$;

$R^{10d}$, at each occurrence, is selected from $C_{1-6}$ alkyl, $C_{2-6}$ alkenyl, $C_{2-6}$ alkynyl, a $C_{3-10}$ carbocyclic residue substituted with 0–3 $R^{10c}$, and a 5–6 membered heterocyclic system containing 1–4 heteroatoms selected from the group consisting of N, O, and S substituted with 0–3 $R^{10c}$;

$R^{10e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{10f}R^{10f}$, and $(CH_2)_r$ phenyl;

$R^{10f}$, at each occurrence, is selected from H, $C_{1-5}$ alkyl, and $C_{3-6}$ cycloalkyl;

alternatively, $R^9$ and $R^{10}$ join to form $C_{3-7}$ cycloalkyl, 5–6-membered cyclic ketal or =O;

with the proviso that when $R^{10}$ is halogen, cyano, nitro, or bonded to the carbon to which it is attached through a heteroatom, $R^9$ is not halogen, cyano, or bonded to the carbon to which it is attached through a heteroatom;

$R^{11}$, is selected from H, $C_{1-6}$ alkyl, $C_{2-8}$ alkenyl, $C_{2-8}$ alkynyl, $(CH_2)_qOH$, $(CH_2)_qSH$, $(CH_2)_qOR^{11d}$, $(CH_2)_q$ $SR^{11d}$, $(CH_2)_qNR^{11a}R^{11a'}$, $(CH_2)_rC(O)OH$, $(CH_2)_rC$ $(O)R^{11b}$, $(CH_2)_rC(O)NR^{11a}R^{11a'}$, $(CH_2)_qNR^{11a}C(O)$ $R^{11a}$, $(CH_2)_qNR^{11a}C(O)NHR^{11a}$, $(CH_2)_rC(O)OR^{11b}$, $(CH_2)_qOC(O)R^{11b}$, $(CH_2)_qS(O)_pR^{11b}$, $(CH_2)_qS(O)_2$ $NR^{11a}R^{11a'}$, $(CH_2)_qNR^{11a}S(O)_2R^{11b}$, $C_{1-6}$ haloalkyl, a $(CH_2)_r$—$C_{3-10}$ carbocyclic residue substituted with 0–5 $R^{11c}$, and a $(CH_2)_r$-5–10 membered heterocyclic system containing 1–4 heteroatoms selected from N, O, and S, substituted with 0–3 $R^{11c}$;

$R^{11a}$ and $R^{11a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{11e}$, and a $(CH_2)_r$-5–10 membered heterocyclic system containing 1–4 heteroatoms selected from N, O, and S, substituted with 0–3 $R^{11e}$;

$R^{11b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–2 $R^{11e}$, and a $(CH_2)_r$-5–6 membered heterocyclic system containing 1–4 heteroatoms selected from N, O, and S, substituted with 0–3 $R^{11e}$;

$R^{11c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF2)_rCF_3$, $NO_2$, CN, $(CH_2)_rNR^{11f}R^{11f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{11b}$, $(CH_2)_rC(O)NR^{11f}R^{11f}$, $(CH_2)_r$ $NR^{11f}C(O)R^{11a}$, $(CH_2)_rC(O)OC_{1-4}$ alkyl, $(CH_2)_rOC$ $(O)R^{11b}$, $(CH_2)_rC(=NR^{11f})NR^{11f}R^{11f}$, $(CH_2)_rNHC$ $(=NR^{11f})NR^{11f}R^{11f}$, $(CH_2)_rS(O)_pR^{11b}$, $(CH_2)_rS(O)_2$ $NR^{11f}R^{11f}$, $(CH_2)_rNR^{11f}S(O)_2R^{11b}$, and $(CH_2)_r$phenyl substituted with 0–3 $R^{11e}$;

$R^{11d}$, at each occurrence, is selected from $C_{1-6}$ alkyl substituted with 0–3 $R^{11e}$, $C_{2-6}$ alkenyl, $C_{2-6}$ alkynyl, and a $C_{3-10}$ carbocyclic residue substituted with 0–3 $R^{11c}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{11f}R^{11f}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-6}$ alkyl, $(CH_2)_qOH$, $(CH_2)_rC_{3-6}$ cycloalkyl, and $(CH_2)$tphenyl substituted with 0–3 $R^{12a}$;

$R^{12a}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{9f}R^{9f}$, and $(CH_2)_r$phenyl;

alternatively, $R^{11}$ and $R^{12}$ join to form $C_{3-7}$ cycloalkyl;

$R^{13}$, at each occurrence, is selected from $C_{1-6}$ alkyl, $C_{2-8}$ alkenyl, $C_{2-8}$ alkynyl, $C_{3-6}$ cycloalkyl, $(CF_2)_wCF_3$, $(CH_2)_rNR^{13a}R^{13a'}$, $(CH_2)_rOH$, $(CH_2)_rOR^{13b}$, $(CH_2)_r$ SH, $(CH_2)_rSR^{13b}$, $(CH_2)_wC(O)OH$, $(CH_2)_wC(O)R^{13b}$, $(CH_2)_wC(O)NR^{13a}R^{13a'}$, $(CH_2)_rNR^{13d}C(O)R^{13a}$, $(CH_2)_wC(O)OR^{13b}$, $(CH_2)_rOC(O)R^{13b}$, $(CH_2)_wS(O)_pR^{13b}$, $(CH_2)_wS(O)_2NR^{13a}R^{13a'}$, $(CH_2)_rNR^{13d}S(O)_2R^{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_r$ $OC_{1-5}$ alkyl, $(CH_2)_rOH$, $(CH_2)_rSC_{1-5}$ alkyl, and $(CH_2)_r$ $NR^{13d}R^{13d}$;

$R^{13d}$, at each occurrence, is selected from H, $C_{1-6}$ alkyl, and $C_{3-6}$ cycloalkyl;

$R^{14}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{14a}R^{14a'}$, $(CHR')_rOH$, $(CHR')_r$ $O(CHR')_rR^{14d}$, $(CHR')_rSH$, $(CHR')_rC(O)H$, $(CHR')_rS$ $(CHR')_rR^{14d}$, $(CHR')_rC(O)OH$, $(CHR')_rC(O)$ $(CHR')_r$ $R^{14b}$, $(CHR')_rC(O)NR^{14a}R^{14a'}$, $(CHR')_rNR^{14f}C(O)$ $(CHR')_rR^{14b}$, $(CHR')_rC(O)O(CHR')_rR^{14d}$, $(CHR')_rOC$ $(O)(CHR')_rR^{14b}$, $(CHR')_rC(=NR^{14f})NR^{14a}R^{14a'}$, $(CHR')_rNHC(=NR^{14f})NR^{14f}R^{14f}$, $(CHR')_rS(O)_p$ $(CHR')_rR^{14b}$, $(CHR')_rS(O)_2NR^{14a}R^{14a'}$, $(CHR')_r$ $NR^{14f}S(O)_2(CHR')_rR^{14b}$, $C_{1-6}$ haloalkyl, $C_{2-8}$ alkenyl substituted with 0–3 R', $C_{2-8}$ alkynyl substituted with 0–3 R', $(CHR')_r$phenyl substituted with 0–3 $R^{14e}$, and a $(CH_2)_r$-5–10 membered heterocyclic system containing 1–4 heteroatoms selected from N, O, and S, substituted with 0–2 $R^{15e}$, or two $R^{14}$ substituents on adjacent atoms on ring A form to join a 5–6 membered heterocyclic system containing 1–3 heteroatoms selected from N, O, and S substituted with 0–2 $R^{15e}$;

alternatively, $R^{14}$ joins with $R^4$ to form a 5, 6 or 7 membered piperidinium spirocycle or pyrrolidinium spirocycle fused to ring A, the spirocycle substituted with 0–3 $R^a$;

R', at each occurrence, is selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with $R^{14e}$;

$R^{14a}$ and $R^{14a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{14e}$, and a $(CH_2)_r$-5–10 membered heterocyclic system containing 1–4 heteroatoms selected from N, O, and S, substituted with 0–2 $R^{14e}$;

$R^{14b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{14e}$, and $(CH_2)_r$-5–6 membered heterocyclic system containing 1–4 heteroatoms selected from N, O, and S, substituted with 0–2 $R^{14e}$;

$R^{14d}$, at each occurrence, is selected from $C_{2-8}$ alkenyl, $C_{2-8}$ alkynyl, $C_{1-6}$ alkyl substituted with 0–3 $R^{14e}$, a $(CH_2)_r$—$C_{3-10}$ carbocyclic residue substituted with 0–3 $R^{14e}$, and a $(CH_2)_r$-5–6 membered heterocyclic system containing 1–4 heteroatoms selected from N, O, and S, substituted with 0–3 $R^{14e}$;

$R^{14e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{14f}R^{14f}$, and $(CH_2)_r$ phenyl;

$R^{14f}$, at each occurrence, is selected from H, $C_{1-6}$ alkyl, $C_{3-6}$ cycloalkyl, and phenyl;

$R^{15}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{15a}R^{15a'}$, $(CHR')_rOH$, $(CHR')_r$ $O(CHR')_rR^{15d}$, $(CHR')_rSH$, $(CHR')_rC(O)H$, $(CHR')_rS$ $(CHR')_rR^{15d}$, $(CHR')_rC(O)OH$, $(CHR')_rC(O)$ $(CHR')_r$ $R^{15b}$, $(CHR')_rC(O)NR^{15a}R^{15a'}$, $(CHR')_rNR^{15f}C(O)$ $(CHR')_rR^{15b}$, $(CHR')_rC(O)O(CHR')_rR^{15d}$, $(CHR')_rOC$ $(O)$ $(CHR')_rR^{15b}$, $(CHR')_rC(=NR^{15f})NR^{15a}R^{15a'}$, $(CHR')_rNHC(=NR^{15f})NR^{15f}R^{15f}$, $(CHR')_rS(O)_p$ $(CHR')_rR^{15b}$, $(CHR')_rS(O)_2NR^{15a}R^{15a'}$, $(CHR')_r$ $NR^{15f}S(O)_2(CHR')_rR^{15b}$, $C_{1-6}$ haloalkyl, $C_{2-8}$ alkenyl substituted with 0–3 R', $C_{2-8}$ alkynyl substituted with 0–3 R', $(CHR')_r$phenyl substituted with 0–3 $R^{15e}$, and a $(CH_2)_r$-5–10 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{15e}$, and a $(CH_2)_r$-5–10 membered heterocyclic system containing 1–4 heteroatoms selected from N, O, and S, substituted with 0–2 $R^{15e}$;

$R^{15b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{15e}$, and $(CH_2)_r$-5–6 membered heterocyclic system containing 1–4 heteroatoms selected from N, O, and S, substituted with 0–2 $R^{15e}$;

$R^{15d}$, at each occurrence, is selected from $C_{2-8}$ alkenyl, $C_{2-8}$ alkynyl, $C_{1-6}$ alkyl substituted with 0–3 $R^{15e}$, a $(CH_2)_r$—$C_{3-10}$ carbocyclic residue substituted with 0–3 $R^{15e}$, and a $(CH_2)_r$-5–6 membered heterocyclic system containing 1–4 heteroatoms selected from N, O, and S, substituted with 0–3 $R^{15e}$;

$R^{15e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{15f}R^{15f}$, and $(CH_2)_r$ phenyl;

$R^{15f}$, at each occurrence, is selected from H, $C_{1-6}$ alkyl, $C_{3-6}$ cycloalkyl, and phenyl;

$R^{16}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a'}$, $(CHR')_rOH$, $(CHR')_r$ $O(CHR')_rR^{16d}$, $(CHR')_rSH$, $(CHR')_rC(O)H$, $(CHR')_rS$ $(CHR')_rR^{16d}$, $(CHR')_rC(O)OH$, $(CHR')_rC(O)$ $(CHR')_r$ $R^{16b}$, $(CHR')_rC(O)NR^{16a}R^{16a'}$, $(CHR')_rNR^{16f}C(O)$ $(CHR')_rR^{16b}$, $(CHR')_rC(O)O(CHR')_rR^{16d}$, $(CHR')_rOC$ $(O)$ $(CHR')_rR^{16b}$, $(CHR')_rC(=NR^{16f})NR^{16a}R^{16a'}$, $(CHR')_rNHC(=NR^{16f})NR^{16f}R^{16f}$, $(CHR')_rS(O)_p$ (CHR')$_t$R$^{16b}$, (CHR')$_t$S(O)$_2$NR$^{16a}$R$^{16a'}$, (CHR')$_t$NR$^{16f}$S(O)$_2$(CHR')$_t$R$^{16b}$, C$_{1-6}$ haloalkyl, C$_{2-8}$ alkenyl substituted with 0–3 R', C$_{2-8}$ alkynyl substituted with 0–3 R', and (CHR')$_t$phenyl substituted with 0–3 R$^{16e}$;

R$^{16a}$ and R$^{16a'}$, at each occurrence, are selected from H, C$_{1-6}$ alkyl, C$_{2-8}$ alkenyl, C$_{2-8}$ alkynyl, a (CH$_2$)$_r$—C$_{3-10}$ carbocyclic residue substituted with 0–5 R$^{16e}$, and a (CH$_2$)$_r$-5–10 membered heterocyclic system containing 1–4 heteroatoms selected from N, O, and S, substituted with 0–2 R$^{16e}$;

R$^{16b}$, at each occurrence, is selected from C$_{1-6}$ alkyl, C$_{2-8}$ alkenyl, C$_{2-8}$ alkynyl, a (CH$_2$)$_r$C$_{3-6}$ carbocyclic residue substituted with 0–3 R$^{16e}$, and a (CH$_2$)$_r$-5–6 membered heterocyclic system containing 1–4 heteroatoms selected from N, O, and S, substituted with 0–2 R$^{16e}$;

R$^{16d}$, at each occurrence, is selected from C$_{2-8}$ alkenyl, C$_{2-8}$ alkynyl, C$_{1-6}$ alkyl substituted with 0–3 R$^{16e}$, a (CH$_2$)$_r$—C$_{3-10}$ carbocyclic residue substituted with 0–3 R$^{16e}$, and a (CH$_2$)$_r$-5–6 membered heterocyclic system containing 1–4 heteroatoms selected from N, O, and S, substituted with 0–3 R$^{16e}$;

R$^{16e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{16f}$R$^{16f}$, and (CH$_2$)$_r$ phenyl;

R$^{16f}$, at each occurrence, is selected from H, C$_{1-6}$ alkyl, and C$_{3-6}$ cycloalkyl, and phenyl;

g is selected from 0, 1, 2, 3, and 4;

t is selected from 1 and 2;

w is selected from 0 and 1;

r is selected from 0, 1, 2, 3, 4, and 5;

q is selected from 1, 2, 3, 4, and 5; and p is selected from 0, 1, 2, and 3.

[16] In a preferred embodiment, the present invention provides a novel method for the modulation of the chemokine receptor CCR-3 comprising the administration of an effective amount of compounds of formula (I), wherein:

E is selected from:

R$^4$ is absent, taken with the nitrogen to which it is attached to form an N-oxide, or selected from C$_{1-8}$ alkyl, (CH$_2$)$_r$C$_{3-6}$ cycloalkyl, and (CH$_2$)$_r$-phenyl substituted with 0–3 R$^{4c}$;

R$^{4c}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$ SC$_{1-5}$ alkyl, (CH$_2$)$_r$NR$^{4a}$R$^{4a'}$, and (CH$_2$)$_r$ phenyl;

alternatively, R$^4$ joins with R$^7$,R$^9$ or R$^{14}$ to form a 5, 6 or 7 membered piperidinium spirocycle substituted with 0–3 R$^a$;

R$^1$ and R$^2$ are independently selected from H and C$_{1-4}$ alkyl;

R$^6$, at each occurrence, is selected from C$_{1-4}$ alkyl, C$_{2-8}$ alkenyl, C$_{2-8}$ alkynyl, (CH$_2$)$_r$C$_{3-6}$ cycloalkyl, (CF$_2$)$_r$CF$_3$, CN, (CH$_2$)$_r$OH, (CH$_2$)$_r$OR$^{6b}$, (CH$_2$)$_r$C(O)R$^{6b}$, (CH$_2$)$_r$C(O)NR$^{6a}$R$^{6a'}$, (CH$_2$)$_r$NR$^{6d}$C(O)R$^{6a}$, and (CH$_2$)$_t$ phenyl substituted with 0–3 R$^{6c}$;

R$^{6a}$ and R$^{6a'}$, at each occurrence, are selected from H, C$_{1-6}$ alkyl, C$_{3-6}$ cycloalkyl, and phenyl substituted with 0–3 R$^{6c}$;

R$^{6b}$, at each occurrence, is selected from C$_{1-6}$ alkyl, C$_{3-6}$ cycloalkyl, and phenyl substituted with 0–3 R$^{6c}$;

R$^6$c, at each occurrence, is selected from C$_{1-6}$ alkyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$SC$_{1-5}$ alkyl, and (CH$_2$)$_r$NR$^{6d}$R$^{6d}$;

R$^{6d}$, at each occurrence, is selected from H, C$_{1-6}$ alkyl, and C$_{3-6}$ cycloalkyl;

R$^7$, is selected from H, C$_{1-3}$ alkyl, (CH$_2$)$_r$C$_{3-6}$ cycloalkyl, (CH$_2$)$_q$OH, (CH$_2$)$_q$OR$^{7d}$, (CH$_2$)$_q$NR$^{7a}$R$^{7a'}$, (CH$_2$)$_q$C(O)R$^{7b}$, (CH$_2$)$_r$C(O)NR$^{7a}$R$^{7a'}$, (CH$_2$)$_q$NR$^{7a}$C(O)R$^{7a}$, C$_{1-6}$ haloalkyl, (CH$_2$)$_r$phenyl with 0–2 R$^{7c}$;

R$^{7a}$ and R$^{7a'}$, at each occurrence, are selected from H, C$_{1-6}$ alkyl, (CH$_2$)$_r$C$_{3-6}$ cycloalkyl, a (CH$_2$)$_r$phenyl substituted with 0–3 R$^{7e}$;

R$^{7b}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, (CH$_2$)$_r$ phenyl substituted with 0–3 R$^{7e}$;

R$^7$c, at each occurrence, is selected from C$_{1-4}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$,CN, (CH$_2$)$_r$NR$^{7f}$R$^{7f}$, (CH$_2$)$_r$OH, (CH$_2$)$_r$OC$_{1-4}$ alkyl, (CH$_2$)$_r$C(O)R$^{7b}$, (CH$_2$)$_r$C(O)NR$^{7f}$R$^{7f}$, (CH$_2$)$_r$NR$^{7f}$C(O)R$^{7a}$, (CH$_2$)$_r$S(O)$_p$R$^{7b}$, (CH$_2$)$_r$ S(O)$_2$NR$^{7f}$R$^{7f}$, (CH$_2$)$_r$NR$^{7f}$S(O)$_2$R$^{7b}$, and (CH$_2$)$_r$ phenyl substituted with 0–2 R$^{7e}$;

R$^{7d}$, at each occurrence, is selected from C$_{1-6}$ alkyl, (CH$_2$)$_r$C$_{3-6}$ cycloalkyl, (CH$_2$)$_r$phenyl substituted with 0–3 R$^{7e}$;

R$^{7e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{7f}$R$^{7f}$, and (CH$_2$)$_r$phenyl;

R$^{7f}$, at each occurrence, is selected from H, C$_{1-5}$ alkyl, and C$_{3-6}$ cycloalkyl;

R$^8$ is H or joins with R$^7$ to form C$_{3-7}$ cycloalkyl or =NR$^{8b}$;

$R^{11}$, is selected from H, $C_{1-6}$ alkyl, $(CH_2)_rC_{3-6}$ cycloalkyl, $(CH_2)_qOH$, $(CH_2)_qOR^{11d}$, $(CH_2)_qNR^{11a}R^{11a'}$, $(CH_2)_rC(O)R^{11b}$, $(CH_2)_rC(O)NR^{11a}R^{11a'}$, $(CH_2)_qNR^{11a}C(O)R^{11a}$, $C_{1-6}$ haloalkyl, $(CH_2)_r$phenyl with 0–2 $R^{11c}$, $(CH_2)_r$-5–10 membered heterocyclic system containing 1–4 heteroatoms selected from N, O, and S, substituted with 0–3 $R^{15}$;

$R^{11a}$ and $R^{11a'}$, at each occurrence, are selected from H, $C_{1-6}$ alkyl, $(CH_2)_rC_{3-6}$ cycloalkyl, a $(CH_2)_r$phenyl substituted with 0–3 $R^{11e}$;

$R^{11b}$, at each occurrence, is selected from $C_{1-6}$ alkyl, $C_{2-8}$ alkenyl, $C_{2-8}$ alkynyl, $(CH_2)_rC_{3-6}$ cycloalkyl, $(CH_2)_r$ phenyl substituted with 0–3 $R^{11e}$;

$R^{11c}$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{11f}R^{11f}$, $(CH_2)_rOH$, $(CH_2)_rOC_{1-4}$ alkyl, $(CH_2)_rC(O)R^{11b}$, $(CH_2)_rC(O)NR^{11f}R^{11f}$, $(CH_2)_rNR^{11f}C(O)R^{11a}$, $(CH_2)_rS(O)_pR^{11b}$, $(CH_2)_rS(O)_2NR^{11f}R^{11f}$, $(CH_2)_rNR^{11f}S(O)_2R^{11b}$, and $(CH_2)_r$phenyl substituted with 0–2 $R^{11e}$;

$R^{11d}$, at each occurrence, is selected from $C_{1-6}$ alkyl, $(CH_2)_rC_{3-6}$ cycloalkyl, $(CH_2)_r$phenyl substituted with 0–3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{11f}R^{11f}$, and $(CH_2)_r$phenyl;

$R^{11f}$, at each occurrence, is selected from H, $C_{1-5}$ alkyl and $C_{3-6}$ cycloalkyl;

$R^{12}$ is H or joins with $R^{11}$ to form $C_{3-7}$ cycloalkyl;

$R^{13}$, at each occurrence, is selected from $C_{1-4}$ alkyl, $C_{3-6}$ cycloalkyl, $(CH_2)NR^{13a}R^{13a'}$, $(CH_2)OH$, $(CH_2)OR^{13b}$, $(CH_2)_wC(O)R^{13b}$, $(CH_2)_wC(O)NR^{13a}R^{13a'}$, $(CH_2)NR^{13d}C(O)R^{13a}$, $(CH_2)_wS(O)_2NR^{13a}R^{13a'}$, $(CH_2)NR^{13d}S(O)_2R^{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, and $(CH_2)_rNR^{13d}R^{13d}$;

$R^{13d}$, at each occurrence, is selected from H, $C_{1-6}$ alkyl, and $C_{3-6}$ cycloalkyl;

q is selected from 1, 2, and 3; and r is selected from 0, 1, 2, and 3.

[17] In a more preferred embodiment, the present invention provides a novel method for the modulation of the chemokine receptor CCR-3 comprising the administration of an effective amount of compounds of formula (I), wherein:

ring A is selected from:

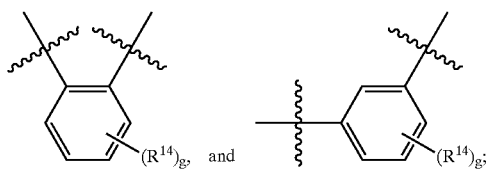
$(R^{14})_g$, and $(R^{14})_g$;

$R^3$ is selected from a $(CR^3'H)_r$-carbocyclic residue substituted with 0–5 $R^{15}$, wherein the carbocyclic residue is selected from phenyl, $C_{3-6}$ cycloalkyl, naphthyl, and adamantyl; and a $(CR^3'H)_r$-heterocyclic system substituted with 0–4 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^5$ is selected from $(CR^{5'}H)_r$-phenyl substituted with 0–5 $R^{16}$; and a $(CR^{5'}H)_r$-heterocyclic system substituted with 0–3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl.

[18] In an even more preferred embodiment, the present invention provides a novel method for the modulation of the chemokine receptor CCR-3 comprising the administration of an effective amount of compounds of formula (I-i), wherein the compound of formula (I-i) is:

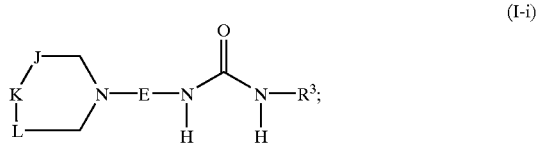
(I-i)

with the proviso that at least one of J, K or L contains an $R^5$;

$R^{16}$, at each occurrence, is selected from $C_{1-8}$ alkyl, $(CH_2)_rC_{3-6}$ cycloalkyl, $CF_3$, Cl, Br, I, F, $(CH_2)_rNR^{16a}R^{16a'}$, $NO_2$, CN, OH, $(CH_2)_rOR^{16d}$, $(CH_2)_rC(O)R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_rNR^{16f}S(O)_2R^{16b}$, and $(CH_2)_r$phenyl substituted with 0–3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl;

$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

[19] In an another even more preferred embodiment, the present invention provides a novel method for the modulation of the chemokine receptor CCR-3 comprising the administration of an effective amount of compounds of formula (I-ii), wherein (I-ii) is:

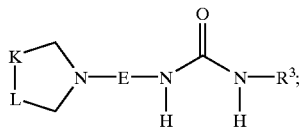

(I-ii)

with the proviso that at least one of K or L contains an $R^5$;

$R^{16}$, at each occurrence, is selected from $C_{1-8}$ alkyl, $(CH_2)_rC_{3-6}$ cycloalkyl, $CF_3$, Cl, Br, I, F, $(CH_2)_r$ $NR^{16a}R^{16a'}$, $NO_2$, CN, OH, $(CH_2)_rOR^{16d}$, $(CH_2)_rC(O)R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_rNR^{16f}S(O)_2R^{16b}$, and $(CH_2)_r$phenyl substituted with 0–3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl;

$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

[20] In a preferred embodiment, the present invention provides a novel method for the modulation of the chemokine receptor CCR-3 comprising the administration of an effective amount of compounds of formula (I-i), wherein:

$R^5$ is $CH_2$phenyl substituted with 0–3 $R^{16}$;

$R^9$, is selected from H, $C_{1-6}$ alkyl, $(CH_2)_rC_{3-6}$ cycloalkyl, F, Cl, CN, $(CH_2)_rOH$, $(CH_2)_rOR^{9d}$, $(CH_2)_rNR^{9a}R^{9a'}$, $(CH_2)_rOC(O)NHR^{9a}$, $(CH_2)_r$phenyl substituted with 0–5 $R^{9e}$, and a heterocyclic system substituted with 0–2 $R^{9e}$, wherein the heterocyclic system is selected from pyridyl, thiophenyl, furanyl, oxazolyl, and thiazolyl;

$R^{9a}$ and $R^{9a'}$, at each occurrence, are selected from H, $C_{1-6}$ alkyl, $C_{3-6}$ cycloalkyl, and $(CH_2)_r$phenyl substituted with 0–3 $R^{9e}$;

$R^{9d}$, at each occurrence, is selected from $C_{1-6}$ alkyl and phenyl;

$R^{9e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{10}$ is selected from H, $C_{1-5}$ alkyl, OH, and $CH_2OH$;

alternatively, $R^9$ and $R^{10}$ join to form $C_{3-7}$ cycloalkyl, 5–6-membered cyclic ketal or =O;

with the proviso that when $R^{10}$ is halogen, cyano, nitro, or bonded to the carbon to which it is attached through a heteroatom, $R^9$ is not halogen, cyano, or bonded to the carbon to which it is attached through a heteroatom;

$R^{11}$ is selected from H, $C_{1-8}$ alkyl, $(CH_2)_r$phenyl substituted with 0–5 $R^{11e}$, and a $(CH_2)_r$-heterocyclic system substituted with 0–2 $R^{11e}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl; and $R^{11e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{12}$ is H;

alternatively, $R^{11}$ and $R^{12}$ join to form $C_{3-7}$ cycloalkyl;

$R^{14}$, at each occurrence, is selected from $C_{1-8}$ alkyl, $(CH_2)_rC_{3-6}$ cycloalkyl, $CF_3$, Cl, Br, I, F, $(CH_2)_r$ $NR^{14a}R^{14a'}$, $NO_2$, CN, OH, $(CH_2)_rOR^{14d}$, $(CH_2)_rC(O)R^{14b}$, $(CH_2)_rC(O)NR^{14a}R^{14a'}$, $(CH_2)_rNR^{14f}C(O)R^{14b}$, $(CH_2)_rS(O)_pR^{14b}$, $(CH_2)_rS(O)_2NR^{14a}R^{14a'}$, $(CH_2)_rNR^{14f}S(O)_2R^{14b}$, $(CH_2)_r$phenyl substituted with 0–3 $R^{14e}$, and a $(CH_2)_r$-5–6 membered heterocyclic system containing 1–4 heteroatoms selected from N, O, and S, substituted with 0–2 $R^{15e}$, or two $R^{14}$ substituents on adjacent atoms on ring A form to join a 5–6 membered heterocyclic system containing 1–3 heteroatoms selected from N, O, and S substituted with 0–2 $R^{15e}$;

$R^{14a}$ and $R^{14a'}$, at each occurrence, are selected from H, $C_{1-6}$ alkyl, $C_{3-6}$ cycloalkyl, and $(CH_2)_r$phenyl substituted with 0–3 $R^{14e}$, and a $(CH_2)_r$-5–6 membered heterocyclic system containing 1–4 heteroatoms selected from N, O, and S, substituted with 0–2 $R^{15e}$;

$R^{14b}$, at each occurrence, is selected from H, $C_{1-6}$ alkyl, $C_{3-6}$ cycloalkyl, and $(CH_2)_r$phenyl substituted with 0–3 $R^{14e}$;

$R^{14d}$, at each occurrence, is selected from $C_{1-6}$ alkyl and phenyl;

$R^{14e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{14f}$, at each occurrence, is selected from H, and $C_{1-5}$ alkyl; and r is selected from 0, 1, and 2.

[21] In a preferred embodiment, the present invention provides a novel method for the modulation of the chemokine receptor CCR-3 comprising the administration of an effective amount of compounds of formula (I-ii), wherein:

$R^5$ is $CH_2$phenyl substituted with 0–3 $R^{16}$;

$R^9$, is selected from H, $C_{1-6}$ alkyl, $(CH_2)_rC_{3-6}$ cycloalkyl, F, Cl, CN, $(CH_2)_rOH$, $(CH_2)_rOR^{9d}$, $(CH_2)_rNR^{9a}R^{9a'}$, $(CH_2)_rOC(O)NHR^{9a}$, $(CH_2)_r$phenyl substituted with 0–5 $R^{9e}$, and a heterocyclic system substituted with 0–2 $R^{9e}$, wherein the heterocyclic system is selected from pyridyl, thiophenyl, furanyl, oxazolyl, and thiazolyl;

$R^{9a}$ and $R^{9a'}$, at each occurrence, are selected from H, $C_{1-6}$ alkyl, $C_{3-6}$ cycloalkyl, and $(CH_2)_r$phenyl substituted with 0–3 $R^{9e}$;

$R^{9d}$, at each occurrence, is selected from $C_{1-6}$ alkyl and phenyl;

$R^{9e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{10}$ is selected from H, $C_{1-8}$ alkyl, OH, and $CH_2OH$;

alternatively, $R^9$ and $R^{10}$ join to form $C_{3-7}$ cycloalkyl, 5–6-membered cyclic ketal or =O;

with the proviso that when $R^{10}$ is halogen, cyano, nitro, or bonded to the carbon to which it is attached through a heteroatom, $R^9$ is not halogen, cyano, or bonded to the carbon to which it is attached through a heteroatom;

$R^{11}$ is selected from H, $C_{1-8}$ alkyl, $(CH_2)_r$phenyl substituted with 0–5 $R^{11e}$, and a $(CH_2)_r$-heterocyclic system substituted with 0–2 $R^{11e}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl; and $R^{11e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{12}$ is H;

alternatively, $R^{11}$ and $R^{12}$ join to form $C_{3-7}$ cycloalkyl;

$R^{14}$, at each occurrence, is selected from $C_{1-8}$ alkyl, $(CH_2)_rC_{3-6}$ cycloalkyl, $CF_3$, Cl, Br, I, F, $(CH_2)_r$ $NR^{14a}R^{14a'}$, $NO_2$, CN, OH, $(CH_2)_rOR^{14d}$, $(CH_2)_rC(O)$ $R^{14b}$, $(CH_2)_rC(O)NR^{14a}R^{14a'}$, $(CH_2)_rNR^{14f}C(O)R^{14b}$, $(CH_2)_rS(O)_pR^{14b}$, $(CH_2)_rS(O)_2NR^{14a}R^{14a'}$, $(CH_2)_r$ $NR^{14f}S(O)_2R^{14b}$, $(CH_2)_r$phenyl substituted with 0–3 $R^{14e}$, and a $(CH_2)_r$-5–6 membered heterocyclic system containing 1–4 heteroatoms selected from N, O, and S, substituted with 0–2 $R^{15e}$, or two $R^{14}$ substituents on adjacent atoms on ring A form to join a 5–6 membered heterocyclic system containing 1–3 heteroatoms selected from N, O, and S substituted with 0–2 $R^{15e}$;

$R^{14a}$ and $R^{14a'}$, at each occurrence, are selected from H, $C_{1-6}$ alkyl, $C_{3-6}$ cycloalkyl, and $(CH_2)_r$phenyl substituted with 0–3 $R^{14e}$;

$R^{14b}$, at each occurrence, is selected from H, $C_{1-6}$ alkyl, $C_{3-6}$ cycloalkyl, and $(CH_2)_r$phenyl substituted with 0–3 $R^{14e}$;

$R^{14d}$, at each occurrence, is selected from $C_{1-6}$ alkyl and phenyl;

$R^{14e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{14f}$, at each occurrence, is selected from H, and $C_{1-5}$ alkyl; and r is selected from 0, 1, and 2.

[22] In a more preferred embodiment, the present invention provides a novel method for the modulation of the chemokine receptor CCR-3 comprising the administration of an effective amount of compounds of formula (I-i), wherein:

J is selected from $CH_2$ and $CHR^5$;

K is selected from $CH_2$ and $CHR^5$;

L is selected from $CH_2$ and $CHR^5$;

with the proviso that at least one of J, K or L is $CHR^5$;

$R^3$ is a $C_{3-10}$ carbocyclic residue substituted with 0–3 $R^{15}$, wherein the carbocyclic residue is selected from cyclopropyl, cyclopentyl, cyclohexyl, phenyl, naphthyl and adamantyl, and a $(CR^3H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{15}$, at each occurrence, is selected from $C_{1-8}$ alkyl, $(CH_2)_rC_{3-6}$ cycloalkyl, $CF_3$, Cl, Br, I, F, $(CH_2)_r$ $NR^{15a}R^{15a'}$, $NO_2$, CN, OH, $(CH_2)_rOR^{15d}$, $(CH_2)_rC(O)$ $R^{15b}$, $(CH_2)_rC(O)NR^{15a}R^{15a'}$, $(CH_2)_rNR^{15f}C(O)R^{15b}$, $(CH_2)_rS(O)_pR^{15b}$, $(CH_2)_rS(O)_2NR^{15a}R^{15a'}$, $(CH_2)_r$ $NR^{15f}S(O)_2R^{15b}$, $(CH_2)_r$phenyl substituted with 0–3 $R^{15e}$, and a $(CH_2)_r$-5–6 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{3-6}$ cycloalkyl, and $(CH_2)_r$phenyl substituted with 0–3 $R^{15e}$;

$R^{15b}$, at each occurrence, is selected from H, $C_{1-6}$ alkyl, $C_{3-6}$ cycloalkyl, and $(CH_2)_r$phenyl substituted with 0–3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H, and $C_{1-5}$ alkyl.

[23] In a more preferred embodiment, the present invention provides a novel method for the modulation of the chemokine receptor CCR-3 comprising the administration of an effective amount of compounds of formula (I-ii), wherein:

K is selected from $CH_2$ and $CHR^5$;

L is selected from $CH_2$ and $CHR^5$;

with the proviso that at least one of K or L is $CHR^5$;

$R^3$ is a $C_{3-10}$ carbocyclic residue substituted with 0–3 $R^{15}$, wherein the carbocyclic residue is selected from cyclopropyl, cyclopentyl, cyclohexyl, phenyl, naphthyl and adamantyl, and a $(CR^3H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{15}$, at each occurrence, is selected from $C_{1-8}$ alkyl, $(CH_2)_rC_{3-6}$ cycloalkyl, $CF_3$, Cl, Br, I, F, $(CH_2)_r$ $NR^{15a}R^{15a'}$, $NO_2$, CN, OH, $(CH_2)_rOR^{15d}$, $(CH_2)_rC(O)$ $R^{15b}$, $(CH_2)_rC(O)NR^{15a}R^{15a'}$, $(CH_2)_rNR^{15f}C(O)R^{15b}$, $(CH_2)_rS(O)_pR^{15b}$, $(CH_2)_rS(O)_2NR^{15a}R^{15a'}$, $(CH_2)_r$ $NR^{15f}S(O)_2R^{15b}$, and $(CH_2)_r$phenyl substituted with 0–3 $R^{15e}$, and a $(CH_2)_r$-5–6 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{3-6}$ cycloalkyl, and $(CH_2)_r$phenyl substituted with 0–3 $R^{15e}$;

$R^{15b}$, at each occurrence, is selected from H, $C_{1-6}$ alkyl, $C_{3-6}$ cycloalkyl, and $(CH_2)_r$phenyl substituted with 0–3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H and $C_{1-5}$ alkyl.

In another embodiment, the present invention provides a pharmaceutical composition, comprising a pharmaceutically acceptable carrier and a therapeutically effective amount of a compound of the present invention.

In another embodiment, the present invention provides a method for modulation of chemokine receptor activity comprising administering to a patient in need thereof a therapeutically effective amount of a compound of the present invention.

In a preferred embodiment, the present invention provides a method for modulation of chemokine receptor activity comprising contacting a CCR3 receptor with an effective inhibitory amount of a compound of the present invention.

In another embodiment, the present invention provides a method for treating inflammatory disorders comprising administering to a patient in need thereof a therapeutically effective amount of a compound of the present invention In another embodiment, the present invention provides a method for treating or preventing disorders selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

In a preferred embodiment, the present invention provides a method for treating or preventing disorders selected from asthma, allergic rhinitis, atopic dermatitis, and inflammatory bowel diseases.

In a more preferred embodiment, the present invention provides a method for treating or preventing disorders wherein the disorder is asthma.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0–2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups "Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example $—C_vF_w$ where v=1 to 3 and w=1 to (2v+1)).

The compounds of Formula I can also be quaternized by standard techniques such as alkylation of the piperidine or pyrrolidine with an alkyl halide to yield quaternary piperidinium salt products of Formula I. Such quaternary piperidinium salts would include a counterion. As used herein, "counterion" is used to represent a small, negatively charged species such as chloride, bromide, hydroxide, acetate, sulfate, and the like.

As used herein, the term "piperidinium spirocycle or pyrrolidinium spirocycle" is intented to mean a stable spirocycle ring system, in which the two rings form a quarternary nitrogene at the ring junction.

As used herein, the term "5–6-membered cyclic ketal" is intended to mean 2,2-disubstituted 1,3-dioxolane or 2,2-disubstituted 1,3-dioxane and their derivatives.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. Preferred heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "prodrugs"are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

Synthesis

The compounds of Formula I can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991).

Generally, compounds described in the scope of this patent application can be synthesized by the route described in Scheme 1. The appropriately substituted pyrrolidine (n=0) or piperidine (n=1) 1 is alkylated by a N-protected alkylhalide (halide=Cl, Br, I), mesylate, tosylate or triflate, 2, (where E represents a linkage described within the scope of this application in its fully elaborated form with the appropriate protecting groups as understood by one skilled in the art or in a precursor form which can be later elaborated into its final form by methods familiar to one skilled in the art) with or without base or an acid scavenger to yield the piperidinyl- or pyrrolidinylalkyl protected amine 3. If the halide is not I, then KI can also be added to facilitate the displacement, provided the solvent is suitable, such as an alcohol, 2-butanone, DMF or DMSO, amongst others. The displacement can be performed at room temperature to the reflux temperature of the solvent. The protecting group is subsequently removed to yield amine 4. Protecting groups include phthalimide which can be removed by hydrazine, a reaction familiar to one skilled in the art; bis-BOC which can be removed by either TFA or HCl dissolved in a suitable solvent, both procedures being familiar to one skilled in the art; a nitro group instead of an amine which can be reduced to yield an amine by conditions familiar to one skilled in the art; 2,4-dimethyl pyrrole (S. P. Breukelman, et al. J. Chem. Soc. Perkin Trans. I, 1984, 2801); N-1,1,4,4-Tetramethyl-disilylazacyclopentane (STABASE) (S. Djuric, J. Venit, and P. Magnus Tet. Lett 1981, 22, 1787) and other protecting groups. Reaction with an isocyanate or isothiocyanate 5 (Z=O,S) yields urea or thiourea 6. Reaction with a chloroformate or chlorothioformate 7 (Z=O,S) such as o-, p-nitrophenyl-chloroformate or phenylchloroformate (or their thiocarbonyl equivalents), followed by diplacement with an amine 9, also yields the corresponding urea or thiourea 6. Likewise, reaction of carbamate 8 (X=H, or 2- or 4-NO2) with disubstituted amine 10 yields trisubstituted urea or thiourea 12. Reaction of the amine 4 with an N,N-disubstituted carbamoyl chloride 11 (or its thiocarbonyl equivalent) yields the corresponding N,N-disubstituted urea or thiourea 12. Amine 4 can also be reductively aminated to yield 13 by conditions familiar to one skilled in the art and by the following conditions: Abdel-Magid, A. F., et al. Tet. Lett. 1990, 31, (39) 5595–5598. This secondary amine can subsequently be reacted with isocyanates or isothiocyanates to yield trisubstituted ureas 14 or with carbamoyl chlorides to yield tetrasubstituted ureas 15.

SCHEME 1

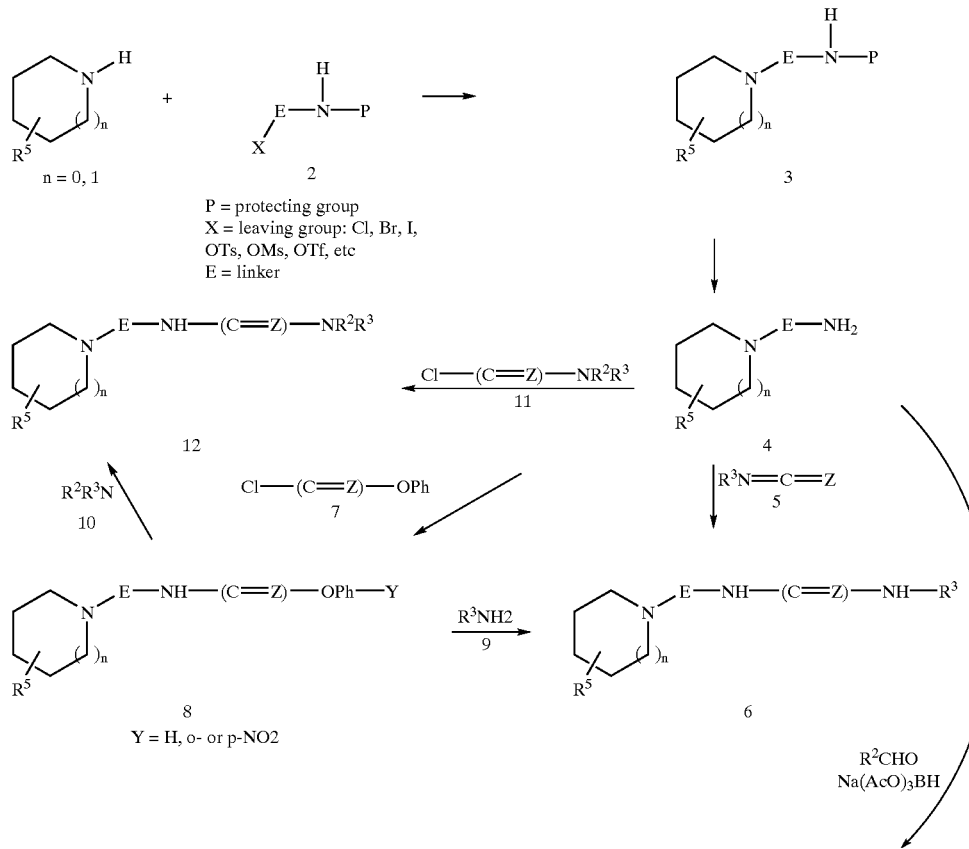

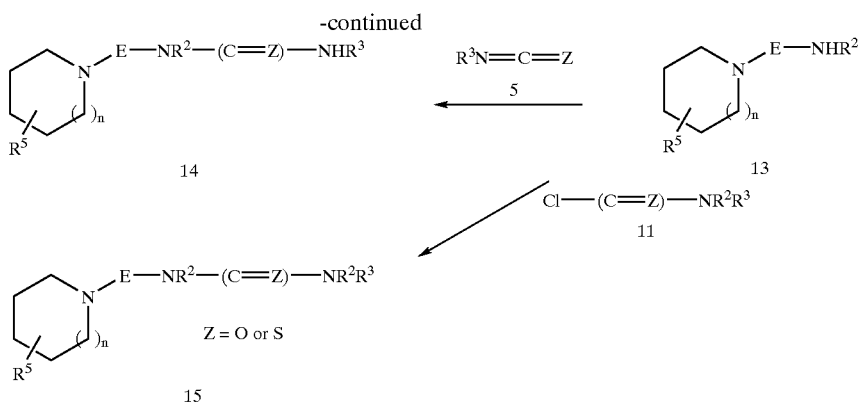

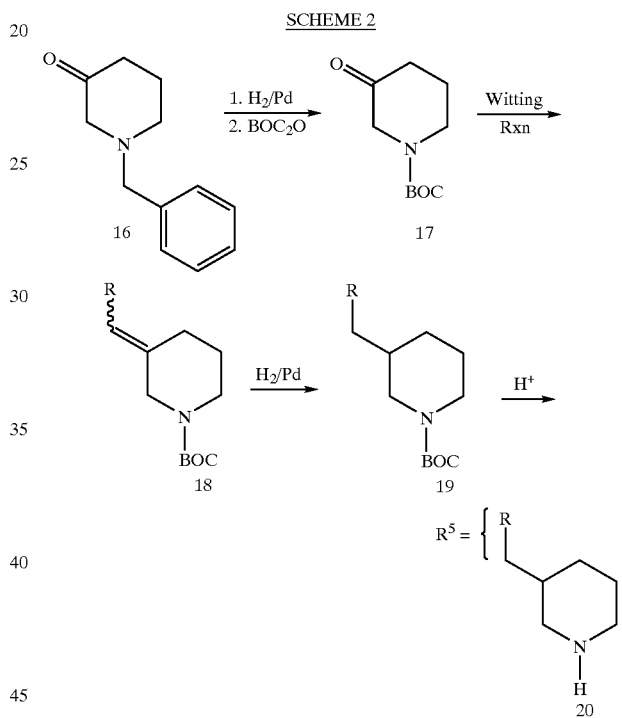

SCHEME 2

One can also convert amine 4 into an isocyanate, isothiocyanate, carbamoyl chloride or its thiocarbonyl equivalent (isocyanate: Nowakowski, J. J Prakt. Chem/Chem-Ztg 1996, 338 (7), 667–671; Knoelker, H.-J. et al., Angew. Chem. 1995, 107 (22), 2746–2749; Nowick, J. S. et al., J. Org. Chem. 1996, 61 (11), 3929–3934; Staab, H. A.; Benz, W.; Angew Chem 1961, 73; isothiocyanate: Strekowski L. et al., J. Heterocycl. Chem. 1996, 33 (6), 1685–1688; Kutschy, Pet al., Synlett. 1997, (3), 289–290) carbamoyl chloride: Hintze, F.; Hoppe, D.; Synthesis (1992) 12, 1216–1218; thiocarbamoyl chloride: Ried, W.; Hillenbrand, H.; Oertel, G.; Justus Liebigs Ann Chem 1954, 590) (these reactions are not shown in Scheme 1). These isocyanates, isothiocyantes, carbamoyl chlorides or thiocarbamoyl chlorides can then be reacted with $R^2R^3NH$ to yield di- or trisubstituted ureas or thioureas 12. An additional urea forming reaction involves the reaction of carbonyldiimidazole (CDI) (Romine, J. L.; Martin, S. W.; Meanwell, N. A.; Epperson, J. R.; Synthesis 1994 (8), 846–850) with 4 followed by reaction of the intermediate imidazolide with 9 or in the reversed sequence (9+CDI, followed by 4). Activation of imidazolide intermediates also facilitates urea formation (Bailey, R. A., et al., Tet. Lett. 1998, 39, 6267–6270). One can also use 13 and 10 with CDI. The urea forming reactions are done in a non-hydroxylic inert solvent such as THF, toluene, DMF, etc., at room temperature to the reflux temperature of the solvent and can employ the use of an acid scavenger or base when necessary such as carbonate and bicarbonate salts, triethylamine, DBU, Hunigs base, DMAP, etc.

Substituted pyrrolidines and piperidines 1 can either be obtained commercially or be prepared as shown in Scheme 2. Commercially available N-benzylpiperid-3-one 16 can be debenzylated and protected with a BOC group employing reactions familiar to one skilled in the art. Subsequent Wittig reaction followed by reduction and deprotection yields piperidine 20 employing reactions familiar to one skilled in the art. Substituted pyrrolidines may be made by a similar reaction sequence. Other isomers and analogs around the piperidine ring can also be made by a similar reaction sequence. Chiral pyrrolidines/piperidines can be synthesized via asymmetric hydrogenation of 18 using chiral catalysts (see Parshall, G. W. Homogeneous Catalysis, John Wiley and Sons, New York: 1980, pp. 43–45; Collman, J. P., Hegedus, L. S. Principles and Applications of Organotransition Metal Chemistry, University Science Books, Mill Valley, Calif., 1980, pp. 341–348).

The cyanoguanidines (Z=N—CN) can be synthesized by the method of K. S. Atwal, et al. and references contained therein (J. Med. Chem. (1998) 41, 217–275). The nitroethylene analog (Z=C—NO2) can be synthesized by the method of F. Moimas, et al. (Synthesis 1985, 509–510) and references contained therein. The malononitrile analog (Z=C(CN)2) may be synthesized by the method of S. Sasho, et al. (J. Med. Chem. 1993, 36, 572–579).

Guanidines (Z=$NR^{1a}$) can be synthesized by the methods outlined in Scheme 3. Compound 21 where Z=S can be methylated to yield the methylisothiourea 22. Displacement of the SMe group with amines yields substituted guanidines 23 (see H. King and I. M. Tonkin J. Chem. Soc. 1946, 1063 and references therein). Alternatively, reaction of thiourea 21 with amines in the presence of triethanolamine and "lac sulfur" which facilitates the removal of $H_2S$ yields substituted guanidines 23 (K. Ramadas, Tet. Lett. 1996, 37, 5161 and references therein). Finally, the use of carbonimidoyldichloride 24, or 25 followed by sequential displacements by amines yields the corresponding substituted guanidine 23

(S. Nagarajan, et al., Syn. Comm. 1992, 22, 1191–8 and references therein). In a similar manner, carbonimidoyldichlorides, $R^2-N=C(Cl)_2$ (not shown in Scheme 3) and $R^3-N=C(Cl)_2$ (not shown) can also be reacted sequentially with amines to yield di- and trisubstituted guanidine 23.

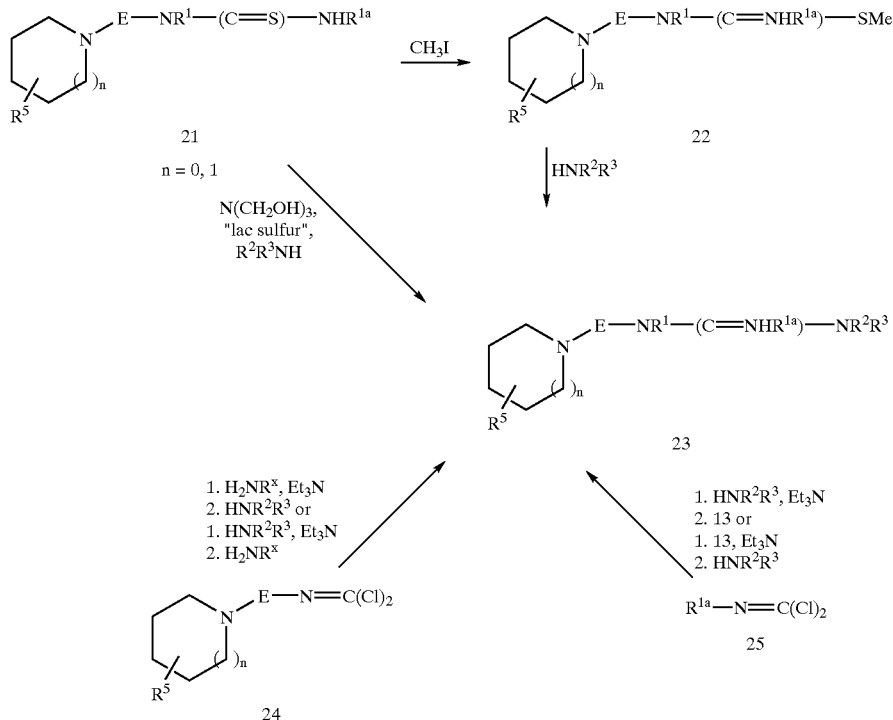

SCHEME 3

A method for introducing substituents in linkage E is that of A. Chesney et al. (Syn. Comm. 1990, 20 (20), 3167–3180) as shown in Scheme 4. Michael reaction of pyrrolidine or piperidine 1 with Michael acceptor 26 yields intermediate 27 which can undergo subsequent reactions in the same pot. For example, reduction yields alcohol 28 which can be elaborated to the amine 29 by standard procedures familiar to one skilled in the art. Some of these include mesylation or tosylation followed by displacement with $NaN_3$ followed by reduction to yield amine 29. Another route as depicted in Scheme 4 involves reaction with diphenylphosphoryl azide followed by reduction of the azide to yield amine 29.

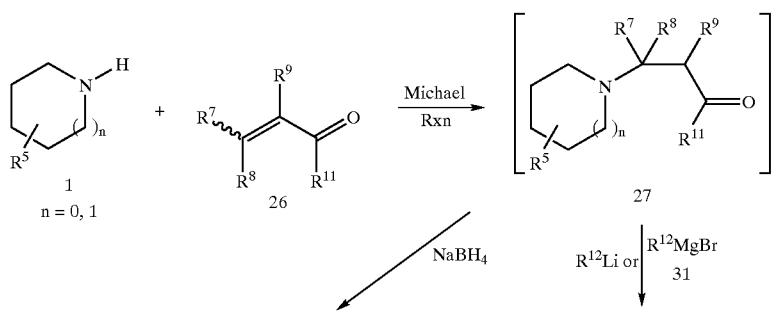

SCHEME 4

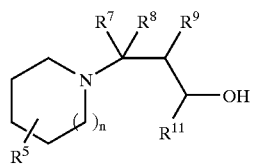

28

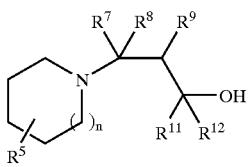

32

|(PhO)₂(P=O)N₃

|(PhO)₂(P=O)N₃

|H₂, Pd/C

|H₂, Pd/C

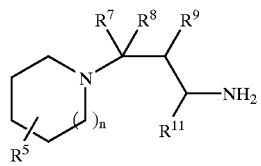

29

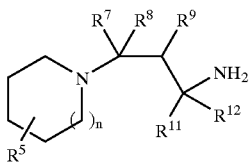

33

|as described previously

|as described previously

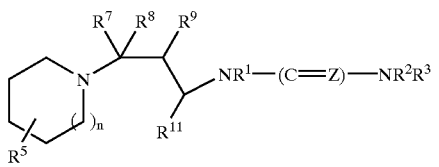

30

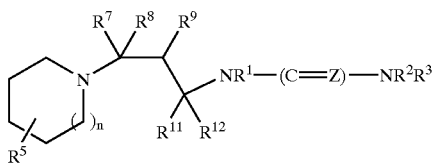

34

The mesylate or tosylate can also be displaced by other nucleophiles such as $NH_3$, $BOC_2N^-$, potassium phthalimide, etc., with subsequent deprotection where necessary to yield amines 29. Finally, 29 can be converted to urea or thiourea 30 by procedures discussed for Scheme 1 or to the compounds of this invention by procedures previously discussed. Similarly, aldehyde 27 may be reacted with a lithium or a Grignard reagent 31 to yield alcohol adduct 32. This in turn can be converted to urea or thiourea 34 in the same way as discussed for the conversion of 28 to 30.

Scheme 5 shows that intermediate 36 can be extended via a Wittig reaction (A. Chesney, et al. Syn. Comm. 1990, 20 (20), 3167–3180) to yield 37. This adduct can be reduced catalytically to yield 38 or by other procedures familiar to one skilled in the art. Alkylation yields 39, followed by saponification and Curtius rearrangement (T. L. Capson and C. D. Poulter, Tet. Lett., (1984) 25, 3515–3518) followed by reduction of the benzyl protecting group yields amine 40 which can be elaborated further as was described earlier in Scheme 1 and elsewhere in this application to make the compounds of this invention. Dialkyllithium cuprate, organocopper, or copper-catalyzed Grignard addition (for a review, see G. H. Posner, "An Introduction to Synthesis Using Organocopper Reagents", J. Wiley, New York, 1980; Organic Reactions, 19, 1 (1972)) to alpha,beta-unsaturated ester 37 yields 41 which can undergo subsequent transformations just discussed to yield amine 43 which can be elaborated further to the compounds of this invention as was described earlier. The intermediate enolate ion obtained upon cuprate addition to 37 can also be trapped by an electrophile to yield 42 (for a review, see R. J. K. Taylor, Synthesis 1985, 364). Likewise, another 2-carbon homologation is reported by A. Chesney et al. (ibid.) on intermediate 36 which involves reacting 36 with an enolate anion to yield aldol condensation product 42 where $R^{12}$=OH. The OH group can undergo synthetic transformations which are familiar to one skilled in the art and which will be discussed in much detail later on in the application. Chiral auxilliaries can also be used to introduce stereo- and enantioselectivity in these aldol condensations, procedures which are familiar to one skilled in the art.

SCHEME 5
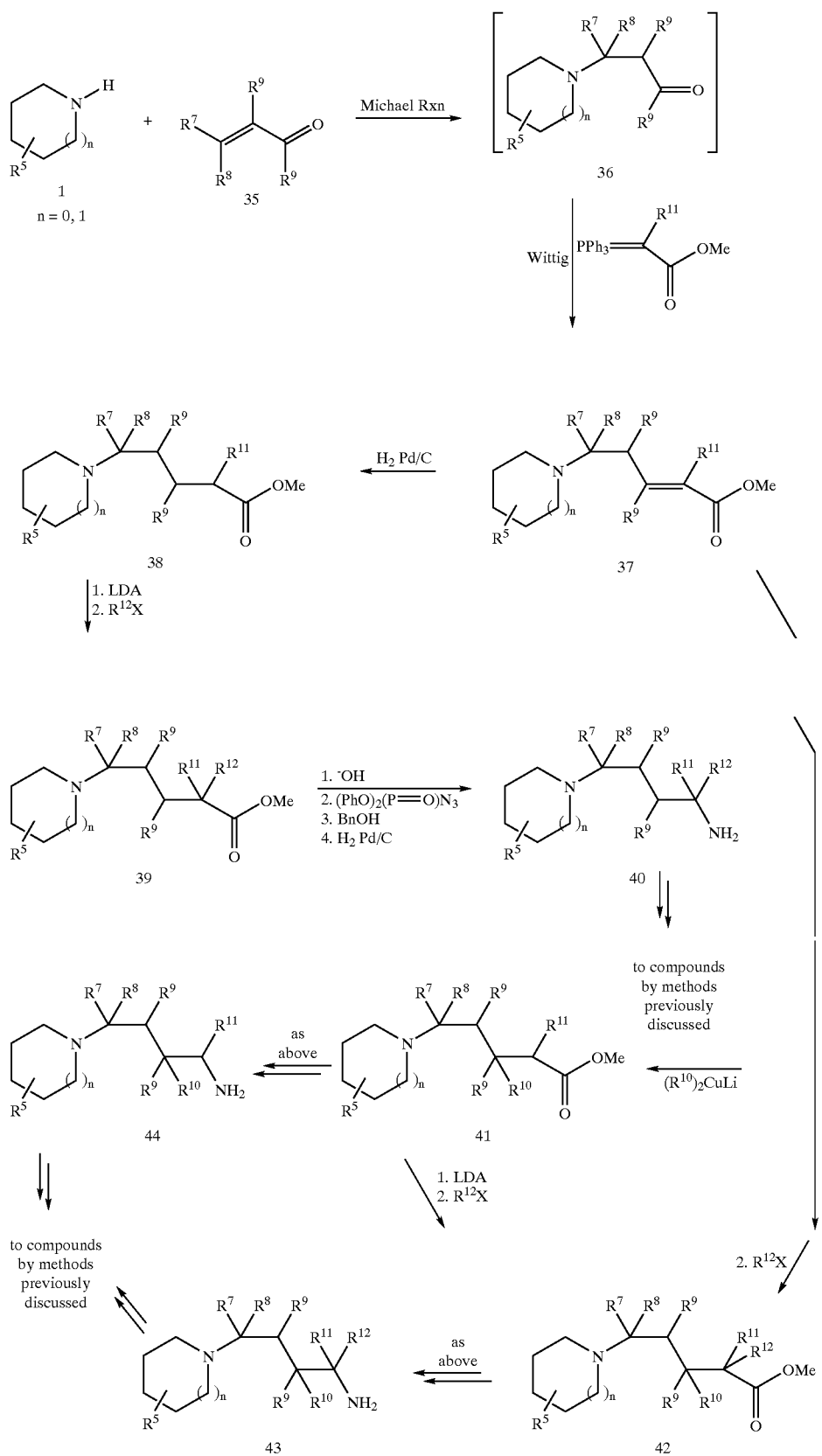

Examples of such methods are taught in D. A. Evans, et al., J. Am. Chem. Soc. 1981, 103, 2127; D. A. Evans, J. Am. Chem. Soc. 1982, 104, 1737; D. A. Evans, J. Am. Chem. Soc. 1986, 108, 2476; D. A. Evans. et al., J. Am. Chem. Soc. 1986, 108, 6757; D. A. Evans, J. Am. Chem. Soc. 1986, 108, 6395; D. A. Evans, J. Am. Chem. Soc. 1985, 107, 4346; A. G. Myers, et al., J. Am. Chem. Soc. 1997, 119, 6496. One can also perform an enantioselective alkylation on esters 38 or 41 with $R^{12}X$ where X is a leaving group as described in Scheme 1, provided the ester is first attached to a chiral auxiliary (see above references of Evans, Myers and Mauricio de L. Vanderlei, J. et al., Synth. Commun. 1998, 28, 3047).

One can also react alpha,beta-unsaturated ester 37 (Scheme 6) with Corey's dimethyloxosulfonium methylide (E. J. Corey and M. Chaykovsky, J. Am. Chem. Soc. 1965, 87, 1345) to form a cyclopropane which can undergo eventual Curtius rearrangement and subsequent elaboration to the compounds of this invention wherein the carbon containing $R^9R^{10}$ is tied up in a cyclopropane ring with the carbon containing $R^{11}R^{12}$. In addition, compound 48 can also undergo the analogous reactions just described to form cyclopropylamine 50 which can be further elaborated into the compounds of this invention as described previously. Compound 48 may be synthesized by an alkylation reaction of pyrrolidine/piperidine 1 with bromide 47 in an inert solvent employing the conditions as described for the alkylation of 2 onto 1 in Scheme 1.

Another way to synthesize the compounds in the scope of this application is shown in Scheme 7. Michael reaction of amine 1 with an acrylonitrile 51 (as described by I. Roufos in J. Med. Chem. 1996, 39, 1514–1520) followed by Raney-Nickel hydrogenation yields amine 53 which can be elaborated to the compounds of this invention as previously described.

SCHEME 6

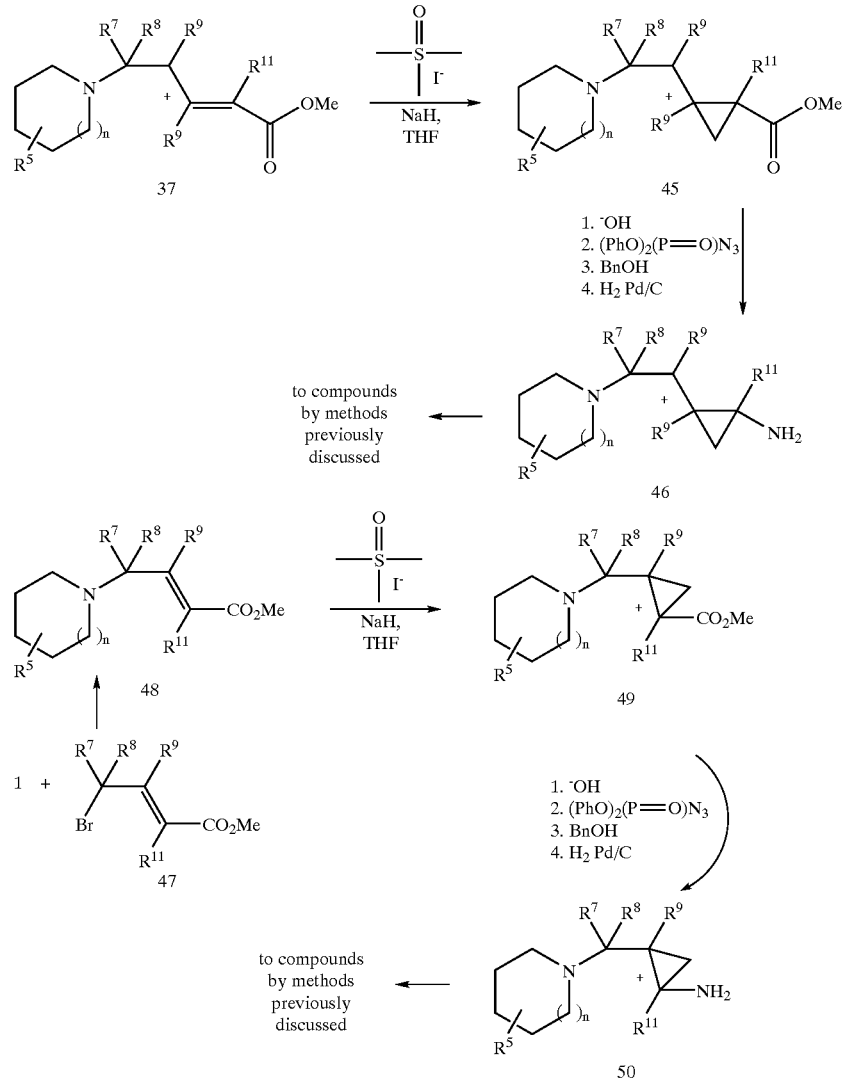

In Schemes 4, 5, and 6, we see that there is no gem-substitution on the alpha-carbon to the electron-withdrawing group of what used to be the Michael acceptor. In other words, in Scheme 4, there is no $R^{10}$ gem to $R^9$; in Scheme 5, there is no $R^{10}$ gem to one of the $R^9$s and in Scheme 7 there is no $R^{10}$ gem to $R^9$. Gem-substitution can be introduced by reacting pyrrolidine or piperidine 1 with the epoxide of Michael acceptors 26, 35, and 51 to yield the corresponding alcohols (for amines reacting with epoxides of Michael acceptors, see Charvillon, F. B.; Amouroux, R.; Tet. Lett. 1996, 37, 5103–5106; Chong, J. M.; Sharpless, K. B.; J Org Chem 1985, 50, 1560). These alcohols eventually can be further elaborated into $R^{10}$ by one skilled in the art, as, for example, by tosylation of the alcohol and cuprate displacement (Hanessian, S.; Thavonekham, B.; DeHoff, B.; J Org. Chem. 1989, 54, 5831), etc., and by other displacement reactions which will be discussed in great detail later on in this application.

SCHEME 7

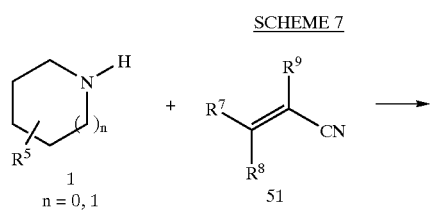

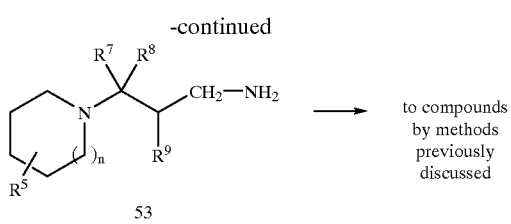

Further use of epoxides to synthesize compounds of this invention are shown in Scheme 8. Reaction of pyrrole or piperidine 1 with epoxide 54 yields protected amino-alcohol 55. This reaction works exceptionaly well when $R^7$ and $R^8$ are H but is not limited thereto. The reaction is performed in an inert solvent at room temperature to the reflux temperature of the solvent. Protecting groups on the nitrogen atom of 54 include BOC and CBZ but are not limited thereto. The hydroxyl group can be optionally protected by a variety of protecting groups familiar to one skilled in the art.

SCHEME 8

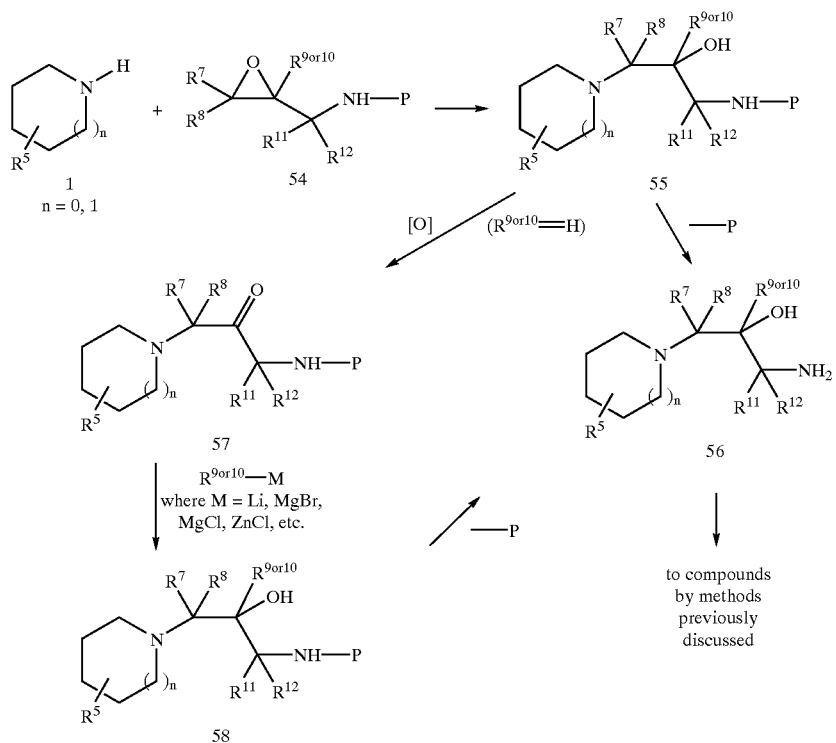

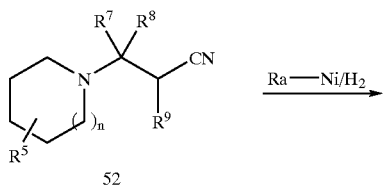

Deprotection of the nitrogen by methods familiar to one skilled in the art yields 56 which can be elaborated to the compounds of this invention by the procedures previously discussed. If $R^9$=H, then oxidation, for example, by using PCC (Corey E. J. and Suggs, J. W., Tet. Lett. 1975, 31, 2647–2650) or with the Dess-Martin periodinane (Dess, D. B. and Martin, J. C., J. Org. Chem. 1983, 48, 4155–4156) yields ketone 57 which may undergo nucleophilic 1,2-addition with organometallic reagents such as alkyl- or aryllithiums, Grignards, or zinc reagents, with or without $CeCl_3$ (T. Imamoto, et al., Tet. Lett. 1985, 26, 4763–4766; T.

Imamoto, et al., Tet. Lett. 1984, 25, 4233–4236) in aprotic solvents such as ether, dioxane, or THF to yield alcohol 58. The hydroxyl group can be optionally protected by a variety of protecting groups familiar to one skilled in the art. Deprotection of the nitrogen yields 56 which can be finally elaborated to the compounds of this invention as previously discussed. Epoxides disclosed by structure 54 may be synthesized enantio-selectively from amino acid starting materials by the methods of Dellaria, et al. J Med Chem 1987, 30 (11), 2137, and Luly, et al. J Org Chem 1987, 52 (8), 1487.

The carbonyl group of ketone 57 in Scheme 8 may undergo Wittig reactions followed by reduction of the double bond to yield alkyl, arylalkyl, heterocyclic-alkyl, cycloalkyl, cycloalkylalkyl, etc. substitution at that position, reactions that are familiar to one skilled in the art. Wittig reagents can also contain functional groups which after reduction of the double bond yield the following functionality: esters (Buddrus, J. Angew Chem., 1968, 80), nitriles (Cativiela, C. et al., Tetrahedron 1996, 52 (16), 5881–5888.), ketone (Stork, G. et al., J Am Chem Soc 1996, 118 (43), 10660–10661), aldehyde and methoxymethyl (Bertram, G. et al., Tetrahedron Lett 1996, 37 (44), 7955–7958.), gamma-butyrolactone Vidari, G. et al., Tetrahedron: Asymmetry 1996, 7 (10), 3009–3020.), carboxylic acids (Svoboda, J. et al., Collect Czech Chem Commun 1996, 61 (10), 1509–1519), ethers (Hamada, Y. et al., Tetrahedron Lett 1984, 25 (47), 5413), alcohols (after hydrogenation and deprotection—Schonauer, K.; Zbiral, E.; Tetrahedron Lett 1983, 24 (6), 573), amines (Marxer, A.; Leutert, T. Helv Chim Acta, 1978, 61) etc., all of which may further undergo transformations familiar to one skilled in the art to form a wide variety of functionality at this position.

Scheme 9 summarizes the displacement chemistry and subsequent elaborations that can be used to synthesize the $R^9$ groups. In Scheme 9 we see that alcohol 55 or 58 may be tosylated, mesylated, triflated, or converted to a halogen by methods familiar to one skilled in the art to produce compound 59. (Note that all of the following reactions in this paragraph can be also performed on the compounds, henceforth called carbon homologs of 55 or 58 where OH can be $(CH_2)_rOH$ and it is also understood that these carbon homologs may have substituents on the methylene groups as well). For example, a hydroxy group may be converted to a bromide by $CBr_4$ and $Ph_3P$ (Takano, S. Heterocycles 1991, 32, 1587). For other methods of converting an alcohol to a bromide or to a chloride or to an iodide see R. C. Larock, Comprehensive Organic Transformations, VCH Publishers, New York, 1989, pp. 354–360. Compound 59 in turn may be displaced by a wide variety of nucleophiles as shown in Scheme 9 including but not limited to azide, cyano, malonate, cuprates, potassium thioacetate, thiols, amines, etc., all nucleophilic displacement reactions being familiar to one skilled in the art. Displacement by nitrile yields a one-carbon homologation product. Nitrile 60 can be reduced with DIBAL to yield aldehyde 61. This aldehyde can undergo reduction to alcohol 62 with, for example, $NaBH_4$ which in turn can undergo all of the $S_N2$ displacement reactions mentioned for alcohol 55 or 58. Alcohol 62 is a one carbon homolog of alcohol 55 or 58. Thus one can envision taking alcohol 62, converting it to a leaving group X as discussed above for compound 55 or 58, and reacting it with NaCN or KCN to form a nitrile, subsequent DIBAL reduction to the aldehyde and subsequent $NaBH_4$ reduction to the alcohol resulting in a two carbon homologation product. This alcohol can undergo activation followed by the same $S_N2$ displacement reactions discussed previously, ad infinitum, to result in 3, 4, 5 . . . etc. carbon homologation products. Aldehyde 61 can also be reacted with a lithium or Grignard reagent to form an alcohol 61a which can also undergo the above displacement reactions. Oxidation by methods familiar to one skilled in the art yields ketone 61b. Displacement by malonate yields malonic ester 63 which can be saponified and decarboxylated to yield carboxylic acid 64, a two carbon homologation product. Conversion to ester 65 (A. Hassner and V. Alexanian, Tet. Lett, 1978, 46, 4475–8) and reduction with LAH yields alcohol 68 which can undergo all of the displacement reactions discussed for alcohol 55 or 58. Alcohols may be converted to the corresponding fluoride 70 by DAST (diethylaminosulfur trifluoride) (Middleton, W. J.; Bingham, E. M.; Org. Synth. 1988, VI, pg. 835). Sulfides 71 can be converted to the corresponding sulfoxides 72 (p=1) by sodium metaperiodate oxidation (N. J. Leonard, C. R. Johnson J. Org. Chem. 1962, 27, 282–4) and to sulfones 72 (p=2) by Oxone® (A. Castro, T. A. Spencer J. Org. Chem. 1992, 57, 3496–9). Sulfones 72 can be converted to the corresponding sulfonamides 73 by the method of H. -C. Huang, E. et al., Tet. Lett. (1994) 35, 7201–7204 which involves first, treatment with base followed by reaction with a trialkylborane yielding a sulfinic acid salt which can be reacted with hydroxylamine-O-sulfonic acid to yield a sulfonamide. Another route to sulfonamides involves reaction of amines with a sulfonyl chloride (G. Hilgetag and A. Martini, Preparative Organic Chemistry, New York: John Wiley and Sons, 1972, p. 679). This sulfonyl chloride (not shown in Scheme 9) can be obtained from the corresponding sulfide (71 where $R^{9d}$=H in Scheme 9, the hydrolysis product after thioacetate displacement), disulfide, or isothiouronium salt by simply reacting with chlorine in water. The isothiouronium salt may be synthesized from the corresponding halide, mesylate or tosylate 59 via reaction with thiourea (for a discussion on the synthesis of sulfonyl chlorides see G. Hilgetag and A. Martini, ibid., p. 670). Carboxylic acid 64 can be converted to amides 66 by standard coupling procedures or via an acid chloride by Schotten-Baumann chemistry or to a Weinreb amide (66: $R^{9a}$=OMe, $R^{9a'}$=Me in Scheme 9) (S. Nahm and S. M. Weinreb, Tet. Lett., 1981, 22, 3815–3818) which can undergo reduction to an aldehyde 67 ($R^{9b}$=H in Scheme 9) with LAH (S. Nahm and S. M. Weinreb, ibid.) or reactions with Grignard reagents to form ketones 67 (S. Nahm and S. M. Weinreb, ibid.). The aldehyde 67 obtained from the Weinreb amide reduction can be reduced to the alcohol with $NaBH_4$. The aldehyde or ketone 67 (or 61 or 61b for that matter) can undergo Wittig reactions as discussed previously followed by optional catalytic hydrogenation of the olefin. This Wittig sequence is one method for synthesizing the carbocyclic and heterocyclic substituted systems at $R^9$ employing the appropriate carbocyclic or heterocyclic Wittig (or Horner-Emmons) reagents. Of course, the Wittig reaction may also be used to synthesize alkenes at $R^9$ and other functionality as well. Ester 65 can also form amides 66 by the method of Weinreb (A. Basha, M. Lipton, and S. M. Weinreb, Tet. Lett. 1977, 48, 4171–74) (J. I. Levin, E. Turos, S. M. Weinreb, Syn. Comm. 1982, 12, 989–993). Alcohol 68 can be converted to ether 69 by procedures familiar to one skilled in the art, for example, NaH, followed by an alkyliodide or by Mitsunobu chemistry (Mitsunobu, O. Synthesis, 1981, 1–28). Alcohol 55 or 58, 62, or 68, can be acylated by procedures familiar to one skilled in the art, for example, by Schotten-Baumann conditions with an acid chloride or by an anhydride with a base such as pyridine to yield 78. Halide, mesylate, tosylate or triflate 59 can undergo displacement with azide followed by reduction to yield amine 74 a procedure familiar to one skilled in the art. This amine can undergo optional reductive amination and acylation to yield 75 or reaction with ethyl formate (usually refluxing ethyl formate) to yield formamide 75. Amine 74 can again undergo optional reductive amination followed by reaction with a sulfonyl chloride to yield 76, for example under Schotten-Baumann conditions as discussed previously. This same sequence may be employed for amine 60a, the reduction product of nitrile 60. Tosylate 59 can undergo displacement with cuprates to yield 77 (Hanessian, S.; Thavonekham, B.; DeHoff, B.; J Org. Chem. 1989, 54, 5831). Aldehyde 61 or its homologous extensions can be reacted with a carbon anion of an aryl (phenyl, naphthalene, etc.) or heterocyclic group to yield an aryl alcohol or a heterocyclic alcohol. If necessary, $CeCl_3$ may be added (T. Imamoto, et al., Tet. Lett. 1985, 26, 4763–4766; T. Imamoto, et al., Tet. Lett. 1984, 25, 4233–4236). This alcohol may be reduced with $Et_3SiH$ and TFA (J. Org. Chem. 1969, 34, 4; J. Org. Chem. 1987, 52, 2226) (see discussion of aryl and heterocyclic anions for Schemes 20–22). These aryl and heterocyclic anions may also be alkylated by 59 (or its carbon homolog) to yield compounds where $R^9$ contains an aryl or heterocyclic group. Compound 59 or its carbon homologs may be alkylated by an alkyne anion to produce alkynes at $R^9$ (see R. C. Larock, Comprehensive Organic Transformations, New York, 1989, VCH Publishers, p 297). In addition, carboxaldehyde 61 or its carbon homologs can undergo 1,2-addition by an alkyne anion (Johnson, A. W. The Chemistry of Acetylenic Compounds. V. 1. "Acetylenic Alcohols," Edward Arnold and Co., London (1946)). Nitro groups can be introduced by displacing bromide 59 (or its carbon homologs) with sodium nitrite in DMF (J. K. Stille and E. D. Vessel J. Org. Chem. 1960, 25, 478–490) or by the action of silver nitrite on iodide 59 or its carbon homologs (Org. Syntheses 34, 37–39).

SCHEME 9

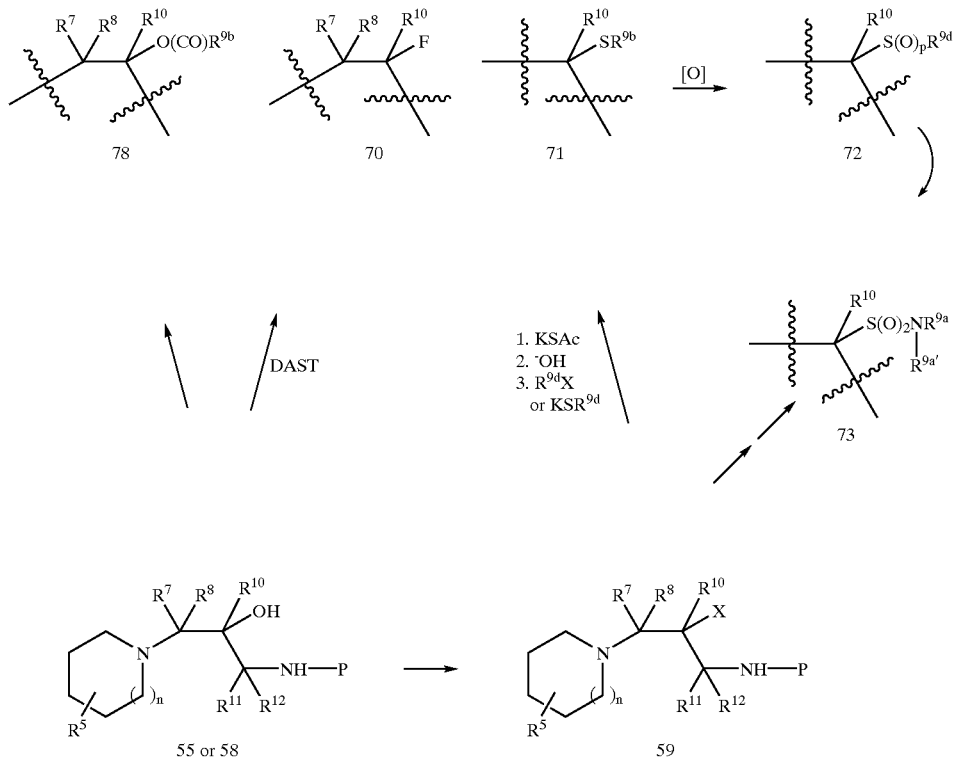

If an anion is made of the pyrrolidine/piperidine 1 with LDA or n-BuLi, etc., then that anion in a suitable nonhydroxylic solvent such as THF, ether, dioxane, etc., can react in a Michael-type fashion (1,4-addition) with an alpha,beta-unsaturated ester to yield an intermediate enolate which can be quenched with an electrophile ($R^9X$) (where X is as described in Scheme 1) (Uyehara, T.; Asao, N.; Yamamoto, Y.; J Chem Soc, Chem Commun 1987, 1410) as shown in Scheme 10.

SCHEME 9 (con't)

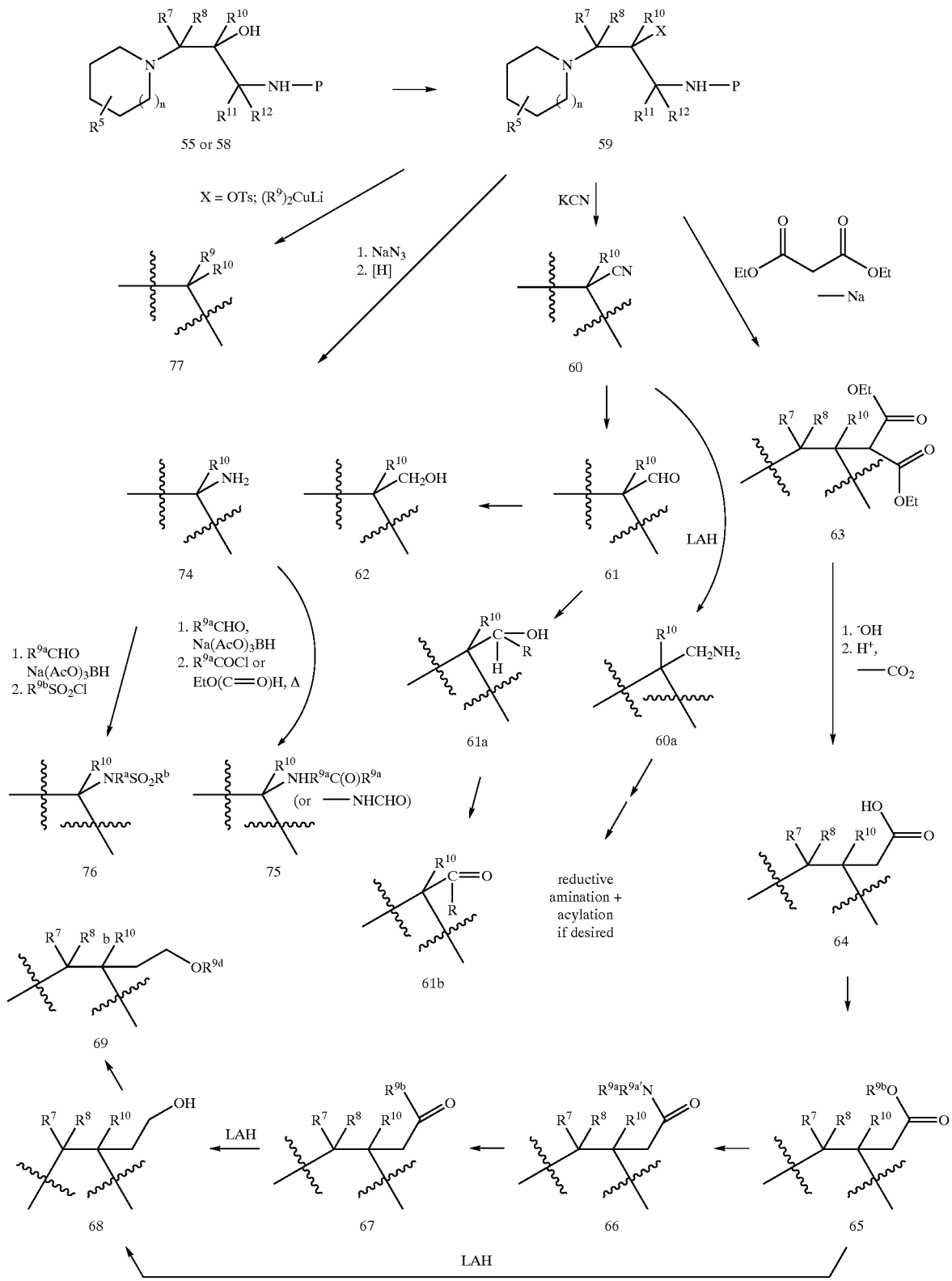

It is to be understood that $R^9$ is either in its final form or in a suitable protected precursor form. This electrophile can be a carbon-based electrophile, some examples being formaldehyde to introduce a $CH_2OH$ group, an aldehyde or a ketone which also introduces a one-carbon homologated alcohol, ethylene oxide (or other epoxides) which introduces a —CH₂CH₂OH group (a two-carbon homologated alcohol), an alkyl halide, etc., all of which can be later elaborated into $R^9$. It can also be an oxygen-based electrophile such as MCPBA, Davis' reagent (Davis, F. A.; Haque, M. S.; J Org Chem 1986, 51 (21),4083; Davis, F. A.; Vishwaskarma, L. C.; Billmers, J. M.; Finn, J.; J Org Chem 1984, 49, 3241) or $MoO_5$ (Martin, T. et al., J Org Chem 1996, 61 (18), 6450–6453) which introduces an OH group. These OH groups can undergo the displacement reactions discussed previously in Scheme 9 or protected by suitable protecting groups and deprotected at a later stage when the displacement reactions decribed in Scheme 9 can be performed. In addition, these OH groups can also undergo displacement reactions with heterocycles as described for Schemes 19–22 to introduce N- or C-substituted heterocycles at this position. Ester 80 can be converted into its Weinreb amide 82 (S. Nahm and S. M. Weinreb, Tet. Lett., 1981, 22, 3815–3818) or Weinreb amide 82 can be synthesized via Michael-type addition of 1 to alpha,beta-unsaturated Weinreb amide 83. Subsequent reaction with a Grignard reagent forms ketone 85. This ketone can also be synthesized in one step directly from 1 and alpha,beta-unsaturated ketone 84 using the same procedure. This ketone may be reduced with LAH, $NaBH_4$ or other reducing agents to form alcohol 86. Or else, ketone 85 can be reacted with an organolithium or Grignard reagents to form tertiary alcohol 87. Or else, ester 80 can be directly reduced with $LiBH_4$ or LAH to yield primary alcohol 88.

SCHEME 10

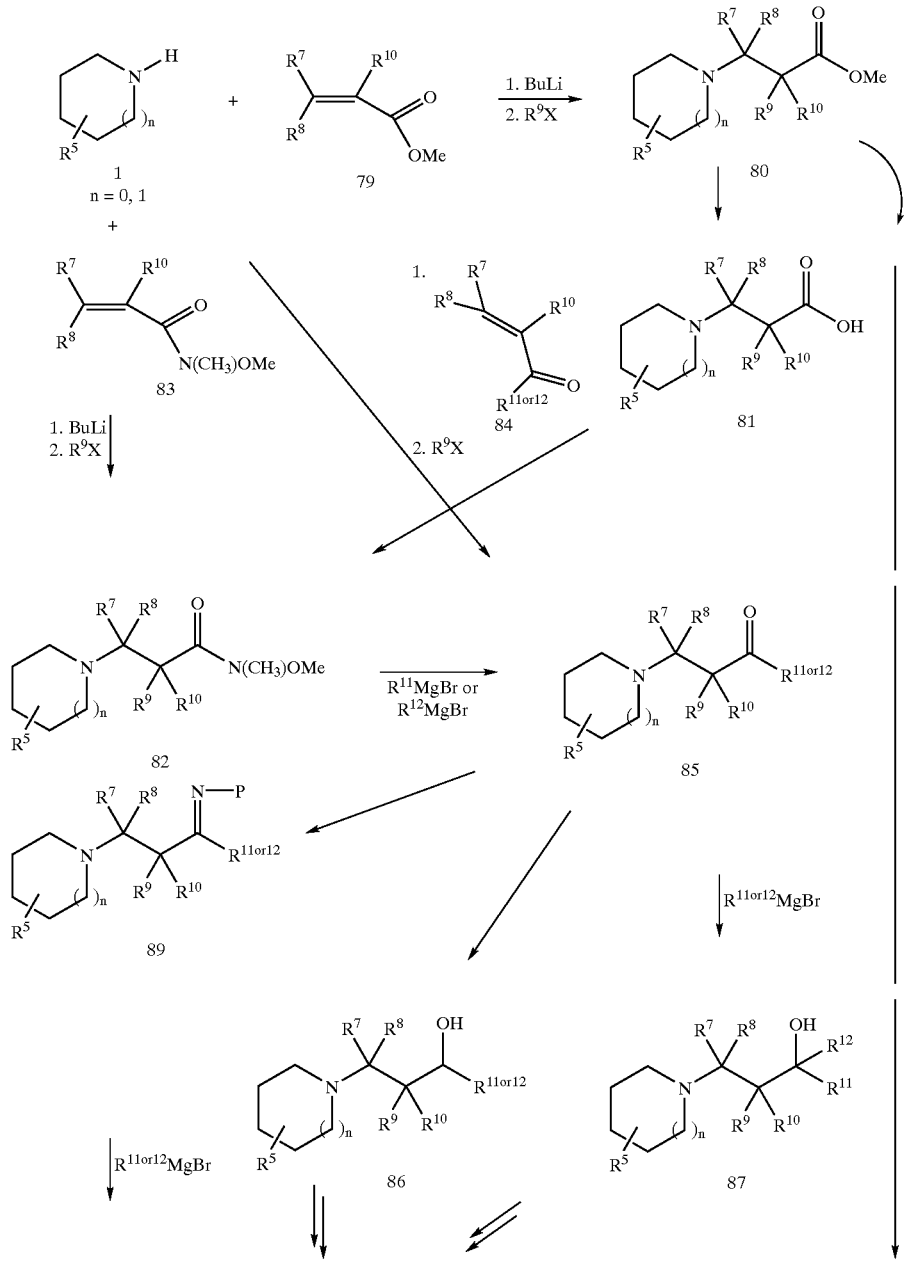

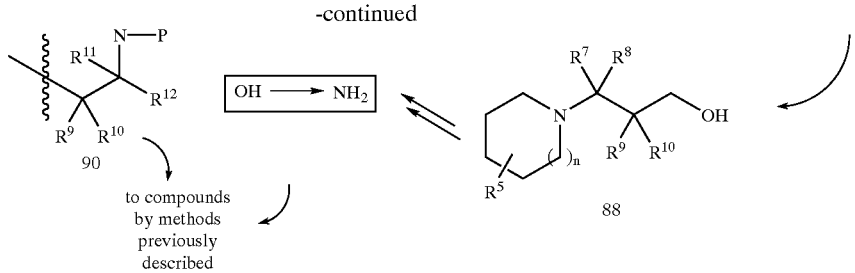

Alcohols 86, 87, and 88 can all be tosylated, mesylated, triflated, or converted to a halogen by methods discussed previously and displaced with an amine nucleophile such as azide, diphenylphosphoryl azide (with or without DEAD and $Ph_3P$), phthalimide, etc. as discussed previously (and which are familiar to one skilled in the art) and after reduction (azide) or deprotection with hydrazine (phthalimide), for example, yield the corresponding amines. These can then be elaborated into the compounds of this invention as discussed previously. Ketone 85 can also be converted into imine 89 which can be reacted with a Grignard reagent or lithium reagent, etc., to form a protected amine 90 which can be deprotected and elaborated into the compounds of this invention as discussed previously. Some protecting groups include benzyl and substituted benzyl which can be removed by hydrogenation, and cyanoethyl, which can be removed with aqueous base, etc. It is to be understood that $R^{7-12}$ in Scheme 10 can be in their final form or in precursor form which can be elaborated into final form by procedures familiar to one skilled in the art.

Magnesium amides of amines have been used to add in a Michael-type manner to alpha,beta-unsaturated esters where the substituents at the beta position of the unsaturated ester are-tied together to form a cyclopentane ring (for example, compound 79 where $R^7$ and $R^8$ are taken together to be —$(CH_2)_4$—) (Kobayashi, K. et al., Bull Chem Soc Jpn, 1997, 70 (7), 1697–1699). Thus reaction of pyrrolidine or piperidine 1 with cycloalkylidine esters 79 as in Scheme 10 yields esters 80 where $R^7$ and $R^8$ are taken together to form a cycloalkyl ring. Subsequent elaboration yields compounds of this invention where $R^7$ and $R^8$ are taken together to form a cycloalkyl ring.

Compounds of structure 95a may also be synthesized from epoxyalcohols which are shown in Scheme 11. Allylic alcohol 91 can be epoxidized either stereoselectively using $VO(acac)_2$ catalyst (for a review, see Evans: Chem. Rev. 1993, 93, 1307) or enantioselectively (Sharpless: J. Am. Chem. Soc. 1987, 109, 5765) to epoxyalcohol 92. $S_N2$ displacement of the alcohol using zinc azide and triphenylphosphine (Yoshida, A. J. Org. Chem. 57, 1992, 1321–1322) or diphenylphosphoryl azide, DEAD, and triphenylphosphine (Saito, A. et al., Tet. Lett. 1997, 38 (22), 3955–3958) yields azidoalcohol 93. Hydrogenation over a Pd catalyst yields aminoalcohol 94. This can be protected in situ or in a subsequent step with $BOC_2O$ to put on a BOC protecting group, or with CBZ-Cl and base to put on a CBZ-group or other protecting groups. Alternatively, the amino group can be reacted with an isocyanate, an isothiocyanate, a carbamoyl chloride, or any reagent depicted in Scheme 1 to form 95 which can be alkylated with 1 to form the compounds of this invention.

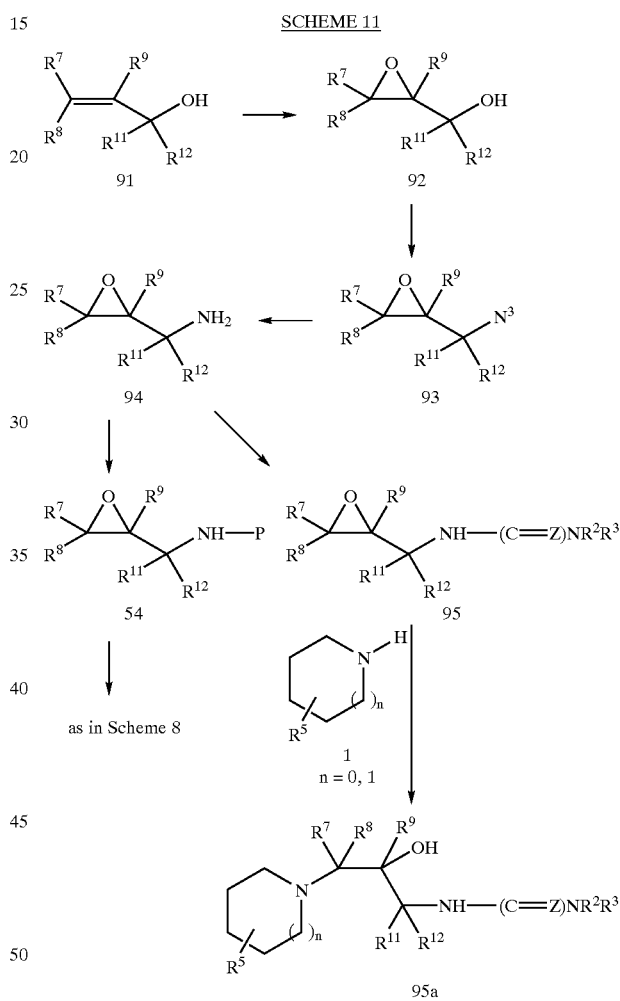

SCHEME 11

Sometimes amine 1 might have to be activated with Lewis acids in order to open the epoxide ring (Fujiwara, M.; Imada, M.; Baba, A.; Matsuda, H.;Tetrahedron Lett 1989, 30, 739; Caron, M.; Sharpless, K. B.; J Org Chem 1985, 50, 1557) or 1 has to be deprotonated and used as a metal amide, for example the lithium amide (Gorzynski-Smith, J.; Synthesis 1984 (8), 629) or MgBr amide (Carre, M. C.; Houmounou, J. P.; Caubere, P.; Tetrahedron Lett 1985, 26, 3107) or aluminum amide (Overman, L. E.; Flippin, L. A.; Tetrahedron Lett 1981, 22, 195).

The quaternary salts (where $R^4$ is present as a substituent) of pyrrolidines and piperidines can be synthesized by simply reacting the amine with an alkylating agent, such as methyl iodide, methyl bromide, ethyl iodide, ethyl bromide, ethyl or methyl bromoacetate, bromoacetonitrile, allyl iodide, allylbromide, benzyl bromide, etc. in a suitable solvent such as THF, DMF, DMSO, etc. at room temperature to the reflux temperature of the solvent. Spiroquaternary salts can be synthesized in a similar manner, the only difference being that the alkylating agent is located intramolecularly as shown in Scheme 12. It is understood by one skilled in the art that functional groups might not be in their final form to permit cyclization to the quaternary ammonium salt and might have to be in precursor form or in protected form to be elaborated to their final form at a later stage. For example, the $NR^1(C=Z)NR^2R^3$ group on the rightmost phenyl ring of compound 104 might exist as a nitro group precursor for ease of manipulation during quaternary salt formation. Subsequent reduction and $NR^1(C=Z)NR^2R^3$ group formation yields product 105. The leaving groups represented by X in Scheme 12 may equal those represented in Scheme 1, but are not limited thereto. N-oxides of pyrrolidines and piperidines can be made by the procedure of L. W. Deady (Syn. Comm. 1977, 7, 509–514). This simply entails reacting the pyrrolidine or piperidine with MCPBA, for example, in an inert solvent such as methylene chloride.

SCHEME 12

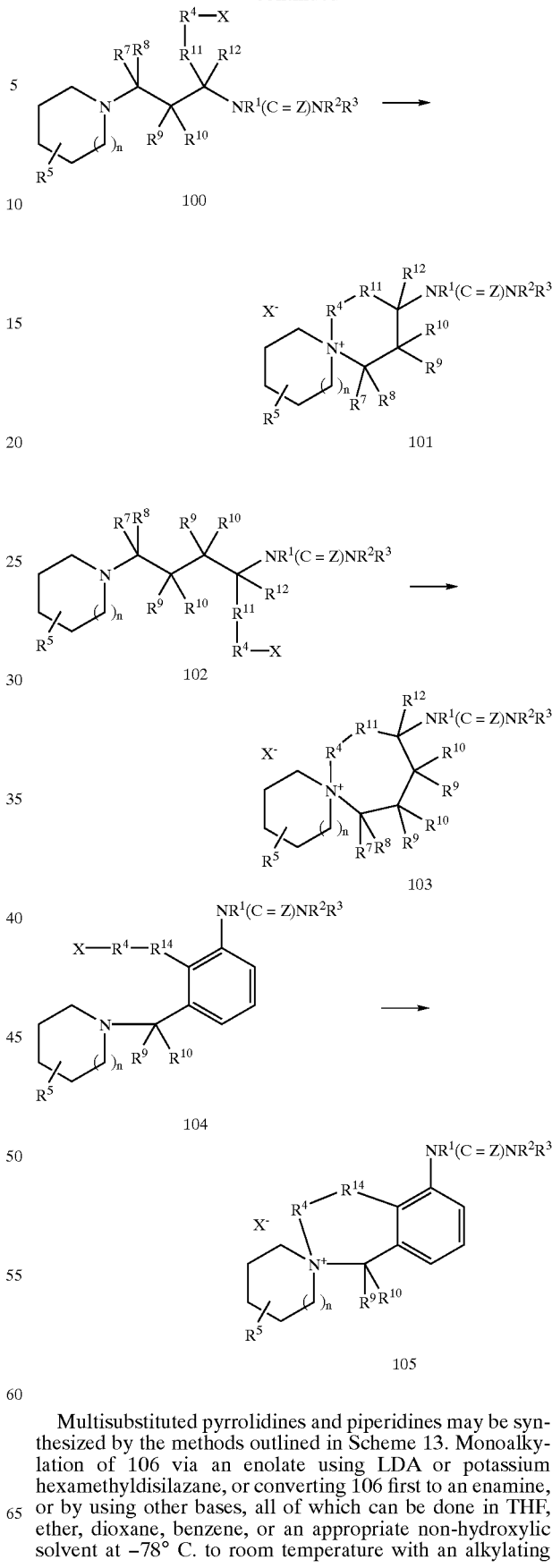

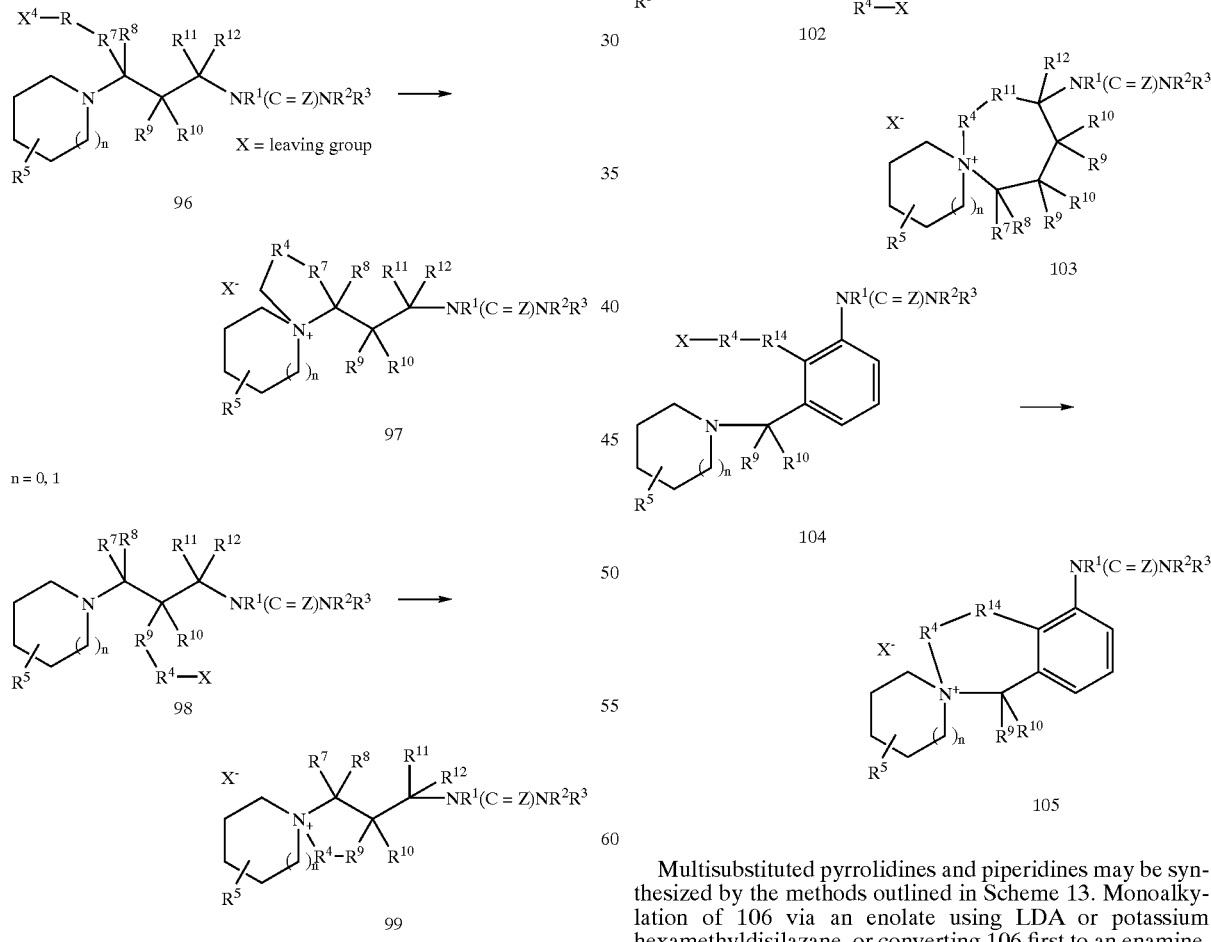

Multisubstituted pyrrolidines and piperidines may be synthesized by the methods outlined in Scheme 13. Monoalkylation of 106 via an enolate using LDA or potassium hexamethyldisilazane, or converting 106 first to an enamine, or by using other bases, all of which can be done in THF, ether, dioxane, benzene, or an appropriate non-hydroxylic solvent at −78° C. to room temperature with an alkylating agent such as methyl iodide, benzyl bromide, etc. where X is as defined in Scheme 1, yields product 107. This product can subsequently undergo alkylation again under thermodynamic or kinetic conditions and afterwards, if need be, can undergo two more alkylations to produce tri- and tetrasubstituted analogs of 107. The thermodynamic or kinetic conditions yield regioselectively alkylated products (for a discussion on thermodynamic vs. kinetic alkylations see H. House Modern Synthetic Reactions, W. A. Benjamin, Inc. (Menlo Park, Calif.: 1972) chapter 9).

SCHEME 13

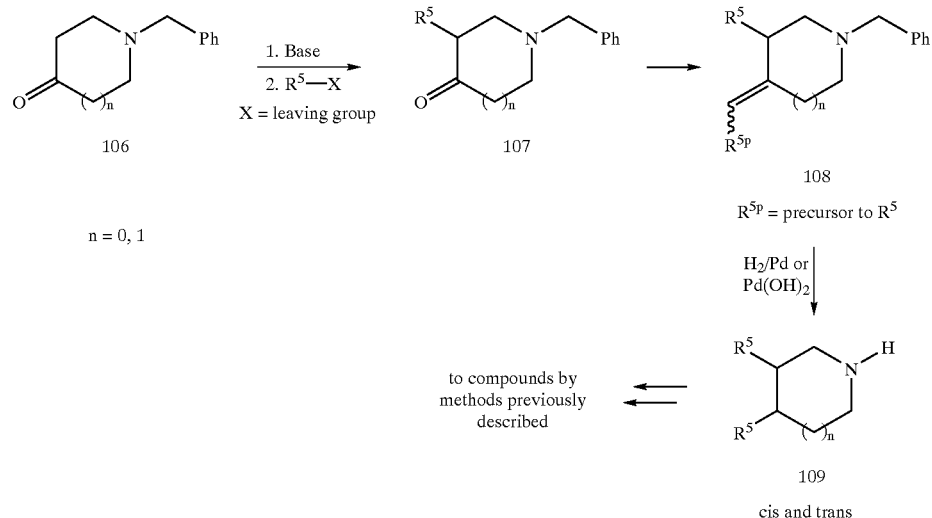

SCHEME 14

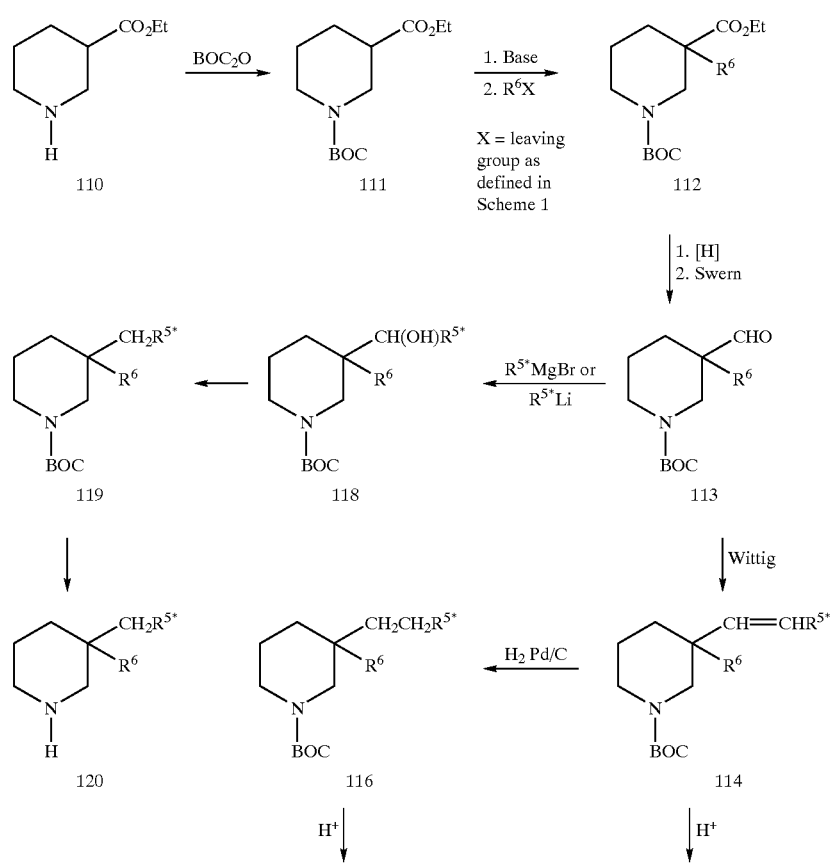

-continued

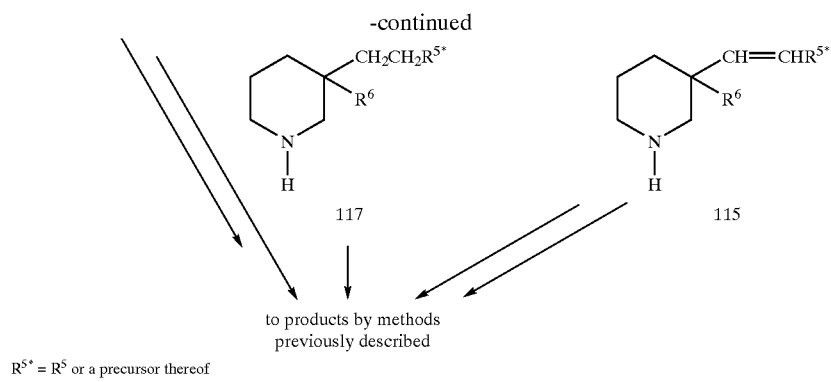

to products by methods
previously described

R⁵* = R⁵ or a precursor thereof

Subsequent Wittig olefination yields compound 108. Hydrogenation (asymmetric hydrogenation is an option here: Parshall, G. W. Homogeneous Catalysis, John Wiley and Sons, New York: 1980, pp. 43–45; Collman, J. P., Hegedus, L. S. Principles and Applications of Organotransition Metal Chemistry, University Science Books, Mill Valley, Calif., 1980, pp. 341–348) yields pyrrolidine or piperidine 109 which can be resolved into its relative and/or absolute isomers at this stage or later on in the synthesis either by crystallization, chromatographic techniques, or other methods familiar to one skilled in the art. The amine 109 an then be elaborated into the compounds of this invention by methods discussed previously (Scheme 1). The carbonyl-containing intermediate 107 in Scheme 13 can also be reduced to the methylene analog via a Wolff-Kishner reduction and modifications thereof, or by other methods familiar to one skilled in the art. The carbonyl group can also be reduced to an OH group, which can undergo all of the reactions described in Scheme 9 to synthesize the R6 groups. This piperidine or pyrrolidine can be deprotected and elaborated to the compounds of this invention by methods discussed earlier. Thus, mono-, di-, tri-, or tetraalkylated carbonyl-containing pyrrolidines or piperidines can be synthesized, which in turn can be reduced to the corresponding —CH2— analogs employing the Wolff-Kishner reduction or other methods.

Another method for synthesizing gem-substituted pyrrolidines and piperidines is shown in Scheme 14. It is understood by one skilled in the art that some of the steps in this scheme can be rearranged. It is also understood that gem-disubstitution is only shown at only one position on the piperidine ring and that similar transformations may be performed on other carbon atoms as well, both for piperidine and pyrrolidine. Thus, 3-carboethoxypiperidine 110 may be BOC-protected and alkylated employing a base such as LDA, KHMDS, LHDMS, etc., in THF, ether, dioxane, etc. at −78° C. to room temperature, and an alkylating agent R⁶X where X is a halide (halide=Cl, Br, I), mesylate, tosylate or triflate, to yield 112. Reduction using DIBAL, for example, and if necessary followed by oxidation such as a Swern oxidation (S. L. Huang, K. Omura, D. Swern J. Org. Chem. 1976, 41, 3329–32) yields aldehyde 113. Wittig olefination (114) followed by deprotection yields 115 which may be elaborated as described previously into the compounds of this invention. Reduction of the Wittig adduct 114 yields 116 which may be deprotected to yield 117 which may be in turn elaborated as described previously into the compounds of this invention. Reaction of aldehyde 113 with an alkyl-lithium or Grignard reagent yields alcohol 118 which may be reduced catalytically or with Et₃SiH/TFA (J. Org. Chem. 1969, 34, 4; J. Org. Chem. 1987, 52, 2226) if R⁵* (R⁵*=R⁵ or a precursor thereof) is aromatic to yield 119. If R⁵* is not aromatic, then the OH may be reduced by the method of Barton (Barton, D. H. R.; Jaszberenyi, J. C. Tet. Lett. 1989, 30, 2619 and other references therein). Once tosylated, the alcohol can also be displaced with dialkyllithium cuprates (not shown) (Hanessian, S.; Thavonekham, B.; DeHoff, B.; J Org. Chem. 1989, 54, 5831). Deprotection if necessary yields 120 which may be elaborated as described previously into the compounds of this invention.

SCHEME 15

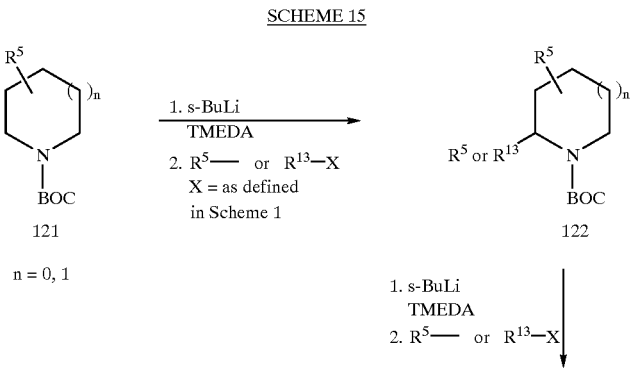

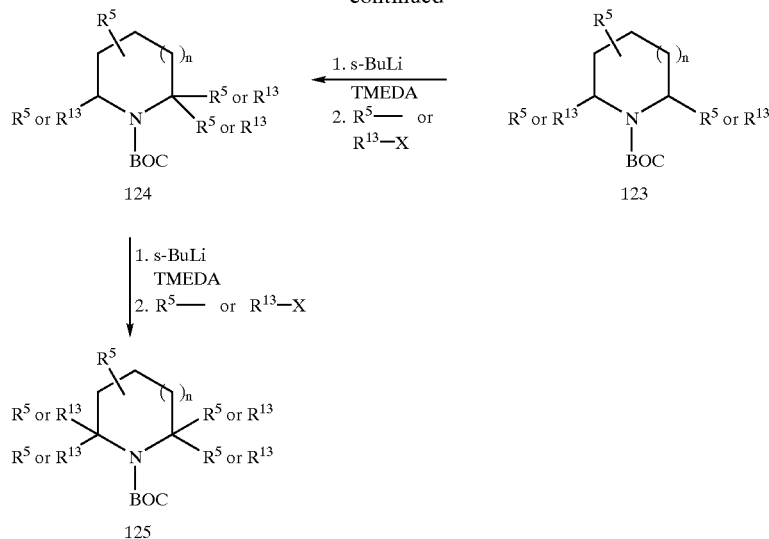

A method for the alkylation of alkyl groups, arylalkyl groups, allylic groups, propargylic groups, etc., and a variety of other electrophiles onto the pyrrolidinyl and/or piperidinyl alpha-carbons (alpha to the ring nitrogen atom) is represented by the work of Peter Beak, et al. as shown in Scheme 15. It is understood by one skilled in the art that the $R^5$ and $R^{13}$ groups are either in their precursor, protected, or final form. Only one $R^5$ group is shown to be substituted on piperidine/pyrrolidine 121. However it is understood by one skilled in the art that additional functionality may be present on the ring in either precursor, protected, or final form. Thus lithiation with an alkyllithium reagent such as n-BuLi or s-BuLi as shown, followed by quenching with an electrophilic species such as $R^5X$ or $R^{13}X$ where X is as defined in Scheme 1 and $R^5$ and $R^{13}$ are in their precursor, protected, or final form, yields monoalkylated piperidine/pyrrolidine 122. This alkylation may occur either stereoselectively (P. Beak and W. K. Lee J. Org. Chem. 1990, 55, 2578–2580) or enantioselectively if sparteine is included as a source of chirality (P. Beak, et al., J. Am. Chem. Soc. 1994, 116, 3231–3239). The alkylation process may be repeated up to three more times as shown in Scheme 15 to result in di-, tri-, and tetrasubstitution at the alpha-positions.

Compounds where $R^9$ and $R^{10}$ form a cyclic 3, 4, 5, 6, or 7-membered ring can be synthesized by the methods disclosed in Scheme 16. These same methods may also be used to synthesize gem-disubstituted compounds in which $R^9$ can be different from $R^{10}$ by step-wise alkylation of the malonate derivative. Of course, this scheme may be used to synthesize compounds where $R^{10}$=H also. For example, a cyclohexyl-fused malonate may be synthesized by Michael addition and alkylation of $I(CH2)_4CH$=$CCO_2Me$ with dimethyl malonate employing NaH/DMF (Desmaele, D.; Louvet, J. -M.; Tet Lett 1994, 35 (16), 2549–2552) or by a double Michael addition (Reddy, D. B., et al., Org. Prep. Proced. Int. 24 (1992) 1, 21–26) (Downes, A. M.; Gill, N. S.; Lions, F.; J Am Chem or by an alkylation followed by a second intromolecular alkylation employing an iodoaldehyde (Suami, T.; Tadano, K.; Kameda, Y.; Iimura, Y.; Chem Lett 1984, 1919), or by an alkylation followed by a second intramolecular alkylation employing an alkyl dihalide (Kohnz, H.; Dull, B.; Mullen, K.; Angew Chem 1989, 101 (10), 1375), etc.

SCHEME 16

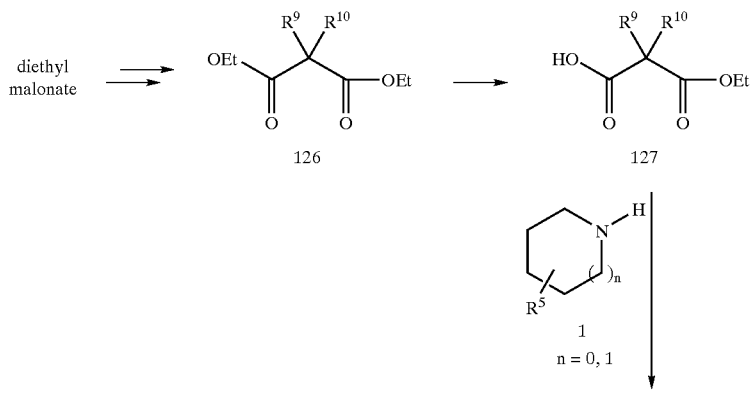

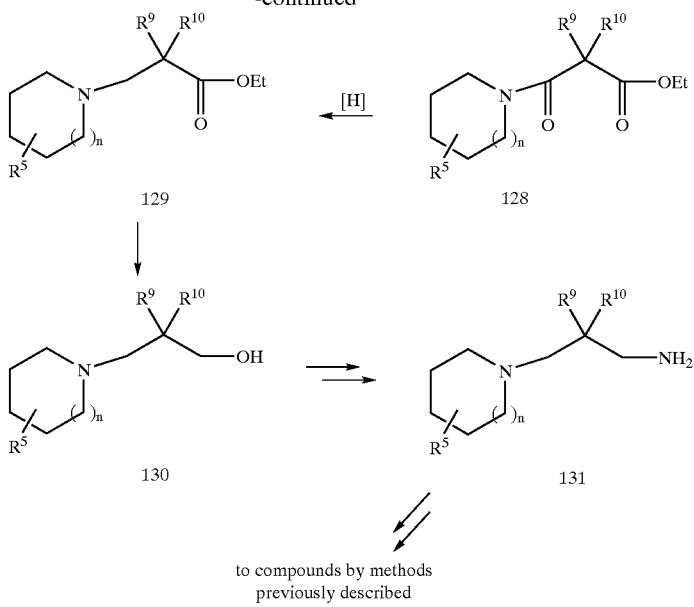

Subsequent monosaponification (Pallai, P. V., Richman, S., Struthers, R. S., Goodman, M. Int. J. Peptide Protein Res. 1983, 21, 84–92; M. Goodman Int. J. Peptide Protein Res. 19831, 17, 72–88), standard coupling with pyrrolidine/piperidine 1 yields 128. Reduction with borane yields 129 followed by reduction with LAH yields 130 which can be then converted to amine 131 and then to the compounds of this invention by procedures as discussed previously. Ester 129 can also be converted to a Weinreb amide and elaborated to the compounds of this invention as described in Scheme 10 for ester 80 which would introduce substituents $R^{11}$ and $R^{12}$.

Scheme 17 describes another method for the synthesis of compounds where $R^9$ and $R^{10}$ are taken together to form cycloalkyl groups. Aminoalcohols 132 are found in the literature (CAS Registry Nos. for n=0, 1, 2, 3, respectively: 45434-02-4, 2041-56-7, 2239-31-8, 2041-57-8). They can easily be protected, as with a BOC group (or CBZ, or any other compatible protecting group) by known procedures familiar to one skilled in the art to yield alcohols 133. The alcohols can then be activated either by conversion to a halide or to a mesylate, tosylate or triflate by methods familiar to one skilled in the art and as discussed previously, and then alkylated with pyrrolidine/piperidine 1 by the conditions described in Scheme 1 to yield 135. Subsequent deprotection yields amine 136 which can be elaborated to the compounds of this invention as described previously. Of course, alcohol 133 can be oxidized to the aldehyde and then reacted with $R^{7\ or\ 8}$MgBr or $R^{7\ or\ 8}$Li with or without $CeCl_3$ to yield the corresponding alcohol 133 where instead of —$CH_2OH$, we would have —$CHR^{7\ or\ 8}OH$. This oxidation-1,2-addition sequence may be repeated to yield a tertiary alcohol. The alcohol may then be tosylated, mesylated, triflated, or converted to Cl, Br, or I by procedures familiar to one skilled in the art to yield 134 and then displaced with pyrrolidine/piperidine 1 to yield 135. Subsequent deprotection yields 136 which may undergo elaboration to the compounds of this invention as discussed previously.

SCHEME 17

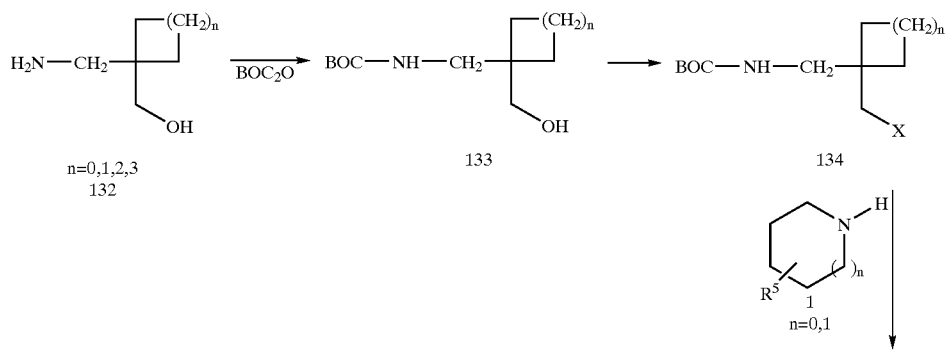

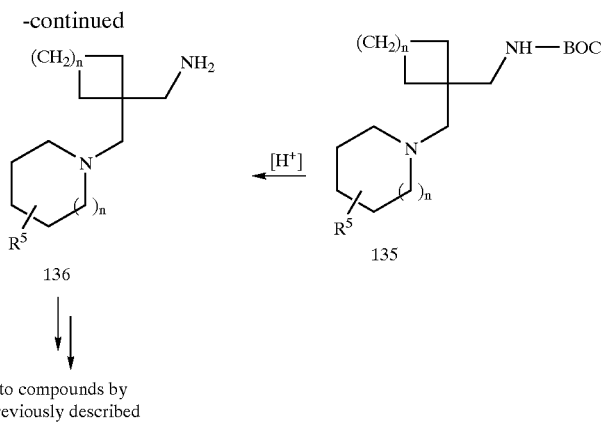

A method to introduce cycloalkyl groups at $R^{11}R^{12}$ is shown in Scheme 18. Protection of the nitrogen of compounds 137 which are commercially available yields 138 (the protecting group may be BOC, CBZ, or any other compatible protecting group) by procedures familiar to one skilled in the art. Esterification by any one of a number of procedures familiar to one skilled in the art (for example A. Hassner and V. Alexanian, Tet. Lett, 1978, 46, 4475–8) followed by reduction with DIBAL (or alternatively reduction to the alcohol with, for example, LiBH$_4$, followed by Swern oxidation (op. cit.)) yields aldehyde 139. One carbon homologation via the Wittig reaction followed by hydrolysis of the vinyl ether yields aldehyde 141. Reductive amination (Abdel-Magid, A. F., et al. Tet. Lett. 1990, 31, (39) 5595–5598) yields 142 followed by deprotection yields amine 143 which can be elaborated to the compounds of this invention by the methods previously discussed. Of course, aldehyde 139 can be reacted with $R^{9 \, or \, 10}$MgBr or $R^{9 \, or \, 10}$Li with or without CeCl$_3$ to yield an alcohol which can be oxidized to a ketone. Wittig one-carbon homologation on this ketone as described above followed by hydrolysis yields 141 where the —CH$_2$CHO is substituted with one $R^{9 \, or \, 10}$ group (—CHR$^{9 \, or \, 10}$CHO).

SCHEME 18

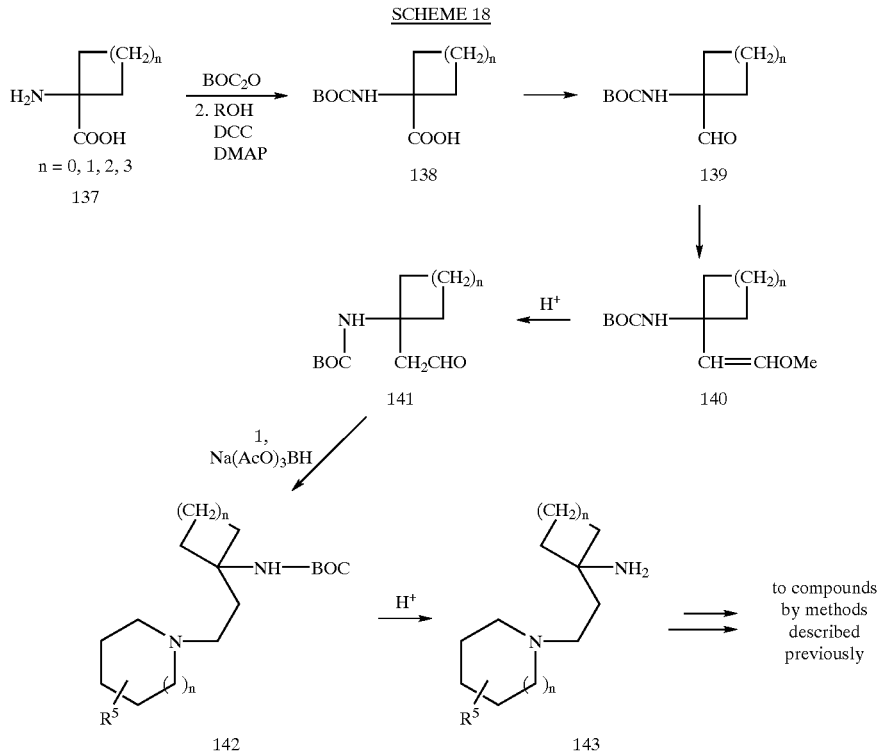

Aldehyde 141 (—CH$_2$CHO) or its monosubstituted analog synthesized above (—CHR$^{9 \, or \, 10}$CHO) can undergo alkylation with $R^{9 \, or \, 10}$X where X is as defined in Scheme 1 to yield compound 141 containing one or both of the $R^9$ and $R^{10}$ substituents alpha to the aldehyde group. Alkylation can be performed using LDA or lithium bistrimethylsilyl amide amongst other bases in an inert solvent such as ether, THF, etc., at −78° C. to room temperature. Aldehyde 141 (—CH$_2$CHO) or its substituted analogs synthesized above (i.e., —CHR$^9$R$^{10}$CHO) can undergo reductive amination with 1 and subsequent elaboration to the compounds of this invention. Aldehyde 141 (—CH$_2$CHO)or its substituted analogs synthesized above (i.e., —CHR$^9$R$^{10}$CHO) can also undergo 1,2-addition with R$^{7\ or\ 8}$MgBr or R$^{7\ or\ 8}$Li to yield the corresponding alcohol —CH$_2$CHR$^{7\ or\ 8}$OH or —CHR$^9$R$^{10}$CHR$^{7\ or\ 8}$OH. The alcohol may then be tosylated, mesylated, triflated, or converted to Cl, Br, or I by procedures familiar to one skilled in the art and displaced with pyrrolidine/piperidine 1 to yield, after subsequent deprotection and elaboration, the compounds of this invention. Or else alcohol —CH$_2$CHR$^{7\ or\ 8}$OH or —CR$^9$R$^{10}$CHR$^{7\ or\ 8}$OH can be oxidized (i.e., Swern, op. cit.) to the ketone and reductively aminated with 1 and subsequently elaborated to the compounds of this invention. Or else alcohol —CH$_2$CHR$^{7\ or\ 8}$OH or —CR$^9$R$^{10}$CHR$^{7\ or\ 8}$OH can be oxidized (i.e., Swern, op. cit.) to the ketone and reacted once more with R$^{7\ or\ 8}$MgBr or R$^{7\ or\ 8}$Li to yield the corresponding alcohol —CH$_2$CR$^7$R$^8$OH or —CR$^9$R$^{10}$CR$^7$R$^8$OH. If the ketone enolizes easily, CeCl$_3$ may be used together with the Grignard or lithium reagent. The alcohol can again be tosylated, mesylated, triflated, or converted to Cl, Br, or I by procedures familiar to one skilled in the art and displaced with pyrrolidine/piperidine 1 to yield, after subsequent deprotection and elaboration, the compounds of this invention. Thus each one of the R$^7$, R$^8$, R$^9$, and R$^{10}$ groups may be introduced into compounds 141, 142 and 143 and and, of course, in the compounds of this invention, by the methods discussed above.

A method for the synthesis of N-substituted heterocycles at R$^5$ is shown in Scheme 19. The heterocycle can be deprotonated with NaH or by other bases familiar to one skilled in the art, in a solvent such as DMF, THF, or another appropriate non-hydroxylic solvent and reacted with piperidine or pyrrolidine 143 at room temperature to the reflux temperature of the solvent. Deprotection and elaboration as described before yields compounds where R$^5$ contains an N-substituted heterocycle. If the nitrogen atom of the heterocycle is sufficiently nucleophilic, then an acid scavenger, such as K$_2$CO$_3$, KHCO$_3$, Na$_2$CO$_3$, NaHCO$_3$, amongst others, can be used in place of NaH, employing THF, DMF, or methyl ethyl ketone as solvents. In this case hydroxylic solvents may be used as well, such as methanol, ethanol, etc. from room temperature to the reflux temperature of the solvent. Compound 143 as well as its other positional isomers are available, for example, from commercially available 4-hydroxymethylpiperidine, 2-, 3-, and 4-carboethoxypiperidine, L- or D-proline ethyl ester, or from methyl 1-benzyl-5-oxo-3-pyrrolidinecarboxylate by methods familiar to one skilled in the art and as discussed previously in this application.

SCHEME 19

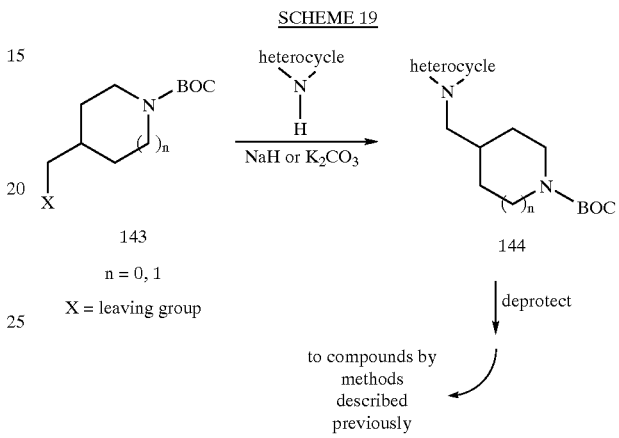

A method for the synthesis of C-substituted heterocycles at R$^5$ is shown in Scheme 20. Many heterocycles such as the ones shown in Scheme 20, but not limited thereto, can be metallated with strong bases such as LDA, n-BuLi, sec-BuLi, t-BuLi, etc. to yield the corresponding anionic species. These anions may also be generated via halogen-metal exchange employing n-BuLi, or other alkyllithium reagents. These reactions may be performed in THF, ether, dioxane, DME, benzene, etc. at −78° C. to room temperature.

SCHEME 20

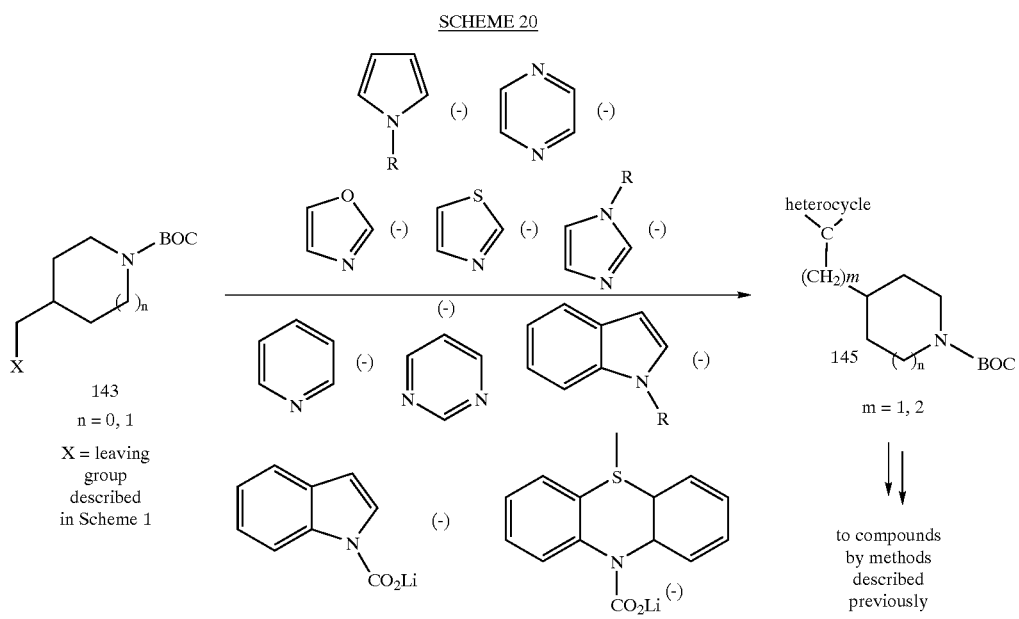

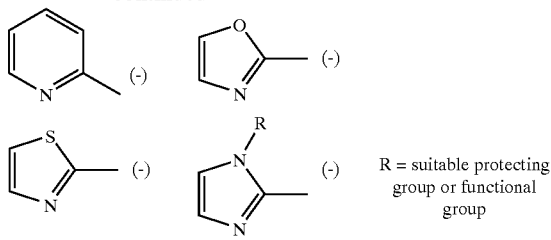

For reviews of these metallations and halogen-metal exchange reactions see Organometallics in Organic Synthesis, FMC Corp., Lithium Division, 1993, pp. 17–39; Lithium Link, FMC Corp., Spring 1993, pp. 2–17; n-Butyllithium in Organic Synthesis, Lithium Corp. of America, 1982, pp. 8–16; G. Heinisch, T. Langer, P. Lukavsky, J. Het. Chem. 1997, 34, 17–19. The anions can then be quenched with electrophile 143 or its positional isomers to yield the corresponding C-alkylated heterocyclic pyrrolidine or piperidine 145.

Org. Chem. 1969, 34, 4; J. Org. Chem. 1987, 52, 2226) amongst others familiar to one skilled in the art. It is understood by one skilled in the art that the aldehyde group can be located in other positions instead of, for example, the 4-position of piperidine in compound 146 as depicted in Scheme 21. It is to be understood that other heterocycles may also be used besides the ones shown in Scheme 20 and 21.

The anions of the methyl-substituted heterocycles may also be reacted with a BOC-protected piperidone or pyrroli-

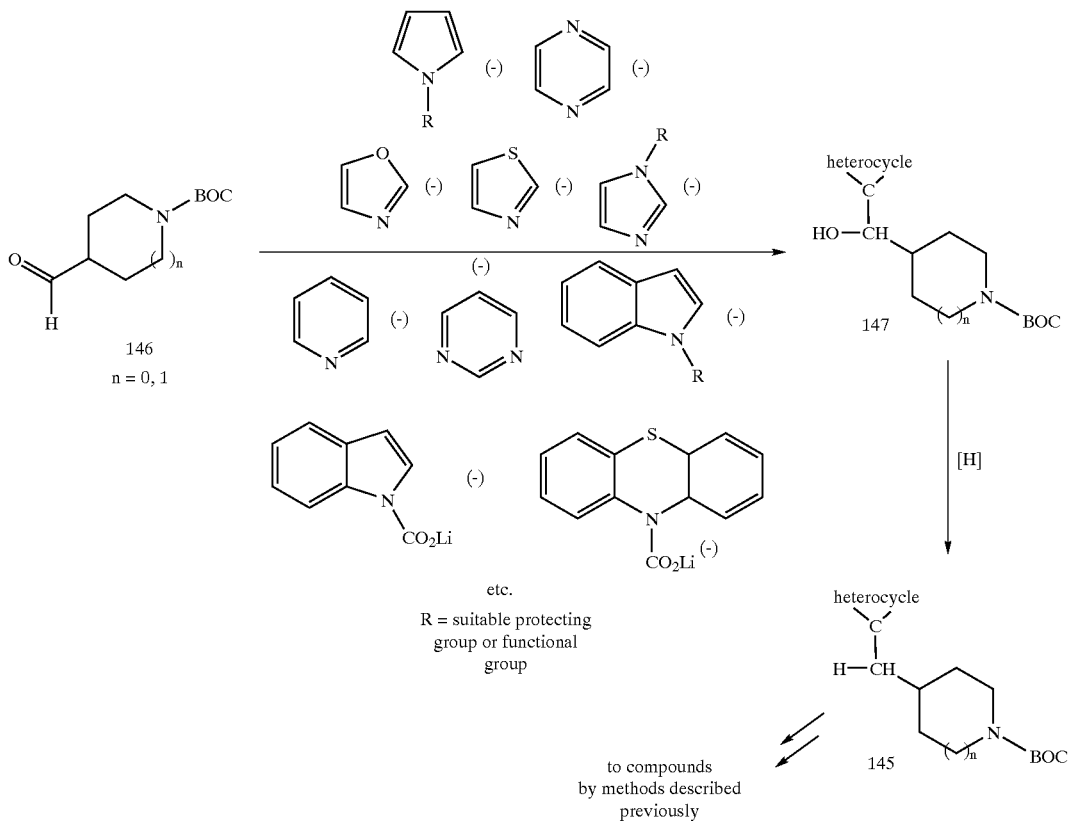

SCHEME 21

Another method for the synthesis of C-substituted heterocyclic-methylpyrrolidines or piperidines is shown in Scheme 21. The protected aldehyde 146 is reacted with the anion of the heterocycle (its generation as described previously) at –78° C. to room temperature with or without $CeCl_3$ in an inert solvent such as THF, ether, dioxane, DME, benzene, etc. to yield carbinol 147. Catalytic hydrogenation of the alcohol yields the corresponding methylene compound 145. Other reduction methods include $Et_3SiH/TFA$ (J.

done (148) to yield alcohols 149 as shown in Scheme 22 (see above reviews on metallations for references). These alcohols may be reduced using $PtO_2$ and TFA (P. E. Peterson and C. Casey, J. Org. Chem. 1964, 29, 2325–9) to yield piperidines and pyrrolidines 150. These can subsequently be taken on to the compounds of this invention as described previously. It is understood by one skilled in the art that the carbonyl group can be located in other positions instead of, for example, the 4-position of piperidine in compound 148 as depicted in Scheme 22. It is to be understood that other heterocycles may also be used besides the ones shown in Scheme 22.

SCHEME 22

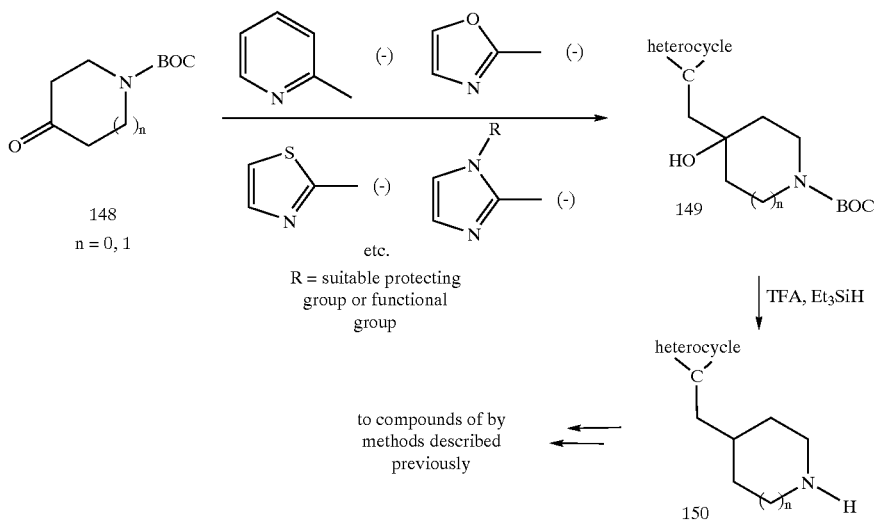

One may also react aryl (phenyl, naphthyl, etc.) anions, generated either by halogen-metal exchange or by ortho-directed metallation (Snieckus, V. Chem. Rev. 1990, 90, 879–933) using n- or s- or t-BuLi in a non-hydroxylic solvent such as THF, ether, etc., with or without TMEDA and allow them to react with compounds 143, 146. and 148 with subsequent elaboration to yield the compounds of this invention by the methods depicted in Schemes 19–22.

Another method for the preparation of C-substituted heterocycles is shown in Scheme 23. Protected piperidone 148 undergoes a Wittig reaction with heterocyclic phosphorous ylides to yield 151. Hydrogenation over a noble metal catalyst such as Pd in an alcoholic solvent or with an optically active transition metal catalyst (see asymmetric hydrogenation references of Parshall and Coleman, op. cit.) yields 152 which can be further elaborated into the compounds of this invention by the procedures described previously. It will be appreciated by one skilled in the art that the carbonyl group can be located in other positions instead of, for example, the 4-position of piperidine in compound 148 as depicted in Scheme 23. It is to be understood that other heterocycles may also be used besides the ones shown in Scheme 23.

Scheme 23

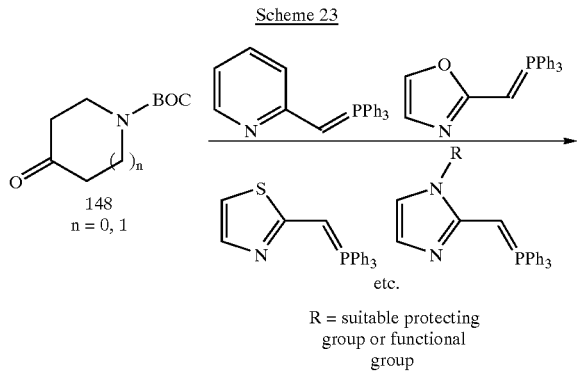

Syntheses of amines 9, 10, and the amines which are precursors to isocyanates or isothiocyanates 5 will now be discussed. For example, 3-nitrobenzeneboronic acid (153: Scheme 24) is commerically available and can undergo Suzuki couplings (Suzuki, A. Pure Appl. Chem. 1991, 63, 419) with a wide variety of substituted iodo- or bromo aryls (aryls such as phenyl, naphthalene, etc.), heterocycles, alkyls, akenyls (Moreno-manas, M., et al., J. Org. Chem., 1995, 60, 2396), or alkynes. It can also undergo coupling with triflates of aryls, heterocycles, etc. (Fu, J. -m, Snieckus, V. Tet. Lett. 1990, 31, 1665–1668). Both of the above reactions can also undergo carbonyl insertion in the presence of an atmosphere of carbon monoxide (Ishiyama, et al., Tet. Lett. 1993, 34, 7595). These nitro-containing compounds (155 and 157) can then be reduced to the corresponding amines either via catalytic hydrogenation, or via a number of chemical methods such as $Zn/CaCl_2$ (Sawicki, E. J Org Chem 1956, 21). The carbonyl insertion compounds (158)

can also undergo reduction of the carbonyl group to either the CHOH or CH2 linkages by methods already discussed (NaBH$_4$ or Et$_3$SiH, TFA, etc.). These amines can then be converted to isocyanate 5 via the following methods (Nowakowski, J. J Prakt Chem/Chem-Ztg 1996, 338 (7), 667–671; Knoelker, H. -J. et al., Angew Chem 1995, 107 (22), 2746–2749; Nowick, J. S. et al., J Org Chem 1996, 61 (11), 3929–3934; Staab, H. A.; Benz, W.; Angew Chem 1961, 73); to isothiocyanate 5 via the following methods (Strekowski L. et al., J Heterocycl Chem 1996, 33 (6), 1685–1688; Kutschy, P et al., Synlett 1997, (3), 289–290); to carbamoyl chloride 11 (after 156 or 158 is reductively aminated with an R$^2$ group) (Hintze, F.; Hoppe, D.; Synthesis (1992) 12, 1216–1218); to thiocarbamoyl chloride 11 (after 156 or 158 is reductively aminated with an R$^2$ group) (Ried, W.; Hillenbrand, H.; Oertel, G.; Justus Liebigs Ann Chem 1954, 590); or just used as 9, or 10 (after 156 or 158 is reductively aminated with an R$^2$ group), in synthesizing the compounds of this invention by the methods depicted in Scheme 1.

SCHEME 24

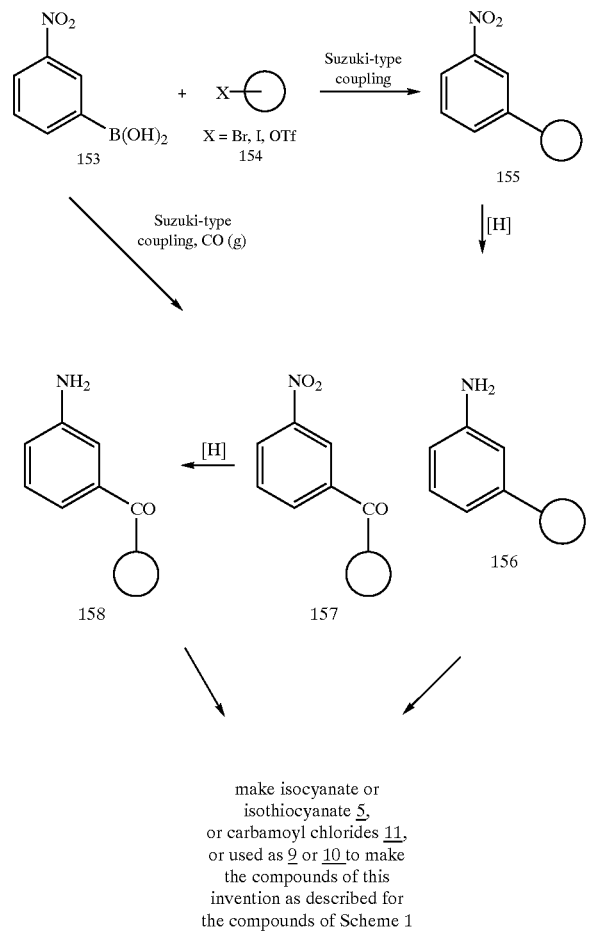

make isocyanate or
isothiocyanate 5,
or carbamoyl chlorides 11,
or used as 9 or 10 to make
the compounds of this
invention as described for
the compounds of Scheme 1

Likewise, protected aminobromobenzenes or triflates or protected aminobromoheterocycles or triflates 159 (Scheme 25) may undergo Suzuki-type couplings with arylboronic acids or heterocyclic boronic acids (160). These same bromides or triflates 159 may also undergo Stille-type coupling (Echavarren, A. M., Stille, J. K. J. Am. Chem. Soc., 1987, 109, 5478–5486) with aryl, vinyl, or heterocyclic stannanes 163. Bromides or triflates 159 may also undergo Negishi-type coupling with other aryl or heterocyclic bromides 164 (Negishi E. Accts. Chem. Res. 1982, 15, 340; M. Sletzinger, et al., Tet. Lett. 1985, 26, 2951). Deprotection of the amino group yields an amine with can be coupled to make a urea and other linkers containing Z as described above and for Scheme 1. Amino protecting groups include phthalimide, 2,4-dimethyl pyrrole (S. P. Breukelman, et al. J. Chem. Soc. Perkin Trans. I, 1984, 2801); N-1,1,4,4-Tetramethyldisilyl-azacyclopentane (STABASE) (S. Djuric, J. Venit, and P. Magnus Tet. Lett 1981, 22, 1787) and others familiar to one skilled in the art.

SCHEME 25

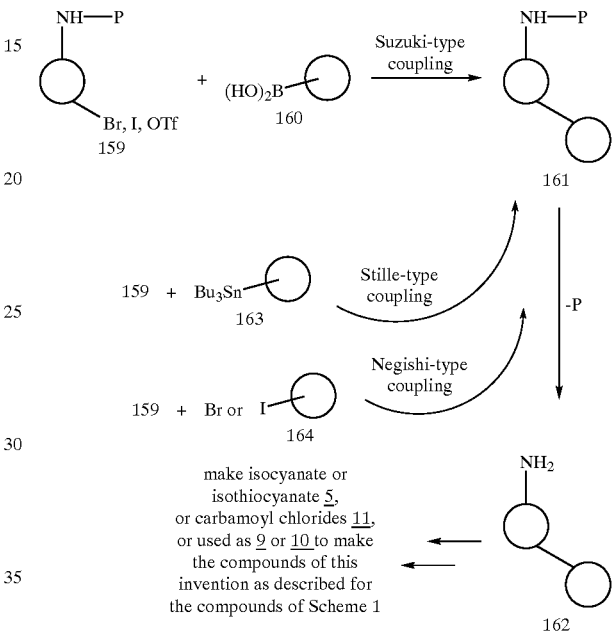

make isocyanate or
isothiocyanate 5,
or carbamoyl chlorides 11,
or used as 9 or 10 to make
the compounds of this
invention as described for
the compounds of Scheme 1

Compounds where R$^7$ and R$^8$ are taken together to form =NR$^{8b}$ can be synthesized by the methods in Scheme 25a. Reacting 1 with nitrile a with CuCl catalysis forms amidine b where R$^{8b}$ is H (Rousselet, G.; Capdevielle, P.; Maumy, M.; Tetrahedron Lett. 1993, 34 (40), 6395–6398). Note that the urea portion may be in final form or in precursor form (for example, a protected nitrogen atom; P=protecting group such as STABASE, bis-BOC, etc., as was discussed previously) which may be subsequently elaborated into the compounds of this invention. Compounds b may be also synthesized by reacting iminoyl chloride c with pyrrolidine/piperidine 1 to yield b where R$^{8b}$ is not H (Povazanec, F., et al., J. J. Heterocycl. Chem., 1992, 29, 6, 1507–1512). Iminoyl chlorides are readily available from the corresponding amide via PCl$_5$ or CCl$_4$/PPh$_3$ (Duncia, J. V. et al., J. Org. Chem., 1991, 56, 2395–2400). Again, the urea portion may be in final form or in precursor form.

Scheme 25a

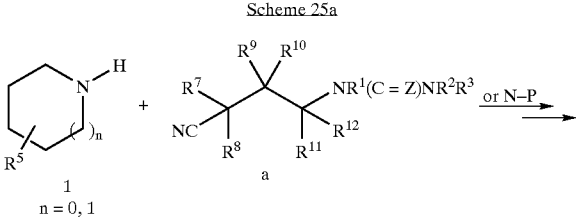

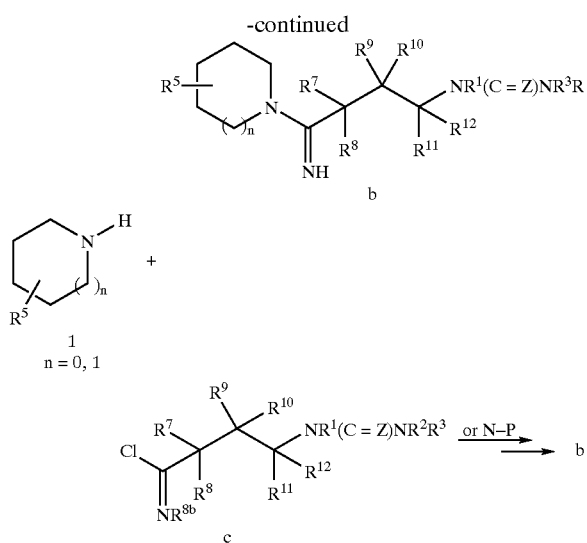

Many amines are commercially available and can be used as 9, 10, or used as precursors to isocyanates or isothiocyanates 5. There are numerous methods for the synthesis of non-commercially available amines familiar to one skilled in the art. For example, aldehydes and ketones may be converted to their O-benzyl oximes and then reduced with LAH to form an amine (Yamazaki, S.; Ukaji, Y.; Navasaka, K.; Bull Chem Soc Jpn 1986, 59, 525). Ketones and trifluoromethylketones undergo reductive amination in the presence of $TiCl_4$ followed by $NaCNBH_4$ to yield amines (Barney, C. L., Huber, E. W., McCarthy, J. R. Tet. Lett. 1990, 31, 5547–5550). Aldehydes and ketones undergo reductive amination with $Na(AcO)_3BH$ as mentioned previously to yield amines (Abdel-Magid, A. F., et al. Tet. Lett. 1990, 31, (39) 5595–5598). Amines may also be synthesized from aromatic and heterocyclic OH groups (for example, phenols) via the Smiles rearrangement (Weidner, J. J., Peet, N. P. J. Het. Chem., 1997, 34, 1857–1860). Azide and nitrile displacements of halides, tosylates, mesylates, triflates, etc. followed by LAH or other types or reduction methods yield amines.

Sodium diformyl amide (Yinglin, H., Hongwen, H. Synthesis 1989 122), potassium phthalimide, and bis-BOC-amine anion can all displace halides, tosylates, mesylates, etc., followed by standard deprotection methods to yield amines, procedures which are familiar to one skilled in the art. Other methods to synthesize more elaborate amines involve the Pictet-Spengler reaction, imine/immonium ion Diels-Alder reaction (Larsen, S. D.; Grieco, P. A. J. Am. Chem. Soc. 1985, 107, 1768–69; Grieco, P. A., et al., J. Org. Chem. 1988, 53, 3658–3662; Cabral, J. Laszlo, P. Tet. Lett. 1989, 30, 7237–7238; amide reduction (with LAH or diborane, for example), organometallic addition to imines (Bocoum, A. et al., J. Chem. Soc. Chem. Comm. 1993, 1542–4) and others all of which are familiar to one skilled in the art.

Compounds containing an alcohol side-chain alpha to the nitrogen of the piperidine/pyrrolidine ring can be synthesized as shown in Scheme 25b. Only the piperidine case is exemplified, and it is to be understood by one skilled in the art that the alpha-substituted pyrrolidines may be synthesized by a similar route. It is also understood that appropriate substituents may be present on the piperidine/pyrrolidine ring. A 4-benzylpiperidine 196 is protected with a BOC group. The BOC-piperidine 197 is then metallated under conditions similar to those Beak, et al. (P. Beak and W. -K. Lee, J. Org. Chem. 1990, 55, 2578–2580, and references therein) and quenched with an aldehyde to yield alcohol 198. The metallation may also be done enantioselectively using sparteine (P. Beak, S. T. Kerrick, S. Wu, J. Chu J. Am. Chem. Soc. 1994, 116, 3231–3239). This alcohol can be deprotonated with NaH and cyclized to carbamate 198a which permits structural assignments of the erythro and threo isomers. Deprotection with base yields aminoalcohol 199. Subsequent N-alkylation yields phthalimidoalkylpiperidine 201. It is to be understood that the alkyl chain does not necessarily have to be n-propyl, but that n-propyl was chosen for demonstration purposes only. Deprotection of the phthalimido group with hydrazine yields amine 202. Finally, reaction with an isocyanate or via any of the previously described conditions described in Scheme 1 yields urea 203. If an isocyanate is used, the isocyanate can add twice to yield urea-carbamate 204.

Scheme 25b

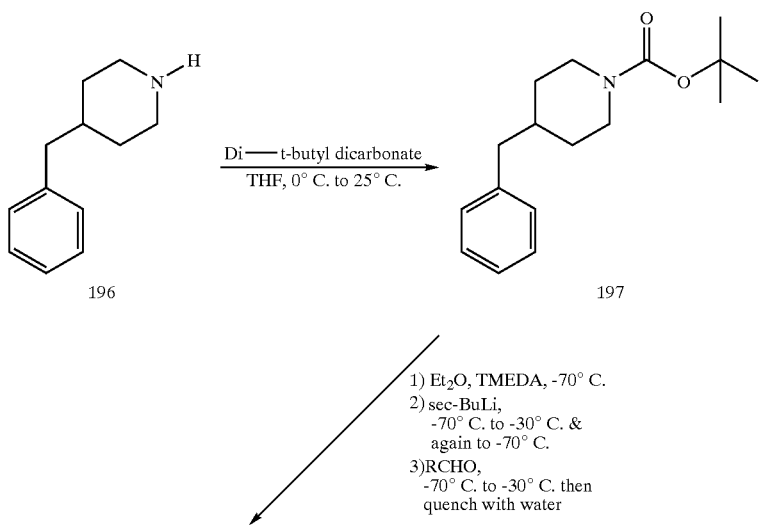

-continued
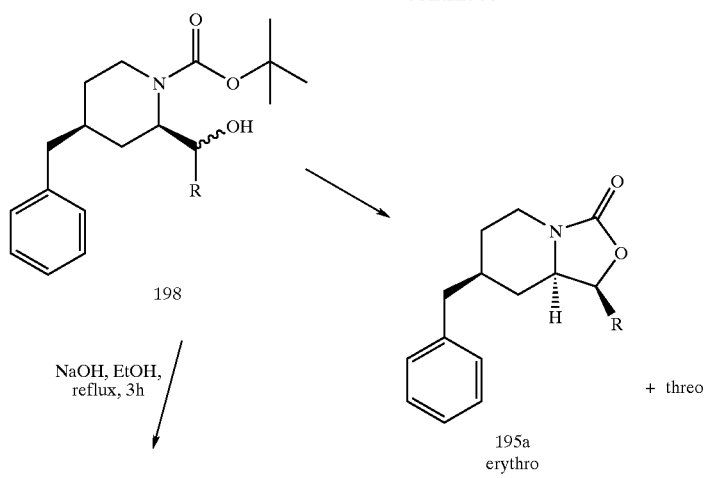
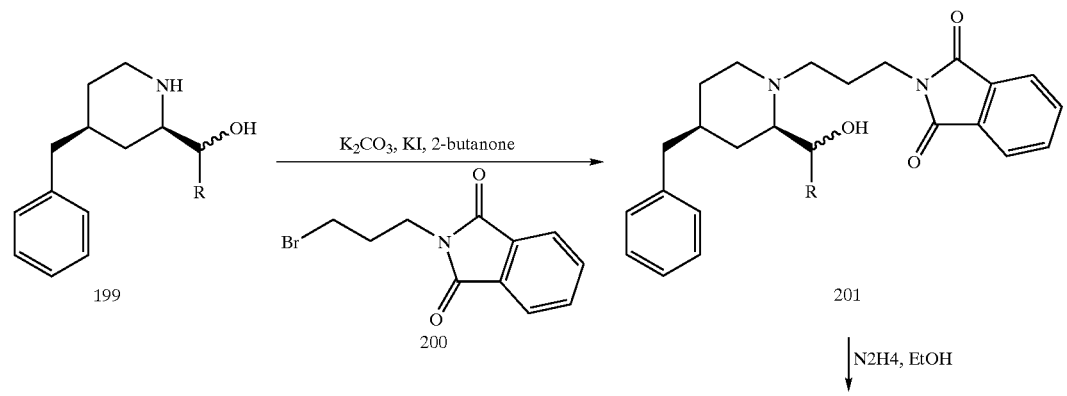
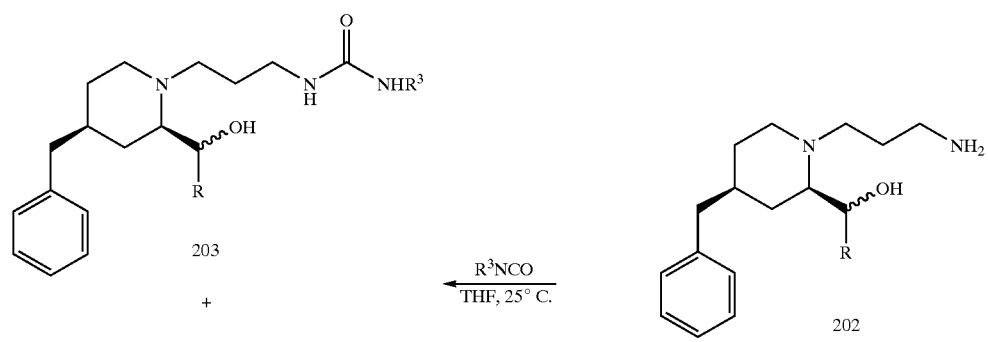
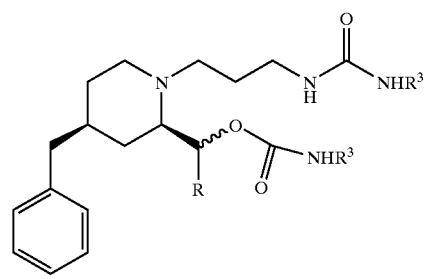

Compounds where Z=N—CN, CHNO$_2$, and C(CN)$_2$ can be synthesized by the methods shown in Scheme 25c. Thus amine 208 reacts with malononitrile 207 neat or in an inert solvent at room temperature to the reflux temperature of the solvent, or at the melting point of the solid/solid mixture, to yield malononitrile 206. This in turn can undergo reaction with amine 205 under similar conditions stated just above to yield molononitrile 209. Likewise, a similar reaction sequence may be used to make 212 and 215 [for Z=C(CN)$_2$, see for example P. Traxler, et al., J. Med. Chem. (1997), 40, 3601–3616; for Z=N—CN, see K. S. Atwal, J. Med. Chem. (1998) 41, 271; for Z=CHNO$_2$, see J. M. Hoffman, et al., J. Med. Chem. (1983) 26, 140–144).

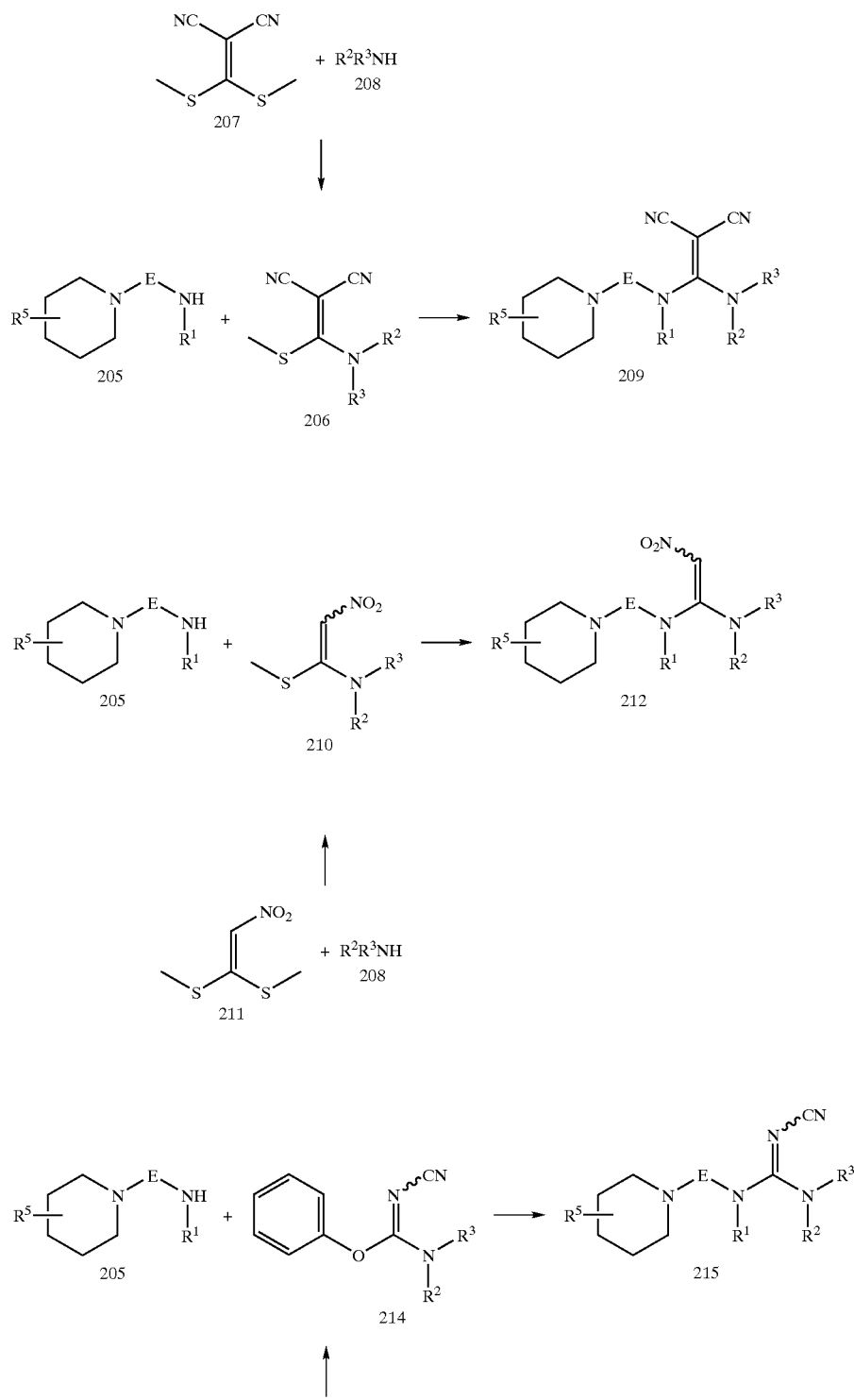

Scheme 25c

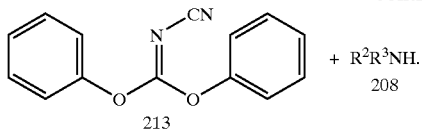 + R²R³NH.
213          208

EXAMPLES

The compounds of this invention and their preparation can be understood further by the following working examples. These examples are meant to be illustrative of the present invention, and are not to be taken as limiting thereof.

Example 1

Part A: Preparation of 4-benzyl-1-(3-N-phthalimido-n-prop-1-yl)piperidine

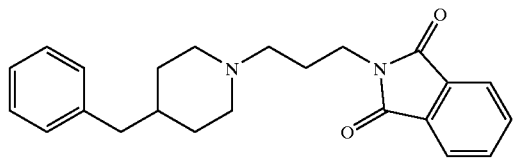

4-benzylpiperidine (8.0 g, 45.6 mmol, 1 eq), N-(3-bromopropyl)-phthalimide (13.5 g, 50.2 mmol, 1.1 eq), potassium iodide (7.6 g, 45.6 mmol, 1 eq) and potassium carbonate (2.6 g, 91.3 mmol, 2 eq) were refluxed in 125 mL of 2-butanone. The reaction was worked up after 5 hours by filtering off the inorganic solids then adding EtOAc and rinsing the organic layer 2× with water. The organic layer was dried over magnesium sulfate then the solvent removed in vacuo to obtain an amber oil. The oil was purified by flash chromatography in 100% EtOAc to remove impurities then 8:2 chloroform/methanol to isolate 3.67 g of the product as a light amber oil. NMR(300 MHz, CDCl₃) δ 8.00–7.80 (m, 2H); 7.80–7.60 (m, 2H); 7.35–7.10 (m, 3H); 7.08 (d, 2H, J=7 Hz); 3.76 (t, 2H, J=7 Hz); 2.83 (d, 2H, J=10 Hz); 2.45–2.30 (m, 4H); 1.95–1.30 (m, 7H); 1.20–0.90 (m, 2H).

Part B: Preparaton of 4-benzyl-1-(3-amino-n-prop-1-yl) piperidine

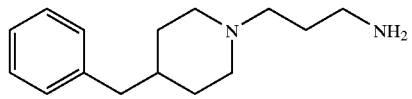

4-benzyl-1-(3-N-phthalimido-n-prop-1-yl)piperidine (13.72 g, 37.9 mmol, 1 eq.) was dissoved in 200 mL of EtOH at 25° C. under $N_2$, the anhydrous hydrazine (2.38 mL, 75.7 mmol, 2 eq.) was added. The solution was then refluxed during which time a white precipitate formed. The reaction was worked up after refluxing 4 hours by filtering off the solids. The solvent was removed in vacuo to obtain an oil which was re-rotovapped from toluene to remove excess hydrazine. Obtained an oil which was stirred in Et₂O. Insoluble material was filtered then the solvent removed in vacuo to obtain 5.55 g of an amber oil as product. NMR (300 MHz, CDCl₃) δ 7.40–7.21 (m, 2H); 7.21–7.05 (m, 3H); 2.92 (d, 2H, J=10 Hz); 2.73 (t, 2H, J=7 Hz); 2.53 (d, 2H, J=7 Hz); 2.40–2.20 (m, 2H); 1.84 (t of t, 2H, J=7,7 Hz); 1.75–1.10 (m, 9H).

Part C: N-(3-cyanophenyl)-N'-[3-[4-(phenylmethyl)-1-piperidinyl]propyl]urea

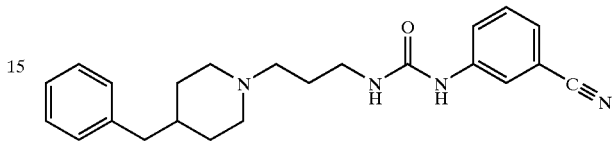

4-benzyl-1-(3-amino-n-prop-1-yl)piperidine (300 mg, 1.29 mmol, 1 eq) was dissoved in THF at 25° C. under $N_2$ then 3-cyanophenyl isocyanate (186 mg, 1.29 mmol, 1 eq) was added. TLC after 30 minutes shows the reaction complete. The solvent was removed in vacuo then the residue was purified over silica gel in 100% EtOAc to 8:2 chloroform/MeOHto yield 437 mg of an amber oil as product. NMR (300 MHz, DMSO-d₆) δ 9.90–9.50 (m, 1H); 9.32 (s, 1H); 7.93 (s, 1H); 7.59 (d, 1H, J=7 Hz); 7.43 (t, 1H, J=7 Hz); 7.40–7.24 (m, 3H); 7.24–7.10 (m, 3H); 6.68 (t, 1H, J=7 Hz); 3.50–3.25 (m, 2H); 3.25–3.07 (m, 2H); 3.07–2.90 (m, 2H); 2.90–2.60 (m, 2H); 2.60–2.40 (m, 2H); 2.00–1.60 (m, 5H); 1.60–1.30 (m, 2H).

Example 2

Part A: Preparation of 4-benzyl-1-carbomethoxymethyl-1-[3-(3-cyanophenylaminocarbonylamino)prop-1-yl] piperidinium

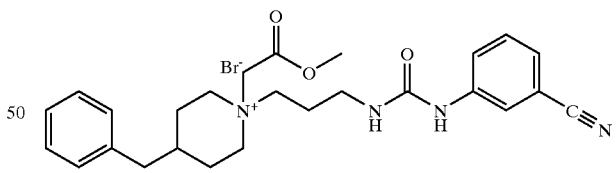

4-benzyl-1-[3-(3-cyanophenylaminocarbonylamino) prop-1-yl]piperidine (50 mg, 0.133 mmol, 1 eq), was dissoved in acetone at 25° C. under $N_2$ then methyl bromoacetate (13 uL, 0.133 mmol, 1 eq),was added. After 16 hours, the solvent was removed in vacuo and the residue was purified over silica gel in 100% EtOAc to 8:2 chloroform/MeOH to yield 50 mg of white solids as product. NMR (300 MHz, CD₃OD) δ 8.00–7.80 (m, 1H); 7.65–7.45 (m, 1H); 7.45–7.33 (m, 1H); 7.33–7.05 (m, 6H); 4.50–4.25 (m, 2H); 4.00–3.60 (m, 5H); 3.50–3.20 (m, 6H); 2.70–2.50 (m, 2H); 2.10–1.60 (m, 7H).

Example 3

Part A: Preparation of 1-(t-Butoxycarbonyl)-3-piperidone

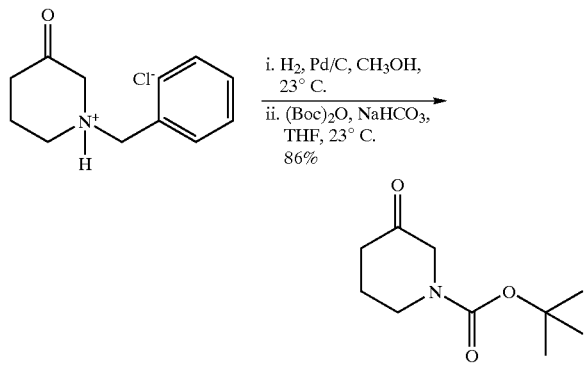

To a deep yellow solution of 1-benzyl-3-piperidone hydrochloride (3.00 g, 1.33 mmol, 1 equiv) in methanol (100 mL) was added 10 wt. % (dry basis) palladium on activated carbon (600 mg) under a stream of nitrogen. The resulting black suspension was deoxygenated by alternate evacuation and flushing with nitrogen (3×) followed by alternate evacuation and flushing with hydrogen (3×). The reaction suspension was then shaken vigorously under a hydrogen atmosphere of 55 psi. After 12 hours, gravity filtration of the supsension and concentration of the resulting filtrate in vacuo yielded crude 3-piperidone as a viscous light green oil. The oil was immediately treated with tetrahydrofuran (150 mL) and di-t-butyldicarbonate (4.73 g, 21.7 mmol, 0.98 equiv). Upon addition of saturated aqueous sodium bicarbonate (25 mL), the oil completely dissolved to give a light yellow suspension. After stirring the suspension vigorously for 2 hours, the now white suspension was poured into aqueous hydrogen chloride (1N, 100 mL), and the layers were separated. The aqueous layer was extracted with ethyl acetate (3×70 mL), and the combined organic layers were washed with saturated aqueous sodium chloride (50 mL), dried over sodium sulfate, and filtered. Concentration of the resulting filtrate in vacuo yielded 1-(t-butoxycarbonyl)-3-piperidone (3.79 g, 86%) as a white oily solid. $^1$H NMR (300 MHz, CDCl$_3$), δ:3.94 (s, 2H), 3.53 (t, 2H, J=6 Hz), 2.41 (t, 2H, J=7 Hz), 1.92 (m, 2H), 1.41 (s, 9H)

Part B: Preparation of 1',3-(2H)-Dehydro-3-benzyl-1-(t-butoxycarbonyl)piperidine

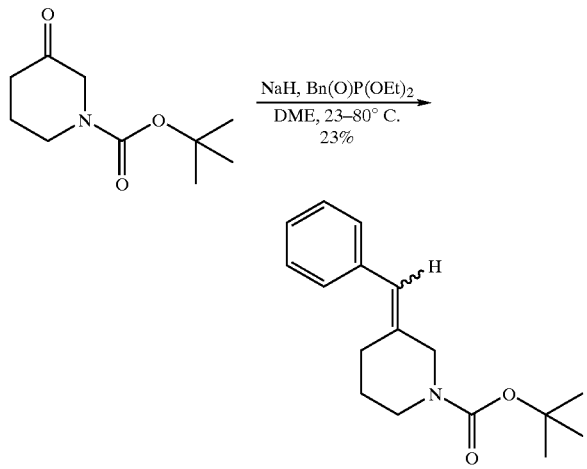

To a flame-dried 100-mL flask charged with sodium hydride (60% wt. dispersion in mineral oil; 601 mg, 15.0 mmol, 2.3 equiv)) and 1,2-dimethoxyethane (20 mL) was added benzyl diethylphosphite (3.42 g, 3.13 mL, 15.0 mmol, 2.3 equiv) dropwise over a period of 5 min. After 10 min, 1-(t-butoxycarbonyl)-3-piperidone was added in one portion to the pale yellow suspension. The flask was fitted with a relfux condensor, and the resulting yellow-gray suspension at heated under reflux conditions for 2 hrs. Upon cooling to 23° C., the reaction was poured into aqueous hydrogen chloride (0.20 N, 100 mL) and diethyl ether (75 mL). The layers were separated and the aqueous layer was basified with saturated aqueous sodium bicarbonate to pH 9. The aqueous layer was extracted with diethyl ether (4×75 mL), and the combined organic layers were dried over sodium sulfate. Filtration, concentration in vacuo, and purification of the resulting residue by flash column chromatography (5% ethyl acetate in hexanes) afforded a mixture of the desired olefin (410 mg, 23%) and the corresponding ethoxy-carbamate (550 mg, 34%) as a clear oil. The ethoxycarbamate was removed in the subsequent step by flash column chromatography. $^1$H NMR (300 MHz, CDCl$_3$), δ: 7.30 (m, 2H), 7.18 (m, 3H), 6.42 (s, 1H), 4.02 (s, 2H), 3.50 (t, 2H, J=6 Hz), 2.51 (t, 2H, J=5 Hz), 1.61 (m, 2H), 1.49 (s, 9H). MS (CI), m$^+$/z: (M+H)$^+$=274, [(M+H)$^+$-(—C(O)OC(CH$_3$)$_3$)] 174.

Part C: Preparation of 1-(t-Butoxycarbonyl)-3-benzylpiperidine

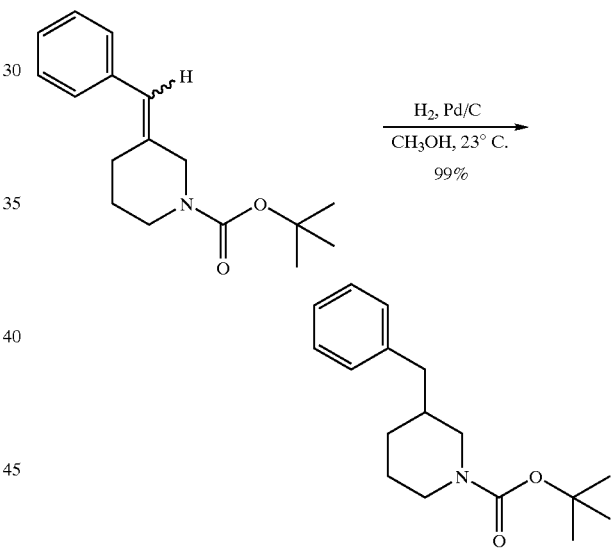

To a solution of impure product (410 mg, 1.50 mmol) obtained in the previous step in methanol (100 mL) was added 10 wt. % (dry basis) palladium on activated carbon (200 mg) under a stream of nitrogen. The resulting black suspension was deoxygenated by alternate evacuation and flushing with nitrogen (3×) followed by alternate evacuation and flushing with hydrogen (3×). The reaction suspension was then shaken vigorously under a hydrogen atmosphere of 55 psi. After 12 hours, gravity filtration of the supsension and concentration of the resulting filtrate in vacuo resulted in a pale yellow residue. Purification of this residue by flash column chromatography afforded 1-(t-butoxycarbonyl)-3-benzyl-piperidine (407 mg, 99%) as a clear oil. $^1$H NMR (300 MHz, CDCl$_3$), δ:7.23 (m, 2H), 7.14 (m, 3H), 3.86 (m, 2H), 2.75 (br m, 1H), 2.51 (m, 3H), 1.70 (br. m, 2H), 1.64 (br. m, 1H), 1.41 (s, 9H), 1.34 (br. m, 1H), 1.09 (br. m, 1H). MS (CI), m$^+$/z: (M$^+$+1) 276, [(M+H)$^+$-(—C(O)OC(CH$_3$)$_3$)]=176.

Part D: 3-Benzylpiperidine hydrochloride

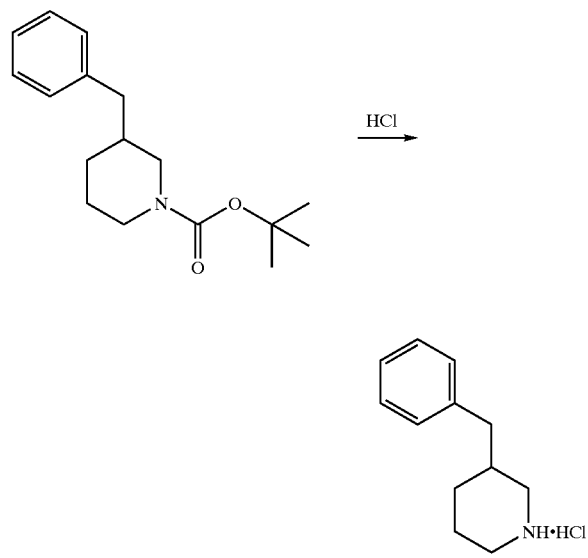

To a solution of 1-(t-butoxycarbonyl)-3-benzylpiperidine (400 mg, 1.45 mmol) in methanol (5 mL) was added hydrogen chloride in dioxane (4M, 15 mL). The resulting yellow solution was stirred for 1 hr, at which time the reaction was concentrated in vacuo to provide 3-benzylpiperidine hydrochloride (308 mg, 100%) as an amorphous solid. $^1$H NMR (300 MHz, CD$_3$OD), δ:7.27 (m, 2H,), 7.19 (m, 3H), 3.29 (br. d, 1H, J=12 Hz), 3.20 (br. d, 1H, J=12 Hz), 2.87 (br. t, 1H, J=12 Hz), 2.67 (m, 1H), 2.60 (d, 2H, J=7 Hz), 2.08 (m, 1H) 1.70–1.87 (m, 3H), 1.26 (m, 1H). MS (CI), m$^+$/z: (M+H)$^+$=176.

Part E: Preparation of N-(3-methoxyphenyl)-N'-[3-[3-[(phenyl)methyl]-1-piperidinyl]propyl]urea

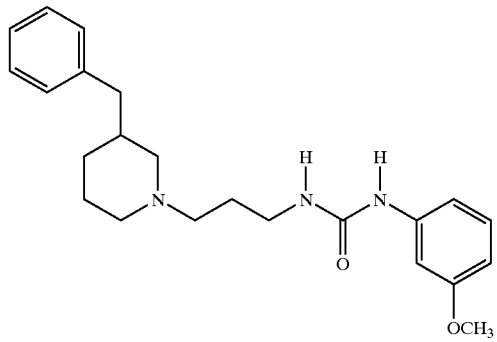

The above compound was prepared by the methods similar to the ones employed in Example 1, part C. $^1$H NMR (300 MHz, CD$_3$OD), δ:7.29–7.13 (m, 4H); 7/07 (d, 1H, J=9 Hz); 7.02 (m, 1H); 6.78 (d, 1H, J=9 Hz); 6.60 (d, 1H, J=9 Hz); 3.77 (s, 3H); 3.30 (m, 2H); 2.80 (m, 2H); 2.53–2.32 (m, 4H); 1.85–1.55 (m, 7H); 1.44–0.78 (m, 2H). MS (ESI), m$^+$/z: (M+H)$^+$=382.

Example 4
Part A: Preparation of a,a'-Dibromo-3-nitro-o-xylene

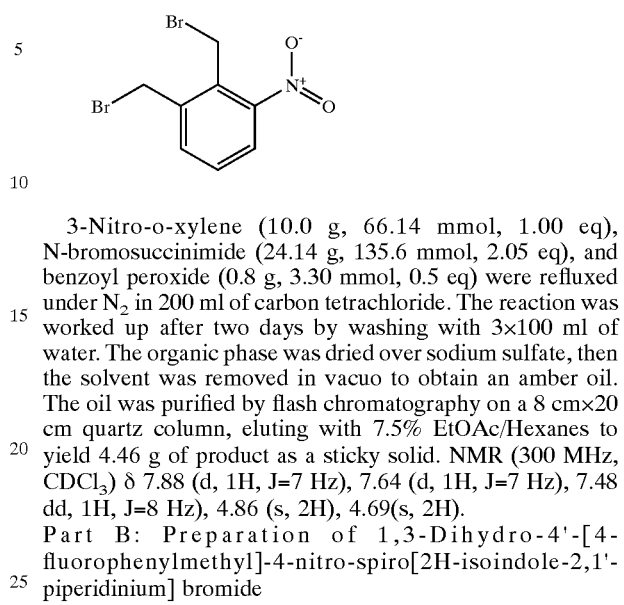

3-Nitro-o-xylene (10.0 g, 66.14 mmol, 1.00 eq), N-bromosuccinimide (24.14 g, 135.6 mmol, 2.05 eq), and benzoyl peroxide (0.8 g, 3.30 mmol, 0.5 eq) were refluxed under N$_2$ in 200 ml of carbon tetrachloride. The reaction was worked up after two days by washing with 3×100 ml of water. The organic phase was dried over sodium sulfate, then the solvent was removed in vacuo to obtain an amber oil. The oil was purified by flash chromatography on a 8 cm×20 cm quartz column, eluting with 7.5% EtOAc/Hexanes to yield 4.46 g of product as a sticky solid. NMR (300 MHz, CDCl$_3$) δ 7.88 (d, 1H, J=7 Hz), 7.64 (d, 1H, J=7 Hz), 7.48 dd, 1H, J=8 Hz), 4.86 (s, 2H), 4.69(s, 2H).

Part B: Preparation of 1,3-Dihydro-4'-[4-fluorophenylmethyl]-4-nitro-spiro[2H-isoindole-2,1'-piperidinium] bromide

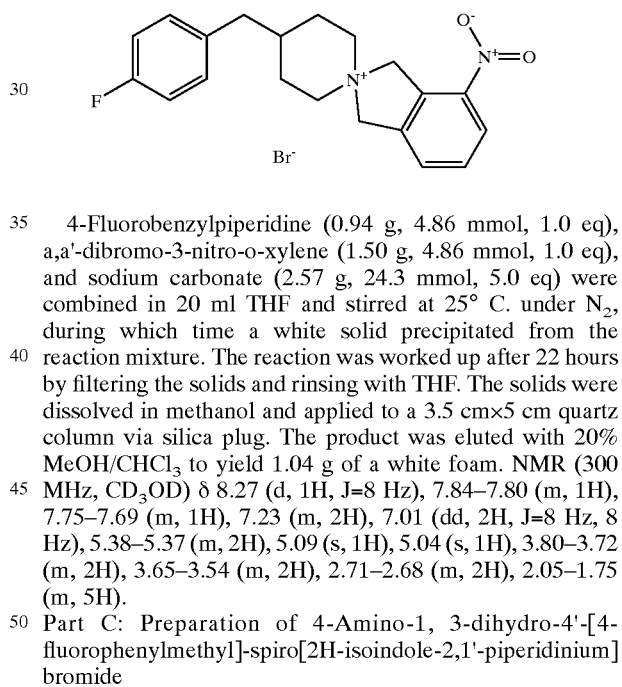

4-Fluorobenzylpiperidine (0.94 g, 4.86 mmol, 1.0 eq), a,a'-dibromo-3-nitro-o-xylene (1.50 g, 4.86 mmol, 1.0 eq), and sodium carbonate (2.57 g, 24.3 mmol, 5.0 eq) were combined in 20 ml THF and stirred at 25° C. under N$_2$, during which time a white solid precipitated from the reaction mixture. The reaction was worked up after 22 hours by filtering the solids and rinsing with THF. The solids were dissolved in methanol and applied to a 3.5 cm×5 cm quartz column via silica plug. The product was eluted with 20% MeOH/CHCl$_3$ to yield 1.04 g of a white foam. NMR (300 MHz, CD$_3$OD) δ 8.27 (d, 1H, J=8 Hz), 7.84–7.80 (m, 1H), 7.75–7.69 (m, 1H), 7.23 (m, 2H), 7.01 (dd, 2H, J=8 Hz, 8 Hz), 5.38–5.37 (m, 2H), 5.09 (s, 1H), 5.04 (s, 1H), 3.80–3.72 (m, 2H), 3.65–3.54 (m, 2H), 2.71–2.68 (m, 2H), 2.05–1.75 (m, 5H).

Part C: Preparation of 4-Amino-1, 3-dihydro-4'-[4-fluorophenylmethyl]-spiro[2H-isoindole-2,1'-piperidinium] bromide

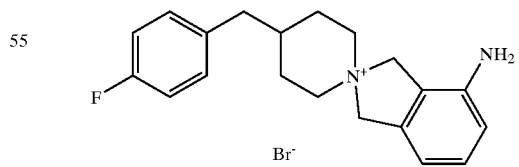

1,3-Dihydro-4'-[4-fluorophenylmethyl]-4-nitro-spiro[2H-isoindole-2,1'-piperidinium] bromide (1.03 g, 2.46 mmol, 1.0 eq), zinc (5.32 g, 81.5 mmol, 33.0 eq), and calcium chloride (0.18 g, 1.60 mmol, 0.65 eq) were refluxed under N$_2$ in 25 ml of a 78% ethanol/water solution. The reaction was worked up after 5 hours by filtering through Celite® and rinsing the cake with methanol. The filtrate was concentrated in vacuo to a mixture of water and an amber oil. The mixture was dissolved in 50 ml of 2-propanol, and concentrated in vacuo to remove excess water. The resulting yellow foam was dissolved in methanol and applied to a 3.5 cm×5 cm quartz column via silica plug. The product was eluted with 20% MeOH/CHCl$_3$ to yield 0.81 g of a yellow foam. NMR (300 MHz, DMSO) δ 7.27–7.05 (m, 5H), 6.61–6.53 (m, 2H), 5.43–5.41 (m, 2H), 4.80 (bs, 1H), 4.74 (bs, 2H), 4.63 (bs, 1H), 3.62–3.43 (m, 4H), 2.60 (bd, 2H, J=7 Hz), 1.98–1.59 (m, 5H).

Part D: Preparation of N-[1,3-Dihydro-4'-[4-fluorophenyl-methyl]spiro[2H-isoindole-2,1'-piperdinium-4-yl]-N'-4-fluorophenylurea bromide

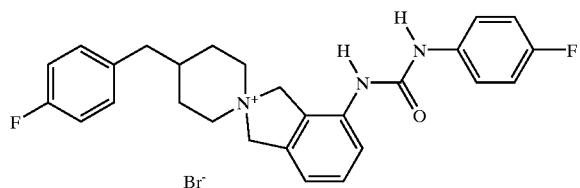

4-Amino-1, 3-dihydro-41-[4-fluorophenylmethyl]-spiro [2H-isoindole-2,1'-piperidinium] bromide (0.33 g, 0.84 mmol, 1.0 eq), and 4-fluorophenyl isocyanate (0.23 g, 1.69 mmol, 2.0 eq) were combined in 3 ml DMF and stirred at 25•C under N$_2$. The reaction was worked up after 22 hours by removing the solvent in vacuo, dissolving the residue in methanol, and applying the mixture to a 3.5 cm×15 cm quartz column via silica plug. The product was eluted with 10% MeOH/CHCl$_3$ to yield 65 mg of a yellow foam. NMR (300 MHz, DMSO) δ 9.18 (s, 1H), 9.00 (s, 1H), 7.49–7.43 (m, 2H), 7.41–7.34 (m, 2H), 7.26–7.21 (m, 2H), 7.17–7.10 (m, 5H), 4.94 (s, 2H), 4.80 (s, 2H), 3.63–3.45 (m, 4H), 2.61 (bd, j=7 Hz), 1.91–1.62 (m, 5H)

Example 5
Part A. Preparation of 4-benzyl-1-(3-hydroxy-3-phenylprop-1-yl)piperidine

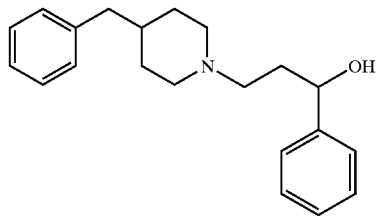

To a flame-dried 3-neck flask under a N$_2$ atmosphere with a magnetic stirring bar, 4-benzylpiperidine (5.00 mL, 28 mmol, 1 eq), DBU (42 µL, 0.28 mmol, 0.01 eq), and THF (100 mL) were added, mixed, and cooled to −15° C. using a CCl$_4$/CO$_2$(s) bath. Acrolein (1.87 mL, 28 mmol, 1 eq) was then syringed in slowly during 10 minutes maintaining the temp. at −15° C. After 0.5 hours at −15° C., phenylmagnesium chloride (2.0 M, 14.0 mL, 28 mmol, 1 eq) was syringed in slowly and the contents allowed to slowly warm to room temperature and then stirred for 48 h. The reaction was worked up by adding 0.1 N NaOH and EtOAc (200 mL each). The viscous magnesium salts were suction filtered through fiberglass filter paper. The layers were separated and the aqueous layer was extracted again with ethyl acetate (2×200 mL). The organic layers were combined, washed with brine (1×200 mL), dried (MgSO$_4$) and the solvent removed in vacuo to yield 7.39 g of an amber oil. Flash chromatography in 100% ethyl actetate yielded 2.48 g of an orange oil. NMR (CDCl$_3$) δ 7.40–7.10 (m, 10H); 4.93 (d of d, 1H, J=3,7 Hz); 3.12–2.96 (m, 2H); 2.68–2.46 (m, 4H); 2.01 (t of d, 1H, J=2, 10 Hz); 1.86–1.26 (m, 8H). ESI MS detects (M+H)$^+$=310.

Part B: Preparation of 4-benzyl-1-(3-azido-3-phenylprop-1-yl)piperidine

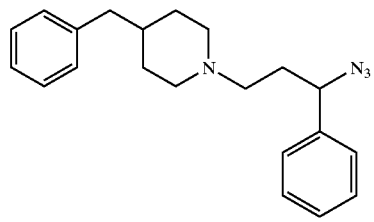

The product from part A (209 mg, 0.675 mmol, 1 eq), DBU (123 mg, 0.810 mmol, 1.2 eq), diphenylphosphoryl azide (0.175 mL, 0.810 mmol, 1.2 eq), and toluene (1.0 mL) were mixed and stirred overnight at room temperature under a N$_2$ atmosphere. The reaction was then worked up by adding ethyl acetate (50 mL), washing with water (3×25 mL), followed by washing with brine (1×25 mL), drying (MgSO$_4$) and removing the solvent in vacuo to yield 277 mg of an amber oil. Flash chromatography in 1:1 hexane/ethyl acetate yielded 84 mg of product as an oil. NMR (CDCl$_3$) δ 7.41–7.09 (m, 10 H); 4.56 (t, 1H, J=7 Hz); 3.83 (m, 2H); 2.52 (d, 2H, J=7 Hz); 2.32 (t, 2H, J=7 Hz); 2.30–1.77 (m, 5H); 2.59 (m, 2H); 1.98 (m, 1H); 1.39–1.26 (m, 4H). IR (neat) 2095 cm$^{-1}$.

Part C: Preparation of 4-benzyl-1-(3-amino-3-phenylprop-1-yl)piperidine

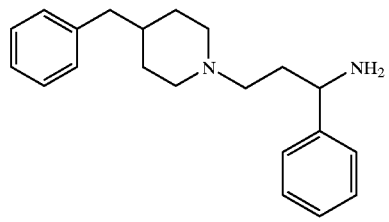

The compound from part B (100 mg), 10% Pd on carbon (120 mg), and methanol (100 mL) were carefully combined in a flask under a N$_2$ atmosphere. The contents were then submitted to 1 atm of H$_2$ being delivered via a sparge tube for 0.5 h at room temperature. Filtration of the contents through Celite® and removal of the solvent in vacuo yielded 70 mg of product. NMR (CDCl$_3$) (key peak only) δ3.94 (t, 1, J=7 Hz). NH$_4$—Cl MS detects (M+H)$^+$=309.

Part D: N-(3-cyanophenyl)-N'-[3-[4-(phenylmethyl)-1-piperidinyl]-1-phenylpropyl]urea

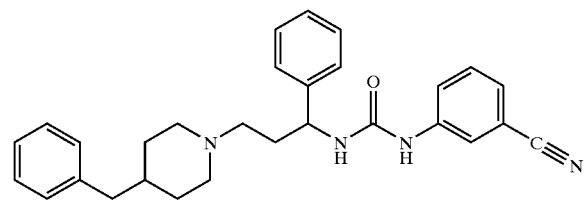

The compound from Part C (57 mg, 0.185 mmol, 1 eq) was mixed and stirred with 3-cyanophenylisocyanate 26.6 mg, 0.185 mmol, 1 eq) in THF (1 mL) overnight at room temperature under a $N_2$ atmosphere. The solvent was removed in vacuo and the residue flash chromatographed on silica gel in 3:1 to 1:1 hexane/ethyl acetate to 100% ethyl acetate to yield 44.3 mg of a yellow oil. NMR (CDCl$_3$) δ7.58 (s, 1H); 7.52 (d, 1H, J=9 Hz); 7.42 (s, 1H); 7.30–7.17 9 m, 8H); 7.12 (m, 3H); 4.82 (m, 1H); 2.97–2.80 (m, 3H); 2.52 (d, 2H, J=7 Hz); 2.35 (m, 2H); 2.05–1.85 (m, 4H); 1.81–1.60 (m, 2H); 1.54 (m, 1H); 1.25 (m, 1H). ESI MS detects $(M+H)^+=453$.

Example 6

Part A: Preparation of 2-benzyloxycarbonylamino-1-phenyl-3-butene.

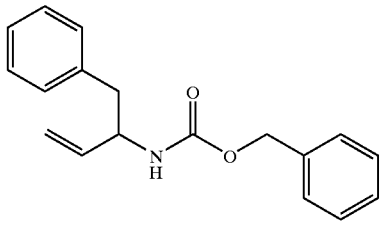

To a stirred suspension of methyltriphenylphosphonium bromide (10.72 g, 0.03 moles) in 100 mL of dry tetrahydrofuran at −78° C. was added dropwise 1.6M n-butyl lithium (17.5 mL, 0.028 moles), and the mixture was stirred for 0.5 hrs at −78~−20° C. Then was added a solution of N-Cbz-phenylalaninal (5.67 g, 0.02 moles) in 50 mL of dry tetrahydrofuran, and the mixture was stirred for 16 hrs at room temperature. After addition of saturated NH4Cl (50 mL) the mixture was extracted with EtOAc, and the extract was washed with water and brine. It was dried over Na2SO4 and evaporated to give an oily residue. The crude product was purified by column chromatograpy on silica gel with elution by 5:95 EtOAc-hexane to give pure 2-benzyloxycarbonylamino-1-phenyl-3-butene.

Part B: Preparation of 2-benzyloxycarbonylamino-1-phenyl-3,4-epoxy-butane.

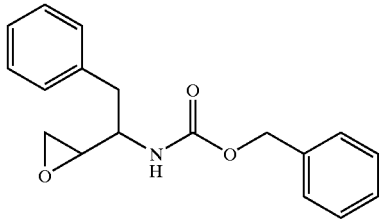

To a stirred solution of 2-benzyloxycarbonylamino-1-phenyl-3-butene (1.43 g, 5.08 mmoles) in 20 mL of CH2Cl2 was added 3-chloroperoxybenzoic acid (2.19 g, 60%, 7.62 mmoles) in several portions, and the mixture was stirred at room temperature for 30 hrs. After addition of EtOAc (60 mL), the mixture was washed with saturated NaHCO3 and brine, and the organic layer was dried over Na2SO4. Evaporation of the solvent afforded an oily residue. The crude product was purified by column chromatography on silica gel with elution by 2:8 EtOAc-hexane to give pure 2-benzyloxycarbonylamino-1-phenyl-3,4-epoxy-butane.

Part C: Preparation of 2-benzyloxycarbonylamino-4-[4-(4-fluorophenyl)methyl-1-piperidinyl]-1-phenyl-butan-3-ol.

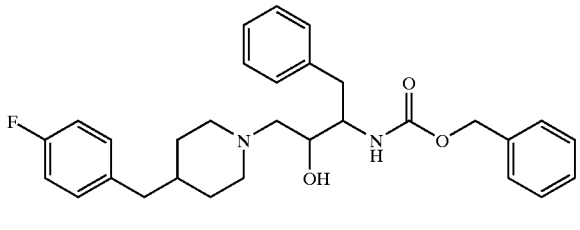

A solution of 4-(4-fluorophenyl)methyl-piperidine (0.515 g, 2.314 mmoles) and 2-benzyloxycarbonylamino-1-phenyl-3,4-epoxy-butane (0.688 g, 2.314 mmoles DMF was stirred for 4 hours at 100° C. and cooled to room temperature. After addition of EtOAc (30 mL), the mixture was washed with water (2x) and brine. The oranic solution was dried over Na2SO4, and evaporated to give an oily residue. It was then purified by passing through a plug of silica gel with elution by EtOAc to give pure product.

Part D: Preparation of 2-amino-4-(4-(4-fluorophenyl) methyl-1-piperidinyl)-1-phenyl-butan-3-ol.

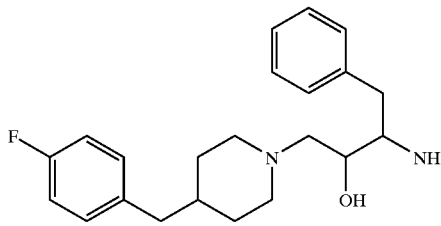

The above product was dissolved in 10 mL of ethanol, and was added 0.1 g of 10% Pd on carbon. The mixture was stirred under hydrogen (1 atm) for 8 hours, and filtered through Celite. Evaporation of the solvent gave the titled product as solid (0.662 g).

Part E: Preparation of N-(3-cyanophenyl)-N'-[1-benzyl-2-hydroxy-3-[4-(4-fluorophenylmethyl)-1-piperidinyl]propyl] urea

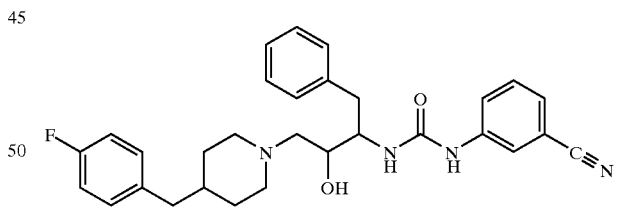

To a solution of 2-amino-4-[4-(4-fluorophenyl)methyl-1-piperidinyl]-1-phenyl-butan-3-ol (50 mg, 0.14 mmoles) in 2.5 mL of dry THF was added 3-cyanophenyl isocyanate (20.2 mg, 0.14 mmoles) and the mixture was stirred for 15 minutes at room temperature. Then the solvent was evaporated off to give an oily residue. It was purified by column chromatography on silica gel with elution by EtOAc to give pure titled compound as an amorphous solid. MS (ES+) for $C_{30}H_{33}FN_4O_2$:501.

The following examples were prepared by the procedures previously described in Schemes 1–25, Examples 1–6 and/or by procedures familiar to one skilled in the art.

TABLE 1*

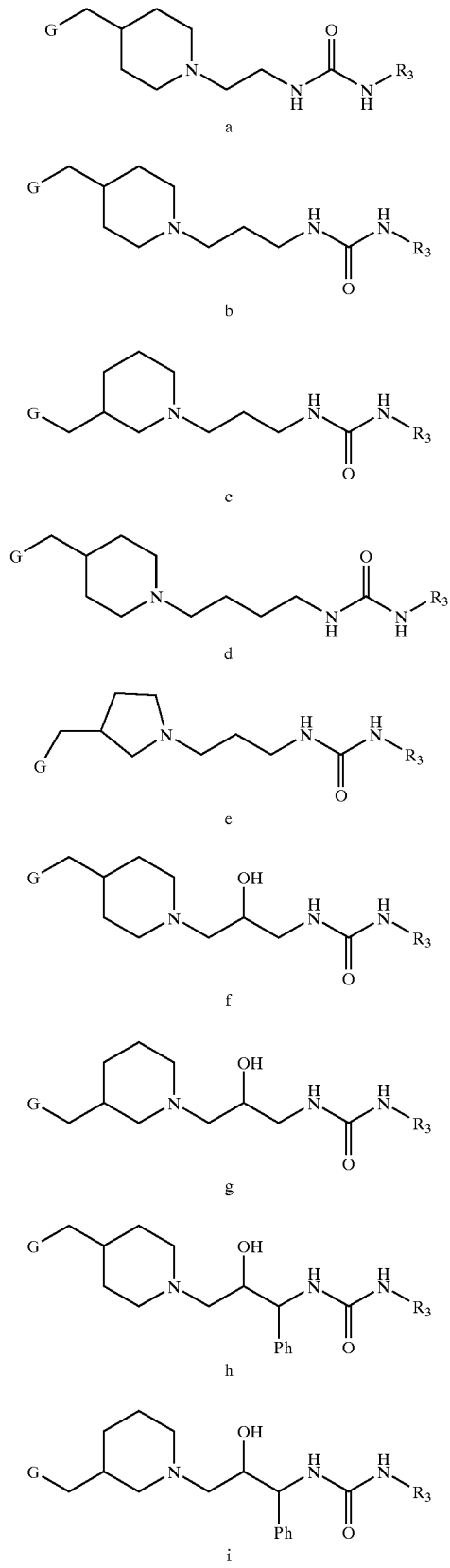

| Ex # | Core | G | R3 | M + 1 |
|---|---|---|---|---|
| 7 | a | Ph | 3-CO2Et—Ph | 410 |
| 8 | a | Ph | 3-I—Ph | 464 |
| 9 | a | Ph | 1-adamantyl | 396 |
| 10 | a | Ph | 3-OCH3—Ph | 368 |
| 11 | a | Ph | Ph | 338 |
| 12 | a | Ph | 4-F—Ph | 356 |
| 13 | a | Ph | 4-CO2Et—Ph | 410 |
| 14 | a | Ph | 4-CN—Ph | 363 |
| 15 | b | Ph | 1-adamantyl | 410 |
| 16 | b | Ph | 2-F-5-CF3—Ph | 438 |
| 17 | b | Ph | 2-naphthyl | 402 |
| 18 | b | Ph | 2-F-5-NO2—Ph | 415 |
| 19 | b | Ph | 4-N(CH3)2—Ph | 395 |
| 20 | b | Ph | 2-NO2—Ph | 397 |
| 21 | b | Ph | 2-C2H5—Ph | 380 |
| 22 | b | Ph | 4-CF4—Ph | 420 |
| 23 | b | Ph | 3,5-diCF3—Ph | 488 |
| 24 | b | Ph | 3-CO2Et—Ph | 424 |
| 25 | b | Ph | 3-CN—Ph | 377 |
| 26 | b | Ph | 4-OBn—Ph | 458 |
| 27 | b | Ph | 2-Ph—Ph | 428 |
| 28 | b | Ph | 2-BrPh | 431 |
| 29 | b | Ph | 4-I—Ph | 478 |
| 30 | b | Ph | 3-I—Ph | 478 |
| 31 | b | Ph | 4-OEt—Ph | 396 |
| 32 | b | Ph | 4-nBu—Ph | 408 |
| 33 | b | Ph | 4-nBuO—Ph | 424 |
| 34 | b | Ph | CH(Bn)CO2Et | 452 |
| 35 | b | Ph | CH(iPr)CO2Et | 404 |
| 36 | b | Ph | nC8H17 | 388 |
| 37 | b | Ph | 3-OCH3—Ph | 382 |
| 38 | b | Ph | Ph | 352 |
| 39 | b | Ph | 4-CO2Et—Ph | 424 |
| 40 | b | Ph | 4-F—Ph | 370 |
| 41 | b | Ph | 2-Phenyl-cyclopropyl | 392 |
| 42 | b | Ph | 2-OCH3—Ph | 382 |
| 43 | b | Ph | 4-OCH3—Ph | 382 |
| 44 | b | 4-F—Ph | 3-CN—Ph | 395 |
| 45 | b | 4-F—Ph | 4-F—Ph | 388 |
| 46 | b | 4-F—Ph | 4-CO2Et—Ph | 442 |
| 47 | b | 3,4-OCH2O—Ph | 3-CN—Ph | 421 |
| 48 | b | 4-F—Ph | 3-OCH3—Ph | 400 |
| 49 | b | 3,4-OCH2O—Ph | 3-CO2Et—Ph | 468 |
| 50 | b | 3,4-OCH2O—Ph | 3-OCH3—Ph | 426 |
| 51 | b | 4-OCH3—Ph | 3-OCH3—Ph | 412 |
| 52 | b | 4-OCH3—Ph | 4-F—Ph | 400 |
| 53 | b | Ph | 4-CN—Ph | 377 |

TABLE 1*-continued

| 54 | b | 3,4-OCH2O—Ph | 4-F—Ph | 414 |
| 55 | b | 4-OCH3—Ph | 4-CN—Ph | 407 |
| 56 | b | 2,4-diF—Ph | 4-F—Ph | 406 |
| 57 | b | 2,4-diF—Ph | 3-OCH3—Ph | 418 |
| 58 | b | 2,4-diF—Ph | 3-CN—Ph | 413 |
| 59 | b | 3-CF3—Ph | 4-F—Ph | 438 |
| 60 | b | 3-CF3—Ph | 3-OCH3—Ph | 450 |
| 61 | b | 4-F—Ph | CH2Ph | 384 |
| 62 | b | 4-F—Ph | CH2CH2Ph | 398 |
| 63 | b | 4-F—Ph | 2-F—Ph | 388 |
| 64 | b | 4-F—Ph | 3-F—Ph | 388 |
| 65 | b | 4-F—Ph | cyclohexyl | 376 |
| 66 | b | 4-F—Ph | iPr | 336 |
| 67 | b | 4-F—Ph | 2-phenyl-cyclopropyl | 410 |
| 68 | b | 4-CF3—Ph | 3-CN—Ph | 445 |
| 69 | b | 3-CF3—Ph | 3-CN—Ph | 445 |
| 70 | b | 4-CH3—Ph | 3-OCH3—Ph | 396 |
| 71 | b | 4-CH3—Ph | 3-CN—Ph | 391 |
| 72 | b | 4-Cl—Ph | 3-CN—Ph | 411 |
| 73 | b | 4-CF3—Ph | 4-CO2Et—Ph | 492 |
| 74 | b | 3-OCH3—Ph | 3-OCH3—Ph | 412 |
| 75 | b | 3-OCH3—Ph | 3-CN—Ph | 407 |
| 76 | b | 4-CO2CH3—Ph | 3-OCH3—Ph | 440 |
| 77 | b | 4-CO2CH3—Ph | 3-CN—Ph | 435 |
| 78 | b | 4-CO2CH3—Ph | 4-F—Ph | 428 |
| 79 | b | 4-CO2CH3—Ph | 4-CO2CH3—Ph | 482 |
| 80 | b | 4-CF3—Ph | 4-F—Ph | 438 |
| 81 | b | 4-CF3—Ph | 3-OCH3—Ph | 450 |
| 82 | b | 3-OCH3—Ph | 4-F—Ph | 400 |
| 83 | b | 3-OCH3—Ph | 4-CO2Et—Ph | 454 |
| 84 | b | 2-F—Ph | 3-CN—Ph | 395 |
| 85 | b | 3-OCH3—Ph | 3-F—Ph | 400 |
| 86 | b | 2-F—Ph | 3-OCH3—Ph | 400 |
| 87 | b | 3-OCH3—Ph | 3-CO2Et—Ph | 454 |
| 88 | b | 2-F—Ph | 3-F—Ph | 388 |
| 89 | b | 2-F—Ph | 4-F—Ph | 388 |
| 90 | b | 2-F—Ph | 3-CO2Et—Ph | 442 |
| 91 | b | 3-F—Ph | 3-CN—Ph | 395 |
| 92 | b | 3,4-diF—Ph | 3-CN—Ph | 413 |
| 93 | b | 3,4-diF—Ph | 3-OCH3—Ph | 418 |
| 94 | b | 4-Cl—Ph | 4-F—Ph | 404 |
| 95 | b | 4-Cl—Ph | 3-OCH3—Ph | 416 |
| 96 | b | 2-F—Ph | 4-CO2Et—Ph | 442 |
| 97 | b | 3-F—Ph | 3-OCH3—Ph | 400 |
| 98 | b | 3-F—Ph | 4-F—Ph | 388 |
| 99 | b | 3-F—Ph | 4-CO2Et—Ph | 442 |
| 100 | b | 3,4-diF—Ph | 4-F—Ph | 406 |
| 101 | b | 3-Cl—Ph | 3-CN—Ph | 411 |
| 102 | b | 4-F—Ph | 3-COCH3—Ph | 412 |
| 103 | b | 3,5-diF—Ph | 3-CN—Ph | 413 |
| 104 | b | 3,5-diF—Ph | 3-OCH3—Ph | 418 |
| 105 | b | 4-F—Ph | 4-COCH3—Ph | 412 |
| 106 | b | 1-naphthyl | 3-CN—Ph | 427 |
| 107 | b | 1-naphthyl | 4-F—Ph | 420 |
| 108 | b | 1-naphthyl | 3-OCH3—Ph | 432 |
| 109 | b | 3-CH3—Ph | 3-CN—Ph | 391 |
| 110 | b | 3-CH3—Ph | 4-F—Ph | 384 |
| 111 | b | 3-CH3—Ph | 3-OCH3—Ph | 396 |
| 112 | b | 4-F—Ph | 2-iPr—Ph | 412 |
| 113 | b | 4-F—Ph | 2-CF3—Ph | 438 |
| 114 | b | 4-F—Ph | 3-Cl—Ph | 404 |
| 115 | b | 4-F—Ph | 3-CF3—Ph | 438 |
| 116 | b | 4-F—Ph | 4-Ph—Ph | 446 |
| 117 | b | 4-F—Ph | 2-Cl—Ph | 404 |
| 118 | b | 4-F—Ph | 2,4-diF—Ph | 406 |
| 119 | c | Ph | 3-CO2Et—Ph | 424 |
| 120 | c | Ph | 3-CN—Ph | 377 |
| 121 | c | Ph | 4-F—Ph | 370 |
| 122 | c | Ph | Ph | 352 |
| 123 | c | Ph | 1-adamantyl | 410 |
| 124 | c | Ph | 4-CO2Et—Ph | 424 |
| 125 | c | 4-F—Ph | Ph | 370 |
| 126 | c | 4-F—Ph | 3-CN—Ph | 395 |
| 127 | c | 4-F—Ph | 1-adamantyl | 428 |
| 128 | c | 4-F—Ph | 3-OCH3—Ph | 400 |
| 129 | c | 4-F—Ph | 3-CO2Et—Ph | 442 |
| 130 | c | 4-F—Ph | 4-F—Ph | 388 |
| 130a | c | 4-F—Ph | 3-COCH3—Ph | 412 |
| 131 | c | 2-F—Ph | Ph | 370 |
| 132 | c | 2-F—Ph | 3-CN—Ph | 395 |
| 133 | c | 2-F—Ph | 3-OCH3—Ph | 400 |
| 134 | c | 2-F—Ph | 4-F—Ph | 388 |
| 135 | c | 3-F—Ph | 3-OCH3—Ph | 400 |
| 136 | c | 3-F—Ph | 3-CN—Ph | 395 |
| 137 | c | 2,4-diF—Ph | 3-CN—Ph | 413 |
| 138 | c | 2,4-diF—Ph | 3-OCH3—Ph | 418 |
| 139 | c | 2,4-diF—Ph | Ph | 388 |
| 140 | c | 2,4-diF—Ph | 4-F—Ph | 406 |
| 141 | c | 2,4-diF—Ph | 3-COCH3—Ph | 430 |
| 142 | d | Ph | 3-CN—Ph | 391 |
| 143 | d | Ph | 3-CO2Et—Ph | 438 |
| 144 | d | Ph | 3-I—Ph | 492 |
| 145 | d | Ph | 4-OCH2Ph—Ph | 472 |
| 146 | d | Ph | 1-adamantyl | 424 |
| 147 | d | Ph | 3-OCH3—Ph | 396 |
| 148 | d | Ph | Ph | 366 |
| 149 | d | Ph | 4-F—Ph | 384 |
| 150 | d | Ph | 4-CO2Et—Ph | 438 |
| 151 | d | Ph | 4-CN—Ph | 391 |
| 152 | e | 4-F—Ph | Ph | 356 |
| 153 | e | 4-F—Ph | 3-CN—Ph | 381 |
| 154 | e | 4-F—Ph | 3-OCH3—Ph | 386 |
| 155 | e | 4-F—Ph | 4-F—Ph | 374 |
| 156 | e | 4-F—Ph | 3-CO2Et—Ph | 428 |
| 157 | e | 4-F—Ph | 4-CO2Et—Ph | 428 |
| 158 | e | 4-F—Ph | 1-adamantyl | 414 |
| 159 | f | 4-F—Ph | 3-CN—Ph | 411 |
| 160 | f | 4-F—Ph | 3-OCH3—Ph | 416 |
| 161 | j | Ph | Ph | 458 |
| 162 | j | Ph | 3-CN—Ph | 483 |
| 163 | j | Ph | 3-OCH3—Ph | 488 |
| 164 | j | 4-F—Ph | 3-OCH3—Ph | 506 |
| 165 | j | 4-F—Ph | 4-F—Ph | 494 |
| 166 | j | 4-F—Ph | 1-adamantyl | 534 |
| 167 | l | Ph | 3-OCH3—Ph | 458 |
| 168 | l | Ph | 1-adamantyl | 486 |
| 169 | c | imidazol-1-yl | 3-OCH3—Ph | 372 |

*All stereocenters are (+/−) unless otherwise indicated

TABLE 2**

| Ex # | Y | Z | R4 | X | R$_{5a}$ | R$_{5b}$ | R$_{5c}$ | R1 | R2 |
|---|---|---|---|---|---|---|---|---|---|
| 170 | H | H | — | — | H | H | H | H | Ph |
| 171 | H | H | — | — | H | H | H | H | CH3 |
| 172 | H | 3-OCH3 | CH2Ph | Br | H | H | H | H | H |
| 173 | H | 3-CN | — | — | CO2Et | H | H | H | H |
| 174 | H | 3-OCH3 | CH3 | I | H | H | H | H | H |
| 175 | H | 3-CN | CH3 | I | H | H | H | H | H |
| 176 | H | 3-CN | CH2Ph | Br | H | H | H | H | H |
| 177 | H | 3-CN | — | — | H | H | H | CH2Ph | H |
| 178 | H | 3-CN | — | — | H | H | H | Et | H |
| 179 | H | 4-F | CH3 | I | H | H | H | H | H |
| 180 | H | 4-F | CH2Ph | Br | H | H | H | H | H |
| 181 | H | 4-F | CH2CO2CH3 | Br | H | H | H | H | H |
| 182 | H | 3-CN | CH2CN | Br | H | H | H | H | H |
| 183 | H | 3-CN | CH2COPh | Br | H | H | H | H | H |
| 184 | H | 2-OCH3 | CH3 | I | H | H | H | H | H |
| 185 | H | 4-OCH3 | CH3 | I | H | H | H | H | H |
| 186 | F | 3-CN | CH3 | I | H | H | H | H | H |
| 187 | H | 3-CN | — | — | H | H | H | H | H |
| 188 | H | 3-OCH3 | O | — | H | H | H | H | H |
| 189 | H | 3-OCH3 | — | — | | | CH2Ph | | |
| 190 | F | 3-CN | CH3 | I | H | H | H | H | H |
| 191 | F | 3-COCH3 | — | — | H | CH2Ph | H | H | H |
| 192 | F | 4-F—Ph | — | — | H | CH2Ph | H | H | H |
| 193 | F | 3-OCH3 | — | — | H | CH2Ph | H | H | H |
| 194 | H | 3-OCH3 | — | — | H | H | H | CH2Ph | H |
| 195 | H | 3-CN | — | — | H | H | H | CH2Ph | H |

**All compounds are amorphous unless otherwise indicted.

TABLE 3**

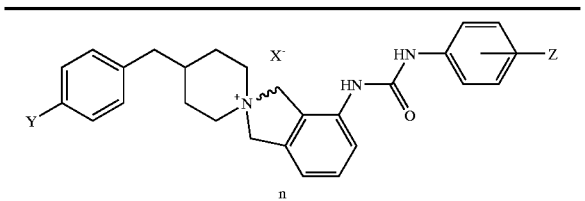

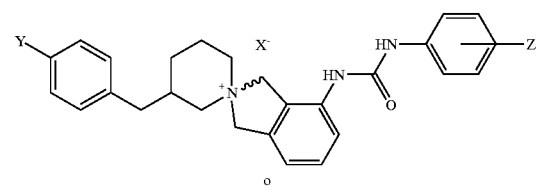

| Ex # | Core | Y | Z | X |
|---|---|---|---|---|
| 196 | n | H | 3-CN | Br |
| 197 | n | H | 3-CN | Br |
| 198 | n | H | 4-F | Br |
| 199 | n | H | 4-F | Br |
| 200 | n | F | 3-CN | Br |
| 201 | n | F | 3-CN | Br |
| 202 | n | F | 3-OCH3 | Br |
| 203 | n | F | 3-OCH3 | Br |
| 204 | o | F | 4-F | Br |

TABLE 3**-continued

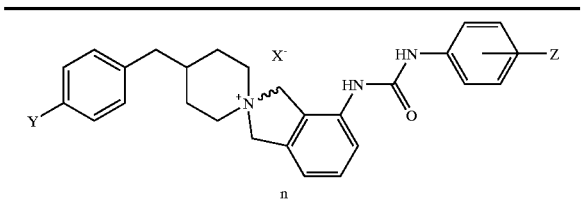

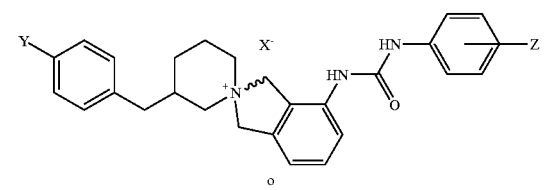

| Ex # | Core | Y | Z | X |
|---|---|---|---|---|
| 205 | o | F | 4-F | Br |
| 206 | o | F | 3-OCH3 | Br |
| 207 | o | F | 3-OCH3 | Br |
| 208 | o | F | 3-CN | Br |
| 209 | o | F | 3-CN | Br |

**All compounds are amorphous unless otherwise indicted.

The compounds of the present invention in which E contains ring A can be prepared in a number of ways well known to one skilled in the art of organic synthesis. As shown in Scheme 26, 4-benzyl piperidine is N-alkylated with an alkylating agent, such as 165 (2-nitro-benzyl bromide (X=Br, $R^{14}$=H), Scheme 26) to give the N-benzyl compound 166. The nitro group of 166 is then reduced using catalytic hydrogenation to give the corresponding aniline 167. The aniline can be converted to the carbamate 168 using chloro-phenyl formate. The carbamate 168 can then be reacted with various amines to give the urea 169. Alternatively, the aniline 167 can be reacted with the appropriate isocyanates to give the urea 169 directly. The saturated ring analogs can also be used. For example, 4-benzyl piperidine can be alkylated with the urea mesylate 185. Scheme 30) to give corresponding cyclohexyl derivative 186.

As shown in Scheme 27, 4-benzyl piperidine can also be N-alkylated with the phenacyl bromide 170 to give the nitro ketone 171. The nitro group of 171 is then reduced using catalytic hydrogenation to give the corresponding aniline 172. The aniline 172 can be reacted with the appropriate isocyantes to give the ketone urea 173. The ketone of 173 can be reduced with $NaBH_4$ to give the alcohol 174.

Alternatively, the epoxide 175 ($R^{14}$=H) can be opened with the 4-benzyl piperidine to give the corresponding nitro benzyl alcohol which is hydrogenated to give the aniline alcohol 176. The aniline 176 may be treated with various isocyanates to give the urea alcohols 174.

The 4-benzyl piperidine can also be N-alkylated with 3-cyanobenzyl bromide (177, Scheme 28) to give the cyano analog 178. The cyano group is reduced using Raney nickel to give the corresponding benzyl amine 179. Treatment of 179 with isocyanates gives the urea 180.

As shown in Scheme 29, treatment of 3-cyano aniline with phenylisocyanate gives the urea 182. The cyano group of 182 is converted to the imidate 183 by HCl/ethanol. Reaction with 4-benzyl piperidine in ethanol then gives the amidine 184.

The saturated ring analogs can also be synthesized using analogous procedures as outlined in Schemes 30 and 31. For example, 4-benzyl piperidine can be alkylated with the urea mesylate 185 (Scheme 29) to give corresponding cyclohexyl derivative 186. Alternatively, starting with the enantiomerically pure amino alcohol 187 [*J. Am. Chem. Soc.* 1996, 118, 5502-5503 and references therein] one can protect the nitrogen to give the N-Cbz alcohol 188. Swern oxidation of the alcohol gives the aldehyde 189. Reductive amination with piperidine analogs gives the cyclohexyl methyl-1-piperidinyl analogue 190. The Cbz group is removed by catalytic hydrogenation to give the free amine 191, which is treated with a phenylisocyanate to give the desired urea analogue 192. Several examples using these synthetic methods are listed in Table 3*a* and Table 3.1.

SCHEME 26

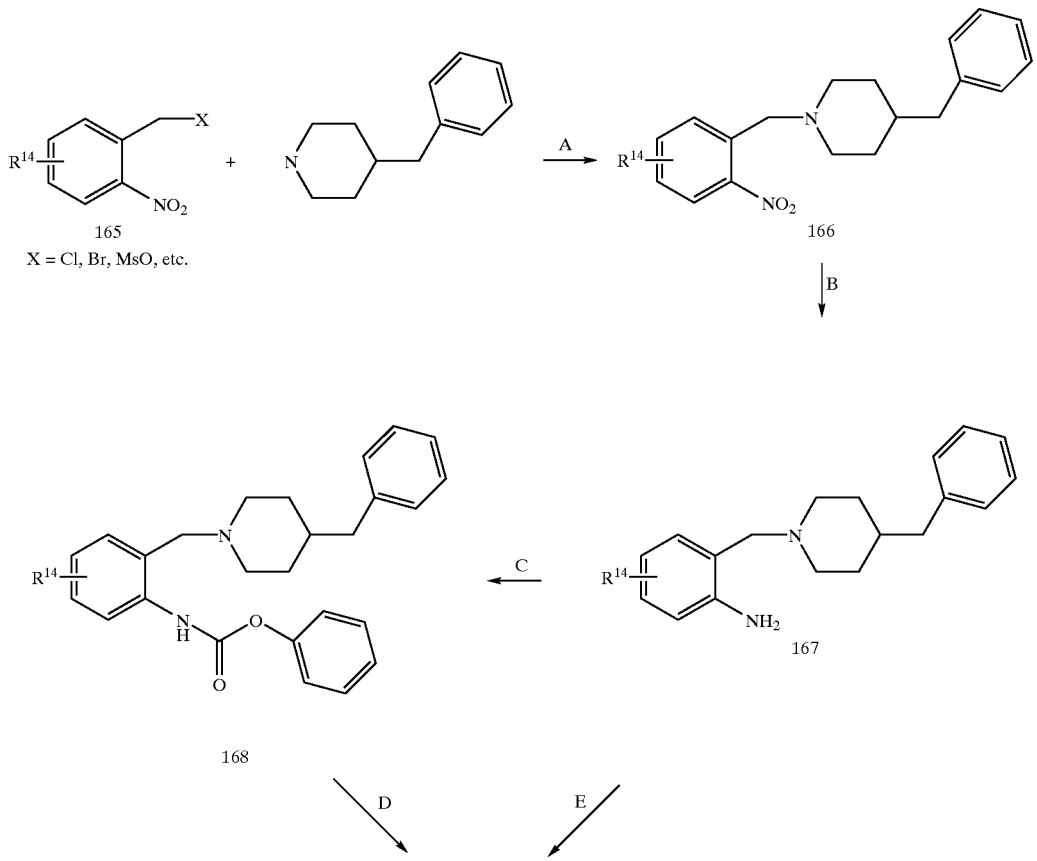

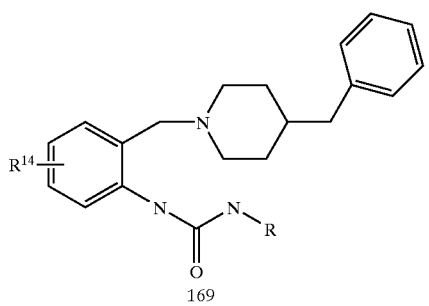
169
A: DMF/K₂CO₃/RT or THF/RT. B: 10% Pd/C, H₂ 50 psi.
C: THF/Et₃N/chlorophenylformate. D: NHR/DMF/50° C.
E: R—N=C=O/THF
SCHEME 27
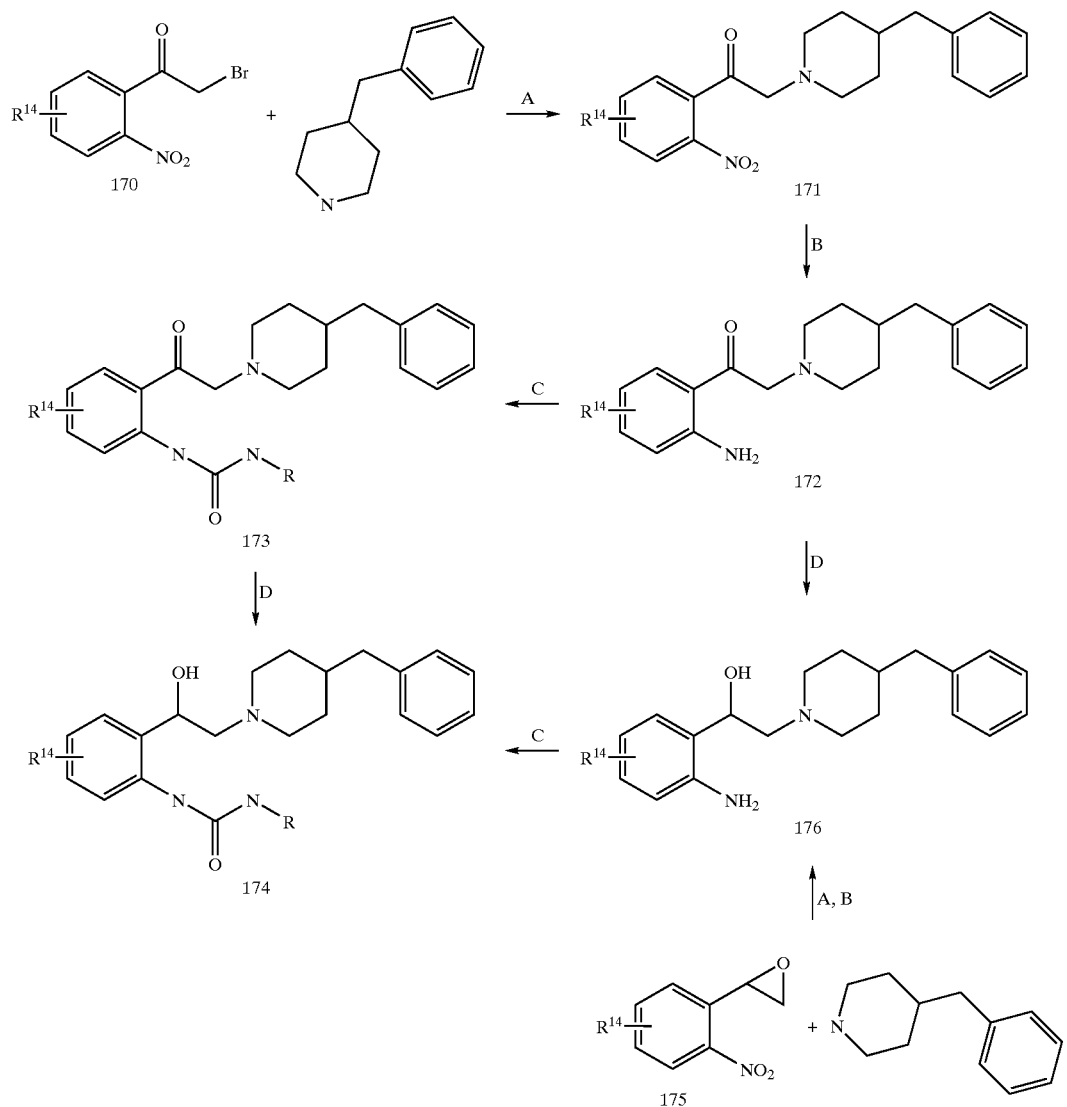
A: DMF/K₂CO₃/RT or DMF/50iC.
B: 10% Pd/C, H₂ 50 psi.
C: R—N=C=O/THF. D: NaBH₄/MeOH/RT

SCHEME 28
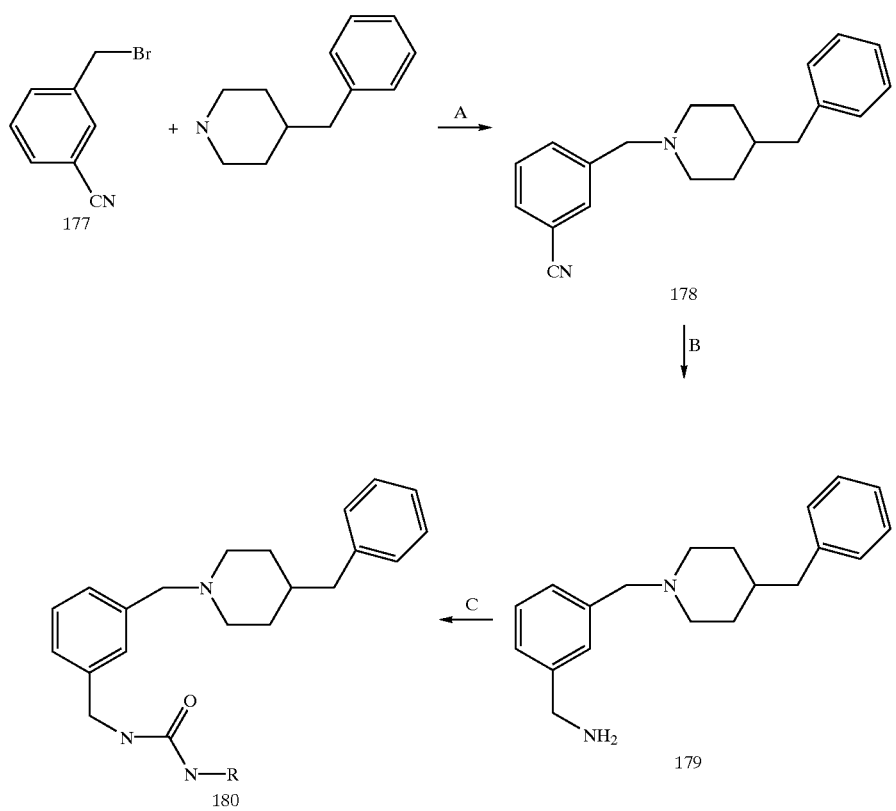
A: DMF/K$_2$CO$_3$ RT  B: Raney nickel, H$_2$ 50 psi.
C: R—N═C═O/THF.
SCHEME 29
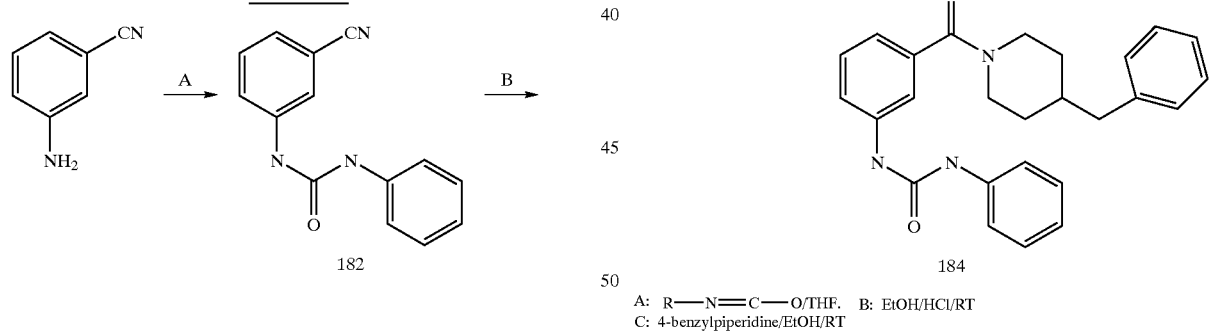
A: R—N═C═O/THF.  B: EtOH/HCl/RT
C: 4-benzylpiperidine/EtOH/RT
SCHEME 30
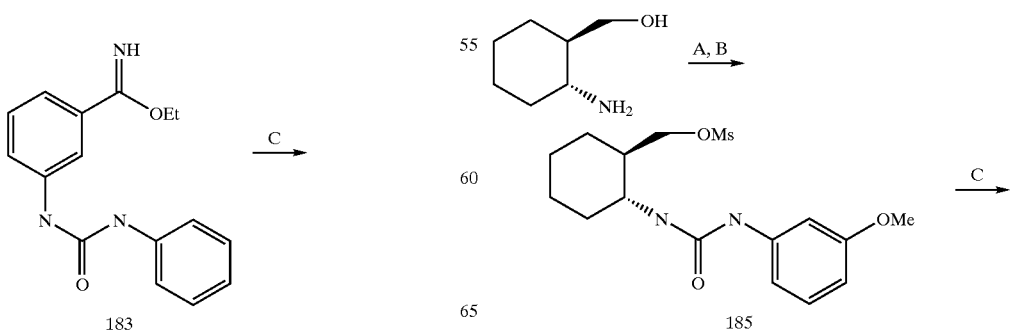

115
-continued
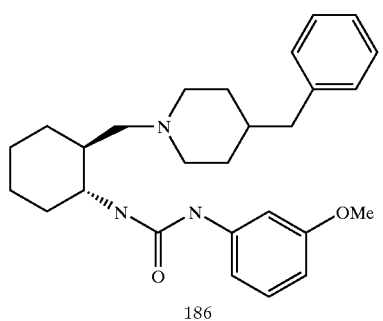
186
A: R—N=C=O/DMF.  B: Ms—Cl/THF
C: 4-benzylpiperidine/DMF/RT
116
-continued
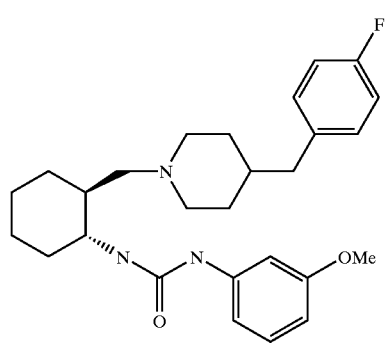
192
a: Benzyl chloroformate/Na$_2$CO$_3$/CH$_2$Cl$_2$. b.Swern
Ox.  c:NaBH(OAc)$_3$ d:H$_2$/10% Pd/C  e: R—N=C=O/THF.
SCHEME 31
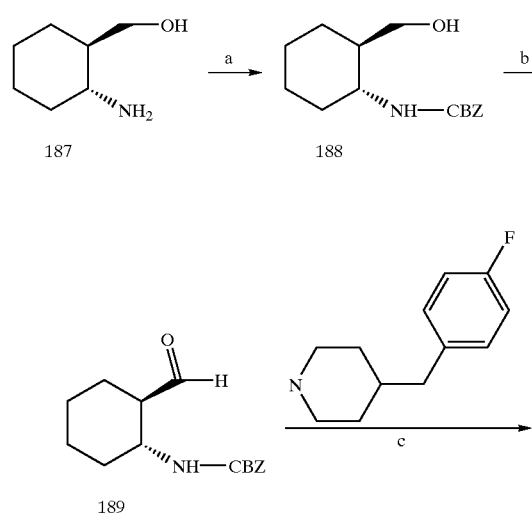
SCHEME 31a
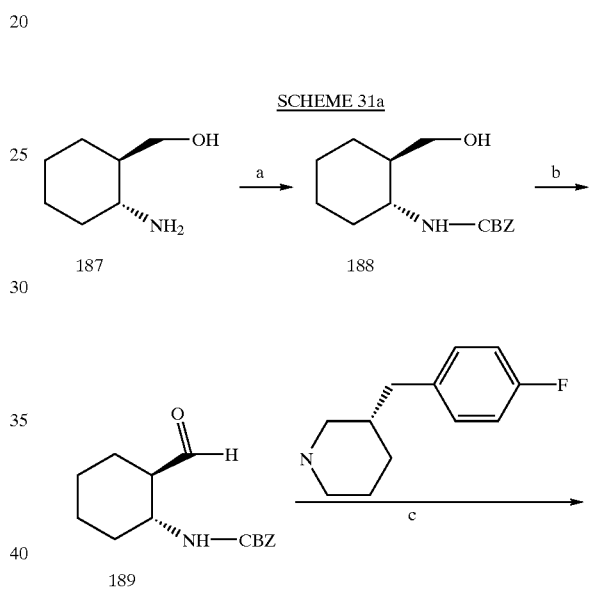
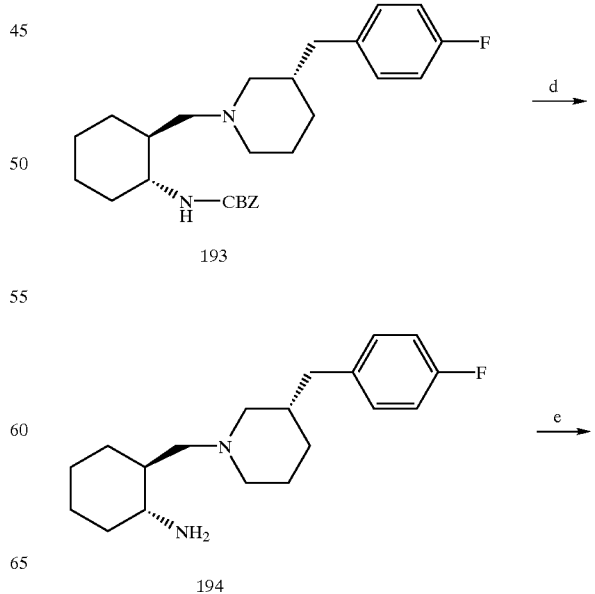

-continued

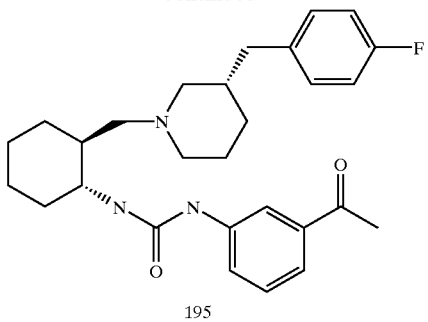

195 a: Benzyl chloroformate/Na₂CO₃/CH₂Cl₂. b.Swern Ox.
c:NaBH(OAc)₃ d:H₂/10% Pd/C  e: R—N═C═O/THF.

The following examples were synthesized using the methods outlined in Schemes 26–31a. These examples are meant to be illustrative of the present invention, and are not to be limiting thereof.

Example 218

N-[1-(phenylmethyl)4-piperidinyl]-N'-[2-[[4-(phenylmethyl)-1-piperidinyl]-methyl]phenyl]urea.

A solution of 4-benzylpiperidine (1.75 g, 10 mmol) in 25 mL of DMF was treated with 2-nitrobenzyl bromide (2.16 g, 10 mmol) and K₂CO₃ (1.38 g, 10 mmol) and the reaction mixture stirred at room temperature for 2 h. The mixture was diluted with water and extracted into ethyl acetate. The organic extracts were washed successively with water and brine, and the organic solvent removed under vacuum on a rotary evaporator to give 166 (Scheme 26, $R^{14}$=H) as a yellow oil.

The oil was re-dissolved in ethyl acetate (50 ml) and treated with 10% Pd/C and hydrogenated at 50 psi hydrogen at room temperature for 40 min. The solution was then filtered and the solvent removed under vacuum to give the aniline 167 as a white solid. The aniline was purified by chromatography (MPLC, 40% ethyl acetate/hexane; silica gel) to give 2.0 g of aniline 167 as a white solid.

A solution of aniline 167 (1.2 g, 4.3 mmol) in THF was treated with Et₃N (1.0 g, 10 mmol) and cooled in an ice bath to 0° C. Chlorophenyl formate (0.71 g, 4.5 mmol) was added to the mixture and stirred for 1 h. The mixture was diluted with water and extracted into ethyl acetate. The extracts were washed with water and brine, and the solvent removed under vacuum to give the phenyl carbamate 168 as an off-white solid. The crude product was used without further purification.

A solution of phenylcarbamate 168 (0.2 g, 0.5 mmol) in DMF is treated with 4-amino-1-benzylpiperidine (95 mg, 0.5 mmol) and K₂CO₃ (138 mg, 1 mmol) and the mixture was heated at 50° C. for 2 h. The mixture was diluted with water and extracted into ethyl acetate. The extracts were washed with water and brine, and the solvent removed under vacuum. The residue was purified by chromatography (MPLC, 0–25% MeOH/ethyl acetate; silica gel) to give 200 mg of the target compound as a white solid. esi ms: $(M+H)^+$=497.

Example 219

N-(2,5-difluorophenyl)-N'-[2-[[4-(phenylmethyl)-1-piperidinyl]-methyl)phenyl]urea A solution of aniline 167 (Scheme 26; ($R^{14}$=H)) (140 mg, 0.5 mmol) in THF is treated with 2,5-difluoro-isocyanate (80 mg, 0.5 mmol) at room temperature for 1 h. The solvent is removed under vacuum and the residue was purified by chromatography (MPLC, 20% EtOAc/Hexane, silica gel) to give the desired urea as a white solid. esi ms: $(M+H)^+$=436.

Example 220

N-(2,5-difluorophenyl)-N'-[[3-[[4-(phenylmethyl)-1-piperidinyl]methyl]phenyl]methyl]urea A solution of 4-benzylpiperidine (1.75 g, 10 mmol) in 25 mL of DMF was treated with 3-cyanobenzyl bromide 177 (1.96 g, 10 mmol) and K₂CO₃ (2.76 g, 20 mmol) and the reaction mixture stirred at room temperature for 2 h. The mixture was diluted with water and extracted into ethyl acetate. The organic extracts were washed successively with water and brine, and the organic solvent removed under vacuum on a rotary evaporator to give 178 (Scheme 28) as a yellow oil.

To a suspension of Raney nickel (2.0 g) in EtOH (saturated with $NH_{3(gas)}$) was added crude 178 (Scheme 28) (1.45 g, 5 mmol) and hydrogenated at 50 psi for 3 days. The solution was then filtered and the solvent removed under vacuum to give the amine 179 as a yellow oil. A solution of amine 179 (200 mg, 0.68 mmol) in THF is treated with 2,5-difluoroisocyanate (115 mg, 0.74 mmol) at room temperature for 1 hour. The solvent is removed under vacuum and the residue is washed with 1 NaOH and water to give the desired urea as a white solid. esi ms: $(M+H)^+$=450.

Example 221

N-(2,5-difluorophenyl)-N'-[2-[[4-(phenylmethyl)-1-piperidinyl]acetyl]phenyl]urea To an ice cold solution of 2-bromo-2'-nitro-acetophenone 170 (2.4 g, 10 mmol) in DMF is added 4-benzylpiperidine (1.75 g, 10 mmol) and stirred for 30 min. The solution was poured into a mixture of K₂CO₃ (1.38 g, 10 mmol) in water/ice and extracted into ethyl acetate. The ethyl acetate extract was washed several times with water. The resultant ethyl acetate solution of crude nitroketone 171 is treated with 10% Pd/C and hydrogenated at 50 psi hydrogen at room temperature for 40 min. The solution was then filter, the solvent removed under vacuum, and the residue purified by chromatography (MPLC, 30% ethyl acetate/hexane; silica gel) to give 1.8 g of aniline 172 as a tan/brown solid.

A solution of aniline 172 (Scheme 27) (310 mg, 1.0 mmol) in THF is treated with 2,5-difluoroisocyanate (160 mg, 1.0 mmol) at room temperature for 1 h. The solvent is removed under vacuum and the residue is purified by chromatography (MPLC, 20% EtOAc/Hexane, silica gel) to give 420 mg of the desired urea-ketone 173 as a white solid. esi ms: $(M+H)^+$=464.

Example 222

N-(2,5-difluorophenyl)-N'-[2-[2-[4-(phenylmethyl)-1-piperidinyl]-1-hydroxyethyl]phenyl]urea A solution of the urea-ketone 173 (260 mg, 0.56 mmol) in MeOH is treated with NaBH₄ (400 mg, 11 mmol) at room temp for 1 hour. The solvent is removed under vacuum and the residue is treated with 1 N NaOH and extracted into EtOAc. The extracts are washed with water, brine and the solvent removed under vacuum to give the desired alcohol 174 as a white solid. esi ms: $(M+H)^+$=466.

Example 223

N-[3-[imino-[4-(phenylmethyl)-1-piperidinyl]methyl]phenyl]-N'-phenylurea

A solution of 3-cyanoaniline (3.54 g, 30 mmol) in THF is treated with phenylisocyanate (3.58 g, 30 mmol) at room temperature for 1 h. The solvent is removed under vacuum and the residue is titurated with hexane to give 7 grams of urea 182 (Scheme 29) as a white solid. Urea 182 (1.0 g, 4.2 mmol) is dissolved in EtOH, cooled in an ice bath while HCl is bubbled-in for 20 min. The solution is left standing at room temperature for 24 h. The solvent is removed under vacuum to give 1.1 g of the imidate 183 as a white solid. The crude imidate (0.5 g, 1.8 mmol) was dissolved in EtOH and treated with 4-benzyl-piperidine (1.8 g, 10 mmol) at room temperature for 2 days. The solvent was removed under vacuum and the residue was purified by chromatography (MPLC, 0 to 30% MeOH/EtOAc, silica gel) to give 200 mg of the desired amidine 184 (Scheme 29) as a white solid. esi ms: (M+H)$^+$=413.

Example 416

N-(3-methoxyphenyl)-N'-[(1R,2S)-2-[[(4-phenylmethyl) piperidinyl]methyl]cyclohexyl]urea Step a: To a solution of (R,R) amino alcohol 187 [*J. Am. Chem. Soc.* 1996, 118, 5502-5503 and references therein] (1.9 g, 14.7 mmol) in CH$_2$Cl$_2$ (50 mL) is added 50 ml of an aqueous solution of Na$_2$CO$_3$ (2.4 g, 28.9 mmol). While stirring, benzyl chloroformate (2.51 g, 14.7 mmol) is added and the mixture is stirred at room temperature for 1 h. The organic layer is separated and washed with water and brine. The solution is concentrated on a rotary evaporator and the residue is chromatographed on silica gel (30% ethyl acetate/hexane) to give 3.1 g (12 mmol) of 188 as a white solid. $^1$H NMR (300 MHz, CDCl$_3$) δ 7.40–7.29 (m, 5 H), 5.11 (s, 2 H), 4.71 (bd, 1 H), 3.76–3.71 (m, 1 H), 3.53–3.28 (m, 3 H), 2.00–1.95 (m, 1 H), 1.90–1.09 (m, 8 H). MS AP$^+$ (M+H)$^+$= 264.3 (100%)

Step b: A solution of DMSO (2.52 g, 30 mmol) in CH$_2$Cl$_2$ (50 mL) is cooled to −78° C. To this solution is added drop-wise oxalyl chloride (1.81 g, 14 mmol) and the resulting solution is stirred for an additional 10 min. Then a solution of alcohol 188 (2.5 g, 9.5 mmol) in CH$_2$Cl$_2$ (70 ml) is added via an addition funnel and stirred for 10 min. Then Et3N (5.0 g, 50 mmol) is added and the solution is allowed to warm to room temperature. The solution is diluted with water and the organic layer washed with water, 1 N HCl, and brine. The organic layer is dried over Na$_2$SO$_4$, filtered, and concentrated to give 2.5 g (9.5 mmol) of the aldehyde 189 as a white solid. $^1$H NMR (300 MHz, CDCl$_3$) δ 9.59 (d, 3.6 Hz, 1 H), 7.38–7.28 (m, 5 H), 5.07 (m, 2 H), 4.69 (m, 1 H), 3.84 (m, 21 H), 2.19–2.11 (m,1 H), 2.09–2.01 (m, 1 H), 1.86–1.75 (m, 3 H), 1.54–1.17 (m, 4 H).

Step c: A solution of aldehyde 189 (2.0 g, 7.7 mmol), 4-(4-fluorophenylmethyl)piperidine hydrochloride (1.8 g, 7.8 mmol) in dichloroethane (80 ml) was treated with Na(OAc)$_3$BH (3.23 g, 15 mmol) and 1 ml AcOH and stirred overnight at room temperature. The resulting solution was diluted with methylene chloride and washed with 1 n NaOH, water, and brine. The organic solvents were removed under vacuum and the residue chromatographed on silica gel (50% EtOAc/hex—100% EtOAc) to give 3.0 g (6.8 mmol) of 190 as an oil.

Step d: A solution of 190 (3.0 g, 6.8 mmol) in MeOH was treated with 1.5 g of 10% Pd/C and hydrogenated at 50 psi overnight in a Parr apparatus. The mixture was filtered and the filtrate concentrated on a rotary evaporator to give 1.8 g (5.9 mmol) of the amine 191 as an oil.

Step e: A solution of amine 191 (200 mg, 0.67 mmol) in THF is treated with 3-methoxyphenyl isocyanate (110 mg, 0.75 mmol) and the mixture is stirred for 30 min. The solvent is removed on a rotary evaporator and the residue is chromatographed on silica gel (50% EtOAc/hex—100% EtOAc) to give 250 mg of urea 192 as a solid. MS esi: (M+H)$^+$=454.4 (100%), HRMS (M+H)$^+$=454.2875.

Example 415

N-(3-acetylphenyl)-N'-[(1R,2S)-2-[[(3S)-3-(4-fluorophenyl)methyl]piperidinyl]methyl]cyclohexyl] urea Step a: To a solution of (R,R) amino alcohol 187 [*J. Org. Chem.* 1996, 61, 5557–5563; *J. Am. Chem. Soc.* 1996, 118, 5502–5503] (9.5 g, 73.8 mmol) in CH$_2$Cl$_2$ (200 mL) is added 200 ml of an aqueous solution of Na$_2$CO$_3$ (15 g, 141 mmol). While stirring, benzyl chloroformate (12.6 g, 73.8 mmol) is added slowly and the mixture is stirred at room temperature for 1 h. The organic layer is separated and washed with water and brine. The organic solvent is removed on a rotary evaporator to give a white solid. The solid is recrystallized from hexane to give 16.3 g (62 mmol) of the alcohol 188 (Scheme 31a) as a white solid. $^1$H NMR (300 MHz, CDCl$_3$) δ 7.40–7.29 (m, 5 H), 5.11 (s, 2 H), 4.71 (bd, 1 H), 3.76–3.71 (m, 1 H), 3.53–3.28 (m, 3 H), 2.00–1.95 (m, 1 H), 1.90–1.09 (m, 8 H). MS AP$^+$ (M+H)$^+$=264.3 (100%)

Step b: A solution of DMSO (36 g, 430 mmol) in CH$_2$Cl$_2$ (200 mL) is cooled to −78° C. To this solution is added drop-wise oxalyl chloride (27.41 g, 216 mmol) and the resulting solution is stirred for an additional 10 min. A solution of alcohol 188 (38 g, 144 mmol) in CH$_2$Cl$_2$ (150 ml) is added via an addition funnel and stirred for 10 min. Then, Et$_3$N (58 g, 570 mmol) is added and the solution is stirred for 20 min and the ice bath removed and stirred for an additional 30 min. The solution is diluted with water and the organic layer separated and washed with water, 1 N HCl, and brine. The organic layer is dried over Na$_2$SO$_4$ filtered, and concentrated to give 38 g of aldehyde 189 as a white solid. The solid is recrystallized from hexane to give 19.7 grams of a first crop of aldehyde 189 as white needles. A second crop gave an additional 11 grams. $^1$H NMR (300 MHz, CDCl$_3$) δ 9.59 (d, 3.6 Hz, 1 H), 7.38–7.28 (m, 5 H), 5.07 (m, 2 H), 4.69 (m, 1 H), 3.84 (m, 21 H), 2.19–2.11 (m,1 H), 2.09–2.01 (m, 1 H), 1.86–1.75 (m, 3 H), 1.54–1.17 (m, 4 H).

Step c: A solution of aldehyde 189 (19.6 g, 75 mmol) and (3S)-3-(4-fluorophenylmethyl)piperidine (14.5 g, 75 mmol) in dichloroethane (400 ml) was treated with Na(OAc)$_3$BH (32 g, 152 mmol) and stirred overnight at room temperature. The resulting solution was poured slowly into a stirred mixture of ice/water/1 N NaOH and stirred for 20 min. The organic layer was separated and washed water, and brine. The solution was dried over MgSO$_4$ and the organic solvent was removed under vacuum and the residue chromatographed on basic alumina (50% EtOAc/hexane) to give 32.1 g (73 mmol) of amine 193 as mixture of (15%) cis and trans isomers. $^1$H NMR (300 MHz, CDCl$_3$) δ 7.79 (bs, 1 H), 7.38–7.29 (m, 5 H), 6.95–6.84 (m, 4 H), 5.08 (m, 2 H), 3.71 (m, 1 H, cis isomer), 3.06 (m, 1 H, trans isomer), 2.80 (m, 1 H), 2.55–2.36 (m, 2 H), 2.30 (dd, J=9 Hz, J=13 Hz, 1 H, trans isomer), 2.05 (dd, J=2 Hz, J=13 Hz, 1 H, trans isomer), 1.81–0.90 (m, 16 H).

Step d: A solution of 193 (32 g, 73 mmol) in MeOH was treated with 8 g of 10% Pd/C and hydrogenated at 50 psi overnight in a Parr apparatus. The mixture was filtered and the filtrate concentrated on a rotary evaporator to give 20 g (65 mmol) of the amine 194, which was used without further purification.

Step e: A solution of amine 194 (10 g, 32.8 mmol) in THF is treated with 3-acetylphenyl isocyanate (5.3 g, 32.8 mmol) and the mixture is stirred for 30 min. The solvent is removed on a rotary evaporator and the residue is chromatographed on silica gel (0.5:4.5:95 NH$_4$OH/MeOH/CH$_2$Cl$_2$) to give 11 g of urea 195 (Example 415) as a solid. Also obtained 2 g of cis isomer (Example 416a). The urea Example 415 was further purified by a second chromatography on silica gel (40:60:1 EtAc/Hex/TEA) and final recrystallization from ether to give crystalline solid. mp 115–117° C., $[\alpha]_D^{25}$=+16.8° (CH$_3$OH, c=0.23 g/dL). $^1$H NMR (300 MHz, CDCl$_3$) δ7.86 (m, 1 H), 7.78 (bs, 1 H), 7.68–7.64 (m, 1 H), 7.62–7.59(m, 1 H), 7.38 (t, J=8 Hz, 1 H), 6.95–6.90 (m, 2 H), 6.79–6.72 (m, 2 H), 6.25 (s, 1 H), 3.21 (dt, J=3 Hz, 11 Hz, 1 H), 3.00–2.97 (m, 1 H), 2.66–2.56 (m, 1 H), 2.61 (s, 3 H), 2.44–2.32 (m, 4 H), 2.06 (dd, J=2 Hz, J=13 Hz, 1 H), 1.80–0.86 (m, 15 H). MS esi: (M+H)$^+$=466.3 (100%). Anal. Calcd for C$_{28}$H$_{36}$N$_3$O$_2$F: C, 72.23; H, 7.70; N, 9.02. Found: C, 72.33; H, 7.91; N, 9.00.

Example 415a

N-(3-acetylphenyl)-N'-[(1R,2S)-2-[[(3S)-3-(4-fluorophenyl)methyl]piperidinyl]methyl]cyclohexyl] urea Hydrochloride A solution of example 415 (15 g, 32 mmol) in 300 ml of THF was cooled in an ice bath and treated drop-wise with 36 ml of a 1 M HCl/ether solution. The resulting solution was stirred for 30 min and concentrated in vacuo. The resulting solid was titurated with ether and the resulting white solid dried under high vacuum overnight to give 16 g of the hydrochloride salt. mp 58–60° C. $[\alpha]_D^{25}$=+20.0° (CH$_3$OH, c=0.23 g/dL). $^1$H NMR (400 MHz, DMSO-D$_6$) δ 9.61 (s, 1 H), 9.15 (s, 1 H), 8.00 (m, 1 H), 7.63–7.61 (m, 1 H), 7.51–7.49(m, 1 H), 7.39–7.34 (m, 1 H), 7.22–7.17 (m, 2 H), 7.09–7.04 (m, 2 H), 6.86 (d, J=8 Hz, 1 H), 3.47–3.31 (m, 4 H), 3.11 (m, 1 H), 2.98–2.82 (m, 2 H), 2.67–2.62 (dd, J=5 Hz, J=13 Hz, 1 H), 2.58–2.50 (m, 2 H), 2.52 (s, 3 H), 2.39 (dd, J=8 Hz, J=13 Hz, 1 H), 2.16–2.06 (m, 2 H), 1.84–1.556 (m, 7 H), 1.30–1.00 (m, 4 H). Anal. Calcd for C$_{28}$H$_{37}$N$_3$O$_2$FCl.H$_2$O.THF$_{0.25}$: C, 64.73; H 7.68; N, 7.81. Found: C, 64.89; H, 7.41; N, 7.81.

Example 415b

N-(3-acetylphenyl)-N'-[(1R,2S)-2-[[(3S)-3-(4-fluorophenyl)methyl]piperidinyl]methyl]cyclohexyl] urea Benzenesulfonate Bezenesulfonic acid monohydrate (1.06 g, 6 mmol) was dried by azeotroping off the water of a benzene solution (twice) and adding the dried acid solution to a solution of example 415 (2.81 g, 6 mmol) in toluene (40 ml). The solvents were removed in vacuo (twice) and the resulting residue recrystallized twice from toluene and dried under high vacuum overnight give 2.77 g of benzenesulfonic acid salt as a white solid. mp 157–159° C. $[\alpha]_D^{25}$=16.9° (CH$_3$OH, c=0.23 g/dL). Anal. Calcd for C$_{34}$H$_{42}$N$_3$O$_5$FS: C, 65.47; H 6.80; N, 6.75; S, 5.14. Found: C, 65.48; H, 6.80; N, 6.70; S, 5.35.

The compounds of Table 3a and Table 3.1 were prepared by procedures described in Schemes 26–31A, other examples and methods taught herein, and procedures familiar to one skilled in the art.

TABLE 3a

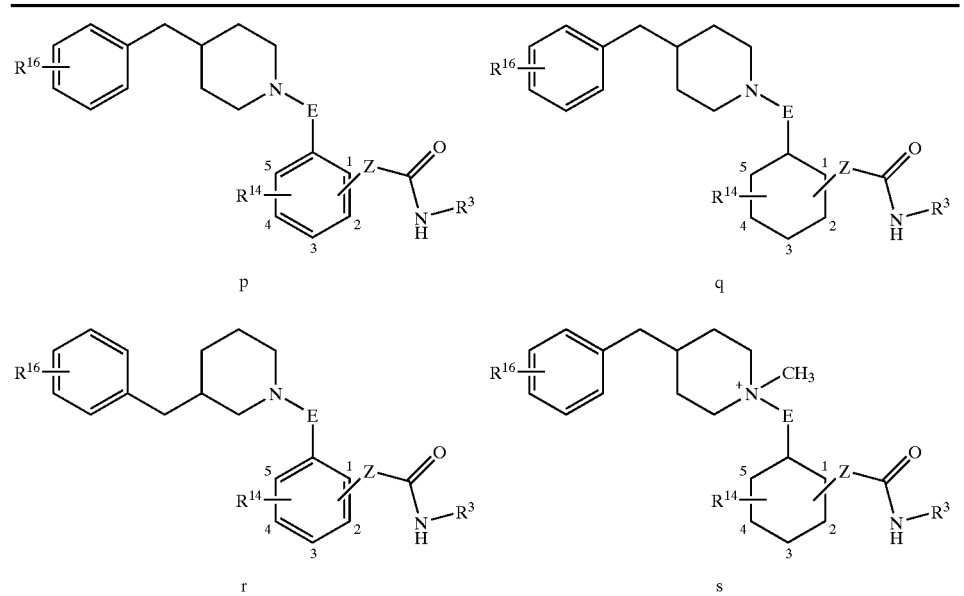

| Ex # | Core | R$^{16}$ | E | Z | R$^{14}$ | R$^3$ | MS M + H$^+$ |
|---|---|---|---|---|---|---|---|
| 218 | p | H | CH$_2$ | (1) NH | H | 1-(phenylmethyl)-4-piperidinyl] | 497 |
| 219 | p | H | CH$_2$ | (1) NH | H | 2,5-difluorophenyl | 436 |
| 220 | p | H | CH$_2$ | (2) CH$_2$NH | H | 2,5-difluorophenyl | 450 |

TABLE 3a-continued

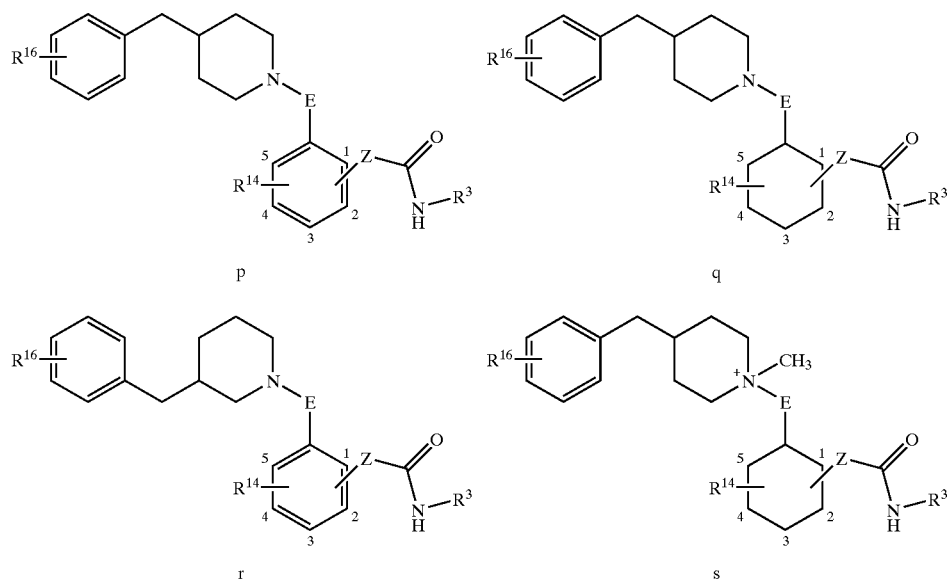

| Ex # | Core | R16 | E | Z | R14 | R3 | MS M + H+ |
|---|---|---|---|---|---|---|---|
| 221 | p | H | (ketone linker) | (1) NH | H | 2,5-difluorophenyl | 464 |
| 222 | p | H | (hydroxyl linker) | (1) NH | H | 2,5-difluorophenyl | 466 |
| 223 | p | H | C=NH | (2) NH | H | phenyl | 413 |
| 224 | p | H | CH2 | (2) NH | H | 1-(phenylmethyl)-4-piperidinyl] | 497 |
| 225 | p | H | CH2 | (1) NH | H | 2-(4-fluorophenyl)-ethyl | 446 |
| 226 | p | H | CH2 | (1) NH | H | 3-hydroxypropyl | 382 |
| 227 | p | H | CH2 | (1) NH | H | 2-(1-piperidinyl)-ethyl | 435 |
| 228 | p | H | CH2 | (1) NH | H | 2-(dimethylamino)-ethyl | 395 |
| 229 | p | H | CH2 | (1) NH | H | 4-(phenylmethyl)-1-piperazine | 483 |
| 230 | p | H | CH2 | (1) NH | H | 4-(phenylmethyl)-1-piperidine | 482 |
| 231 | p | H | CH2 | (1) NH | H | (1,3-benzodioxol-5-ylmethyl) | 458 |
| 232 | p | H | CH2 | (1) NH | H | 2,2-(diphenyl)ethyl | 504 |
| 233 | p | H | CH2 | (1) NH | H | 4-(4-chlorophenyl)-4-hydroxy-1-piperidine | 518 |
| 234 | p | H | CH2 | (1) NH | H | 4-phenyl-4-hydroxy-1-piperidine | 484 |
| 235 | p | H | CH2 | (1) NH | H | 4-phenyl-1-piperidine | 468 |
| 236 | p | H | CH2 | (1) NH | H | (1H)-indazol-5-yl | 440 |
| 237 | p | H | CH2 | (1) NH | H | (1H)-indazol-6-yl | 440 |
| 238 | p | H | CH2 | (1) NH | H | phenylmethyl | 414 |
| 239 | p | H | CH2 | (1) NH | H | 1,3-benzodioxol-5-yl | 444 |

TABLE 3a-continued

Cores p, q, r, s (structures shown).

| Ex # | Core | R16 | E | Z | R14 | R3 | MS M + H+ |
|---|---|---|---|---|---|---|---|
| 240 | p | H | CH2 | (1) NH | (3-4) dioxolane | 1-(phenylmethyl)-4-piperidinyl] | 541 |
| 241 | p | H | CH2 | (1) NH | (3-4) dioxolane | 2-(4-fluorophenyl)ethyl | 490 |
| 242 | p | H | CH2 | (1) NH | (3-4) dioxolane | 4-((2-phenyl)ethyl)-1-piperazine | 541 |
| 243 | p | H | CH2 | (1) NH | (3-4) dioxolane | (1H)-indazol-5-yl | 484 |
| 244 | p | H | CH2 | (1) NH | (3-4) dioxolane | (1H)-indazol-6-yl | 484 |

TABLE 3a-continued

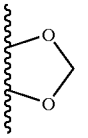

| Ex # | Core | R16 | E | Z | R14 | R3 | MS M + H+ |
|---|---|---|---|---|---|---|---|
| 245 | p | H | CH2 | (1) NH | (3-4) ⟨dioxolane⟩ | benzothiazol-6-yl | 501 |
| 246 | p | H | CH2 | (1) NH | (4) OH | [2-(4-fluorophenyl)-ethyl | 462 |
| 247 | p | H | CH2 | (1) NH | (4) OH | 1-(phenylmethyl)-4-piperidinyl] | 513 |
| 248 | p | H | CH2 | (1) NH | (3-4) ⟨dioxolane⟩ | 3-phenylpropyl | 486 |
| 249 | p | H | CH2 | (2) NH | H | (1H)-indazol-5-yl | 440 |
| 250 | p | H | CH2 | (2) NH | H | [2-(4-fluorophenyl)-ethyl | 446 |
| 251 | p | H | bond | (1) NH | H | 2,5-difluorophenyl | 422 |
| 252 | p | H | CH2 | (1) NH | H | Phenyl | 400 |
| 253 | p | H | CH2 | (1) NH | H | 4-methoxyphenyl | 430 |
| 254 | p | H | CH2 | (1) NH | H | 3-methoxyphenyl | 430 |
| 255 | q | 4-F | CH2 | (2) NH | H | 3-methoxyphenyl | 454 |
| 256 | q | 4-F | CH2 | (2) NH | H | 3-acetylphenyl | 466 |
| 257 | r | H | CH2 | (1) NH | H | 3-methoxyphenyl | 430 |
| 258 | p | H | CH2 | (2) NH | H | 3-cyanophenyl | 425 |
| 259 | p | H | CH2 | (3) NH | H | 3-cyanophenyl | 425 |
| 260 | p | H | CH2 | (3) NH | H | 4-methoxyphenyl | 430 |
| 261 | p | H | CH2 | (3) NH | H | 2-phenylethyl | 428 |
| 262 | p | H | CH2 | (1) NH | H | 3-carboethoxy-phenyl | 472 |
| 263 | p | H | CH2 | (1) NH | H | 3-cyanophenyl | 425 |
| 264 | p | 4-F | CH2 | (1) NH | H | phenyl | 418 |
| 265 | p | H | CH2 | (1) N-Benzyl | H | phenyl | 490 |
| 266 | p | H | CH2 | (1) N-Benzyl | H | 3-cyanophenyl | 515 |
| 267 | p | H | CH2 | (1) NH | H | 2-phenylethyl | 428 |

TABLE 3a-continued
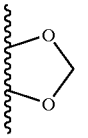
| Ex # | Core | R[16] | E | Z | R[14] | R[3] | MS M + H[+] |
|------|------|-------|---|---|-------|------|-------------|
| 268 | p | H | $CH_2$ | (1) NH | (3-4) 1,3-dioxolane | 3-cyanophenyl | 469 |
| 269 | p | H | $CH_2$ | (1) NH | (3-4) 1,3-dioxolane | 3-carboethoxy-phenyl | 516 |
| 270 | p | H | $CH_2$ | (1) NH | (3-4) 1,3-dioxolane | 4-carboethoxy-phenyl | 516 |
| 271 | p | H | $CH_2$ | (1) NH | (4) OH | phenyl | 416 |
| 272 | p | H | $CH_2$ | (1) NH | (4) OH | 3-cyanophenyl | 441 |
| 273 | p | H | $CH_2$ | (1) NH | (4) $-O-S(=O)_2-CH_3$ | 3-methoxyphenyl | 524 |
| 274 | p | H | $CH_2$ | (1) NH | (4) $-O-S(=O)_2-CH_3$ | Trans-2-phenyl-cyclopropyl | 534 |
| 275 | p | H | $CH_2$ | (1) NH | (3) $CO_2Me$ | 3-cyanophenyl | 483 |
| 276 | p | H | $CH_2$ | (1) NH | (3) $CO_2Me$ | 3-methoxyphenyl | 488 |

TABLE 3a-continued

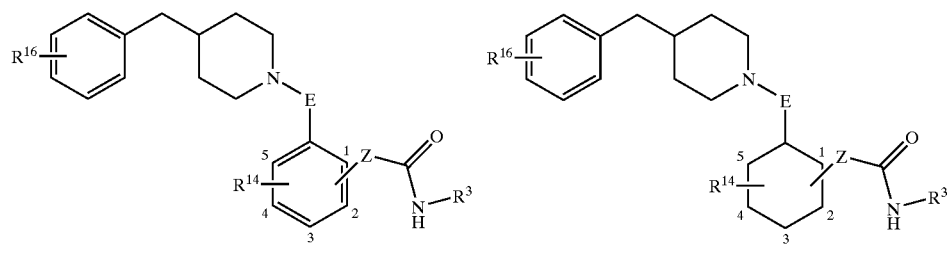

p                q

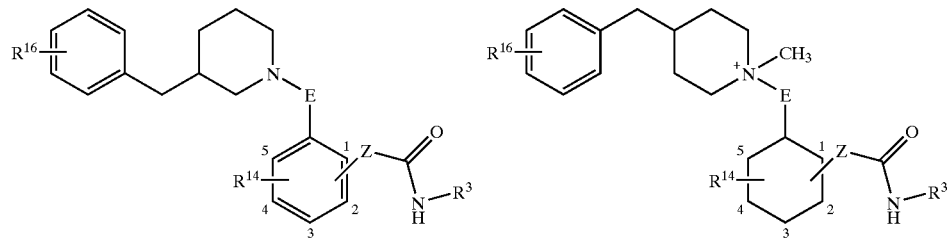

r                s

| Ex # | Core | R16 | E | Z | R14 | R3 | MS M + H+ |
|---|---|---|---|---|---|---|---|
| 277 | p | H | CH2 | (1) NH | (4) —O—S(=O)(=O)—CH3 | 3-cyanophenyl | 519 |
| 278 | p | H | CH2 | (1) NH | (3) ⌁OH | 3-methoxyphenyl | 460 |
| 279 | p | H | CH2 | (1) NH | (3) ⌁OH | 3-cyanophenyl | 455 |
| 280 | p | 4-F | CH2 | (1) NH | (4) CO2Me | 3-cyanophenyl | 501 |
| 280a | p | 4-F | CH2 | (1) NH | (5) CO2Me | 3-cyanophenyl | 501 |
| 280b | p | 4-F | CH2 | (1) NH | (5) CONMe | 3-cyanophenyl | 500 |
| 280c | p | 4-F | CH2 | (1) NH | (5) CONH2 | 3-cyanophenyl | 486 |
| 280d | p | 4-F | CH2 | (1) NH | (5) CO2Me | 3-(1-hydroxyethyl)-phenyl | 520 |
| 280e | r | H | CH2 | (1) NH | (5) CO2Me | phenyl | 458 |
| 280f | p | 4-F | CH2 | (1) NH | (5) CO2H | phenyl | 462 |
| 280g | r | H | CH2 | (1) NH | (5) CO2Me | 3-cyanophenyl | 483 |
| 280h | r | H | CH2 | (1) NH | (5) CO2Me | 3-methoxyphenyl | 488 |
| 280i | r | H | CH2 | (1) NH | (5) CO2Me | 3-acetylphenyl | 500 |
| 280j | p | 4-F | CH2 HCl(salt) | (1) NH | (5) CO2Me | 3-acetylphenyl | 518 |
| 280k | p | 4-F | CH2 HCl(salt) | (1) NH | (5) CO2Me | 3-cyanophenyl | 501 |
| 281 | p | 4-F | CH2 | (1) NH | (4) CO2Me | phenyl | 476 |
| 281a | p | 4-F | CH2 | (1) NH | (5) CO2Me | phenyl | 476 |
| 281b | p | 4-F | CH2 | (1) NH | (5) CONMe | phenyl | 475 |
| 281c | p | 4-F | CH2 | (1) NH | (5) CONH2 | phenyl | 461 |
| 282 | p | 4-F | CH2 | (1) NH | (4) CO2Me | 3-methoxyphenyl | 506 |
| 282a | p | 4-F | CH2 | (1) NH | (5) CO2Me | 3-methoxyphenyl | 506 |
| 282b | p | 4-F | CH2 | (1) NH | (5) CONMe | 3-methoxyphenyl | 505 |
| 282c | p | 4-F | CH2 | (1) NH | (5) CO2Me | 3-acetylphenyl | 518 |
| 282d | p | 4-F | CH2 | (1) NH | (5) CONMe | 3-acetylphenyl | 517 |
| 282e | p | 4-F | CH2 | (1) NH | (5) CONH2 | 3-acetylphenyl | 503 |
| 283 | p | 4-F | CH2 | (1) NH | (4) ⌁OH | 3-cyanophenyl | 473 |
| 284 | p | 4-F | CH2 | (1) NH | (3-4) fused Phenyl | 3-cyanophenyl | 493 |

TABLE 3a-continued

| Ex # | Core | $R^{16}$ | E | Z | $R^{14}$ | $R^3$ | MS M + H⁺ |
|---|---|---|---|---|---|---|---|
| 285 | p | 4-F | CH₂ | (1) NH | (3-4) fused Phenyl | 3-methoxyphenyl | 498 |
| 286 | p | 4-F | CH₂ | (1) NH | (4) —CONPh | 3-cyanophenyl | 562 |
| 286a | p | 4-F | CH₂ | (1) NH | (5) —CONPh | 3-cyanophenyl | 562 |
| 286b | p | 4-F | CH₂ | (1) NH | (5) —CONPh | 3-acetylphenyl | 579 |
| 287 | p | 4-F | CH₂ | (1) NH | (4) ⌇OH | 3-methoxyphenyl | 478 |
| 288 | p | 4-F | CH₂ | (1) NH | (4) CONMe | 3-cyanophenyl | 500 |
| 288a | p | 4-F | CH₂ HCl(salt) | (1) NH | (4) CONMe | 3-cyanophenyl | 500 |
| 288b | p | 4-F | CH₂ HCl(salt) | (1) NH | (5) CONMe | 3-acetylphenyl | 517 |
| 288c | p | 4-F | CH₂ | (1) NH | (5) CON(CH₂)₂NMe₂ | 3-acetylphenyl | 574 |
| 288d | p | 4-F | CH₂ | (1) NH | (5) CON(CH₂)₂NMe₂ | 3-acetylphenyl | 557 |
| 288e | p | 4-F | CH₂ | (1) NH | (5) CONC₃H₅ | 3-acetylphenyl | 453 |
| 288f | p | 4-F | CH₂ | (1) NH | (5) CONC₃H₅ | 3-acetylphenyl | 531 |
| 288g | p | 4-F | CH₂ | (1) NH | (5) CONMe₂ | 3-methoxyphenyl | 519 |
| 288h | p | 4-F | CH₂ | (1) NH | (5) CONMe₂ | 3-acetylphenyl | 531 |
| 288i | p | 4-F | CH₂ | (1) NH | (5) CON(2-pyridinyl) | 3-acetylphenyl | 580 |
| 288j | p | 4-F | CH₂ | (1) NH | (5) CONMe₂ | 3-methoxyphenyl | 568 |
| 289 | p | H | CH₂ | (1) CH₂NH | H | 2,5-difluorophenyl | 450 |
| 290 | p | H | CH₂ | (1) CH₂NH | H | 3-cyanophenyl | 439 |
| 291 | p | H | CH₂ | (1) CH₂NH | H | 3-carboethoxy-phenyl | 486 |
| 292 | p | H | CH₂ | (1) CH₂NH | H | 3-methoxyphenyl | 444 |
| 293 | p | H | CH₂ | (1) CH₂NH | H | 4-methoxyphenyl | 444 |
| 294 | p | H | 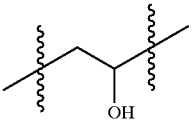 | (1) NH | H | 3-methoxyphenyl | 460 |

TABLE 3a-continued
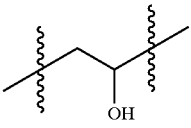
p
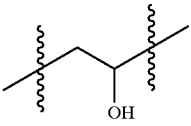
q
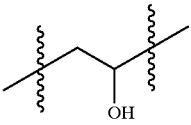
r
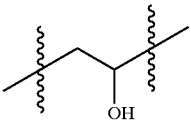
s
| Ex # | Core | R16 | E | Z | R14 | R3 | MS M + H+ |
|---|---|---|---|---|---|---|---|
| 295 | r | H |  OH | (1) NH | H | 3-methoxyphenyl | 460 |
| 296 | p | H |  OH | (1) NH | H | 3-cyanophenyl | 455 |
| 297 | p | H |  OH | (1) NH | H | 3-carboethoxy-phenyl | 502 |
| 298 | p | H |  OH | (1) NH | H | phenyl | 430 |
| 299 | p | 4-F | CH2 | (1) NH | (5) 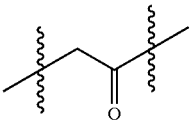 OH | phenyl | 448 |
| 300 | p | H | 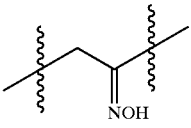 NOH | (1) NH | H | phenyl | 443 |
| 301 | p | H | 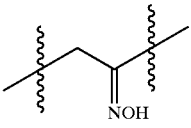 O | (2) NH | H | phenyl | 428 |

TABLE 3a-continued
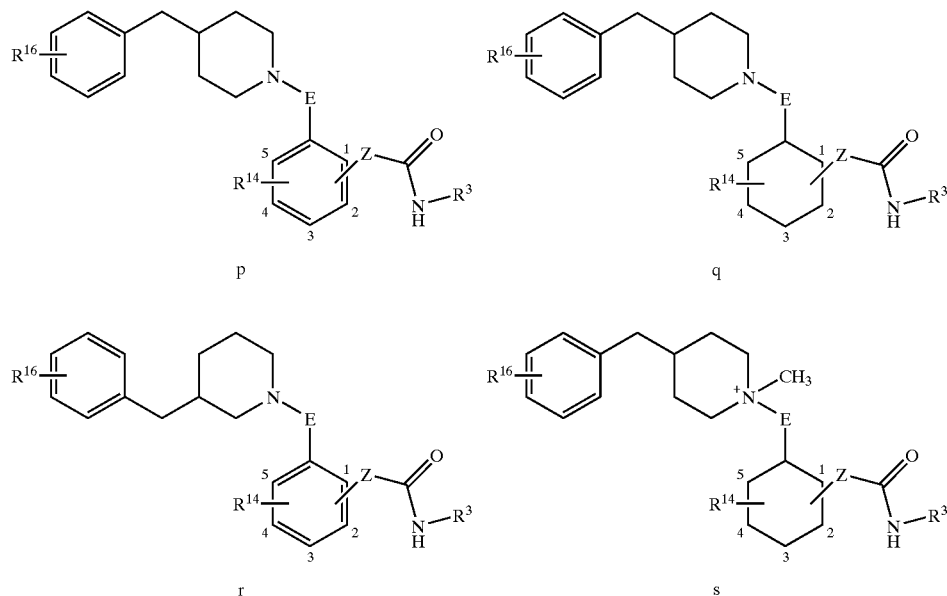
| Ex # | Core | R16 | E | Z | R14 | R3 | MS M + H+ |
|------|------|-----|---|---|-----|-----|-----------|
| 302 | p | H | CH2-CH(OH)- | (2) NH | H | phenyl | 430 |
| 303 | p | 4-F | CH2-CH(OH)- | (1) NH | H | phenyl | 448 |
| 304 | p | 4-F | CH2-CH(OH)- | (1) NH | H | 3-methoxyphenyl | 478 |
| 305 | p | 4-F | CH2-CH(OH)- | (1) NH | H | 3-cyanophenyl | 473 |
| 306 | p | H | CH2-CH(OH)- | (1) NH | (3-4) 1,3-dioxolane | 3-cyanophenyl | 499 |
| 307 | p | H | CH2—CH2 | (1) NH | H | 3-cyanophenyl | 439 |
| 308 | p | 4-F | CH2—CH2 | (1) NH | H | 3-cyanophenyl | 457 |

TABLE 3a-continued

Structures p, q, r, s shown.

| Ex # | Core | R$^{16}$ | E | Z | R$^{14}$ | R$^3$ | MS M + H$^+$ |
|---|---|---|---|---|---|---|---|
| 309 | p | H | CH$_2$—CH$_2$ | (1) NH | H | 3-methoxyphenyl | 444 |
| 310 | p | 4-F | CH$_2$—CH$_2$ | (1) NH | H | 3-methoxyphenyl | 462 |
| 311 | r | H | CH$_2$—CH$_2$ | (1) NH | H | 3-methoxyphenyl | 444 |
| 312 | p | 4-F | CH$_2$—CH$_2$ | (1) NH | H | 3-acetylphenyl | 474 |
| 313 | p | 4-F | CH$_2$—CH$_2$ | (1) NH | H | 4-fluorophenyl | 450 |
| 314 | p | 4-F | CH$_2$—CH$_2$ | (1) NH | H | 1-adamantyl | 490 |
| 315 | s | H | CH$_2$ | (1) NH | (3-4) 1,3-dioxolane | 3-cyanophenyl | 483(M+) |
| 316 | s | H | CH$_2$ | (1) NH | (4) OH | 3-cyanophenyl | 455(M+) |
| 317 | s | H | CH$_2$ | (1) NH | (4) O-(2-THP) | 3-cyanophenyl | 539(M+) |

TABLE 3.1

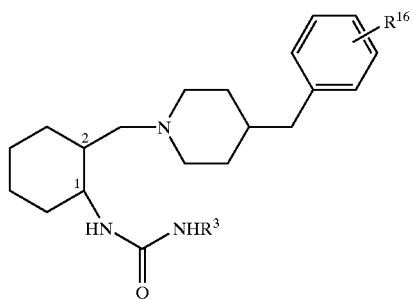

a

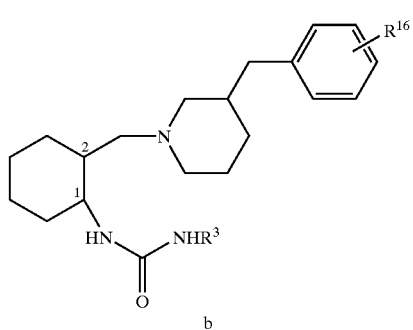

b

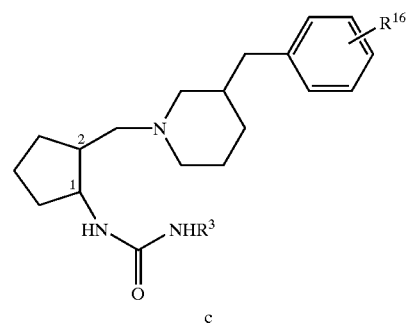

c

| Ex # | Core | $R^{16}$ | Stereo-chemistry | Salt Form | $R^3$ | MS M + H$^+$ |
|---|---|---|---|---|---|---|
| 400 | a | H | 1,2 trans racemic | — | 3-methoxylphenyl | 436 |
| 401 | a | 4-F | 1,2 trans racemic | — | 3-methoxylphenyl | 454 |
| 402 | a | H | 1,2 cis racemic | — | 3-methoxylphenyl | 436 |
| 403 | a | 4-F | 1,2 trans racemic | — | 3-cyanophenyl | 449 |
| 403a | a | 4-F | 1,2 trans racemic | — | 3-acetylphenyl | 466 |
| 403b | a | 4-F | 1,2 trans racemic | — | 3-nitrophenyl | 469 |
| 403c | a | 4-F | 1,2 trans racemic | — | 4-nitrophenyl | 469 |
| 403d | a | 4-F | 1,2 trans racemic | — | 4-pyridinyl | 425 |
| 403e | a | 4-F | 1,2 trans racemic | HCl | 3-acetylphenyl | 466 |
| 403f | a | 4-F | 1,2 trans racemic | — | (1H)-indazol-5-yl | 464 |
| 404 | a | 4-F | 1S, 2R | — | 3-acetylphenyl | 466 |
| 405 | a | 4-F | 1S, 2R | — | 3-cyanophenyl | 449 |
| 406 | a | 4-F | 1S, 2R | — | 3-methoxylphenyl | 454 |
| 407 | a | 4-F | 1S, 2R | — | phenyl | 424 |
| 408 | a | 4-F | 1R, 2S | — | 3-acetylphenyl | 466 |
| 409 | a | 4-F | 1R, 2S | — | 3-cyanophenyl | 449 |
| 410 | a | 4-F | 1R, 2S | — | 3-methoxyphenyl | 454 |

TABLE 3.1-continued

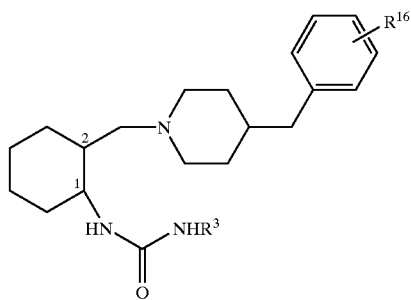

a

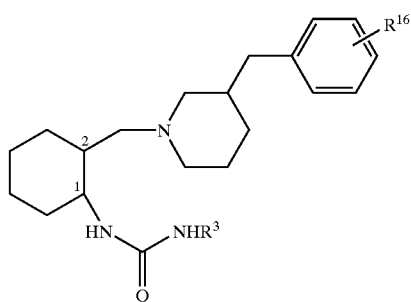

b

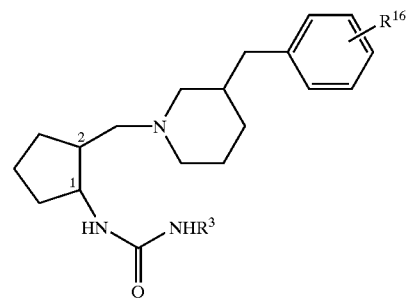

c

| Ex # | Core | R16 | Stereo-chemistry | Salt Form | R3 | MS M + H+ |
|---|---|---|---|---|---|---|
| 411 | a | 4-F | 1R, 2S | — | phenyl | 424 |
| 412 | a | 4-F | 1R, 2S | — | phenylmethyl | 438 |
| 413 | a | 4-F | 1R, 2S | — | (1H)-indazol-5-yl | 464 |
| 414 | a | 4-F | 1R, 2S | — | (1H)-indol-5-yl | 463 |
| 414a | b | H | 1,2 trans (3RS) racemic | — | 3-methoxyphenyl | 464 |
| 414b | b | H | 1,2 trans (3RS) racemic | — | 3-cyanophenyl | 431 |
| 414c | b | H | 1,2 trans (3RS) racemic | — | 3-acetylphenyl | 448 |
| 414d | b | 4-F | 1,2 trans (3RS) racemic | — | 3-acetylphenyl | 466 |
| 414e | b | 4-F | 1,2 trans (3RS) racemic | — | 3-cyanophenyl | 449 |
| 414f | b | 4-F | 1,2 trans (3RS) racemic | — | 3-methoxyphenyl | 454 |
| 414g | b | 4-F | 1,2 trans (3RS) racemic | — | 3-nitrophenyl | 469 |
| 415 | b | 4-F | 1R, 2S, 3S | — | 3-acetylphenyl | 466 |
| 415a | b | 4-F | 1R, 2S, 3S | HCl | 3-acetylphenyl | 466 |
| 415b | b | 4-F | 1R, 2S, 3S | Besyl | 3-acetylphenyl | 466 |
| 416 | b | 4-F | 1R, 2S, 3R | — | 3-acetylphenyl | 466 |
| 416a | b | 4-F | 1R, 2R, 3S | — | 3-acetylphenyl | 466 |
| 416b | b | 4-F | 1R, 2S, 3R | HCl | 3-acetylphenyl | 466 |
| 417 | b | 4-F | 1R, 2S, 3S | — | 3-cyanophenyl | 449 |
| 418 | b | 4-F | 1R, 2S, 3R | — | 3-cyanophenyl | 449 |
| 419 | b | 4-F | 1R, 2S, 3S | — | 3-methoxylphenyl | 454 |

TABLE 3.1-continued

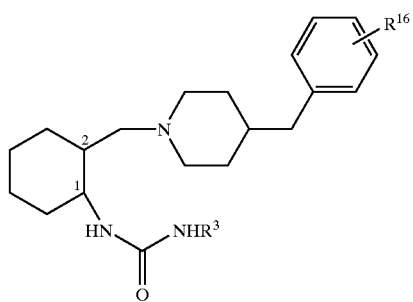

a

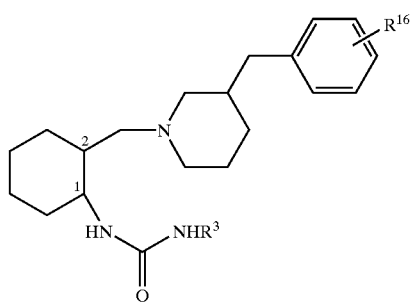

b

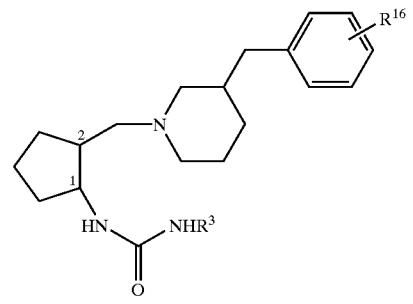

c

| Ex # | Core | R16 | Stereo-chemistry | Salt Form | R3 | MS M + H+ |
|---|---|---|---|---|---|---|
| 420 | b | 4-F | 1R, 2S, 3R | — | 3-methoxylphenyl | 454 |
| 421 | b | 4-F | 1R, 2S, 3S | — | 4-fluorophenyl | 442 |
| 422 | b | 4-F | 1R, 2S, 3R | — | 4-fluorophenyl | 442 |
| 423 | b | 4-F | 1R, 2S, 3S | — | phenyl | 424 |
| 424 | b | 4-F | 1R, 2S, 3S | — | (1H)-indazol-5-yl | 464 |
| 425 | b | 4-F | 1R, 2S, 3S | — | (1H)-indazol-6-yl | 464 |
| 426 | b | 4-F | 1R, 2S, 3S | — | benzthiazol-6-yl | 481 |
| 427 | b | 4-F | 1R, 2S, 3S | — | (1H)-indol-5-yl | 463 |
| 428 | b | 4-F | 1R, 2S, 3S | — | (1H)-indol-6-yl | 463 |
| 429 | b | 4-F | 1R, 2S, 3S | — | (1H)-2,3-dimethylindol-5-yl | 491 |
| 430 | b | 4-F | 1R, 2S, 3S | — | benzimidazol-5-yl | 464 |
| 431 | b | 4-F | 1R, 2S, 3S | — | indolin-5-yl | 465 |
| 432 | b | 4-F | 1R, 2S, 3S | — | 3-cyano-4-fluorophenyl | 467 |
| 433 | b | 4-F | 1R, 2S, 3S | — | 3-acetyl-4-fluorophenyl | 484 |
| 434 | b | 4-F | 1R, 2S, 3S | — | 3,5-diacetylphenyl | 508 |
| 435 | b | 4-F | 1R, 2S, 3S | — | 3-(1-hydroxyethyl)-phenyl | 468 |
| 436 | b | 4-F | 1R, 2S, 3S | — | 4-methyl-thiazol-2-yl | 445 |
| 437 | b | 4-F | 1R, 2S, 3S | — | 4-methyl-5-acetyl-thiazol-2-yl | 487 |
| 438 | b | 4-F | 1R, 2S, 3S | — | 1,3,4-thiadiazol-2-yl | 432 |
| 439 | b | 4-F | 1R, 2S, 3S | — | 4-chlorol-benzthiazol-2-yl | 515 |
| 440 | b | 4-F | 1R, 2S, 3S | — | thiazol-2-yl | 431 |
| 441 | b | 4-F | 1R, 2S, 3S | — | 5-methyl-isoxazol-3-yl | 429 |

TABLE 3.1-continued

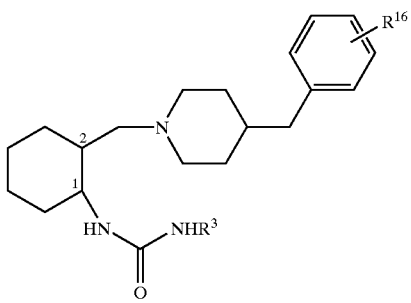

a

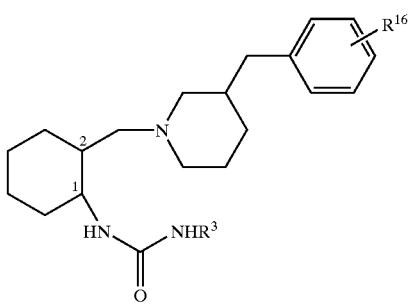

b

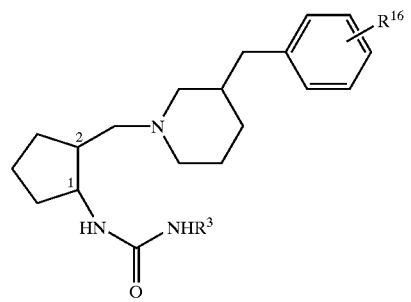

c

| Ex # | Core | R[16] | Stereo-chemistry | Salt Form | R[3] | MS M + H[+] |
|---|---|---|---|---|---|---|
| 442 | b | 4-F | 1R, 2S, 3S | — | 1-methyl-pyrazol-3-yl | 428 |
| 443 | b | 4-F | 1R, 2S, 3S | — | 4-(1,2,4-triazol-1-yl)phenyl | 491 |
| 443a | b | 4-F | 1R, 2R, 3S | — | 4-(1,2,4-triazol-1-yl)phenyl | 491 |
| 444 | b | 4-F | 1R, 2S, 3S | — | (1H)-3-chloro-indazol-5-yl | 499 |
| 445 | b | 4-F | 1R, 2S, 3S | — | 4-fluorophenyl | 492 |
| 446 | b | 4-F | 1R, 2S, 3S | — | 4-chlorophenyl | 458 |
| 447 | b | 4-F | 1R, 2S, 3S | — | 4-bromophenyl | 502 |
| 448 | b | 4-F | 1R, 2S, 3S | — | 3-bromophenyl | 502 |
| 449 | b | 4-F | 1R, 2S, 3S | — | 3-fluorophenyl | 442 |
| 450 | b | 4-F | 1R, 2S, 3S | — | 3,4-difluorophenyl | 460 |
| 451 | b | 4-F | 1R, 2S, 3S | — | 3-chloro-4-fluorophenyl | 476 |
| 452 | b | 4-F | 1R, 2S, 3S | — | 3,5-dichlorophenyl | 492 |
| 453 | c | 4-F | 1R, 2S, 3S | — | 3-acetylphenyl | 452 |
| 454 | c | 4-F | 1R, 2S, 3R | — | 3-acetylphenyl | 452 |
| 455 | c | 4-F | 1R, 2R, 3S | — | 3-acetylphenyl | 452 |
| 456 | c | 4-F | 1R, 2S, 3S | — | 3-cyanophenyl | 435 |
| 457 | c | 4-F | 1R, 2S, 3R | — | 3-cyanophenyl | 435 |
| 458 | c | 4-F | 1R, 2R, 3S | — | 3-cyanophenyl | 435 |
| 458a | c | 4-F | 1R, 2R, 3R | — | 3-cyanophenyl | 435 |
| 459 | c | 4-F | 1R, 2S, 3S | — | phenyl | 410 |
| 460 | c | 4-F | 1R, 2S, 3R | — | phenyl | 410 |
| 461 | c | 4-F | 1R, 2R, 3S | — | phenyl | 410 |
| 462 | b | 4-F | 1R, 2S, 3S | — | (1H)-5-amino-indazol- | 464 |

TABLE 3.1-continued

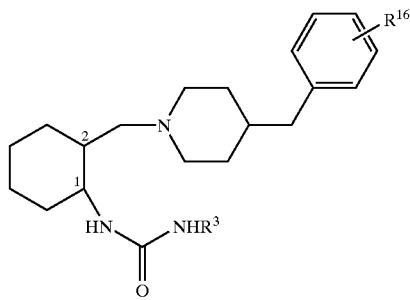

a

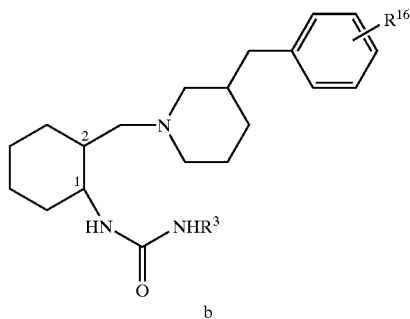

b

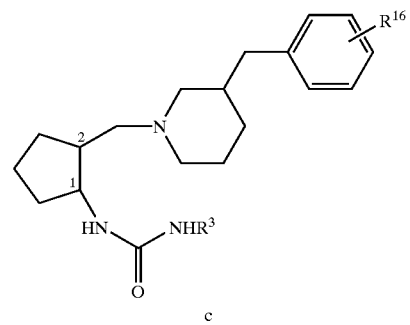

c

| Ex # | Core | R$^{16}$ | Stereo-chemistry | Salt Form | R$^3$ | MS M + H$^+$ |
|---|---|---|---|---|---|---|
| 463 | b | 4-F | 1R, 2S, 3S | — | 1-yl 3-chlorophenyl | 458 |
| 464 | b | 4-F | 1R, 2S, 3S | — | 3-fluoro-4-methylphenyl | 456 |
| 465 | b | 4-F | 1R, 2S, 3S | — | 3-cyano-4-(1-pyrazolyl)phenyl | 515 |
| 466 | b | 4-F | 1R, 2S, 3S | — | 2-methylphenyl | 454 |
| 467 | b | 4-F | 1R, 2S, 3S | — | 2-methylphenyl | 438 |
| 468 | b | 4-F | 1R, 2S, 3S | — | 2,4-dimethylphenyl | 452 |
| 469 | b | 4-F | 1R,,2S, 3S | — | 2,4-dimethoxyphenyl | 484 |
| 470 | b | 4-F | 1R, 2S, 3S | — | 2,5-dimethoxyphenyl | 484 |
| 471 | b | 4-F | 1R, 2S, 3S | — | 2-methoxy-5-methylphenyl | 468 |
| 472 | b | 4-F | 1R, 2S, 3S | — | 2-methyl-5-fluorophenyl | 456 |
| 473 | b | 4-F | 1R, 2S, 3S | — | 3,5-bis((1H)-1-methyltetrazol-5-yl)phenyl | 588 |
| 474 | b | 4-F | 1R, 2S, 3S | — | (3-((1H)-1-methyltetrazol-5-yl)phenyl | 506 |
| 475 | b | 4-F | 1R, 2S, 3S | — | (4-(carboethoxymethyl)thiazol-2-yl | 517 |
| 476 | b | 4-F | 1R, 2S, 3S | — | 5-bromothiazol-2-yl | 509 |
| 477 | b | 4-F | 1R, 2S, 3S | — | 4,5-di(4-fluorophenyl)thiazol-2-yl | 619 |
| 478 | b | 4-F | 1R, 2S, 3S | — | 2-fluorophenyl | 442 |

TABLE 3.1-continued

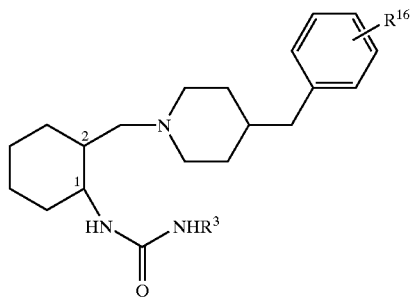

a

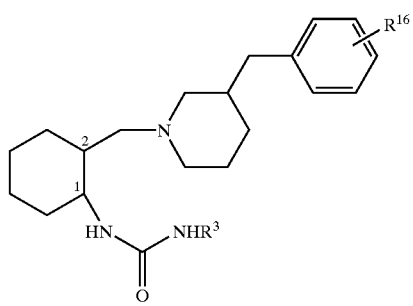

b

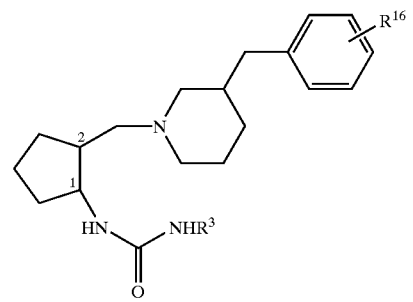

c

| Ex # | Core | $R^{16}$ | Stereo-chemistry | Salt Form | $R^3$ | MS M + H⁺ |
|---|---|---|---|---|---|---|
| 479 | b | 4-F | 1R, 2S, 3S | — | 2-chlorophenyl | 458 |
| 480 | b | 4-F | 1R, 2S, 3S | $CF_3CO_2H$ | indanon-6-yl | 478 |
| 481 | b | 4-F | 1R, 2S, 3S | $CF_3CO_2H$ | indanon-4-yl | 478 |
| 482 | b | 4-F | 1R, 2S, 3S | $CF_3CO_2H$ | 4-(isopropyl)phenyl | 466 |
| 483 | b | 4-F | 1R, 2S, 3S | $CF_3CO_2H$ | 3-nitro-4-methylphenyl | 483 |
| 484 | b | 4-F | 1R, 2S, 3S | $CF_3CO_2H$ | trans-2-phenylcycloprop-1-yl | 464 |
| 485 | b | 4-F | 1R, 2S, 3S | $CF_3CO_2H$ | 2,4-difluorophenyl | 460 |
| 486 | b | 4-F | 1R, 2S, 3S | $CF_3CO_2H$ | 2,5-difluorophenyl | 460 |
| 487 | b | 4-F | 1R, 2S, 3S | $CF_3CO_2H$ | 2,4-dichlorophenyl | 492 |
| 488 | b | 4-F | 1R, 2S, 3S | $CF_3CO_2H$ | 2,5-dichlorophenyl | 492 |
| 489 | b | 4-F | 1R, 2S, 3S | $CF_3CO_2H$ | 2-methoxyphenyl | 454 |
| 490 | b | 4-F | 1R, 2S, 3S | $CF_3CO_2H$ | 2,4-dimethoxy-phenyl | 484 |
| 491 | b | 4-F | 1R, 2S, 3S | $CF_3CO_2H$ | 2,5-dimethoxyphenyl | 484 |
| 492 | b | 4-F | 1R, 2S, 3S | $CF_3CO_2H$ | 2-trifluoromethylphenyl | 492 |
| 493 | b | 4-F | 1R, 2S, 3S | $CF_3CO_2H$ | 2-methylphenyl | 438 |
| 494 | b | 4-F | 1R, 2S, 3S | $CF_3CO_2H$ | 3-trifluoromethyly-phenyl | 492 |
| 495 | b | 4-F | 1R, 2S, 3S | $CF_3CO_2H$ | 3-methylphenyl | 438 |
| 496 | b | 4-F | 1R, 2S, 3S | $CF_3CO_2H$ | 4-methoxyphenyl | 454 |
| 497 | b | 4-F | 1R, 2S, 3S | $CF_3CO_2H$ | 4-carboethoxy-phenyl | 496 |
| 498 | b | 4-F | 1R, 2S, 3S | $CF_3CO_2H$ | 4-trifluoromethyly-phenyl | 492 |
| 499 | b | 4-F | 1R, 2S, 3S | $CF_3CO_2H$ | 4-methylphenyl | 438 |
| 500 | b | 4-F | 1R, 2S, 3S | $CF_3CO_2H$ | 2-fluorophenyl | 442 |
| 501 | b | 4-F | 1R, 2S, 3S | $CF_3CO_2H$ | 2-chlorophenyl | 458 |

TABLE 3.1-continued

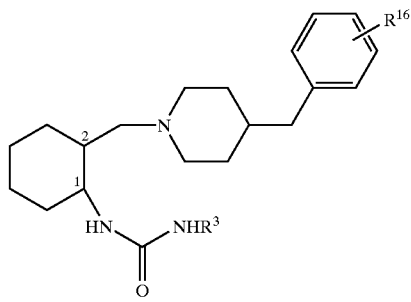

a

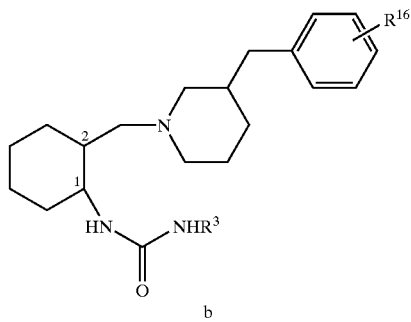

b

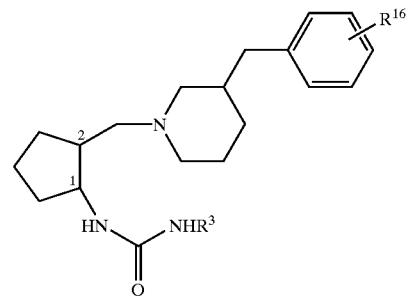

c

| Ex # | Core | R$^{16}$ | Stereo-chemistry | Salt Form | R$^3$ | MS M + H$^+$ |
|---|---|---|---|---|---|---|
| 502 | b | 4-F | 1R, 2S, 3S | CF$_3$CO$_2$H | 2-nitrophenyl | 469 |
| 503 | b | 4-F | 1R, 2S, 3S | CF$_3$CO$_2$H | 2,4-dichlorophenyl | 563 |
| 504 | b | 4-F | 1R, 2S, 3S | CF$_3$CO$_2$H | 3-nitrophenyl | 469 |
| 505 | b | 4-F | 1R, 2S, 3S | CF$_3$CO$_2$H | 3,5-di (trifluoromethyly)-phenyl | 560 |
| 506 | b | 4-F | 1R, 2S, 3S | CF$_3$CO$_2$H | 2,4-dimethylphenyl | 452 |
| 507 | b | 4-F | 1R, 2S, 3S | CF$_3$CO$_2$H | 2,4-dimethoxy-5-chlorophenyl | 518 |
| 508 | b | 4-F | 1R, 2S, 3S | CF$_3$CO$_2$H | 3,4,5-trimethoxyphenyl | 514 |
| 509 | b | 4-F | 1R, 2S, 3S | CF$_3$CO$_2$H | 3,5-dimethylphenyl | 452 |
| 510 | b | 4-F | 1R, 2S, 3S | CF$_3$CO$_2$H | 3-trifluoromethyl-4-chlorophenyl | 526 |
| 511 | b | 4-F | 1R, 2S, 3S | CF$_3$CO$_2$H | 4-phenoxyphenyl | 516 |
| 512 | b | 4-F | 1R, 2S, 3S | CF$_3$CO$_2$H | 4-ethoxyphenyl | 468 |
| 513 | b | 4-F | 1R, 2S, 3S | CF$_3$CO$_2$H | 4-thiomethylphenyl | 470 |
| 514 | b | 4-F | 1R, 2S, 3S | CF$_3$CO$_2$H | 2-naphthyl | 474 |
| 515 | b | 4-F | 1R, 2S, 3S | CF$_3$CO$_2$H | 4-acetylphenyl | 466 |
| 516 | b | 4-F | 1R, 2S, 3S | CF$_3$CO$_2$H | 2,6-dichloro-pyridin-4-yl | 493 |
| 517 | b | 4-F | 1R, 2S, 3S | CF$_3$CO$_2$H | 5-indan-4-yl | 464 |
| 518 | b | 4-F | 1R, 2S, 3S | CF$_3$CO$_2$H | 4-chloronaphth-1-yl | 508 |
| 519 | b | 4-F | 1R, 2S, 3S | CF$_3$CO$_2$H | 3-fluoro-4-methoxyphenyl | 472 |
| 520 | b | 4-F | 1R, 2S, 3S | CF$_3$CO$_2$H | 4-(methylsulfonyl)-phenyl) | 502 |
| 521 | b | 4-F | 1R, 2S, 3S | CF$_3$CO$_2$H | 3-(methylsulfonyl)-phenyl | 502 |

TABLE 3.1-continued

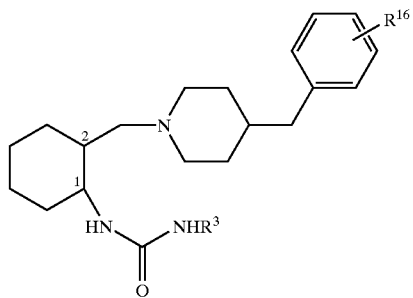

a

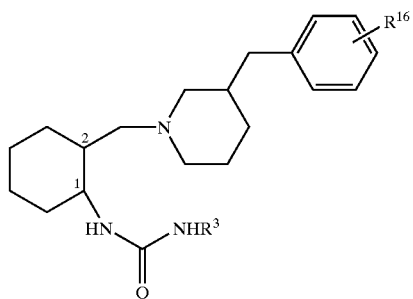

b

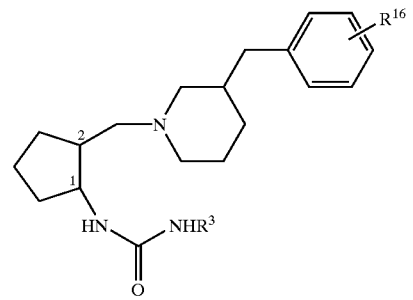

c

| Ex # | Core | R16 | Stereo-chemistry | Salt Form | R3 | MS M + H+ |
|---|---|---|---|---|---|---|
| 522 | b | 4-F | 1R, 2S, 3S | CF$_3$CO$_2$H | 2-((1H)-pyrrol-1-yl)phenyl | 489 |
| 523 | b | 4-F | 1R, 2S, 3S | CF$_3$CO$_2$H | 1,3-benzodioxol-5-yl | 468 |
| 524 | b | 4-F | 1R, 2S, 3S | CF$_3$CO$_2$H | 1-acetylindolin-6-yl | 507 |
| 525 | b | 4-F | 1R, 2S, 3S | CF$_3$CO$_2$H | 4-(6-methylbenzothiazol-2-yl)phenyl | 571 |
| 526 | b | 4-F | 1R, 2S, 3S | CF$_3$CO$_2$H | 4-((2,2-dimethylpropanoyl)amino)phenyl | 523 |
| 527 | b | 4-F | 1R, 2S, 3S | CF$_3$CO$_2$H | 4-(1-methyltetrazol-5-yl)phenyl | 506 |
| 528 | b | 4-F | 1R, 2S, 3S | CF$_3$CO$_2$H | 4-(1-morpholino)phenyl | 509 |
| 529 | b | 4-F | 1R, 2S, 3S | CF$_3$CO$_2$H | quinolin-8-yl | 475 |
| 530 | b | 4-F | 1R, 2S, 3S | CF$_3$CO$_2$H | 3-hydroxyphenyl | 440 |
| 531 | b | 4-F | 1R, 2S, 3S | CF$_3$CO$_2$H | 4-(acetylamino)-phenyl | 481 |
| 532 | b | 4-F | 1R, 2S, 3S | CF$_3$CO$_2$H | 4-hydroxyphenyl | 440 |
| 533 | b | 4-F | 1R, 2S, 3S | CF$_3$CO$_2$H | 3-hydroxy-4-methoxyphenyl | 470 |
| 534 | b | 4-F | 1R, 2S, 3S | CF$_3$CO$_2$H | 3-(acetylamino)-phenyl | 481 |
| 535 | b | 4-F | 1R, 2S, 3S | CF$_3$CO$_2$H | 4-fluoro-3-methylphenyl | 456 |
| 536 | b | 4-F | 1R, 2S, 3S | CF$_3$CO$_2$H | 3-methoxy-4-methylphenyl | 468 |
| 537 | b | 4-F | 1R, 2S, 3S | CF$_3$CO$_2$H | 4-chloro-3-methylphenyl | 472 |
| 538 | b | 4-F | 1R, 2S, 3S | CF$_3$CO$_2$H | 4-(N- | 481 |

TABLE 3.1-continued

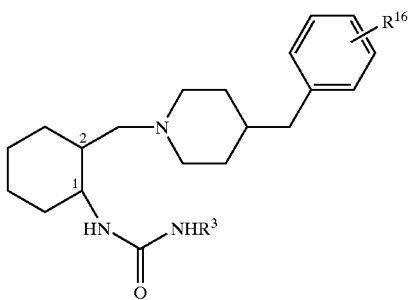

a

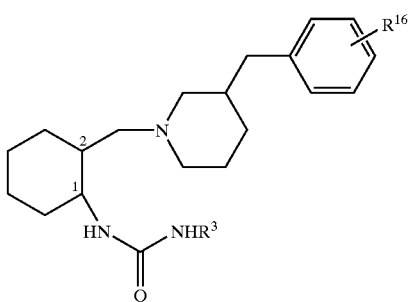

b

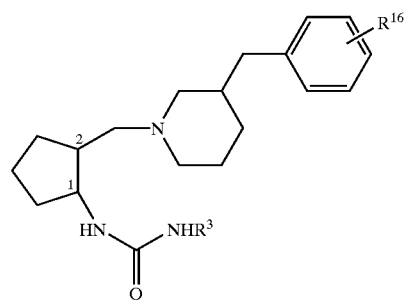

c

| Ex # | Core | $R^{16}$ | Stereo-chemistry | Salt Form | $R^3$ | MS M + H$^+$ |
|---|---|---|---|---|---|---|
| | | | | | methylcarboxamide)phenyl | |
| 539 | b | 4-F | 1R, 2S, 3S | CF$_3$CO$_2$H | 1-adamantyl | 482 |
| 540 | b | 4-F | 1R, 2S, 3S | CF$_3$CO$_2$H | quinolin-5-yl | 475 |
| 541 | b | 4-F | 1R, 2S, 3S | CF$_3$CO$_2$H | quinolin-6-yl | 475 |
| 542 | b | 4-F | 1R, 2S, 3S | CF$_3$CO$_2$H | 1,4-benzodioxan-6-yl | 482 |
| 543 | b | 4-F | 1R, 2S, 3S | CF$_3$CO$_2$H | isoquinolin-5-yl | 475 |
| 544 | b | 4-F | 1R, 2S, 3S | CF$_3$CO$_2$H | 4-(sulfonamide)-phenyl | 503 |
| 545 | b | 4-F | 1R, 2S, 3S | CF$_3$CO$_2$H | benzotriazol-5-yl | 465 |
| 546 | b | 4-F | 1R, 2S, 3S | CF$_3$CO$_2$H | 2-hydroxy-4-methylphenyl | 454 |
| 547 | b | 4-F | 1R, 2s,3s | CF$_3$CO$_2$H | 3-hydroxy-4-methylphenyl | 454 |
| 548 | b | 4-F | 1R, 2S, 3S | CF$_3$CO$_2$H | 2-methyl-benzothiazol-5-yl | 495 |
| 549 | b | 4-F | 1R, 2S, 3S | CF$_3$CO$_2$H | (4-methoxylphenyl)-methyl | 468 |
| 550 | b | 4-F | 1R, 2S, 3S | CF$_3$CO$_2$H | (4-fluorophenyl)-methyl | 456 |
| 551 | b | 4-F | 1R, 2s, 3S | CF$_3$CO$_2$H | (4-methylphenyl)-methyl | 452 |
| 552 | b | 4-F | 1R, 2S, 3S | CF$_3$CO$_2$H | (1R)-1-(phenyl)ethyl | 452 |
| 553 | b | 4-F | 1R, 2S, 3S | CF$_3$CO$_2$H | 1-acetylindolin-5-yl | 507 |
| 554 | b | 4-F | 1R, 2S, 3S | CF$_3$CO$_2$H | 5,6,7,8-tetrahydronaphth-1-yl | 478 |
| 555 | b | 4-F | 1R, 2S, 3S | CF$_3$CO$_2$H | 3-acetyl-4-hydroxyphenyl | 482 |
| 556 | b | 4-F | 1R, 2S, 3S | CF$_3$CO$_2$H | 4-(piperidin-1- | 507 |

TABLE 3.1-continued

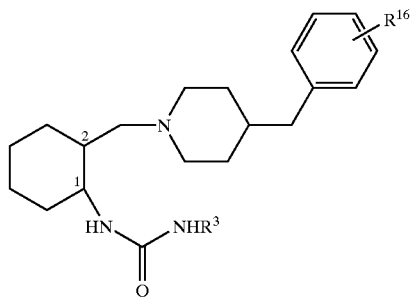

a

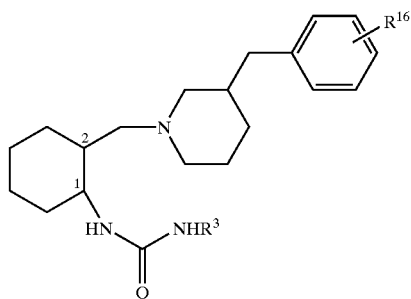

b

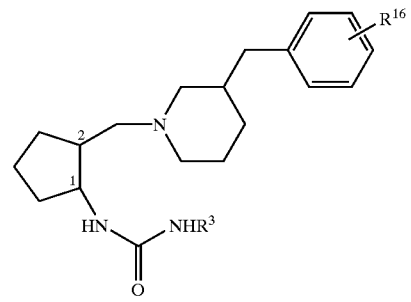

c

| Ex # | Core | $R^{16}$ | Stereo-chemistry | Salt Form | $R^3$ | MS M + H$^+$ |
|---|---|---|---|---|---|---|
| | | | | | yl)phenyl | |
| 557 | b | 4-F | 1R, 2S, 3S | CF$_3$CO$_2$H | cyclohexyl | 430 |
| 558 | b | 4-F | 1R, 2S, 3S | CF$_3$CO$_2$H | 2-methoxyphenyl | 468 |
| 559 | b | 4-F | 1R, 2S, 3S | CF$_3$CO$_2$H | 2,6-dimethylphenyl | 452 |
| 560 | b | 4-F | 1R, 2S, 3S | CF$_3$CO$_2$H | 2-ethylphenyl | 452 |
| 561 | b | 4-F | 1R, 2S, 3S | CF$_3$CO$_2$H | 2,4,6-trimethylphenyl | 466 |
| 562 | b | 4-F | 1R, 2S, 3S | CF$_3$CO$_2$H | 2,5-dimethoxyphenyl | 484 |
| 563 | b | 4-F | 1R, 2S, 3S | CF$_3$CO$_2$H | t-butyl | 404 |
| 564 | b | 4-F | 1R, 2S, 3S | CF$_3$CO$_2$H | i-propyl | 390 |
| 565 | b | 4-F | 1R, 2S, 3s | CF$_3$CO$_2$H | Ethoxycarbonyl-methyl) | 434 |
| 566 | b | 4-F | 1R, 2S, 3S | CF$_3$CO$_2$H | 2-trifluoromethoxy-phenyl | 508 |
| 567 | b | 4-F | 1R, 2S, 3S | CF$_3$CO$_2$H | (1R,S)-1-(methoxycarbonyl)-2-methyl-propyl | 462 |
| 568 | b | 4-F | 1R, 2S, 3S | CF$_3$CO$_2$H | [(1S)-1-(methoxycarbonyl)-2-phenylethyl | 510 |
| 569 | b | 4-F | 1R, 2S, 3S | CF$_3$CO$_2$H | 2,4,4-trimethyl-2-pentyl | 460 |
| 570 | b | 4-F | 1R, 2S, 3S | CF$_3$CO$_2$H | 2-phenylethyl | 452 |
| 571 | b | 4-F | 1R, 2S, 3S | CF$_3$CO$_2$H | 3-acetylphenyl | 466 |
| 572 | b | 4-F | 1R, 2S, 3S | CF$_3$CO$_2$H | 2-carbomethoxy-phenyl | 482 |
| 573 | b | 4-F | 1R, 2S, 3S | CF$_3$CO$_2$H | (1S)-1-(phenyl)ethyl | 452 |
| 574 | b | 4-F | 1R, 2S, 3S | CF$_3$CO$_2$H | 4-(phenyl)phenyl | 500 |
| 575 | b | 4-F | 1R, 2S, 3S | CF$_3$CO$_2$H | 1-naphthyl | 474 |
| 576 | b | 4-F | 1R, 2S, 3S | CF$_3$CO$_2$H | 2-(phenyl)phenyl | 500 |

TABLE 3.1-continued

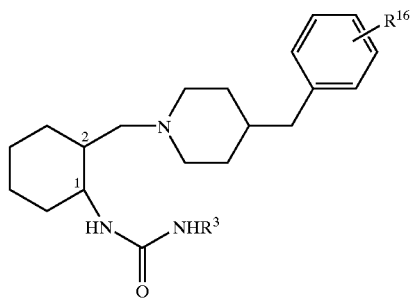

a

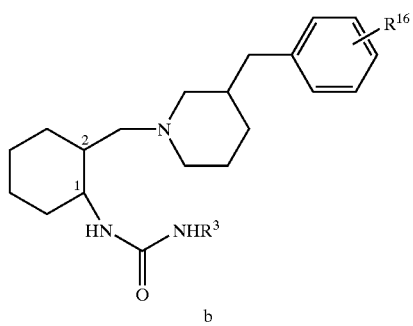

b

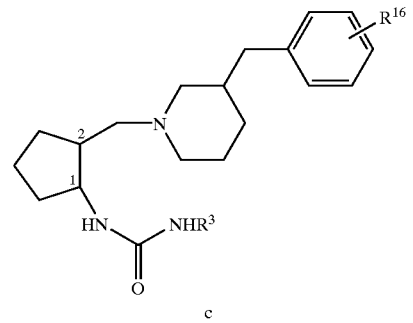

c

| Ex # | Core | $R^{16}$ | Stereo-chemistry | Salt Form | $R^3$ | MS M + H⁺ |
|---|---|---|---|---|---|---|
| 577 | b | 4-F | 1R, 2S, 3S | CF₃CO₂H | Phenylmethoxy | 454 |
| 578 | b | 4-F | 1R, 2S, 3S | CF₃CO₂H | 3,4-dimethoxyphenyl | 484 |
| 579 | b | 4-F | 1R, 2S, 3S | CF₃CO₂H | (3H)-2-ethylquinazolin-4-on-3-yl | 520 |
| 580 | b | 4-F | 1R, 2S, 3S | CF₃CO₂H | 3-pyridinyl | 425 |
| 581 | b | 4-F | 1R, 2S, 3S | CF₃CO₂H | 6-methoxy-3-pyridinyl | 455 |
| 582 | b | 4-F | 1R, 2S, 3S | CF₃CO₂H | 2-methylquinolin-8-yl | 489 |
| 583 | b | 4-F | 1R, 2S, 3S | CF₃CO₂H | 2-methylnaphth-1-yl | 488 |
| 584 | b | 4-F | 1R, 2S, 3S | CF₃CO₂H | 4-((1H)-1-propyl-tetrazol-5-yl)phenyl | 534 |
| 585 | b | 4-F | 1R, 2S, 3S | CF₃CO₂H | 3-aminophenyl | 439 |
| 586 | b | 4-F | 1R, 2S, 3S | — | 3-(acetylamino)-phenyl | 481 |
| 587 | b | 4-F | 1R, 2S, 3S | CF₃CO₂H | 3-(N-methylcarbamoyl)-phenyl | 481 |
| 588 | b | 4-F | 1R, 2S, 3S | CF₃CO₂H | 2-nitro-4-methoxyphenyl | 499 |
| 589 | b | 4-F | 1R, 2S, 3S | CF₃CO₂H | 8-hydroxyquinolin-5-yl | 491 |
| 590 | b | 4-F | 1R, 2S, 3S | CF₃CO₂H | 3-methylpyridin-2-yl | 439 |
| 591 | b | 4-F | 1R, 2S, 3S | CF₃CO₂H | isoquinolin-1-yl | 475 |

Example 318

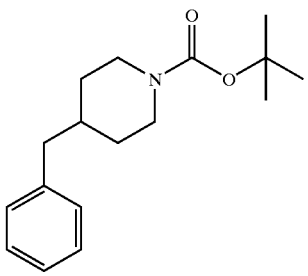

Part A: Preparation of 1-t-butyloxycarbonyl-4-benzylpiperidine 4-benzylpiperidine (10.0 g, 57.1 mmol, 1.0 eq.) was dissolved in 100 mL of THF under $N_2$ and subsequently cooled to 0° C. Di-tert-butyl dicarbonate (11.21 g, 51.3 mmol, 0.9 eq.) dissolved in 50 mL of THF, was added dropwise. Gas evolution was observed. Once gas evolution ceased, the ice bath was removed. After 20 hours, the THF was removed in vacuo then the residue was dissolved in EtOAc and rinsed 3× with 1N citric acid, 1× with brine. The organic was dried over magnesium sulfate and stripped to yield 15.4 g of colorless oil as product. Yield=97.9%. NMR (300 MHz, $CDCl_3$)δ 7.35–7.17 (m,3H); 7.14 (d, 2H, J=7 Hz); 4.20–3.90 (m, 2H); 2.75–2.55 (m, 2H); 2.54 (d, 2H, J=7 Hz); 1.70–1.50 (m, 3H); 1.46 (s, 9H); 1.20–1.00 (m, 2H).

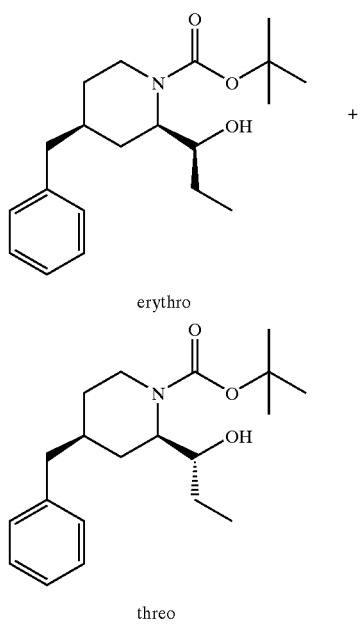

Part B: Preparation of erythro-and threo-cis-4-benzyl-1-t-butoxycarbonyl-•-ethylpiperidinemethanol 1-t-butyloxycarbonyl-4-benzylpiperidine (5.0 g, 18.2 mmol, 1.0 eq.) was dissolved in $Et_2O$ at 25° C. under $N_2$ and cooled to −78° C. N,N,N',N'-Tetramethylethylenediamine (TMEDA) (3.29 mL, 21.8 mmol, 1.2 eq.) was added followed by the dropwise addition of sec-butyllithium (16.76 mL, 21.8 mmol, 1.2 eq.). The reaction was allowed to warm and stir at −30° C. for 30 minutes then again cooled to −78° C. Once cool, propionaldehyde (1.31 mL, 20.0 mmol, 1.1 eq.) was added neat. The reaction was allowed warmed to warm to −30° C. then immediately quenched with 10 mL of water and the organic layer was separated. The aqueous layer was extracted 2× more with $Et_2O$. The organic layers were combined, dried over magnesium sulfate and the solvent removed in vacuo to yield a colorless oil which was purified by flash chromatography in 4:1 to 1:1 hexane/EtOAc. Obtained 0.68 g of a colorless oil as isomer A, yield=11.2% and 0.91 g of a colorless oil as isomer B, yield=15.0%.

Isomer A NMR (300 MHz, $CDCl_3$)δ7.40–7.25 (m, 2H); 7.21 (d, 1H, J=7 Hz); 7.16 (d, 2H, J=7 Hz); 3.60–3.30 (m, 2H); 2.56 (d, 2H J=7 Hz); 1.90–1.00 (m, 7H); 1.46 (s, 9H); 1.00–0.70 (m, 5H).

Isomer B NMR (300 MHz, $CDCl_3$)δ7.30–7.23 (m, 2H); 7.20 (d, 1H, J=7 Hz); 7.14 (d, 2H, J=7 Hz.); 3.60–3.20 (m, 2H); 2.60–2.40 (m, 2H); 1.90–1.00 (m, 9H); 1.44 (s, 9H); 0.96 (t, 3H, J=7 Hz).

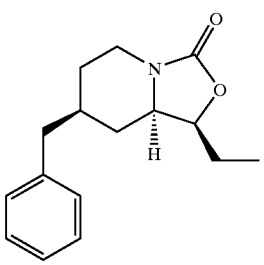

erythro

Part C: Structure determination of Isomer B via cyclization to 4α,6α,7α-4-benzyl-7-ethyl-8-oxa-1-azabicyclo[4.3.0]nonane-9-one Isomer B (60 mg, 0.18 mmol, 1 eq.) was dissolved in DMF at 25° C. under $N_2$ then NaH (7.9 mg, 0.198 mmol, 1 eq.) was added. After 20 hours, 2 mL of water was added followed by EtOAc. The layers were separated. The aqueous layer was extracted 2× more with EtOAc. The organic layers were combined, dried over magnesium sulfate, and the solvent removed in vacuo to yield an oil which was purified over silica gel in 9:1 to 1:1 hexane/EtOAc. Obtained 30 mg. Yield=64%. Product structure confirmed by N.O.E. NMR (300 MHz, $CDCl_3$) δ 7.40–7.20 (m, 3H); 7.16 (d, 2H, J=7 Hz); 4.45–4.25 (m, 1H); 4.00–3.80 (m, 1H); 3.65–3.45 (m, 1H); 2.95–2.70 (m, 1H); 2.65–2.45 (m, 2H); 1.85–1.40 (m, 4H); 1.40–1.00 (m, 6H).

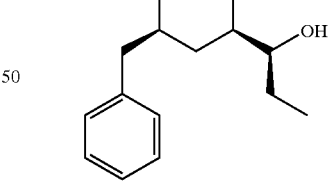

Part D: Preparation of erythro-cis-4-benzyl-α-ethylpiperidinemethanol

Erythro-cis-4-benzyl-1-t-butoxycarbonyl-•-ethylpiperidinemethanol (isomer B from part B) (815 mg, 2.44 mmol, 1 eq.) was dissolved in 8 mL of ethanol at 25° C. under $N_2$. NaOH (391 mg, 9.78 mmol, 4 eq.) was added and the mixture refluxed for 4 hours. The solvent was removed in vacuo to yield an oil. Water was added followed by EtOAc. The layers were separated. The aqueous layer was extracted 2× more with EtOAc. The organic layers were combined dried over magnesium sulfate, and the solvent removed in vacuo to yield 390 mg of an oil. Yield=68%.

NMR (300 MHz, CDCl₃) • 7.35–7.20 (m, 2H); 7.23–7.00 (m, 3H); 3.75–3.65 (m, 1H); 3.20–3.00 (m, 1H); 2.90–2.40 (m, 4H); 1.70–1.50 (m, 2H); 1.50–1.30 (m, 1H); 1.20–0.80 (m, 5H).

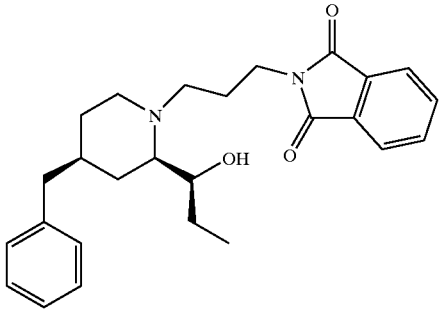

Part E: Preparation of erythro-cis-4-benzyl-α-ethyl-1-(3-N-phthalimido-n-prop-1-yl)piperidinemethanol Erythro-cis-4-benzyl-α-ethylpiperidinemethanol (195 mg, 0.84 mmol, 1 eq.), N-(3-bromopropyl)phthalimide (224 mg, 0.84 mmol, 1 eq.), potassium iodide (139 mg, 0.84 mmol, 1 eq.), and potassium carbonate (231 mg, 0.84 mmol, 1 eq.) were refluxed in 10 mL of 2-butanone for 3 hours. The reaction was worked up by filtering off the inorganic solids. The filtrate solvent was removed in vacuo to yield an oil. Purified by flash chromatography in 100% EtOAc then 4:1 chloroform/MeOH. Obtained 200 mg. Yield=57%. NMR (300 MHz, CDCl₃) δ 7.95–7.80 (m, 2H); 7.80–7.65 (m, 2H); 7.35–7.00 (m, 5H); 3.90–3.60 (m, 3H); 3.20–2.90 (m, 2H); 2.65–2.30 (m, 3H); 2.20–2.00 (m, 2H); 2.00–1.75 (m, 2H); 1.70–1.40 (m, 4H); 1.35–0.90 (m, 3H); 0.96 (t, 3H, J=7 Hz).

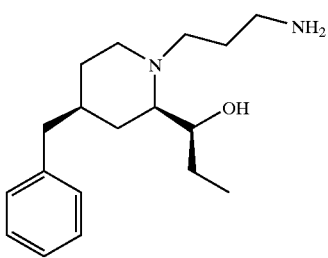

Part F: Preparation of erythro-cis-1-(3-amino-n-prop-1-yl)-4-benzyl-α-ethylpiperidinemethanol Erythro-cis-4-benzyl-α-ethyl-1-(3-N-phthalimido-n-prop-1-yl)piperidinemethanol(200 mg, 0.48 mmol, 1 eq.) was dissolved in 5 mL of ethanol at 25° C. under N₂. Anhydrous hydrazine (0.03 mL, 0.95 mmol, 2 eq.) was added and the reaction refluxed for 3 hours during which time a white precipitate (phthalhydrazide) formed. Once cool, The solids were filtered. The filtrate solvent was removed in vacuo to yield an oil which was stirred in Et₂O. The triturated solids were filtered and the filtrate solvent was removed in vacuo to yield 120 mg of an oil. Yield=87%. NMR (300 MHz, CDCl₃) δ 7.27 (t, 2H, J=7 Hz); 7.17 (d, 1H, J=7 Hz); 7.13 (d, 2H, J=7 Hz); 3.70–3.30 (m, 2H); 3.20–3.00 (m, 2H); 3.00–2.70 (m, 2H); 2.70–2.40 (m, 2H); 2.30–2.10 (m, 1H); 2.10–1.90 (m, 2H); 1.90–1.40 (m, 5H); 1.40–1.00 (m, 3H); 0.96 (t, 3H, J=7 Hz).

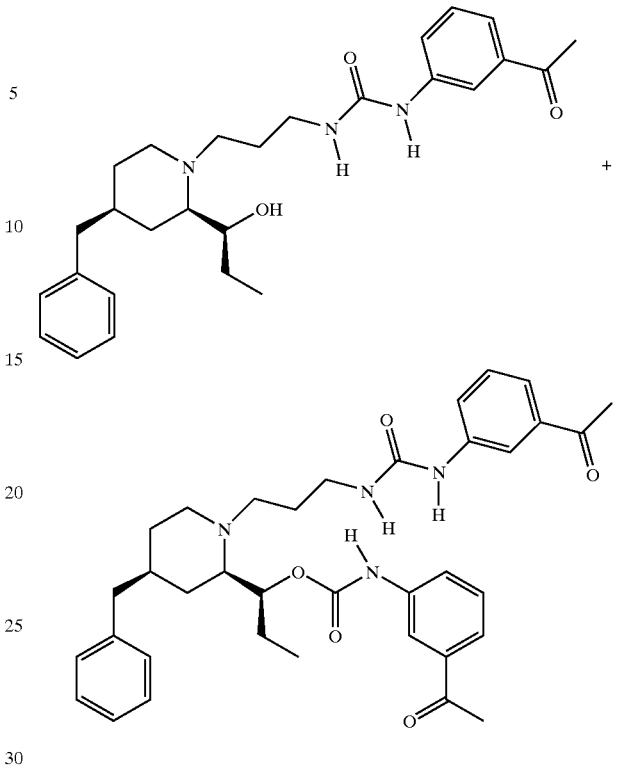

Part G: preparation of erythro-cis-1-[3-(3-acetylphenylaminocarbonylamino)-n-prop-1-yl]-4-benzyl-α-ethylpiperidinemethanol and erythro-cis-1-[3-(3-acetylphenylaminocarbonylamino)-n-prop-1-yl]-2-[1-(3-acetylphenylaminocarbonyloxy)-n-prop-1-yl)-4-benzylpiperidine Erythro-cis-1-(3-amino-n-prop-1-yl)-4-benzyl-α-ethylpiperidinemethanol (120 mg, 0.41 mmol, 1 eq.) was dissolved in 5 mL of THF at 25° C. under N₂ then 3-acetylphenyl isocyanate added neat. After 1 hour the solvent was removed in vacuo to yield an oil. Purified by flash chromatography in 100% EtOAc to 4:1 chloroform/MeOH. Isolated mono-addition product (product A) along with an additional bis-addition product (product B). Prouct A yielded 81 mg of an oil. Yield=43%. Product B yielded 43 mg of an oil.

Product A NMR (300 MHz, CDCl₃) δ 7.86 (bs, 1H); 7.73 (d, 1H, J=7 Hz); 7.60 (s, 1H); 7.56 (d, 1H, J=7 Hz); 7.40–7.15 (m, 4H); 7.12 (d, 2H, J=7 Hz); 6.30–6.05 (m, 1H); 4.00–3.80 (m, 1H); 3.50–3.30 (m, 1H); 3.30–2.90 (m, 5H); 2.60–2.40 (m, 2H); 2.57 (s, 3H); 2.30–2.10 (m, 1H); 2.10–1.90 (m, 2H); 1.80–1.40 (m, 5H); 1.30–1.05 (m, 2H); 0.94 (t, 3H, J=7 Hz).

Product B NMR (300Mhz, CDCl₃) δ 10.80–10.60 (m, 1H); 8.20–8.00 (m,1H); 7.91 (bs, 1H); 7.80–7.18 (m, 9H); 7.11 (d, 2H, J=7 Hz); 6.20–6.00 (m, 1H); 5.20–5.00 (m, 1H); 3.50–3.00 (m, 4H); 2.57 (s, 3H); 2.56 (s, 3H); 2.55–2.00 (m, 5H); 2.00–1.00 (m, 10H); 1.00–0.80 (m, 3H)

Product A was seperated into its enantiomers employing a Daicel Chiral Pack AD column, eluting with 0.1% diethylamine in methanol. (−)-isomer [α]$_D^{25}$ (c=0.300 g/dL, MeOH)=−14.9°. (+)-isomer [α]$_D^{25}$ (c=0.290 g/dL, MeOH=+20.2°.

The following compounds can be synthesized by the methods discussed previously.

TABLE 3b

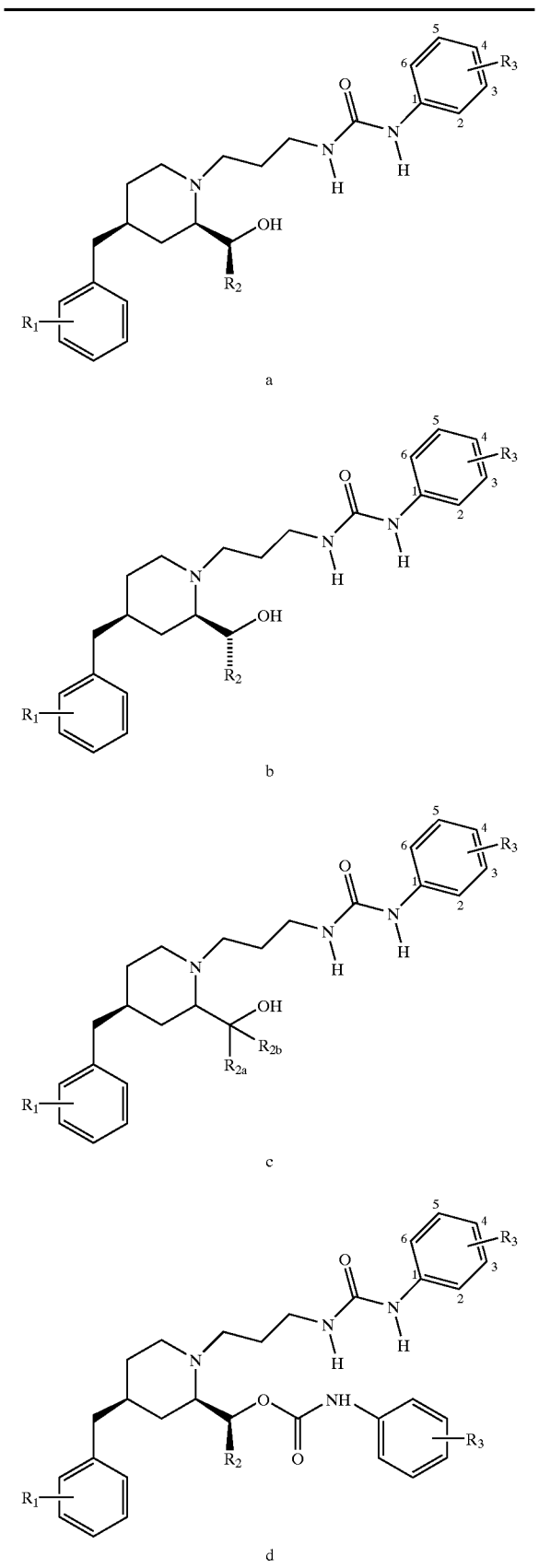

| Cores | R1 | R2 | R2a, R2b | R3 | M + 1 |
|---|---|---|---|---|---|
| 319 a, b | H | CH3 | — | 3-COCH3 | 438 |
| 320 a, b | H | CH3 | — | 4-NO2 | 441 |
| 321 a, b | H | CH3CH2 | — | 3-COCH3 | 452 |
| 322 c | H | — | CH3, CH3 | 3-COCH3 | 452 |
| 323 a, b | H | CH3CH2CH2 | — | 3-COCH3 | 466 |
| 324 a, b | H | (CH3)2CH | — | 3-COCH3 | 466 |
| 325 a, b | H | CH3CH2CH2CH2 | — | 3-COCH3 | 480 |
| 326 a, b | H | (CH3)2CHCH2 | — | 3-COCH3 | 480 |
| 327 d, e | H | CH3CH2 | — | 3-COCH3 | 613 |
| 328 d, e | H | CH3CH2CH2 | — | 3-COCH3 | 627 |
| 329 d, e | H | (CH3)2CH | — | 3-COCH3 | 627 |
| 330 d, e | H | CH3CH2CH2CH2 | — | 3-COCH3 | 641 |
| 331 d, e | H | (CH3)2CHCH2 | — | 3-COCH3 | 641 |

Example 332

Part A Preparation of N-cyano-N'-3-methoxyphenylcarbamimidic acid, phenyl ester

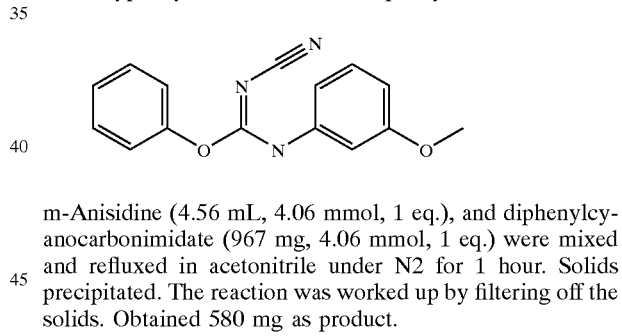

m-Anisidine (4.56 mL, 4.06 mmol, 1 eq.), and diphenylcyanocarbonimidate (967 mg, 4.06 mmol, 1 eq.) were mixed and refluxed in acetonitrile under N2 for 1 hour. Solids precipitated. The reaction was worked up by filtering off the solids. Obtained 580 mg as product.

M.P.=170.0–171.0° C. NMR (300 MHz, DMSO-$d_6$) 67 8.70–8.50 (m, 1H); 7.43 (t, 2H, J=7 Hz); 7.40–7.20 (m, 2H); 7.14 (d, 2H, J=7 Hz); 7.00–6.80 (m, 2H); 6.80–6.70 (m, 1H); 3.80 (s, 3H).

Part B Preparation of N"-cyano-N'-(3-[4-(4-fluorobenzyl)piperidinel]propyl-N-(3-methoxyphenyl)quanidine

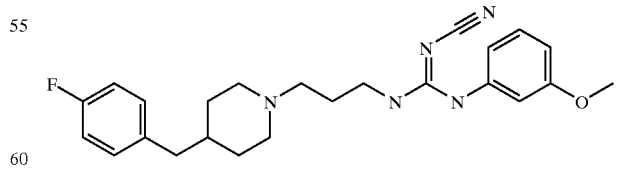

3-(4-(4-fluorophenylmethyl)piperidin-1-yl)propylamine, (synthesized in a similar fashion to the previously described des-fluoro compound) (53 mg, 0.20 mmol, 1 eq.) and the product from Part A (50 mg, 0.20 mmol, 1 eq.) were mixed and refluxed in 2-propanol under $N_2$ for 1 hour. The reaction was stripped and the residue then purified over silica gel in 100% ethyl acetate followed by 8:2 chloroform/methanol. Obtained 55 mg of off-white solids as product. NMR (300 MHz, CDCl₃) δ 7.33 (t, 1H, J=7 Hz); 7.10–6.90 (m, 4H); 6.90–6.80 (m, 3H); 3.83 (s, 3H); 3.50–3.35 (m, 2H); 2.90–2.70 (m, 2H); 1.50–1.20 (m, 3H). Mass Spec detects 424 (M+H).

Example 334
Part A: Preparation of [(Methylthio)(3-acetylphenyl amino)]methylenepropanedinitrile

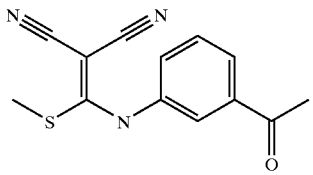

[Bis(methylthio)methylene]propanedinitrile 3.00 g, 17.6 mmol, 1 eq.), and 3' amino-acetophenone (2.38 g, 17.6 mmol, 1 eq.), were mixed and refluxed under N₂ in ethanol for 16 hours. Solids precipitated while cooling to 25° C. The solids were filtered. Obtained 1.86 g of tan solids.

M.P.=165.0–166.5° C. NMR (300 MHz, DMSO-d₆) δ 10.66 (m, 1H); 7.90–7.80 (m, 2H); 7.60–7.50 (m, 2H); 2.60 (s, 3H); 2.54 (s, 3H).

Part B: Preparation of 2-[(3-acetylanilino)({3-[4-(4-fluorobenzyl)-1-piperidinyl]propyl}amino)methylene]malononitrile

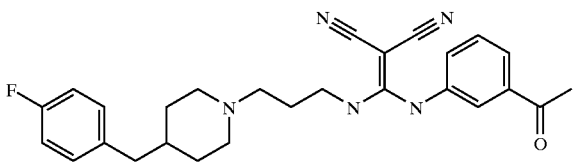

3-(4-(4-fluorophenylmethyl)piperidin-1-yl)propylamine, 49 mg, 0.194 mmol, 1 eq.) and the product from Part A (50 mg, 0.194 mmol, 1 eq.) were mixed then stirred under N2 overnight. The reaction was stripped and the residue purified over chloroform/methanol. Obtained 17 mg of a white amphorphous solid. NMR (300 MHz, CDCl₃) δ 7.82 (d, 1H, J=7 Hz); 7.73(s, 1H); 7.51 (t, 1H, J=7 Hz); 7.34 (d, 1H, J=7Hz); 7.10–6.80 (m, 4H); 3.28 (m, 2H); 2.62 (s, 3H); 2.64–2.40 (m,2H); 2.40–2.25 (m, 2H); 2.05–1.70 (m, 2H); 1.70–1.35 (m, 3H); 1.20–0.80 (m, 2H). Mass Spec detects 460 (M+H).

Example 335
Part A: Preparation of N-[1-(methylthio)-2-nitroethenyl]-3-acetylbenzenamine

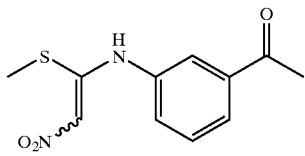

A neat mixture of 1,1-bismethylthio-2-nitroethylene (6.5 g, 38.5 mmol, 10 eq) and 3-aminoacetophenone (0.5 g, 3.85 mmol, 1 eq) was melted together and heated at 140° C. for four hours. The mixture was cooled to room temperature, then subjected to flash chromatography, eluting with 50% ethyl acetate/hexanes, to yield 0.63 g of a yellow powder as product. Yield=65%. NMR (300 MHz, CDCl₃) δ 11.82 (bs, 1H), 7.95–7.91 (m, 2H), 7.59–7.48 (m, 2H), 6.73 (s, 1H), 2.65 (s, 3H), 2.41 (s, 3H).

Part B: Preparation of 1-(3-{[(E)-1-({-[4-(4-fluorobenzyl)-1-piperidinyl]propyl}amino)-2-nitroethylenyl]amino}phenyl)ethanone

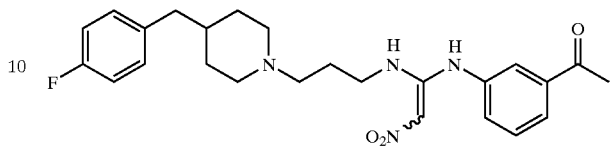

To a suspension of N-[1-(methylthio)-2-nitroethenyl]-3-acetylbenzenamine (0.30 g, 1.19 mmol, 1.00 eq) in 20 ml of methanol was added 3-(4-fluorobenzyl)piperidin-1-yl) propylamine (0.31 g, 1.25 mmol, 1.05 eq), and the mixture was stirred at room temperature. After three days, a colorless solution was observed. The solvent was removed in-vacuo, and the residue was subjected to flash chromatography, eluting with 10% methanol/chloroform, to yield 0.38 g of an orange glass as product. Yield=70%.

NMR (300 MHz, CDCl₃) δ 10.51 (bs, 1H), 7.92 (d, 1H, j=8 Hz), 7.72 (bs, 1H), 7.54 (dd, 1H, j=8 Hz, 8 Hz), 7.35 (bd, 1H), 6.90–6.88 (m, 5H), 6.17 (s, 1H), 3.54 (bs, 2H), 2.92–2.84 (m, 2H), 2.63 (s, 3H), 2.51 (m, 2H), 1.99–1.91 (m, 4H), 1.55–1.50 (m, 3H), 0.88–0.85 (m, 2H). MS (ESI) detects (M+H)⁺=455.

The following compounds can be prepared by procedures described previously:

TABLE 3c

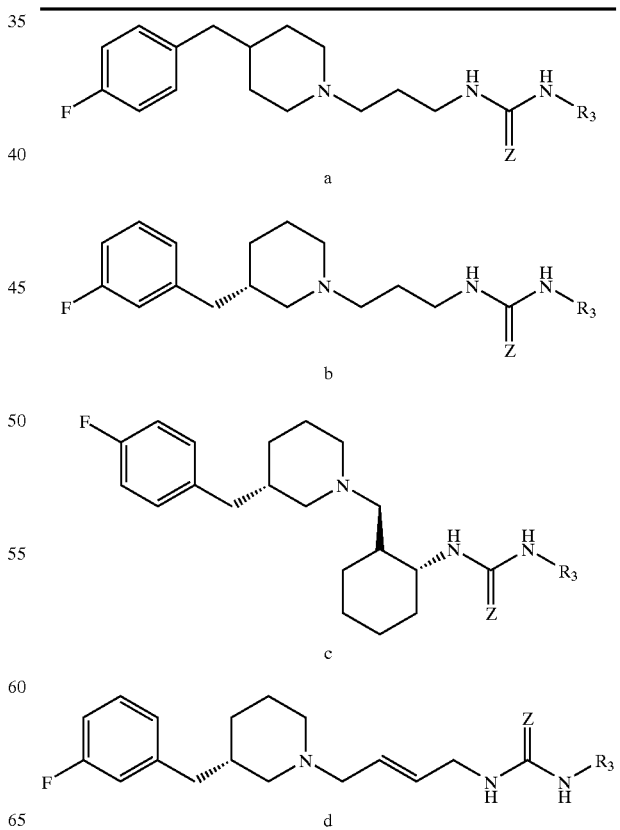

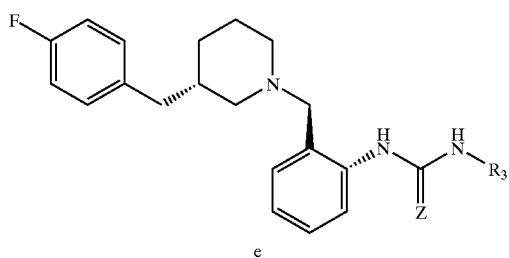

e

| Core | Z | R3 | Mass Spec M + 1 |
|---|---|---|---|
| 332 | a | N—CN | 3-methoxyphenyl | 424 |
| 333 | a | N—CN | 3-acetylphenyl | 460 |
| 334 | a | C(CN)2 | 3-acetylphenyl | 460 |
| 335 | a | CHNO2 | 3-acetylphenyl | 455 |
| 336 | b | N—CN | 3-acetylphenyl | 436 |
| 337 | b | C(CN)2 | 3-acetylphenyl | 460 |
| 338 | b | NCONH2 | 3-acetylphenyl | 454 |
| 339 | b | CHNO2 | 3-acetylphenyl | 455 |
| 340 | b | N—CN | 3,5-diacetylphenyl | 478 |
| 341 | b | NCONH2 | 3,5-diacetylphenyl | 496 |
| 342 | b | NCO2CH3 | 3,5-diacetylphenyl | 511 |
| 343 | b | C(CN)2 | 3,5-diacetylphenyl | |
| 344 | b | N—CN | 3-(1-methyl-1H-tetrazol-5-yl)phenyl | 476 |
| 345 | b | C(CN)2 | 3-(1-methyl-1H-tetrazol-5-yl)phenyl | 500 |
| 346 | b | NCONH2 | 3-(1-methyl-1H-tetrazol-5-yl)phenyl | 494 |
| 347 | b | N—CN | 2,4-dimethoxy-phenyl | 454 |
| 348 | b | N—CN | 5-acetyl-2-methoxy-phenyl | 466 |
| 349 | d | N—CN | 3-(1-methyl-1H-tetrazol-5-yl)phenyl | 488 |
| 350 | c | N—CN | phenyl | 448 |
| 351 | c | N—CN | 3-acetylphenyl | 490 |
| 352 | c | N—CN | 3-cyanophenyl | 473 |
| 353 | c | N—CN | 2,4-dimethoxyphenyl | 508 |
| 354 | c | N—CN | 2,5-dimethoxyphenyl | 508 |
| 355 | c | N—CN | 5-acetyl-2-methoxy-phenyl | 520 |
| 356 | c | N—CN | 2,4-dimethylphenyl | 476 |
| 357 | c | N—CN | 4-(1-methyl-1H-tetrazol-5-yl)phenyl | 530 |
| 358 | c | N—CN | 4-(1-propyl-1H-tetrazol-5-yl)phenyl | 558 |
| 359 | c | N—CN | 5,6,7,8-tetrahydro-naphthy-2-yl-phenyl | 502 |
| 360 | c | N—CN | 4-(4-morpholinyl)-phenyl | 533 |
| 361 | C | N—CN | 2,5-dimethylphenyl | |
| 362 | c | N—CN | 4-hydroxy-2-methylphenyl | |
| 363 | c | N—CN | 2-methylphenyl | |
| 364 | c | N—CN | 2-phenylethyl | |
| 365 | c | N—CN | 1-adamantyl | |
| 366 | c | N—CN | 2-adamantyl | |
| 367 | c | C(CN)2 | 3-acetylphenyl | 514 |
| 368 | c | C(CN)2 | 5-acetyl-2-methoxy-phenyl | 544 |
| 369 | c | CHNO2 | 3-acetylphenyl | 509 |
| 370 | e | CHNO2 | 3-acetylphenyl | 560 |
| 371 | e | N—CN | 3,5-diacetylphenyl | 583 |
| 372 | e | N—CN | 3-acetylphenyl | 541 |
| 373 | e | N—CN | 4-(1-propyl-1H-tetrazol-5-yl)phenyl | 581 |

The following tables contain representative examples of the present invention, and may be prepared by procedures described above, or methods familiar to one skilled in the art. Each entry in each table is intended to be paired with each formulae at the start of the table. For example, Entry 1 in Table 4 is intended to be paired with each of formulae 1a-44.

TABLE 4*

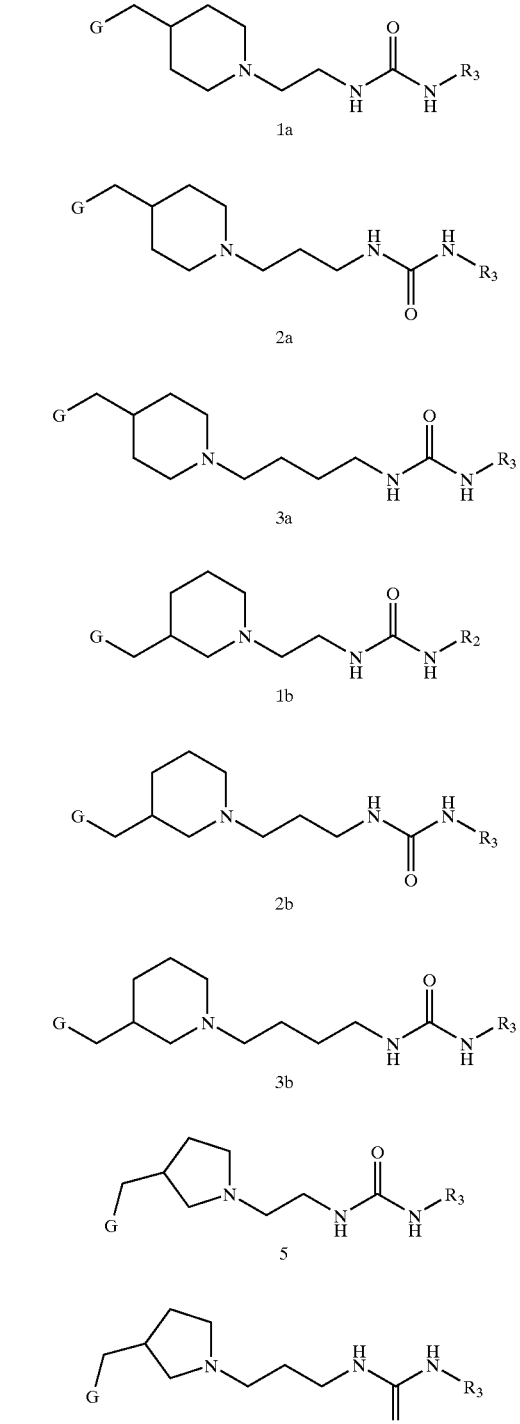

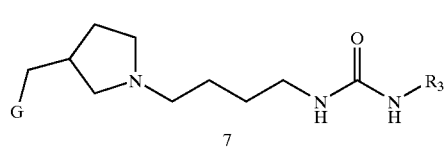

TABLE 4*-continued
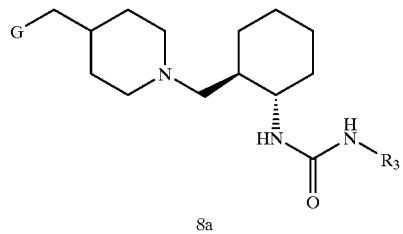
8a
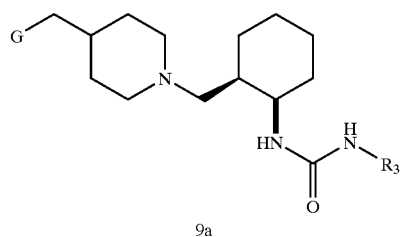
9a
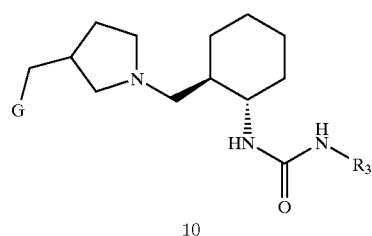
10
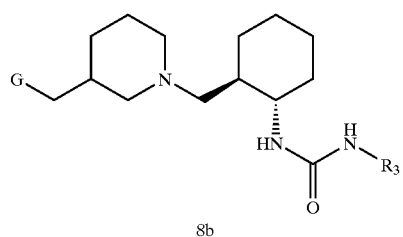
8b
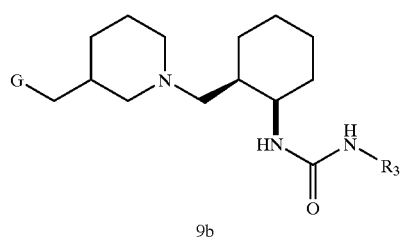
9b
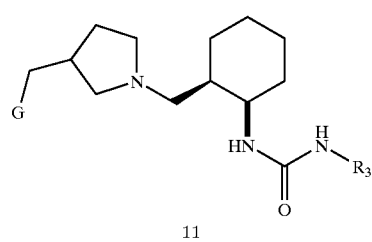
11
TABLE 4*-continued
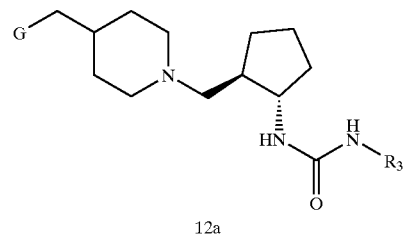
12a
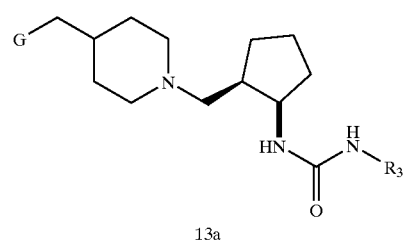
13a
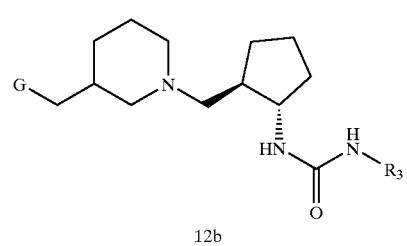
12b
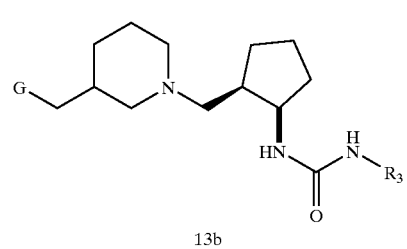
13b
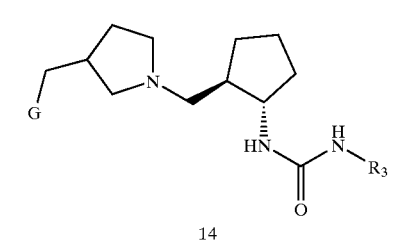
14
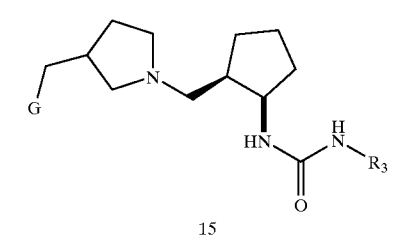
15

TABLE 4*-continued
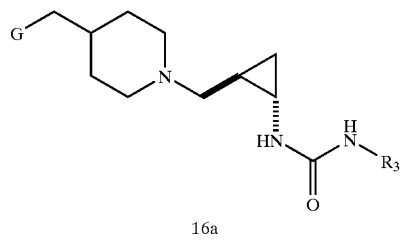
16a
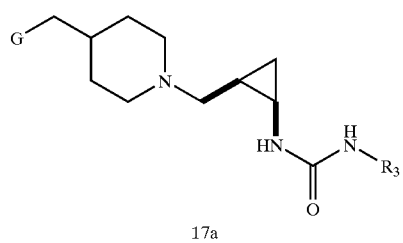
16b
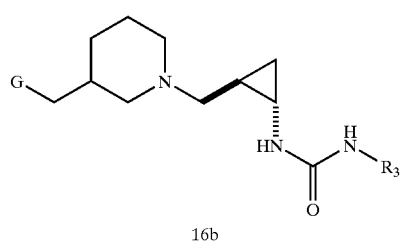
17a
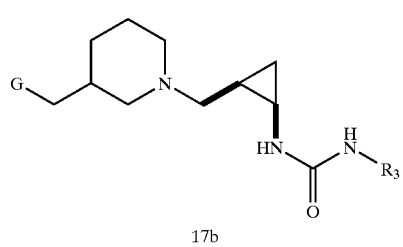
17b
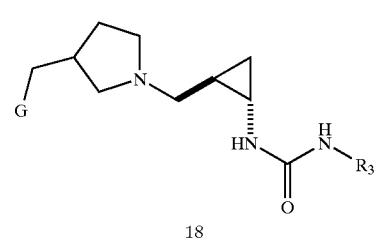
18
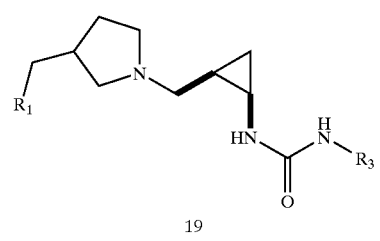
19
TABLE 4*-continued
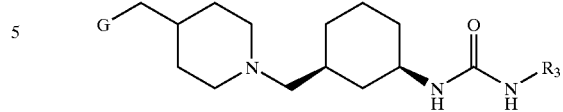
20a
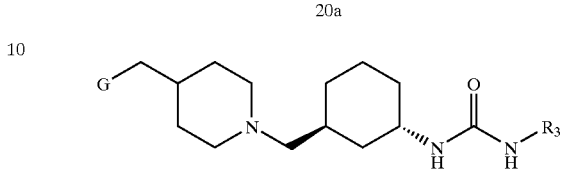
20b
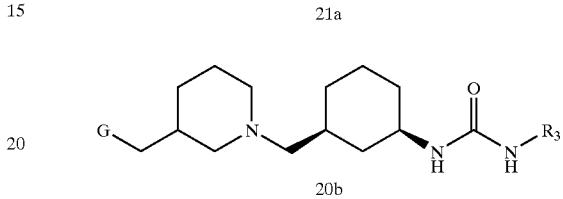
21a
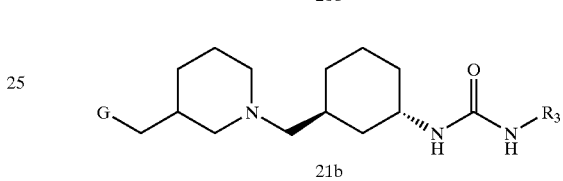
21b
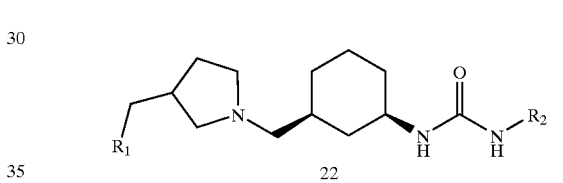
22
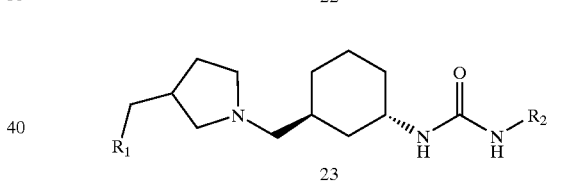
23
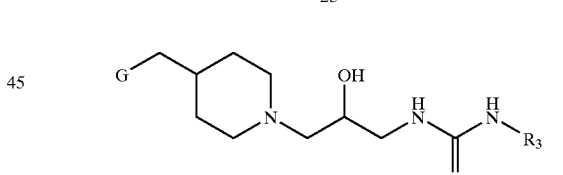
24
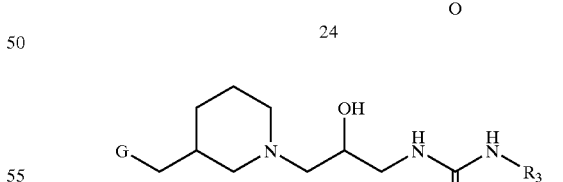
25
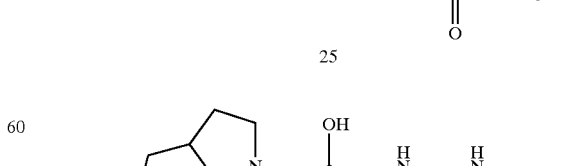
26

TABLE 4*-continued

TABLE 4*-continued

[Structure 43: piperidine-based compound with G, OH, Ph, and R3 urea substituents]

[Structure 44: pyrrolidine-based compound with G, OH, Ph, and R3 urea substituents]

| Entry | G | R3 |
|---|---|---|
| 1 | 4-F—Ph | Ph |
| 2 | 4-F—Ph | 3-CN—Ph |
| 3 | 4-F—Ph | 3-COCH3—Ph |
| 4 | 4-F—Ph | 3-CO2Me—Ph |
| 5 | 4-F—Ph | 3-CO2Et—Ph |
| 6 | 4-F—Ph | 3-CO2H—Ph |
| 7 | 4-F—Ph | 3-CONH2—Ph |
| 8 | 4-F—Ph | 3-CONHMe—Ph |
| 9 | 4-F—Ph | 3-F—Ph |
| 10 | 4-F—Ph | 3-Cl—Ph |
| 11 | 4-F—Ph | 3-Br—Ph |
| 12 | 4-F—Ph | 3-NO2—Ph |
| 13 | 4-F—Ph | 3-NH2—Ph |
| 14 | 4-F—Ph | 3-NHMe—Ph |
| 15 | 4-F—Ph | 3-NMe2—Ph |
| 16 | 4-F—Ph | 3-NHCOCH3—Ph |
| 17 | 4-F—Ph | 3-SO2NH2—Ph |
| 18 | 4-F—Ph | 3-SO2NHMe—Ph |
| 19 | 4-F—Ph | 3-CF3—Ph |
| 20 | 4-F—Ph | 3-OCH3—Ph |
| 21 | 4-F—Ph | 3-OPh—Ph |
| 22 | 4-F—Ph | 3-OCF3—Ph |
| 23 | 4-F—Ph | 3-SCH3—Ph |
| 24 | 4-F—Ph | 3-SOCH3—Ph |
| 25 | 4-F—Ph | 3-SO2CH3—Ph |
| 26 | 4-F—Ph | 3-OH—Ph |
| 27 | 4-F—Ph | 3-CH2OH—Ph |
| 28 | 4-F—Ph | 3-CHOHCH3—Ph |
| 29 | 4-F—Ph | 3-COH(CH3)2—Ph |
| 30 | 4-F—Ph | 3-CHOHPh—Ph |
| 31 | 4-F—Ph | 3-CH3—Ph |
| 32 | 4-F—Ph | 3-C2H5—Ph |
| 33 | 4-F—Ph | 3-iPr-Ph |
| 34 | 4-F—Ph | 3-tBu-Ph |
| 35 | 4-F—Ph | 3-Ph—Ph |
| 36 | 4-F—Ph | 3-CH2Ph—Ph |
| 37 | 4-F—Ph | 3-CH2CO2Me—Ph |
| 38 | 4-F—Ph | 3-(1-piperidinyl)-Ph |
| 39 | 4-F—Ph | 3-(1-pyrrolidinyl)-Ph |
| 40 | 4-F—Ph | 3-(2-imidazolyl)-Ph |
| 41 | 4-F—Ph | 3-(1-imidazolyl)-Ph |
| 42 | 4-F—Ph | 3-(2-thiazolyl)-Ph |
| 43 | 4-F—Ph | 3-(3-pyrazolyl)-Ph |
| 44 | 4-F—Ph | 3-(1-pyrazolyl)-Ph |
| 45 | 4-F—Ph | 3-(1-tetrazolyl)-Ph |
| 46 | 4-F—Ph | 3-(5-tetrazolyl)-Ph |
| 47 | 4-F—Ph | 3-(2-pyridyl)-Ph |
| 48 | 4-F—Ph | 3-(2-thienyl)-Ph |
| 49 | 4-F—Ph | 3-(2-furanyl)-Ph |
| 50 | 4-F—Ph | 4-CN—Ph |
| 51 | 4-F—Ph | 4-COCH3—Ph |
| 52 | 4-F—Ph | 4-CO2Me—Ph |
| 53 | 4-F—Ph | 4-CO2Et—Ph |
| 54 | 4-F—Ph | 4-CO2H—Ph |
| 55 | 4-F—Ph | 4-CONH2—Ph |
| 56 | 4-F—Ph | 4-CONHMe—Ph |
| 57 | 4-F—Ph | 4-CONHPh—Ph |
| 58 | 4-F—Ph | 4-NHCONH2—Ph |
| 59 | 4-F—Ph | 4-F—Ph |
| 60 | 4-F—Ph | 4-Cl—Ph |
| 61 | 4-F—Ph | 4-Br—Ph |
| 62 | 4-F—Ph | 4-NO2—Ph |
| 63 | 4-F—Ph | 4-NH2—Ph |
| 64 | 4-F—Ph | 4-NHMe—Ph |
| 65 | 4-F—Ph | 4-NMe2—Ph |
| 66 | 4-F—Ph | 4-NHCOCH3—Ph |
| 67 | 4-F—Ph | 4-SO2NH2—Ph |
| 68 | 4-F—Ph | 4-SO2NHMe—Ph |
| 69 | 4-F—Ph | 4-CF3—Ph |
| 70 | 4-F—Ph | 4-OCH3—Ph |
| 71 | 4-F—Ph | 4-OPh—Ph |
| 72 | 4-F—Ph | 4-OCF3—Ph |
| 73 | 4-F—Ph | 4-SCH3—Ph |
| 74 | 4-F—Ph | 4-SOCH3—Ph |
| 75 | 4-F—Ph | 4-SO2CH3—Ph |
| 76 | 4-F—Ph | 4-OH—Ph |
| 77 | 4-F—Ph | 4-CH2OH—Ph |
| 78 | 4-F—Ph | 4-CHOHCH3—Ph |
| 79 | 4-F—Ph | 4-COH(CH3)2—Ph |
| 80 | 4-F—Ph | 4-CH3—Ph |
| 81 | 4-F—Ph | 4-C2H5—Ph |
| 82 | 4-F—Ph | 4-iPr-Ph |
| 83 | 4-F—Ph | 4-tBu-Ph |
| 84 | 4-F—Ph | 4-Ph—Ph |
| 85 | 4-F—Ph | 4-CH2Ph—Ph |
| 86 | 4-F—Ph | 4-CH2CO2Me—Ph |
| 87 | 4-F—Ph | 4-(1-piperidinyl)-Ph |
| 88 | 4-F—Ph | 4-(1-pyrrolidinyl)-Ph |
| 89 | 4-F—Ph | 4-(2-imidazolyl)-Ph |
| 90 | 4-F—Ph | 4-(1-imidazolyl)-Ph |
| 91 | 4-F—Ph | 4-(2-thiazolyl)-Ph |
| 92 | 4-F—Ph | 4-(3-pyrazolyl)Ph |
| 93 | 4-F—Ph | 4-(1-pyrazolyl)-Ph |
| 94 | 4-F—Ph | 4-(1-tetrazolyl)-Ph |
| 95 | 4-F—Ph | 4-(5-tetrazolyl)-Ph |
| 96 | 4-F—Ph | 4-(2-pyridyl)-Ph |
| 97 | 4-F—Ph | 4-(2-thienyl)-Ph |
| 98 | 4-F—Ph | 4-(2-furanyl)-Ph |
| 99 | 4-F—Ph | 2-CN—Ph |
| 100 | 4-F—Ph | 2-COCH3—Ph |
| 101 | 4-F—Ph | 2-CO2Me—Ph |
| 102 | 4-F—Ph | 2-CO2Et—Ph |
| 103 | 4-F—Ph | 2-CO2H—Ph |
| 104 | 4-F—Ph | 2-CONH2—Ph |
| 105 | 4-F—Ph | 2-CONHMe—Ph |
| 106 | 4-F—Ph | 2-F—Ph |
| 107 | 4-F—Ph | 2-Cl—Ph |
| 108 | 4-F—Ph | 2-Br—Ph |
| 109 | 4-F—Ph | 2-NO2—Ph |
| 110 | 4-F—Ph | 2-NH2—Ph |
| 111 | 4-F—Ph | 2-NHMe—Ph |
| 112 | 4-F—Ph | 2-NMe2—Ph |
| 113 | 4-F—Ph | 2-NHCOCH3—Ph |
| 114 | 4-F—Ph | 2-SO2NH2—Ph |
| 115 | 4-F—Ph | 2-SO2NHMe—Ph |
| 116 | 4-F—Ph | 2-CF3—Ph |
| 117 | 4-F—Ph | 2-OCH3—Ph |
| 118 | 4-F—Ph | 2-OPh—Ph |
| 119 | 4-F—Ph | 2-OCF3—Ph |
| 120 | 4-F—Ph | 2-SCH3—Ph |
| 121 | 4-F—Ph | 2-SOCH3—Ph |
| 122 | 4-F—Ph | 2-SO2CH3—Ph |
| 123 | 4-F—Ph | 2-OH—Ph |
| 124 | 4-F—Ph | 2-CH2OH—Ph |
| 125 | 4-F—Ph | 2-CHOHCH3—Ph |
| 126 | 4-F—Ph | 2-COH(CH3)2—Ph |
| 127 | 4-F—Ph | 2-CHOHPh—Ph |
| 128 | 4-F—Ph | 2-CH3—Ph |
| 129 | 4-F—Ph | 2-C2H5—Ph |
| 130 | 4-F—Ph | 2-iPr-Ph |
| 131 | 4-F—Ph | 2-tBu-Ph |
| 132 | 4-F—Ph | 2-Ph—Ph |
| 133 | 4-F—Ph | 2-CH2Ph—Ph |
| 134 | 4-F—Ph | 2-CH2CO2Me—Ph |
| 135 | 4-F—Ph | 2-(1-piperidinyl)-Ph |
| 136 | 4-F—Ph | 2-(1-pyrrolidinyl)-Ph |

TABLE 4*-continued

| | | |
|---|---|---|
| 137 | 4-F—Ph | 2-(2-imidazolyl)-Ph |
| 138 | 4-F—Ph | 2-(1-imidazolyl)-Ph |
| 139 | 4-F—Ph | 2-(2-thiazolyl)-Ph |
| 140 | 4-F—Ph | 2-(3-pyrazolyl)-Ph |
| 141 | 4-F—Ph | 2-(1-pyrazolyl)-Ph |
| 142 | 4-F—Ph | 2-(1-tetrazolyl)-Ph |
| 143 | 4-F—Ph | 2-(5-tetrazolyl)-Ph |
| 144 | 4-F—Ph | 2-(2-pyridyl)-Ph |
| 145 | 4-F—Ph | 2-(2-thienyl)-Ph |
| 146 | 4-F—Ph | 2-(2-furanyl)-Ph |
| 147 | 4-F—Ph | 2,4-diF—Ph |
| 148 | 4-F—Ph | 2,5-diF—Ph |
| 149 | 4-F—Ph | 2,6-diF—Ph |
| 150 | 4-F—Ph | 3,4-diF—Ph |
| 151 | 4-F—Ph | 3,5-diF—Ph |
| 152 | 4-F—Ph | 2,4-diCl—Ph |
| 153 | 4-F—Ph | 2,5-diCl—Ph |
| 154 | 4-F—Ph | 2,6-diCl—Ph |
| 155 | 4-F—Ph | 3,4-diCl—Ph |
| 156 | 4-F—Ph | 3,5-diCl—Ph |
| 157 | 4-F—Ph | 3,4-diCF3—Ph |
| 158 | 4-F—Ph | 3,5-diCF3—Ph |
| 159 | 4-F—Ph | 5-Cl-2-MeO—Ph |
| 160 | 4-F—Ph | 5-Cl-2-Me—Ph |
| 161 | 4-F—Ph | 2-F-5-Me—Ph |
| 162 | 4-F—Ph | 2-F-5-NO2—Ph |
| 163 | 4-F—Ph | 3,4-OCH2O—Ph |
| 164 | 4-F—Ph | 3,4-OCH2CH2O—Ph |
| 165 | 4-F—Ph | 2-MeO-4-Me—Ph |
| 166 | 4-F—Ph | 2-MeO-5-Me—Ph |
| 167 | 4-F—Ph | 1-naphthyl |
| 168 | 4-F—Ph | 2-naphthyl |
| 169 | 4-F—Ph | 2-thienyl |
| 170 | 4-F—Ph | 3-thienyl |
| 171 | 4-F—Ph | 2-furanyl |
| 172 | 4-F—Ph | 3-furanyl |
| 173 | 4-F—Ph | 2-pyridyl |
| 174 | 4-F—Ph | 3-pyridyl |
| 175 | 4-F—Ph | 4-pyridyl |
| 176 | 4-F—Ph | 2-indolyl |
| 177 | 4-F—Ph | 3-indolyl |
| 178 | 4-F—Ph | 5-indolyl |
| 179 | 4-F—Ph | 6-indolyl |
| 180 | 4-F—Ph | 3-indazolyl |
| 181 | 4-F—Ph | 5-indazolyl |
| 182 | 4-F—Ph | 6-indazolyl |
| 183 | 4-F—Ph | 2-imidazolyl |
| 184 | 4-F—Ph | 3-pyrazolyl |
| 185 | 4-F—Ph | 2-thiazolyl |
| 186 | 4-F—Ph | 5-tetrazolyl |
| 187 | 4-F—Ph | 2-benzimidazolyl |
| 188 | 4-F—Ph | 5-benzimidazolyl |
| 189 | 4-F—Ph | 2-benzothiazolyl |
| 190 | 4-F—Ph | 5-benzothiazolyl |
| 191 | 4-F—Ph | 2-benzoxazolyl |
| 192 | 4-F—Ph | 5-benzoxazolyl |
| 193 | 4-F—Ph | 1-adamantyl |
| 194 | 4-F—Ph | 2-adamantyl |
| 195 | 4-F—Ph | t-Bu |
| 196 | 2-F—Ph | 3-CN—Ph |
| 197 | 2-F—Ph | 3-COCH3—Ph |
| 198 | 2-F—Ph | 3-CO2Me—Ph |
| 199 | 2-F—Ph | 3-CO2Et—Ph |
| 200 | 2-F—Ph | 3-CO2H—Ph |
| 201 | 2-F—Ph | 3-CONH2—Ph |
| 202 | 2-F—Ph | 3-F—Ph |
| 203 | 2-F—Ph | 3-Cl—Ph |
| 204 | 2-F—Ph | 3-NH2—Ph |
| 205 | 2-F—Ph | 3-SO2NH2—Ph |
| 206 | 2-F—Ph | 3-CF3—Ph |
| 207 | 2-F—Ph | 3-OCH3—Ph |
| 208 | 2-F—Ph | 3-OEt—Ph |
| 209 | 2-F—Ph | 3-OCF3—Ph |
| 210 | 2-F—Ph | 3-SO2CH3—Ph |
| 211 | 2-F—Ph | 3-OH—Ph |
| 212 | 2-F—Ph | 3-CH3—Ph |
| 213 | 2-F—Ph | 3-C2H5—Ph |
| 214 | 2-F—Ph | 4-CN—Ph |
| 215 | 2-F—Ph | 4-COCH3—Ph |
| 216 | 2-F—Ph | 4-CO2Me—Ph |
| 217 | 2-F—Ph | 4-CO2Et—Ph |
| 218 | 2-F—Ph | 4-CO2H—Ph |
| 219 | 2-F—Ph | 4-CONH2—Ph |
| 220 | 2-F—Ph | 4-F—Ph |
| 221 | 2-F—Ph | 4-Cl—Ph |
| 222 | 2-F—Ph | 4-NH2—Ph |
| 223 | 2-F—Ph | 4-SO2NH2—Ph |
| 224 | 2-F—Ph | 4-CF3—Ph |
| 225 | 2-F—Ph | 4-OCH3—Ph |
| 226 | 2-F—Ph | 4-OEt—Ph |
| 227 | 2-F—Ph | 4-OCF3—Ph |
| 228 | 2-F—Ph | 4-SO2CH3—Ph |
| 229 | 2-F—Ph | 4-OH—Ph |
| 230 | 2-F—Ph | 4-CH3—Ph |
| 231 | 2-F—Ph | 4-C2H5—Ph |
| 232 | 2-F—Ph | 2,4-diF—Ph |
| 233 | 2-F—Ph | 2,5-diF—Ph |
| 234 | 2-F—Ph | 3,4-diF—Ph |
| 235 | 2-F—Ph | 3,5-diF—Ph |
| 236 | 2-F—Ph | 2,4-diCl—Ph |
| 237 | 2-F—Ph | 2,5-diCl—Ph |
| 238 | 2-F—Ph | 3,4-diCl—Ph |
| 239 | 2-F—Ph | 3,5-diCl—Ph |
| 240 | 2-F—Ph | 3,4-OCH2O—Ph |
| 241 | 2-F—Ph | 3,4-OCH2CH2O—Ph |
| 242 | 2-F—Ph | 2-thienyl |
| 243 | 2-F—Ph | 2-furanyl |
| 244 | 2-F—Ph | 2-pyridyl |
| 245 | 2-F—Ph | 4-pyridyl |
| 246 | 2-F—Ph | 2-imidazolyl |
| 247 | 2-F—Ph | 3-pyrazolyl |
| 248 | 2-F—Ph | 2-thiazolyl |
| 249 | 2-F—Ph | 5-tetrazolyl |
| 250 | 2-F—Ph | 1-adamantyl |
| 251 | 2,4-diF—Ph | 3-CN—Ph |
| 252 | 2,4-diF—Ph | 3-COCH3—Ph |
| 253 | 2,4-diF—Ph | 3-CO2Me—Ph |
| 254 | 2,4-diF—Ph | 3-CO2Et—Ph |
| 255 | 2,4-diF—Ph | 3-CO2H—Ph |
| 256 | 2,4-diF—Ph | 3-CONH2—Ph |
| 257 | 2,4-diF—Ph | 3-F—Ph |
| 258 | 2,4-diF—Ph | 3-Cl—Ph |
| 259 | 2,4-diF—Ph | 3-NH2—Ph |
| 260 | 2,4-diF—Ph | 3-SO2NH2—Ph |
| 261 | 2,4-diF—Ph | 3-CF3—Ph |
| 262 | 2,4-diF—Ph | 3-OCH3—Ph |
| 263 | 2,4-diF—Ph | 3-OEt—Ph |
| 264 | 2,4-diF—Ph | 3-OCF3—Ph |
| 265 | 2,4-diF—Ph | 3-SO2CH3—Ph |
| 266 | 2,4-diF—Ph | 3-OH—Ph |
| 267 | 2,4-diF—Ph | 3-CH3—Ph |
| 268 | 2,4-diF—Ph | 3-C2H5—Ph |
| 269 | 2,4-diF—Ph | 4-CN—Ph |
| 270 | 2,4-diF—Ph | 4-COCH3—Ph |
| 271 | 2,4-diF—Ph | 4-CO2Me—Ph |
| 272 | 2,4-diF—Ph | 4-CO2Et—Ph |
| 273 | 2,4-diF—Ph | 4-CO2H—Ph |
| 274 | 2,4-diF—Ph | 4-CONH2—Ph |
| 275 | 2,4-diF—Ph | 4-F—Ph |
| 276 | 2,4-diF—Ph | 4-Cl—Ph |
| 277 | 2,4-diF—Ph | 4-NH2—Ph |
| 278 | 2,4-diF—Ph | 4-SO2NH2—Ph |
| 279 | 2,4-diF—Ph | 4-CF3—Ph |
| 280 | 2,4-diF—Ph | 4-OCH3—Ph |
| 281 | 2,4-diF—Ph | 4-OEt—Ph |
| 282 | 2,4-diF—Ph | 4-OCF3—Ph |
| 283 | 2,4-diF—Ph | 4-SO2CH3—Ph |
| 284 | 2,4-diF—Ph | 4-OH—Ph |
| 285 | 2,4-diF—Ph | 4-CH3—Ph |
| 286 | 2,4-diF—Ph | 4-C2H5—Ph |
| 287 | 2,4-diF—Ph | 2,4-diF—Ph |
| 288 | 2,4-diF—Ph | 2,5-diF—Ph |
| 289 | 2,4-diF—Ph | 3,4-diF—Ph |
| 290 | 2,4-diF—Ph | 3,5-diF—Ph |
| 291 | 2,4-diF—Ph | 2,4-diCl—Ph |
| 292 | 2,4-diF—Ph | 2,5-diCl—Ph |
| 293 | 2,4-diF—Ph | 3,4-diCl—Ph |
| 294 | 2,4-diF—Ph | 3,5-diCl—Ph |

TABLE 4*-continued

| | | |
|---|---|---|
| 295 | 2,4-diF—Ph | 3,4-OCH2O—Ph |
| 296 | 2,4-diF—Ph | 3,4-OCH2CH2O—Ph |
| 297 | 2,4-diF—Ph | 2-thienyl |
| 298 | 2,4-diF—Ph | 2-furanyl |
| 299 | 2,4-diF—Ph | 2-pyridyl |
| 300 | 2,4-diF—Ph | 4-pyridyl |
| 301 | 2,4-diF—Ph | 2-imidazolyl |
| 302 | 2,4-diF—Ph | 3-pyrazolyl |
| 303 | 2,4-diF—Ph | 2-thiazolyl |
| 304 | 2,4-diF—Ph | 5-tetrazolyl |
| 305 | 2,4-diF—Ph | 1-adamantyl |
| 306 | 4-Cl—Ph | Ph |
| 307 | 4-Cl—Ph | 3-CN—Ph |
| 308 | 4-Cl—Ph | 3-COCH3—Ph |
| 309 | 4-Cl—Ph | 3-CO2Me—Ph |
| 310 | 4-Cl—Ph | 3-CO2Et—Ph |
| 311 | 4-Cl—Ph | 3-CO2H—Ph |
| 312 | 4-Cl—Ph | 3-CONH2—Ph |
| 313 | 4-Cl—Ph | 3-CONHMe—Ph |
| 314 | 4-Cl—Ph | 3-F—Ph |
| 315 | 4-Cl—Ph | 3-Cl—Ph |
| 316 | 4-Cl—Ph | 3-Br—Ph |
| 317 | 4-Cl—Ph | 3-NO2—Ph |
| 318 | 4-Cl—Ph | 3-NH2—Ph |
| 319 | 4-Cl—Ph | 3-NHMe—Ph |
| 320 | 4-Cl—Ph | 3-NMe2—Ph |
| 321 | 4-Cl—Ph | 3-NHCOCH3—Ph |
| 322 | 4-Cl—Ph | 3-SO2NH2—Ph |
| 323 | 4-Cl—Ph | 3-SO2NHMe—Ph |
| 324 | 4-Cl—Ph | 3-CF3—Ph |
| 325 | 4-Cl—Ph | 3-OCH3—Ph |
| 326 | 4-Cl—Ph | 3-OPh—Ph |
| 327 | 4-Cl—Ph | 3-OCF3—Ph |
| 328 | 4-Cl—Ph | 3-SCH3—Ph |
| 329 | 4-Cl—Ph | 3-SOCH3—Ph |
| 330 | 4-Cl—Ph | 3-SO2CH3—Ph |
| 331 | 4-Cl—Ph | 3-OH—Ph |
| 332 | 4-Cl—Ph | 3-CH2OH—Ph |
| 333 | 4-Cl—Ph | 3-CHOHCH3—Ph |
| 334 | 4-Cl—Ph | 3-COH(CH3)2—Ph |
| 335 | 4-Cl—Ph | 3-CHOHPh—Ph |
| 336 | 4-Cl—Ph | 3-CH3—Ph |
| 337 | 4-Cl—Ph | 3-C2H5—Ph |
| 338 | 4-Cl—Ph | 3-iPr-Ph |
| 339 | 4-Cl—Ph | 3-tBu-Ph |
| 340 | 4-Cl—Ph | 3-Ph—Ph |
| 341 | 4-Cl—Ph | 3-CH2Ph—Ph |
| 342 | 4-Cl—Ph | 3-CH2CO2Me—Ph |
| 343 | 4-Cl—Ph | 3-(1-piperidinyl)-Ph |
| 344 | 4-Cl—Ph | 3-(1-pyrrolidinyl)-Ph |
| 345 | 4-Cl—Ph | 3-(2-imidazolyl)-Ph |
| 346 | 4-Cl—Ph | 3-(1-imidazolyl)-Ph |
| 347 | 4-Cl—Ph | 3-(2-thiazolyl)-Ph |
| 348 | 4-Cl—Ph | 3-(3-pyrazolyl)-Ph |
| 349 | 4-Cl—Ph | 3-(1-pyrazolyl)-Ph |
| 350 | 4-Cl—Ph | 3-(1-tetrazolyl)-Ph |
| 351 | 4-Cl—Ph | 3-(5-tetrazolyl)-Ph |
| 352 | 4-Cl—Ph | 3-(2-pyridyl)-Ph |
| 353 | 4-Cl—Ph | 3-(2-thienyl)-Ph |
| 354 | 4-Cl—Ph | 3-(2-furanyl)-Ph |
| 355 | 4-Cl—Ph | 4-CN—Ph |
| 356 | 4-Cl—Ph | 4-COCH3—Ph |
| 357 | 4-Cl—Ph | 4-CO2Me—Ph |
| 358 | 4-Cl—Ph | 4-CO2Et—Ph |
| 359 | 4-Cl—Ph | 4-CO2H—Ph |
| 360 | 4-Cl—Ph | 4-CONH2—Ph |
| 361 | 4-Cl—Ph | 4-CONHMe—Ph |
| 362 | 4-Cl—Ph | 4-CONHPh—Ph |
| 363 | 4-Cl—Ph | 4-NHCONH2—Ph |
| 364 | 4-Cl—Ph | 4-F—Ph |
| 365 | 4-Cl—Ph | 4-Cl—Ph |
| 366 | 4-Cl—Ph | 4-Br—Ph |
| 367 | 4-Cl—Ph | 4-NO2—Ph |
| 368 | 4-Cl—Ph | 4-NH2—Ph |
| 369 | 4-Cl—Ph | 4-NHMe—Ph |
| 370 | 4-Cl—Ph | 4-NMe2—Ph |
| 371 | 4-Cl—Ph | 4-NHCOCH3—Ph |
| 372 | 4-Cl—Ph | 4-SO2NH2—Ph |
| 373 | 4-Cl—Ph | 4-SO2NHMe—Ph |
| 374 | 4-Cl—Ph | 4-CF3—Ph |
| 375 | 4-Cl—Ph | 4-OCH3—Ph |
| 376 | 4-Cl—Ph | 4-OPh—Ph |
| 377 | 4-Cl—Ph | 4-OCF3—Ph |
| 378 | 4-Cl—Ph | 4-SCH3—Ph |
| 379 | 4-Cl—Ph | 4-SOCH3—Ph |
| 380 | 4-Cl—Ph | 4-SO2CH3—Ph |
| 381 | 4-Cl—Ph | 4-OH—Ph |
| 382 | 4-Cl—Ph | 4-CH2OH—Ph |
| 383 | 4-Cl—Ph | 4-CHOHCH3—Ph |
| 384 | 4-Cl—Ph | 4-COH(CH3)2—Ph |
| 385 | 4-Cl—Ph | 4-CH3—Ph |
| 386 | 4-Cl—Ph | 4-C2H5—Ph |
| 387 | 4-Cl—Ph | 4-iPr-Ph |
| 388 | 4-Cl—Ph | 4-tBu-Ph |
| 389 | 4-Cl—Ph | 4-Ph—Ph |
| 390 | 4-Cl—Ph | 4-CH2Ph—Ph |
| 391 | 4-Cl—Ph | 4-CH2CO2Me—Ph |
| 392 | 4-Cl—Ph | 4-(1-piperidinyl)-Ph |
| 393 | 4-Cl—Ph | 4-(1-pyrrolidinyl)-Ph |
| 394 | 4-Cl—Ph | 4-(2-imidazolyl)-Ph |
| 395 | 4-Cl—Ph | 4-(1-imidazolyl)-Ph |
| 396 | 4-Cl—Ph | 4-(2-thiazolyl)-Ph |
| 397 | 4-Cl—Ph | 4-(3-pyrazolyl)-Ph |
| 398 | 4-Cl—Ph | 4-(1-pyrazolyl)-Ph |
| 399 | 4-Cl—Ph | 4-(1-tetrazolyl)-Ph |
| 400 | 4-Cl—Ph | 4-(5-tetrazolyl)-Ph |
| 401 | 4-Cl—Ph | 4-(2-pyridyl)-Ph |
| 402 | 4-Cl—Ph | 4-(2-thienyl)-Ph |
| 403 | 4-Cl—Ph | 4-(2-furanyl)-Ph |
| 404 | 4-Cl—Ph | 2-CN—Ph |
| 405 | 4-Cl—Ph | 2-COCH3—Ph |
| 406 | 4-Cl—Ph | 2-CO2Me—Ph |
| 407 | 4-Cl—Ph | 2-CO2Et—Ph |
| 408 | 4-Cl—Ph | 2-CO2H—Ph |
| 409 | 4-Cl—Ph | 2-CONH2—Ph |
| 410 | 4-Cl—Ph | 2-CONHMe—Ph |
| 411 | 4-Cl—Ph | 2-F—Ph |
| 412 | 4-Cl—Ph | 2-Cl—Ph |
| 413 | 4-Cl—Ph | 2-Br—Ph |
| 414 | 4-Cl—Ph | 2-NO2—Ph |
| 415 | 4-Cl—Ph | 2-NH2—Ph |
| 416 | 4-Cl—Ph | 2-NHMe—Ph |
| 417 | 4-Cl—Ph | 2-NMe2—Ph |
| 418 | 4-Cl—Ph | 2-NHCOCH3—Ph |
| 419 | 4-Cl—Ph | 2-SO2NH2—Ph |
| 420 | 4-Cl—Ph | 2-SO2NHMe—Ph |
| 421 | 4-Cl—Ph | 2-CF3—Ph |
| 422 | 4-Cl—Ph | 2-OCH3—Ph |
| 423 | 4-Cl—Ph | 2-OPh—Ph |
| 424 | 4-Cl—Ph | 2-OCF3—Ph |
| 425 | 4-Cl—Ph | 2-SCH3—Ph |
| 426 | 4-Cl—Ph | 2-SOCH3—Ph |
| 427 | 4-Cl—Ph | 2-SO2CH3—Ph |
| 428 | 4-Cl—Ph | 2-OH—Ph |
| 429 | 4-Cl—Ph | 2-CH2OH—Ph |
| 430 | 4-Cl—Ph | 2-CHOHCH3—Ph |
| 431 | 4-Cl—Ph | 2-COH(CH3)2—Ph |
| 432 | 4-Cl—Ph | 2-CHOHPh—Ph |
| 433 | 4-Cl—Ph | 2-CH3—Ph |
| 434 | 4-Cl—Ph | 2-C2H5—Ph |
| 435 | 4-Cl—Ph | 2-iPr-Ph |
| 436 | 4-Cl—Ph | 2-tBu-Ph |
| 437 | 4-Cl—Ph | 2-Ph—Ph |
| 438 | 4-Cl—Ph | 2-CH2Ph—Ph |
| 439 | 4-Cl—Ph | 2-CH2CO2Me—Ph |
| 440 | 4-Cl—Ph | 2-(1-piperidinyl)-Ph |
| 441 | 4-Cl—Ph | 2-(1-pyrrolidinyl)-Ph |
| 442 | 4-Cl—Ph | 2-(2-imidazolyl)-Ph |
| 443 | 4-Cl—Ph | 2-(1-imidazolyl)-Ph |
| 444 | 4-Cl—Ph | 2-(2-thiazolyl)-Ph |
| 445 | 4-Cl—Ph | 2-(3-pyrazolyl)-Ph |
| 446 | 4-Cl—Ph | 2-(1-pyrazolyl)-Ph |
| 447 | 4-Cl—Ph | 2-(1-tetrazolyl)-Ph |
| 448 | 4-Cl—Ph | 2-(5-tetrazolyl)-Ph |
| 449 | 4-Cl—Ph | 2-(2-pyridyl)-Ph |
| 450 | 4-Cl—Ph | 2-(2-thienyl)-Ph |
| 451 | 4-Cl—Ph | 2-(2-furanyl)-Ph |
| 452 | 4-Cl—Ph | 2,4-diF—Ph |

TABLE 4*-continued

| | | |
|---|---|---|
| 453 | 4-Cl—Ph | 2,5-diF—Ph |
| 454 | 4-Cl—Ph | 2,6-diF—Ph |
| 455 | 4-Cl—Ph | 3,4-diF—Ph |
| 456 | 4-Cl—Ph | 3,5-diF—Ph |
| 457 | 4-Cl—Ph | 2,4-diCl—Ph |
| 458 | 4-Cl—Ph | 2,5-diCl—Ph |
| 459 | 4-Cl—Ph | 2,6-diCl—Ph |
| 460 | 4-Cl—Ph | 3,4-diCl—Ph |
| 461 | 4-Cl—Ph | 3,5-diCl—Ph |
| 462 | 4-Cl—Ph | 3,4-diCF3—Ph |
| 463 | 4-Cl—Ph | 3,5-diCF3—Ph |
| 464 | 4-Cl—Ph | 5-Cl-2-MeO—Ph |
| 465 | 4-Cl—Ph | 5-Cl-2-Me—Ph |
| 466 | 4-Cl—Ph | 2-F-5-Me—Ph |
| 467 | 4-Cl—Ph | 2-F-5-NO2—Ph |
| 468 | 4-Cl—Ph | 3,4-OCH2O—Ph |
| 469 | 4-Cl—Ph | 3,4-OCH2CH2O—Ph |
| 470 | 4-Cl—Ph | 2-MeO-4-Me—Ph |
| 471 | 4-Cl—Ph | 2-MeO-5-Me—Ph |
| 472 | 4-Cl—Ph | 1-naphthyl |
| 473 | 4-Cl—Ph | 2-naphthyl |
| 474 | 4-Cl—Ph | 2-thienyl |
| 475 | 4-Cl—Ph | 3-thienyl |
| 476 | 4-Cl—Ph | 2-furanyl |
| 477 | 4-Cl—Ph | 3-furanyl |
| 478 | 4-Cl—Ph | 2-pyridyl |
| 479 | 4-Cl—Ph | 3-pyridyl |
| 480 | 4-Cl—Ph | 4-pyridyl |
| 481 | 4-Cl—Ph | 2-indolyl |
| 482 | 4-Cl—Ph | 3-indolyl |
| 483 | 4-Cl—Ph | 5-indolyl |
| 484 | 4-Cl—Ph | 6-indolyl |
| 485 | 4-Cl—Ph | 3-indazolyl |
| 486 | 4-Cl—Ph | 5-indazolyl |
| 487 | 4-Cl—Ph | 6-indazolyl |
| 488 | 4-Cl—Ph | 2-imidazolyl |
| 489 | 4-Cl—Ph | 3-pyrazolyl |
| 490 | 4-Cl—Ph | 2-thiazolyl |
| 491 | 4-Cl—Ph | 5-tetrazolyl |
| 492 | 4-Cl—Ph | 2-benzimidazolyl |
| 493 | 4-Cl—Ph | 5-benzimidazolyl |
| 494 | 4-Cl—Ph | 2-benzothiazolyl |
| 495 | 4-Cl—Ph | 5-benzothiazolyl |
| 496 | 4-Cl—Ph | 2-benzoxazolyl |
| 497 | 4-Cl—Ph | 5-benzoxazolyl |
| 498 | 4-Cl—Ph | 1-adamantyl |
| 499 | 4-Cl—Ph | 2-adamantyl |
| 500 | 4-Cl—Ph | t-Bu |
| 501 | 2-Cl—Ph | 3-CN—Ph |
| 502 | 2-Cl—Ph | 3-COCH3—Ph |
| 503 | 2-Cl—Ph | 3-CO2Me—Ph |
| 504 | 2-Cl—Ph | 3-CO2Et—Ph |
| 505 | 2-Cl—Ph | 3-CO2H—Ph |
| 506 | 2-Cl—Ph | 3-CONH2—Ph |
| 507 | 2-Cl—Ph | 3-F—Ph |
| 508 | 2-Cl—Ph | 3-Cl—Ph |
| 509 | 2-Cl—Ph | 3-NH2—Ph |
| 510 | 2-Cl—Ph | 3-SO2NH2—Ph |
| 511 | 2-Cl—Ph | 3-CF3—Ph |
| 512 | 2-Cl—Ph | 3-OCH3—Ph |
| 513 | 2-Cl—Ph | 3-OEt—Ph |
| 514 | 2-Cl—Ph | 3-OCF3—Ph |
| 515 | 2-Cl—Ph | 3-SO2CH3—Ph |
| 516 | 2-Cl—Ph | 3-OH—Ph |
| 517 | 2-Cl—Ph | 3-CH3—Ph |
| 518 | 2-Cl—Ph | 3-C2H5—Ph |
| 519 | 2-Cl—Ph | 4-CN—Ph |
| 520 | 2-Cl—Ph | 4-COCH3—Ph |
| 521 | 2-Cl—Ph | 4-CO2Me—Ph |
| 522 | 2-Cl—Ph | 4-CO2Et—Ph |
| 523 | 2-Cl—Ph | 4-CO2H—Ph |
| 524 | 2-Cl—Ph | 4-CONH2—Ph |
| 525 | 2-Cl—Ph | 4-F—Ph |
| 526 | 2-Cl—Ph | 4-Cl—Ph |
| 527 | 2-Cl—Ph | 4-NH2—Ph |
| 528 | 2-Cl—Ph | 4-SO2NH2—Ph |
| 529 | 2-Cl—Ph | 4-CF3—Ph |
| 530 | 2-Cl—Ph | 4-OCH3—Ph |
| 531 | 2-Cl—Ph | 4-OEt—Ph |
| 532 | 2-Cl—Ph | 4-OCF3—Ph |
| 533 | 2-Cl—Ph | 4-SO2CH3—Ph |
| 534 | 2-Cl—Ph | 4-OH—Ph |
| 535 | 2-Cl—Ph | 4-CH3—Ph |
| 536 | 2-Cl—Ph | 4-C2H5—Ph |
| 537 | 2-Cl—Ph | 2,4-diF—Ph |
| 538 | 2-Cl—Ph | 2,5-diF—Ph |
| 539 | 2-Cl—Ph | 3,4-diF—Ph |
| 540 | 2-Cl—Ph | 3,5-diF—Ph |
| 541 | 2-Cl—Ph | 2,4-diCl—Ph |
| 542 | 2-Cl—Ph | 2,5-diCl—Ph |
| 543 | 2-Cl—Ph | 3,4-diCl—Ph |
| 544 | 2-Cl—Ph | 3,5-diCl—Ph |
| 545 | 2-Cl—Ph | 3,4-OCH2O—Ph |
| 546 | 2-Cl—Ph | 3,4-OCH2CH2O—Ph |
| 547 | 2-Cl—Ph | 2-thienyl |
| 548 | 2-Cl—Ph | 2-furanyl |
| 549 | 2-Cl—Ph | 2-pyridyl |
| 550 | 2-Cl—Ph | 4-pyridyl |
| 551 | 2-Cl—Ph | 2-imidazolyl |
| 552 | 2-Cl—Ph | 3-pyrazolyl |
| 553 | 2-Cl—Ph | 2-thiazolyl |
| 554 | 2-Cl—Ph | 5-tetrazolyl |
| 555 | 2-Cl—Ph | 1-adamantyl |
| 556 | 2,4-diCl—Ph | 3-CN—Ph |
| 557 | 2,4-diCl—Ph | 3-COCH3—Ph |
| 558 | 2,4-diCl—Ph | 3-CO2Me—Ph |
| 559 | 2,4-diCl—Ph | 3-CO2Et—Ph |
| 560 | 2,4-diCl—Ph | 3-CO2H—Ph |
| 561 | 2,4-diCl—Ph | 3-CONH2—Ph |
| 562 | 2,4-diCl—Ph | 3-F—Ph |
| 563 | 2,4-diCl—Ph | 3-Cl—Ph |
| 564 | 2,4-diCl—Ph | 3-NH2—Ph |
| 565 | 2,4-diCl—Ph | 3-SO2NH2—Ph |
| 566 | 2,4-diCl—Ph | 3-CF3—Ph |
| 567 | 2,4-diCl—Ph | 3-OCH3—Ph |
| 568 | 2,4-diCl—Ph | 3-OEt—Ph |
| 569 | 2,4-diCl—Ph | 3-OCF3—Ph |
| 570 | 2,4-diCl—Ph | 3-SO2CH3—Ph |
| 571 | 2,4-diCl—Ph | 3-OH—Ph |
| 572 | 2,4-diCl—Ph | 3-CH3—Ph |
| 573 | 2,4-diCl—Ph | 3-C2H5—Ph |
| 574 | 2,4-diCl—Ph | 4-CN—Ph |
| 575 | 2,4-diCl—Ph | 4-COCH3—Ph |
| 576 | 2,4-diCl—Ph | 4-CO2Me—Ph |
| 577 | 2,4-diCl—Ph | 4-CO2Et—Ph |
| 578 | 2,4-diCl—Ph | 4-CO2H—Ph |
| 579 | 2,4-diCl—Ph | 4-CONH2—Ph |
| 580 | 2,4-diCl—Ph | 4-F—Ph |
| 581 | 2,4-diCl—Ph | 4-Cl—Ph |
| 582 | 2,4-diCl—Ph | 4-NH2—Ph |
| 583 | 2,4-diCl—Ph | 4-SO2NH2—Ph |
| 584 | 2,4-diCl—Ph | 4-CF3—Ph |
| 585 | 2,4-diCl—Ph | 4-OCH3—Ph |
| 586 | 2,4-diCl—Ph | 4-OEt—Ph |
| 587 | 2,4-diCl—Ph | 4-OCF3—Ph |
| 588 | 2,4-diCl—Ph | 4-SO2CH3—Ph |
| 589 | 2,4-diCl—Ph | 4-OH—Ph |
| 590 | 2,4-diCl—Ph | 4-CH3—Ph |
| 591 | 2,4-diCl—Ph | 4-C2H5—Ph |
| 592 | 2,4-diCl—Ph | 2,4-diF—Ph |
| 593 | 2,4-diCl—Ph | 2,5-diF—Ph |
| 594 | 2,4-diCl—Ph | 3,4-diF—Ph |
| 595 | 2,4-diCl—Ph | 3,5-diF—Ph |
| 596 | 2,4-diCl—Ph | 2,4-diCl—Ph |
| 597 | 2,4-diCl—Ph | 2,5-diCl—Ph |
| 598 | 2,4-diCl—Ph | 3,4-diCl—Ph |
| 599 | 2,4-diCl—Ph | 3,5-diCl—Ph |
| 600 | 2,4-diCl—Ph | 3,4-OCH2O—Ph |
| 601 | 2,4-diCl—Ph | 3,4-OCH2CH2O—Ph |
| 602 | 2,4-diCl—Ph | 2-thienyl |
| 603 | 2,4-diCl—Ph | 2-furanyl |
| 604 | 2,4-diCl—Ph | 2-pyridyl |
| 605 | 2,4-diCl—Ph | 4-pyridyl |
| 606 | 2,4-diCl—Ph | 2-imidazolyl |
| 607 | 2,4-diCl—Ph | 3-pyrazolyl |
| 608 | 2,4-diCl—Ph | 2-thiazolyl |
| 609 | 2,4-diCl—Ph | 5-tetrazolyl |
| 610 | 2,4-diCl—Ph | 1-adamantyl |

TABLE 4*-continued

| | | |
|---|---|---|
| 611 | 3-OCH3—Ph | 3-CN—Ph |
| 612 | 3-OCH3—Ph | 3-COCH3—Ph |
| 613 | 3-OCH3—Ph | 3-CO2Me—Ph |
| 614 | 3-OCH3—Ph | 3-CO2Et—Ph |
| 615 | 3-OCH3—Ph | 3-CO2H—Ph |
| 616 | 3-OCH3—Ph | 3-CONH2—Ph |
| 617 | 3-OCH3—Ph | 3-F—Ph |
| 618 | 3-OCH3—Ph | 3-Cl—Ph |
| 619 | 3-OCH3—Ph | 3-NH2—Ph |
| 620 | 3-OCH3—Ph | 3-SO2NH2—Ph |
| 621 | 3-OCH3—Ph | 3-CF3—Ph |
| 622 | 3-OCH3—Ph | 3-OCH3—Ph |
| 623 | 3-OCH3—Ph | 3-OEt—Ph |
| 624 | 3-OCH3—Ph | 3-OCF3—Ph |
| 625 | 3-OCH3—Ph | 3-SO2CH3—Ph |
| 626 | 3-OCH3—Ph | 3-OH—Ph |
| 627 | 3-OCH3—Ph | 3-CH3—Ph |
| 628 | 3-OCH3—Ph | 3-C2H5—Ph |
| 629 | 3-OCH3—Ph | 4-CN—Ph |
| 630 | 3-OCH3—Ph | 4-COCH3—Ph |
| 631 | 3-OCH3—Ph | 4-CO2Me—Ph |
| 632 | 3-OCH3—Ph | 4-CO2Et—Ph |
| 633 | 3-OCH3—Ph | 4-CO2H—Ph |
| 634 | 3-OCH3—Ph | 4-CONH2—Ph |
| 635 | 3-OCH3—Ph | 4-F—Ph |
| 636 | 3-OCH3—Ph | 4-Cl—Ph |
| 637 | 3-OCH3—Ph | 4-NH2—Ph |
| 638 | 3-OCH3—Ph | 4-SO2NH2—Ph |
| 639 | 3-OCH3—Ph | 4-CF3—Ph |
| 640 | 3-OCH3—Ph | 4-OCH3—Ph |
| 641 | 3-OCH3—Ph | 4-OEt—Ph |
| 642 | 3-OCH3—Ph | 4-OCF3—Ph |
| 643 | 3-OCH3—Ph | 4-SO2CH3—Ph |
| 644 | 3-OCH3—Ph | 4-OH—Ph |
| 645 | 3-OCH3—Ph | 4-CH3—Ph |
| 646 | 3-OCH3—Ph | 4-C2H5—Ph |
| 647 | 3-OCH3—Ph | 2,4-diF—Ph |
| 648 | 3-OCH3—Ph | 2,5-diF—Ph |
| 649 | 3-OCH3—Ph | 3,4-diF—Ph |
| 650 | 3-OCH3—Ph | 3,5-diF—Ph |
| 651 | 3-OCH3—Ph | 2,4-diCl—Ph |
| 652 | 3-OCH3—Ph | 2,5-diCl—Ph |
| 653 | 3-OCH3—Ph | 3,4-diCl—Ph |
| 654 | 3-OCH3—Ph | 3,5-diCl—Ph |
| 655 | 3-OCH3—Ph | 3,4-OCH2O—Ph |
| 656 | 3-OCH3—Ph | 3,4-OCH2CH2O—Ph |
| 657 | 3-OCH3—Ph | 2-thienyl |
| 658 | 3-OCH3—Ph | 2-furanyl |
| 659 | 3-OCH3—Ph | 2-pyridyl |
| 660 | 3-OCH3—Ph | 4-pyridyl |
| 661 | 3-OCH3—Ph | 2-imidazolyl |
| 662 | 3-OCH3—Ph | 3-pyrazolyl |
| 663 | 3-OCH3—Ph | 2-thiazolyl |
| 664 | 3-OCH3—Ph | 5-tetrazolyl |
| 665 | 3-OCH3—Ph | 1-adamantyl |
| 666 | 2-thienyl | 3-CN—Ph |
| 667 | 2-thienyl | 3-COCH3—Ph |
| 668 | 2-thienyl | 3-F—Ph |
| 669 | 2-thienyl | 3-Cl—Ph |
| 670 | 2-thienyl | 3-NH2—Ph |
| 671 | 2-thienyl | 3-OCH3—Ph |
| 672 | 2-thienyl | 3-OH—Ph |
| 673 | 2-thienyl | 4-CN—Ph |
| 674 | 2-thienyl | 4-COCH3—Ph |
| 675 | 2-thienyl | 4-F—Ph |
| 676 | 2-thienyl | 4-Cl—Ph |
| 677 | 2-thienyl | 4-NH2—Ph |
| 678 | 2-thienyl | 4-OCH3—Ph |
| 679 | 2-thienyl | 4-OH—Ph |
| 680 | 2-thienyl | 3,4-diF—Ph |
| 681 | 2-thienyl | 3,5-diF—Ph |
| 682 | 2-thienyl | 3,4-diCl—Ph |
| 683 | 2-thienyl | 3,5-diCl—Ph |
| 684 | 2-thienyl | 3,4-OCH2O—Ph |
| 685 | 2-thienyl | 3,4-OCH2CH2O—Ph |
| 686 | 3-thienyl | 3-CN—Ph |
| 687 | 3-thienyl | 3-COCH3—Ph |
| 688 | 3-thienyl | 3-F—Ph |
| 689 | 3-thienyl | 3-Cl—Ph |
| 690 | 3-thienyl | 3-NH2—Ph |
| 691 | 3-thienyl | 3-OCH3—Ph |
| 692 | 3-thienyl | 3-OH—Ph |
| 693 | 3-thienyl | 4-CN—Ph |
| 694 | 3-thienyl | 4-COCH3—Ph |
| 695 | 3-thienyl | 4-F—Ph |
| 696 | 3-thienyl | 4-Cl—Ph |
| 697 | 3-thienyl | 4-NH2—Ph |
| 698 | 3-thienyl | 4-OCH3—Ph |
| 699 | 3-thienyl | 4-OH—Ph |
| 700 | 3-thienyl | 3,4-diF—Ph |
| 701 | 3-thienyl | 3,5-diF—Ph |
| 702 | 3-thienyl | 3,4-diCl—Ph |
| 703 | 3-thienyl | 3,5-diCl—Ph |
| 704 | 3-thienyl | 3,4-OCH2O—Ph |
| 705 | 3-thienyl | 3,4-OCH2CH2O—Ph |
| 706 | 2-furanyl | 3-CN—Ph |
| 707 | 2-furanyl | 3-COCH3—Ph |
| 708 | 2-furanyl | 3-F—Ph |
| 709 | 2-furanyl | 3-Cl—Ph |
| 710 | 2-furanyl | 3-NH2—Ph |
| 711 | 2-furanyl | 3-OCH3—Ph |
| 712 | 2-furanyl | 3-OH—Ph |
| 713 | 2-furanyl | 4-CN—Ph |
| 714 | 2-furanyl | 4-COCH3—Ph |
| 715 | 2-furanyl | 4-F—Ph |
| 716 | 2-furanyl | 4-Cl—Ph |
| 717 | 2-furanyl | 4-NH2—Ph |
| 718 | 2-furanyl | 4-OCH3—Ph |
| 719 | 2-furanyl | 4-OH—Ph |
| 720 | 2-furanyl | 3,4-diF—Ph |
| 721 | 2-furanyl | 3,5-diF—Ph |
| 722 | 2-furanyl | 3,4-diCl—Ph |
| 723 | 2-furanyl | 3,5-diCl—Ph |
| 724 | 2-furanyl | 3,4-OCH2O—Ph |
| 725 | 2-furanyl | 3,4-OCH2CH2O—Ph |
| 726 | 3-furanyl | 3-CN—Ph |
| 727 | 3-furanyl | 3-COCH3—Ph |
| 728 | 3-furanyl | 3-F—Ph |
| 729 | 3-furanyl | 3-Cl—Ph |
| 730 | 3-furanyl | 3-NH2—Ph |
| 731 | 3-furanyl | 3-OCH3—Ph |
| 732 | 3-furanyl | 3-OH—Ph |
| 733 | 3-furanyl | 4-CN—Ph |
| 734 | 3-furanyl | 4-COCH3—Ph |
| 735 | 3-furanyl | 4-F—Ph |
| 736 | 3-furanyl | 4-Cl—Ph |
| 737 | 3-furanyl | 4-NH2—Ph |
| 738 | 3-furanyl | 4-OCH3—Ph |
| 739 | 3-furanyl | 4-OH—Ph |
| 740 | 3-furanyl | 3,4-diF—Ph |
| 741 | 3-furanyl | 3,5-diF—Ph |
| 742 | 3-furanyl | 3, 4-diCl—Ph |
| 743 | 3-furanyl | 3,5-diCl—Ph |
| 744 | 3-furanyl | 3,4-OCH2O—Ph |
| 745 | 3-furanyl | 3,4-OCH2CH2O—Ph |
| 746 | 2-pyridyl | 3-CN—Ph |
| 747 | 2-pyridyl | 3-COCH3—Ph |
| 748 | 2-pyridyl | 3-F—Ph |
| 749 | 2-pyridyl | 3-Cl—Ph |
| 750 | 2-pyridyl | 3-NH2—Ph |
| 751 | 2-pyridyl | 3-OCH3—Ph |
| 752 | 2-pyridyl | 3-OH—Ph |
| 753 | 2-pyridyl | 4-CN—Ph |
| 754 | 2-pyridyl | 4-COCH3—Ph |
| 755 | 2-pyridyl | 4-F—Ph |
| 756 | 2-pyridyl | 4-Cl—Ph |
| 757 | 2-pyridyl | 4-NH2—Ph |
| 758 | 2-pyridyl | 4-OCH3—Ph |
| 759 | 2-pyridyl | 4-OH—Ph |
| 760 | 2-pyridyl | 3,4-diF—Ph |
| 761 | 2-pyridyl | 3,5-diF—Ph |
| 762 | 2-pyridyl | 3,4-diCl—Ph |
| 763 | 2-pyridyl | 3,5-diCl—Ph |
| 764 | 2-pyridyl | 3,4-OCH2O—Ph |
| 765 | 2-pyridyl | 3,4-OCH2CH2O—Ph |
| 766 | 3-pyridyl | 3CN—Ph |
| 767 | 3-pyridyl | 3-COCH3—Ph |
| 768 | 3-pyridyl | 3-F—Ph |

TABLE 4*-continued

| | | |
|---|---|---|
| 769 | 3-pyridyl | 3-Cl—Ph |
| 770 | 3-pyridyl | 3-NH2—Ph |
| 771 | 3-pyridyl | 3-OCH3—Ph |
| 772 | 3-pyridyl | 3-OH—Ph |
| 773 | 3-pyridyl | 4-CN—Ph |
| 774 | 3-pyridyl | 4-COCH3—Ph |
| 775 | 3-pyridyl | 4-F—Ph |
| 776 | 3-pyridyl | 4-Cl—Ph |
| 777 | 3-pyridyl | 4-NH2—Ph |
| 778 | 3-pyridyl | 4-OCH3—Ph |
| 779 | 3-pyridyl | 4-OH—Ph |
| 780 | 3-pyridyl | 3,4-diF—Ph |
| 781 | 3-pyridyl | 3,5-diF—Ph |
| 782 | 3-pyridyl | 3,4-diCl—Ph |
| 783 | 3-pyridyl | 3,5-diCl—Ph |
| 784 | 3-pyridyl | 3,4-OCH2O—Ph |
| 785 | 3-pyridyl | 3,4-OCH2CH2O—Ph |
| 786 | 4-pyridyl | 3-CN—Ph |
| 787 | 4-pyridyl | 3-COCH3—Ph |
| 788 | 4-pyridyl | 3-F—Ph |
| 789 | 4-pyridyl | 3-Cl—Ph |
| 790 | 4-pyridyl | 3-NH2—Ph |
| 791 | 4-pyridyl | 3-OCH3—Ph |
| 792 | 4-pyridyl | 3-OH—Ph |
| 793 | 4-pyridyl | 4-CN—Ph |
| 794 | 4-pyridyl | 4-COCH3—Ph |
| 795 | 4-pyridyl | 4-F—Ph |
| 796 | 4-pyridyl | 4-Cl—Ph |
| 797 | 4-pyridyl | 4-NH2—Ph |
| 798 | 4-pyridyl | 4-OCH3—Ph |
| 799 | 4-pyridyl | 4-OH—Ph |
| 800 | 4-pyridyl | 3,4-diF—Ph |
| 801 | 4-pyridyl | 3, 5-diF—Ph |
| 802 | 4-pyridyl | 3,4-diCl—Ph |
| 803 | 4-pyridyl | 3,5-diCl—Ph |
| 804 | 4-pyridyl | 3,4-OCH2O—Ph |
| 805 | 4-pyridyl | 3,4-OCH2CH2O—Ph |
| 806 | 3-indolyl | 3-CN—Ph |
| 807 | 3-indolyl | 3-COCH3—Ph |
| 808 | 3-indolyl | 3-F—Ph |
| 809 | 3-indolyl | 3-Cl—Ph |
| 810 | 3-indolyl | 3-NH2—Ph |
| 811 | 3-indolyl | 3-OCH3—Ph |
| 812 | 3-indolyl | 3-OH—Ph |
| 813 | 3-indolyl | 4-CN—Ph |
| 814 | 3-indolyl | 4-COCH3—Ph |
| 815 | 3-indolyl | 4-F—Ph |
| 816 | 3-indolyl | 4-Cl—Ph |
| 817 | 3-indolyl | 4-NH2—Ph |
| 818 | 3-indolyl | 4-OCH3—Ph |
| 819 | 3-indolyl | 4-OH—Ph |
| 820 | 3-indolyl | 3,4-diF—Ph |
| 821 | 3-indolyl | 3,5-diF—Ph |
| 822 | 3-indolyl | 3,4-diCl—Ph |
| 823 | 3-indolyl | 3,5-diCl—Ph |
| 824 | 3-indolyl | 3,4-OCH2O—Ph |
| 825 | 3-indolyl | 3,4-OCH2CH2O—Ph |
| 826 | 5-indolyl | 3-CN—Ph |
| 827 | 5-indolyl | 3-COCH3—Ph |
| 828 | 5-indolyl | 3-F—Ph |
| 829 | 5-indolyl | 3-Cl—Ph |
| 830 | 5-indolyl | 3-NH2—Ph |
| 831 | 5-indolyl | 3-OCH3—Ph |
| 832 | 5-indolyl | 3-OH—Ph |
| 833 | 5-indolyl | 4-CN—Ph |
| 834 | 5-indolyl | 4-COCH3—Ph |
| 835 | 5-indolyl | 4-F—Ph |
| 836 | 5-indolyl | 4-Cl—Ph |
| 837 | 5-indolyl | 4-NH2—Ph |
| 838 | 5-indolyl | 4-OCH3—Ph |
| 839 | 5-indolyl | 4-OH—Ph |
| 840 | 5-indolyl | 3,4-diF—Ph |
| 841 | 5-indolyl | 3,5-diF—Ph |
| 842 | 5-indolyl | 3,4-diCl—Ph |
| 843 | 5-indolyl | 3,5-diCl—Ph |
| 844 | 5-indolyl | 3,4-OCH2O—Ph |
| 845 | 5-indolyl | 3,4-OCH2CH2O—Ph |
| 846 | 5-indazolyl | 3-CN—Ph |
| 847 | 5-indazolyl | 3-COCH3—Ph |
| 848 | 5-indazolyl | 3-F—Ph |
| 849 | 5-indazolyl | 3-Cl—Ph |
| 850 | 5-indazolyl | 3-NH2—Ph |
| 851 | 5-indazolyl | 3-OCH3—Ph |
| 852 | 5-indazolyl | 3-OH—Ph |
| 853 | 5-indazolyl | 4-CN—Ph |
| 854 | 5-indazolyl | 4-COCH3—Ph |
| 855 | 5-indazolyl | 4-F—Ph |
| 856 | 5-indazolyl | 4-Cl—Ph |
| 857 | 5-indazolyl | 4-NH2—Ph |
| 858 | 5-indazolyl | 4-OCH3—Ph |
| 859 | 5-indazolyl | 4-OH—Ph |
| 860 | 5-indazolyl | 3,4-diF—Ph |
| 861 | 5-indazolyl | 3,5-diF—Ph |
| 862 | 5-indazolyl | 3,4-diCl—Ph |
| 863 | 5-indazolyl | 3,5-diCl—Ph |
| 864 | 5-indazolyl | 3,4-OCH2O—Ph |
| 865 | 5-indazolyl | 3,4-OCH2CH2O—Ph |
| 866 | 5-benzimidazolyl | 3-CN—Ph |
| 867 | 5-benzimidazolyl | 3-COCH3—Ph |
| 868 | 5-benzimidazolyl | 3-F—Ph |
| 869 | 5-benzimidazolyl | 3-Cl—Ph |
| 870 | 5-benzimidazolyl | 3-NH2—Ph |
| 871 | 5-benzimidazolyl | 3-OCH3—Ph |
| 872 | 5-benzimidazolyl | 3-OH—Ph |
| 873 | 5-benzimidazolyl | 4-CN—Ph |
| 874 | 5-benzimidazolyl | 4-COCH3—Ph |
| 875 | 5-benzimidazolyl | 4-F—Ph |
| 876 | 5-benzimidazolyl | 4-Cl—Ph |
| 877 | 5-benzimidazolyl | 4-NH2—Ph |
| 878 | 5-benzimidazolyl | 4-OCH3—Ph |
| 879 | 5-benzimidazolyl | 4-OH—Ph |
| 880 | 5-benzimidazolyl | 3,4-diF—Ph |
| 881 | 5-benzimidazolyl | 3,5-diF—Ph |
| 882 | 5-benzimidazolyl | 3,4-diCl—Ph |
| 883 | 5-benzimidazolyl | 3,5-diCl—Ph |
| 884 | 5-benzimidazolyl | 3,4-OCH2O—Ph |
| 885 | 5-benzimidazolyl | 3,4-OCH2CH2O—Ph |
| 886 | 5-benzothiazolyl | 3-CN—Ph |
| 887 | 5-benzothiazolyl | 3-COCH3—Ph |
| 888 | 5-benzothiazolyl | 3-F—Ph |
| 889 | 5-benzothiazolyl | 3-Cl—Ph |
| 890 | 5-benzothiazolyl | 3-NH2—Ph |
| 891 | 5-benzothiazolyl | 3-OCH3—Ph |
| 892 | 5-benzothiazolyl | 3-OH—Ph |
| 893 | 5-benzothiazolyl | 4-CN—Ph |
| 894 | 5-benzothiazolyl | 4-COCH3—Ph |
| 895 | 5-benzothiazolyl | 4-F—Ph |
| 896 | 5-benzothiazolyl | 4-Cl—Ph |
| 897 | 5-benzothiazolyl | 4-NH2—Ph |
| 898 | 5-benzothiazolyl | 4-OCH3—Ph |
| 899 | 5-benzothiazolyl | 4-OH—Ph |
| 900 | 5-benzothiazolyl | 3,4-diF—Ph |
| 901 | 5-benzothiazolyl | 3,5-diF—Ph |
| 902 | 5-benzothiazolyl | 3,4-diCl—Ph |
| 903 | 5-benzothiazolyl | 3,5-diCl—Ph |
| 904 | 5-benzothiazolyl | 3,4-OCH2O—Ph |
| 905 | 5-benzothiazolyl | 3,4-OCH2CH2O—Ph |
| 906 | 5-benzoxazolyl | 3-CN—Ph |
| 907 | 5-benzoxazolyl | 3-COCH3—Ph |
| 908 | 5-benzoxazolyl | 3-F—Ph |
| 909 | 5-benzoxazolyl | 3-Cl—Ph |
| 910 | 5-benzoxazolyl | 3-NH2—Ph |
| 911 | 5-benzoxazolyl | 3-OCH3—Ph |
| 912 | 5-benzoxazolyl | 3-OH—Ph |
| 913 | 5-benzoxazolyl | 4-CN—Ph |
| 914 | 5-benzoxazolyl | 4-COCH3—Ph |
| 915 | 5-benzoxazolyl | 4-F—Ph |
| 916 | 5-benzoxazolyl | 4-Cl—Ph |
| 917 | 5-benzoxazolyl | 4-NH2—Ph |
| 918 | 5-benzoxazolyl | 4-OCH3—Ph |
| 919 | 5-benzoxazolyl | 4-OH—Ph |
| 920 | 5-benzoxazolyl | 3,4-diF—Ph |
| 921 | 5-benzoxazolyl | 3,5-diF—Ph |
| 922 | 5-benzoxazolyl | 3,4-diCl—Ph |
| 923 | 5-benzoxazolyl | 3,5-diCl—Ph |
| 924 | 5-benzoxazolyl | 3,4-OCH2O—Ph |
| 925 | 5-benzoxazolyl | 3,4-OCH2CH2O—Ph |

TABLE 6*
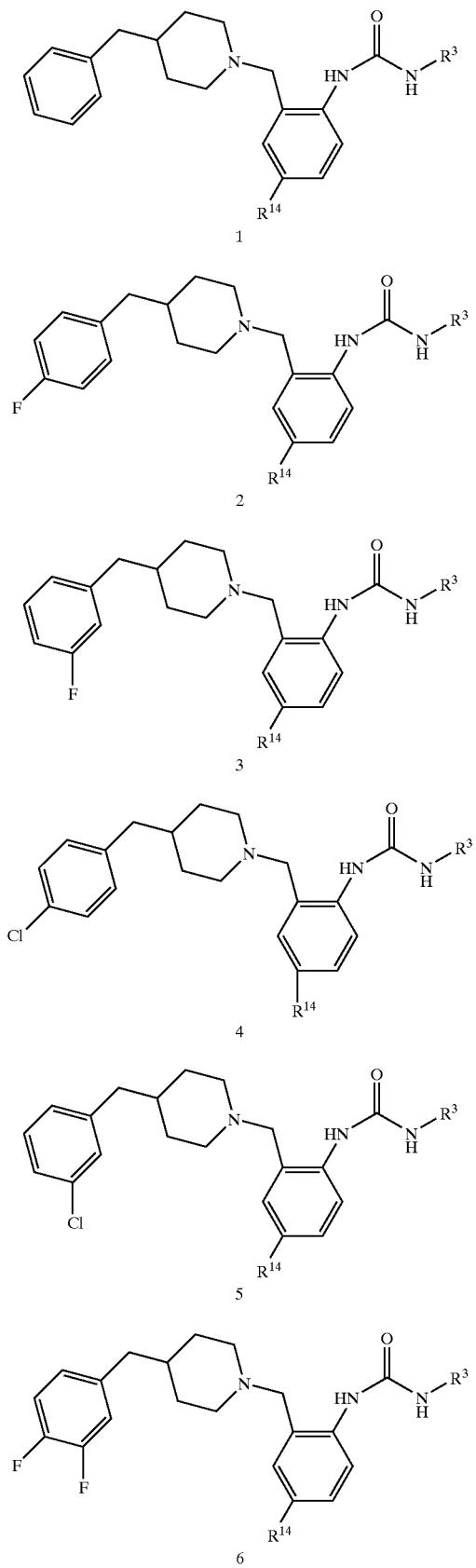
TABLE 6*-continued
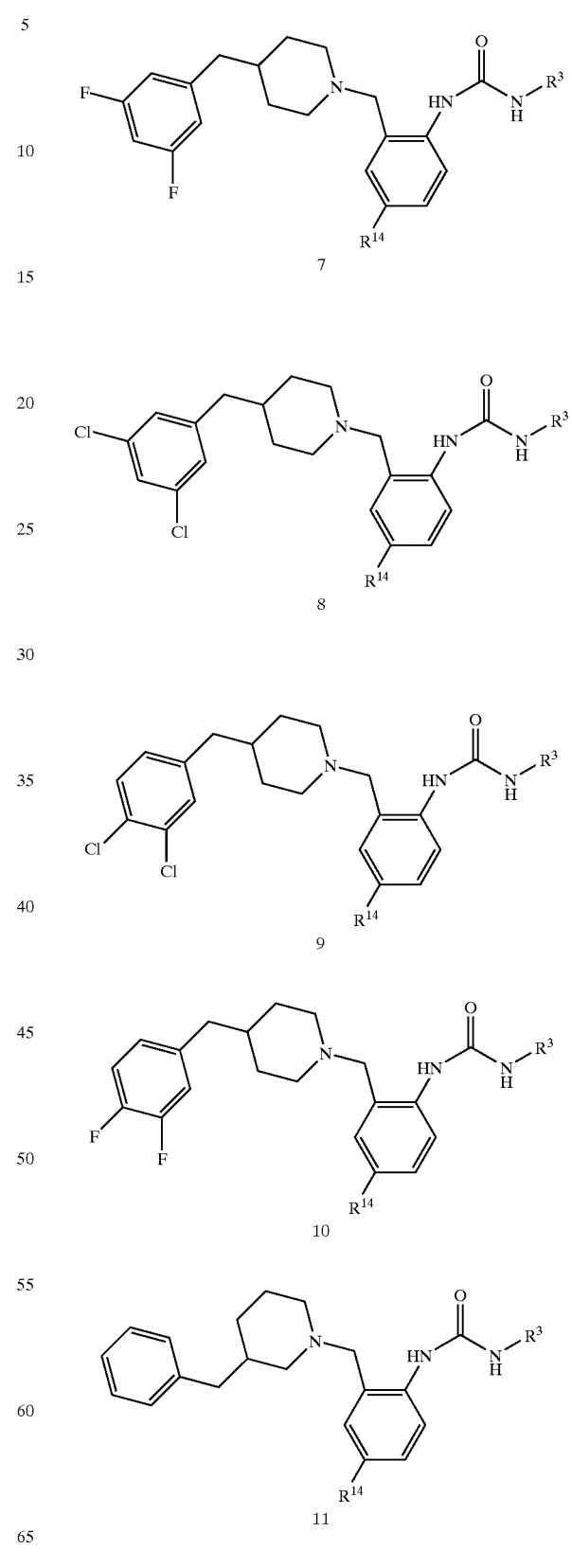

TABLE 6*-continued
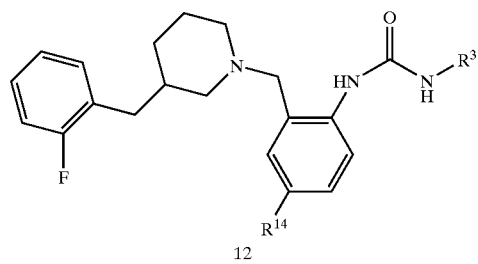
12
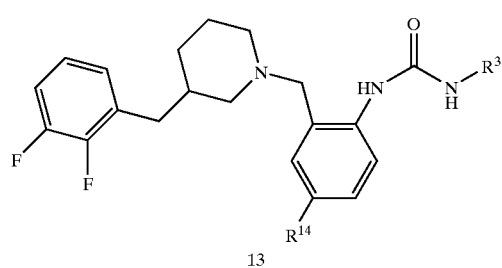
13
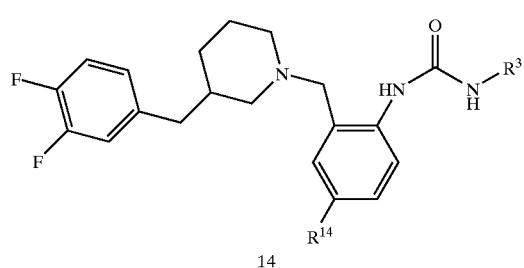
14
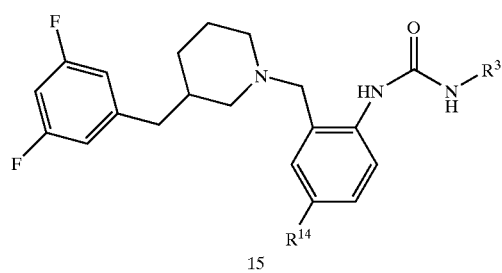
15
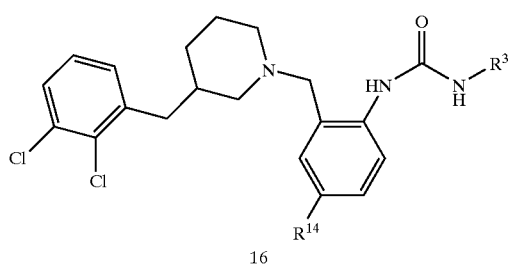
16
TABLE 6*-continued
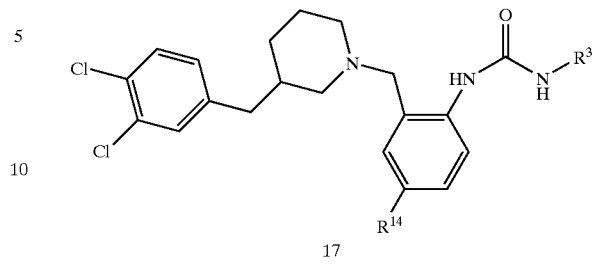
17
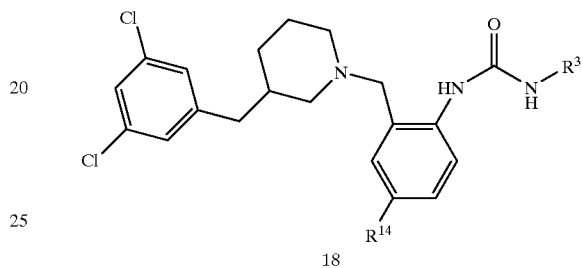
18
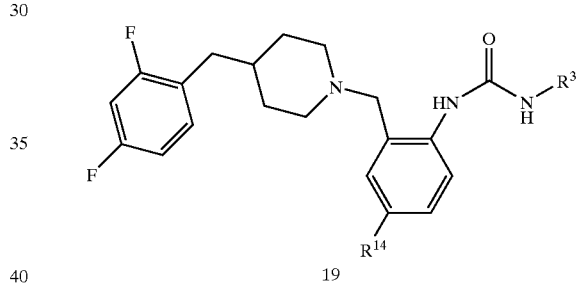
19
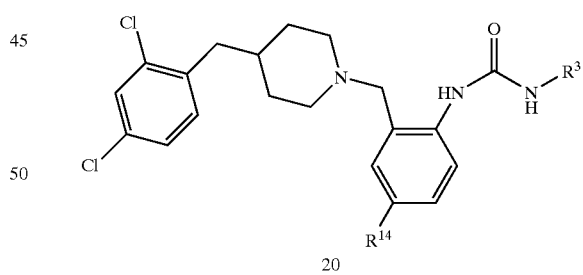
20
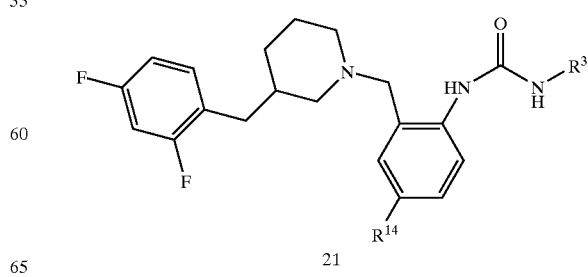
21

TABLE 6*-continued
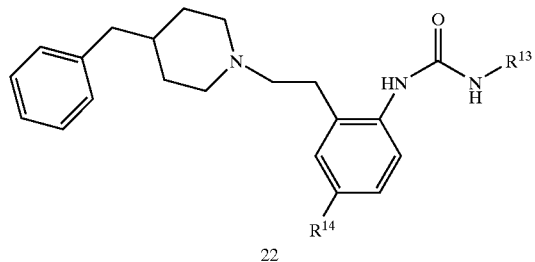
22
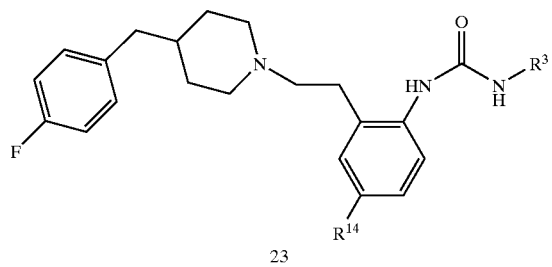
23
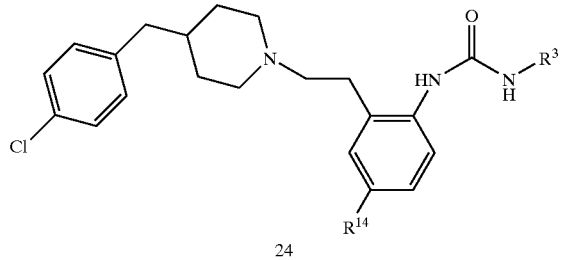
24
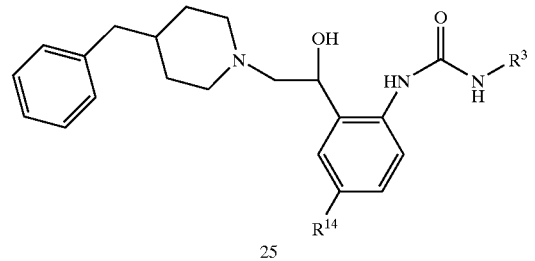
25
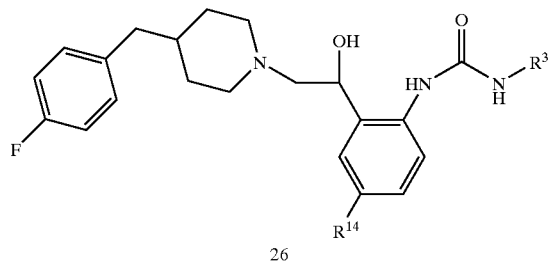
26
TABLE 6*-continued
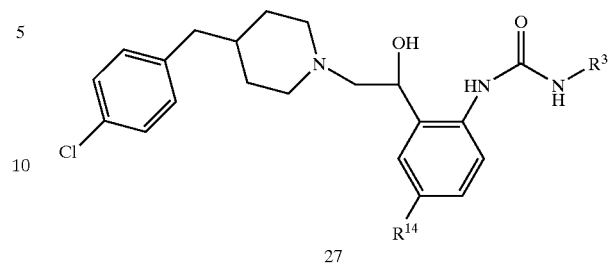
27
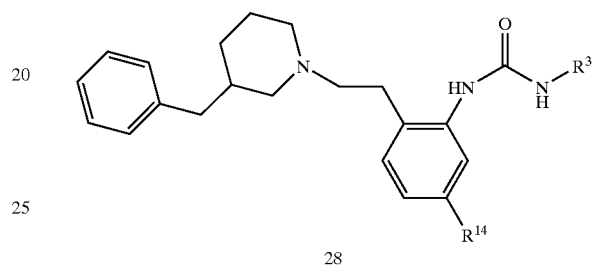
28
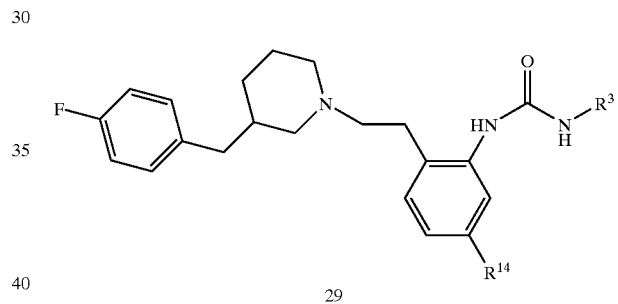
29
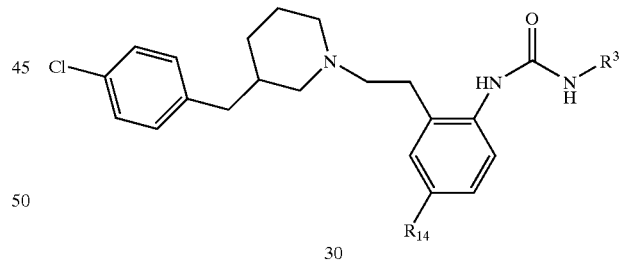
30
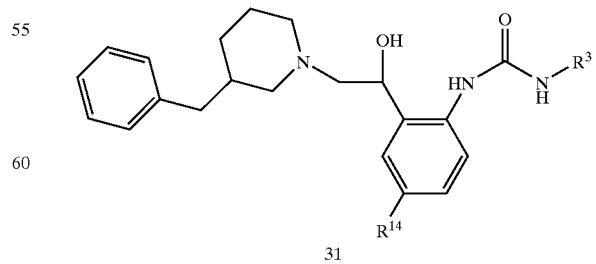
31

TABLE 6*-continued
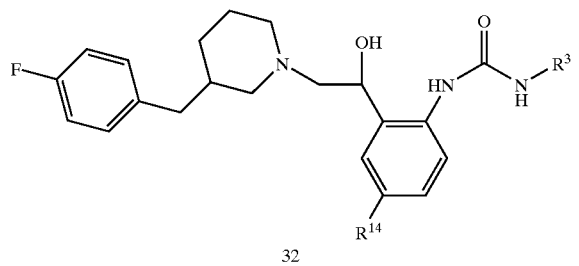
32
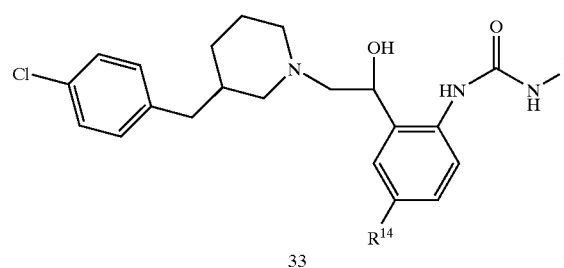
33
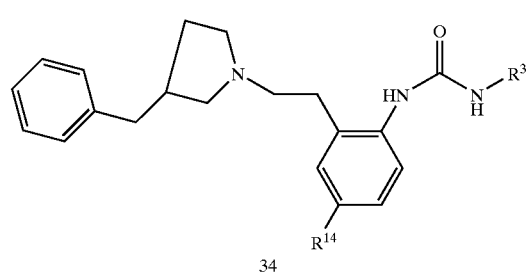
34
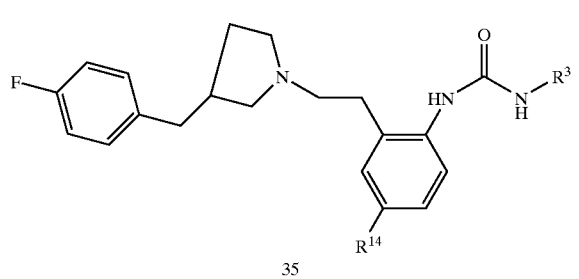
35
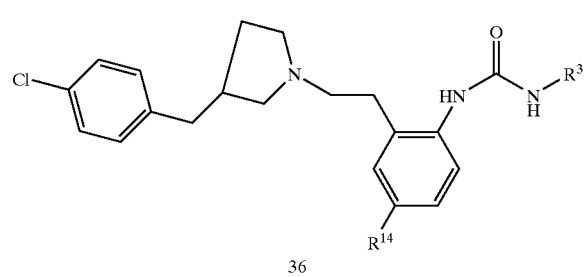
36
TABLE 6*-continued
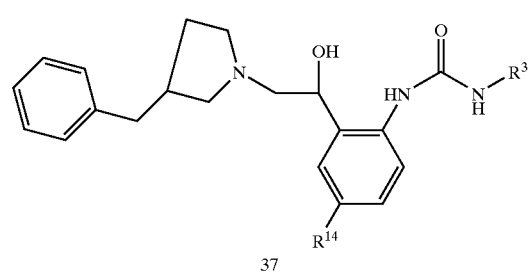
37
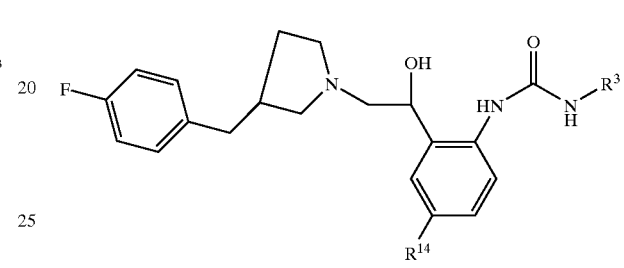
38
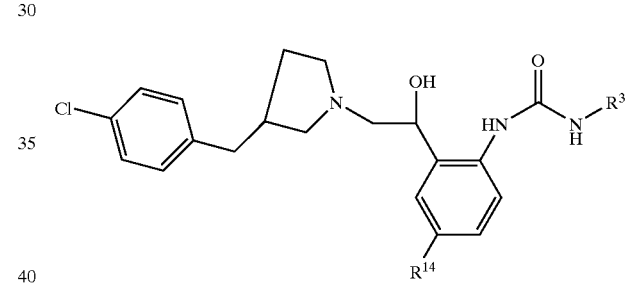
39
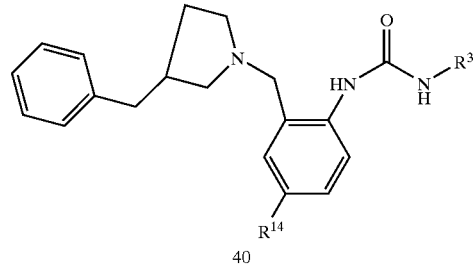
40
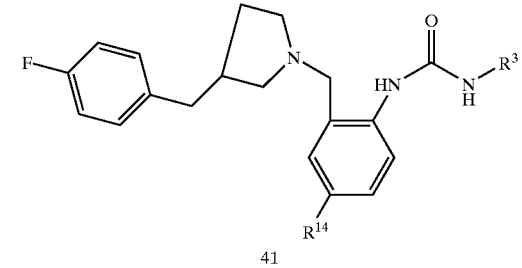
41

TABLE 6*-continued
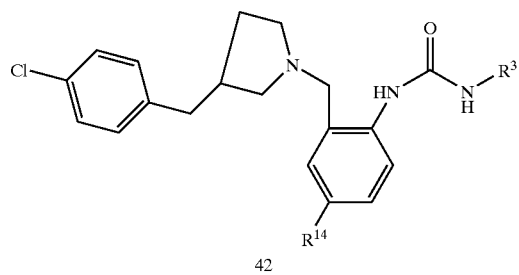
42
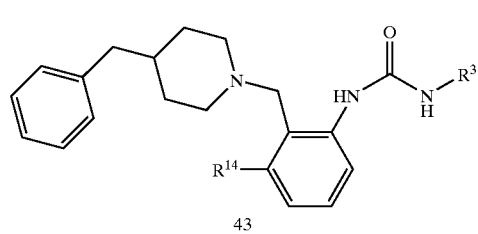
43
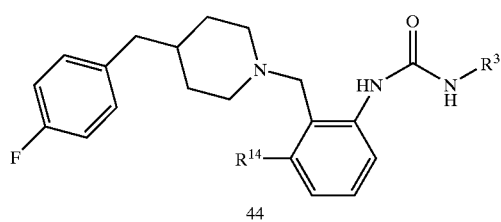
44
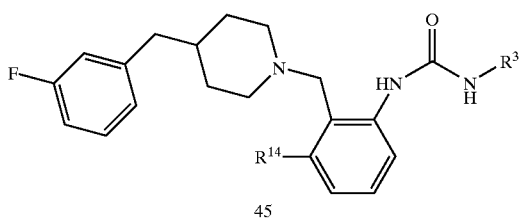
45
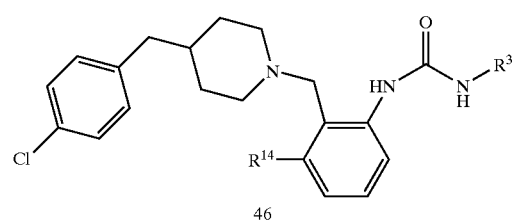
46
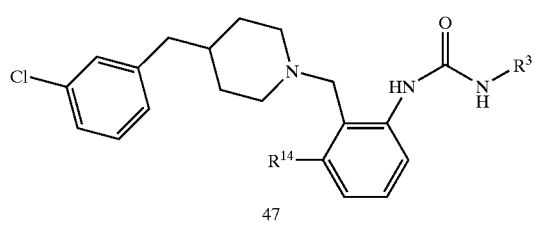
47
TABLE 6*-continued
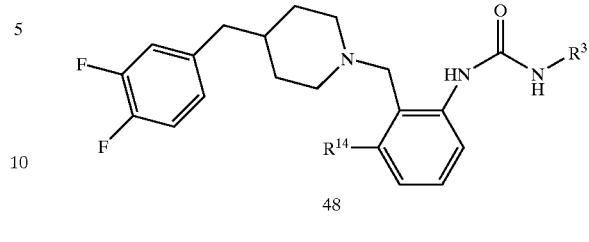
48
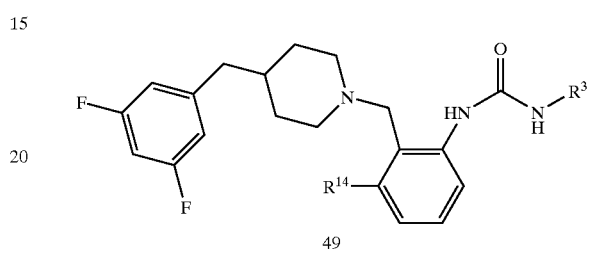
49
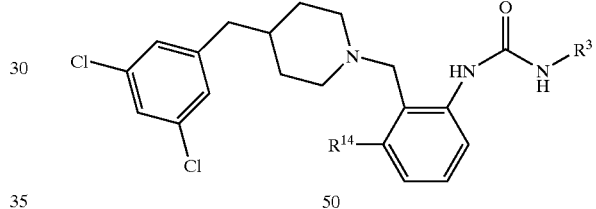
50
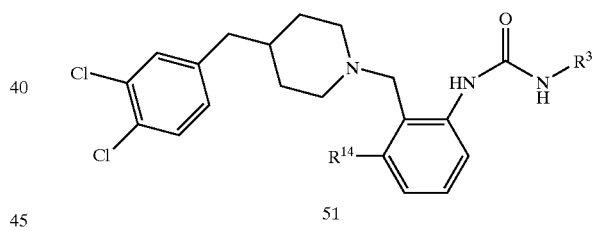
51
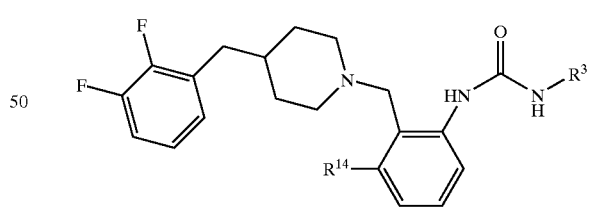
52
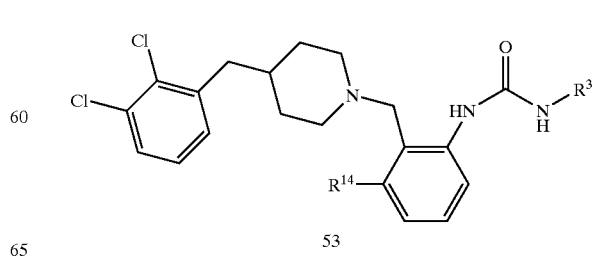
53

TABLE 6*-continued

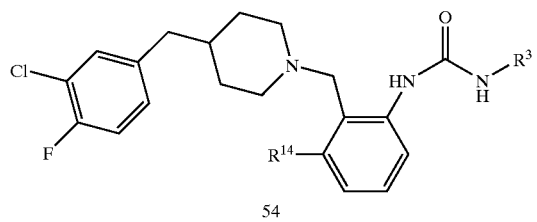
54

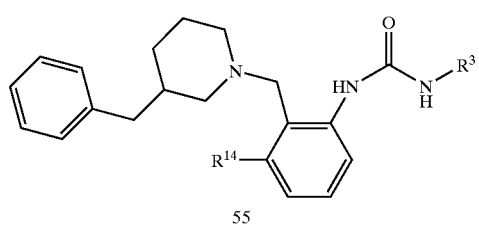
55

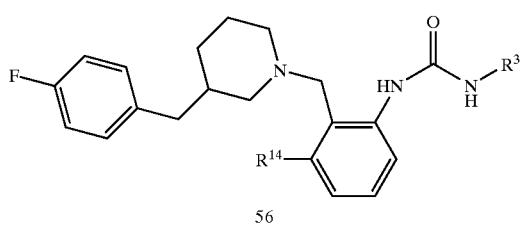
56

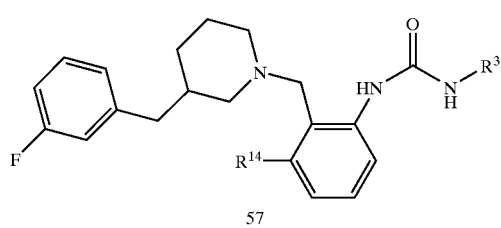
57

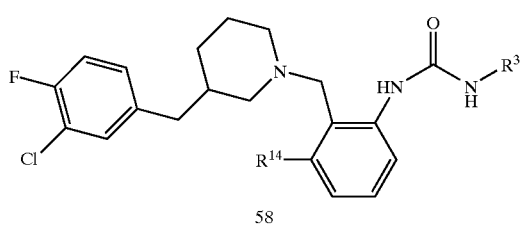
58

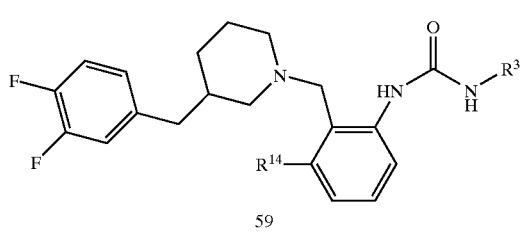
59

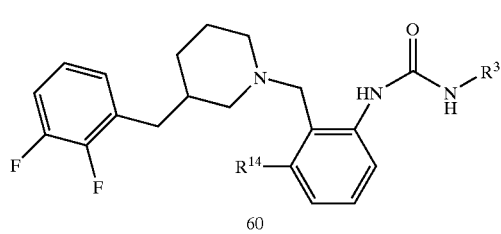
60

TABLE 6*-continued

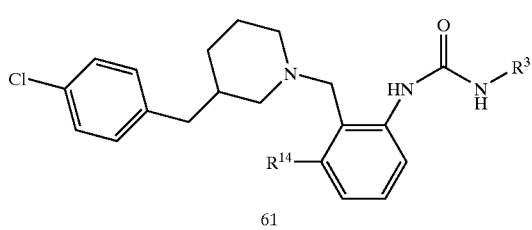
61

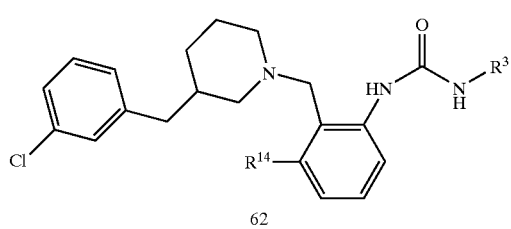
62

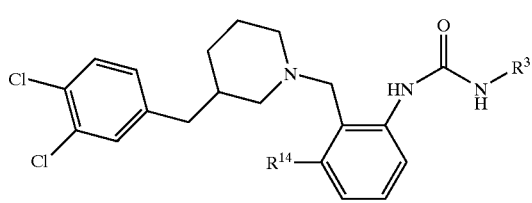
63

| Entry | $R^3$ | $R^{14}$ |
|---|---|---|
| 1 | Ph | CN |
| 2 | Ph | F |
| 3 | Ph | Cl |
| 4 | Ph | CH2OH |
| 5 | Ph | OH |
| 6 | Ph | NH2 |
| 7 | Ph | CO2Me |
| 8 | Ph | CO2Et |
| 9 | Ph | CONH2 |
| 10 | Ph | NHPh |
| 11 | Ph | NHMe |
| 12 | Ph | OMe |
| 13 | Ph | C(O)(2-imidazolyl) |
| 14 | Ph | C(O)(4-imidazolyl) |
| 15 | Ph | C(O)(2-thiazolyl) |
| 16 | Ph | C(O)(4-thiazolyl) |
| 17 | Ph | C(O)(2-oxazolyl) |
| 18 | Ph | C(O)(4-oxazolyl) |
| 19 | Ph | C(O)(3-pyrazolyl) |
| 20 | Ph | C(O)(4-pyrazolyl) |
| 21 | Ph | C(O)(5-tetrazolyl) |
| 22 | Ph | C(O)(2-pyridyl) |
| 23 | Ph | C(O)(3-pyridyl) |
| 24 | Ph | C(O)(4-pyridyl) |
| 25 | Ph | C(O)(2-thienyl) |
| 26 | Ph | C(O)(3-thienyl) |
| 27 | Ph | C(O)(2-furanyl) |
| 28 | Ph | C(O)(3-furanyl) |
| 29 | Ph | 2-thienyl |
| 30 | Ph | 3-thienyl |
| 31 | Ph | 2-furanyl |
| 32 | Ph | 3-furanyl |
| 33 | Ph | 2-pyridyl |
| 34 | Ph | 3-pyridyl |
| 35 | Ph | 4-pyridyl |
| 36 | Ph | 1-imidazolyl |
| 37 | Ph | 2-imidazolyl |
| 38 | Ph | 4-imidazolyl |
| 39 | Ph | 1-pyrazolyl |
| 40 | Ph | 3-pyrazolyl |
| 41 | Ph | 4-pyrazolyl |

TABLE 6*-continued

| | | |
|---|---|---|
| 42 | Ph | 2-thiazolyl |
| 43 | Ph | 4-thiazolyl |
| 44 | Ph | 5-tetrazolyl |
| 45 | Ph | 2-oxazolyl |
| 46 | Ph | 4-oxazolyl |
| 47 | Ph | C(O)N(2-imidazolyl) |
| 48 | Ph | C(O)N(4-imidazolyl) |
| 49 | Ph | C(O)N(2-thiazolyl) |
| 50 | Ph | C(O)14(4-thiazolyl) |
| 51 | Ph | C(O)N(2-oxazolyl) |
| 52 | Ph | C(O)N(4-oxazolyl) |
| 53 | Ph | C(O)N(3-pyrazolyl) |
| 54 | Ph | C(O)N(4-pyrazolyl) |
| 55 | Ph | C(O)N(2-pyridyl) |
| 56 | Ph | C(O)N(3-pyridyl) |
| 57 | Ph | C(O)N(4-pyridyl) |
| 58 | Ph | C(O)N(2-thienyl) |
| 59 | Ph | C(O)N(3-thienyl) |
| 60 | Ph | C(O)N(2-furanyl) |
| 61 | Ph | C(O)N(3-furanyl) |
| 62 | Ph | C(O)N(2-pyrrolyl) |
| 63 | Ph | C(O)N(3-pyrrolyl) |
| 64 | Ph | CH2(1-imidazolyl) |
| 65 | Ph | CH2(1-(1,2,3-triazolyl)) |
| 66 | Ph | CH2(2-(1,2,3-triazolyl)) |
| 67 | Ph | CH2(1-(1,2,4-triazolyl)) |
| 68 | Ph | CH2(1-pyrazolyl) |
| 69 | 3-CN—Ph | CN |
| 70 | 3-CN—Ph | F |
| 71 | 3-CN—Ph | Cl |
| 72 | 3-CN—Ph | CH2OH |
| 73 | 3-CN—Ph | OH |
| 74 | 3-CN—Ph | NH2 |
| 75 | 3-CN—Ph | CO2Me |
| 76 | 3-CN—Ph | CO2Et |
| 77 | 3-CN—Ph | CONH2 |
| 78 | 3-CN—Ph | NHPh |
| 79 | 3-CN—Ph | NHMe |
| 80 | 3-CN—Ph | OMe |
| 81 | 3-CN—Ph | C(O)(2-imidazolyl) |
| 82 | 3-CN—Ph | C(O)(4-imidazolyl) |
| 83 | 3-CN—Ph | C(O)(2-thiazolyl) |
| 84 | 3-CN—Ph | C(O)(4-thiazolyl) |
| 85 | 3-CN—Ph | C(O)(2-oxazolyl) |
| 86 | 3-CN—Ph | C(O)(4-oxazolyl) |
| 87 | 3-CN—Ph | C(O)(3-pyrazolyl) |
| 88 | 3-CN—Ph | C(O)(4-pyrazolyl) |
| 89 | 3-CN—Ph | C(O)(5-tetrazolyl) |
| 90 | 3-CN—Ph | C(O)(2-pyridyl) |
| 91 | 3-CN—Ph | C(O)(3-pyridyl) |
| 92 | 3-CN—Ph | C(O)(4-pyridyl) |
| 93 | 3-CN—Ph | C(O)(2-thienyl) |
| 94 | 3-CN—Ph | C(O)(3-thienyl) |
| 95 | 3-CN—Ph | C(O)(2-furanyl) |
| 96 | 3-CN—Ph | C(O)(3-furanyl) |
| 97 | 3-CN—Ph | 2-thienyl |
| 98 | 3-CN—Ph | 3-thienyl |
| 99 | 3-CN—Ph | 2-furanyl |
| 100 | 3-CN—Ph | 3-furanyl |
| 101 | 3-CN—Ph | 2-pyridyl |
| 102 | 3-CN—Ph | 3-pyridyl |
| 103 | 3-CN—Ph | 4-pyridyl |
| 104 | 3-CN—Ph | 1-imidazolyl |
| 105 | 3-CN—Ph | 2-imidazolyl |
| 106 | 3-CN—Ph | 4-imidazolyl |
| 107 | 3-CN—Ph | 1-pyrazolyl |
| 108 | 3-CN—Ph | 3-pyrazolyl |
| 109 | 3-CN—Ph | 4-pyrazolyl |
| 110 | 3-CN—Ph | 2-thiazolyl |
| 111 | 3-CN—Ph | 4-thiazolyl |
| 112 | 3-CN—Ph | 5-tetrazolyl |
| 113 | 3-CN—Ph | 2-oxazolyl |
| 114 | 3-CN—Ph | 4-oxazolyl |
| 115 | 3-CN—Ph | C(O)N(2-imidazolyl) |
| 116 | 3-CN—Ph | C(O)N(4-imidazolyl) |
| 117 | 3-CN—Ph | C(O)N(2-thiazolyl) |
| 118 | 3-CN—Ph | C(O)N(4-thiazolyl) |
| 119 | 3-CN—Ph | C(O)N(2-oxazolyl) |
| 120 | 3-CN—Ph | C(O)N(4-oxazolyl) |
| 121 | 3-CN—Ph | C(O)N(3-pyrazolyl) |
| 122 | 3-CN—Ph | C(O)N(4-pyrazolyl) |
| 123 | 3-CN—Ph | C(O)N(2-pyridyl) |
| 124 | 3-CN—Ph | C(O)N(3-pyridyl) |
| 125 | 3-CN—Ph | C(O)N(4-pyridyl) |
| 126 | 3-CN—Ph | C(O)N(2-thienyl) |
| 127 | 3-CN—Ph | C(O)N(3-thienyl) |
| 128 | 3-CN—Ph | C(O)N(2-furanyl) |
| 129 | 3-CN—Ph | C(O)N(3-furanyl) |
| 130 | 3-CN—Ph | C(O)N(2-pyrrolyl) |
| 131 | 3-CN—Ph | C(O)N(3-pyrrolyl) |
| 132 | 3-CN—Ph | CH2(1-imidazolyl) |
| 133 | 3-CN—Ph | CH2(1-(1,2,3-triazolyl)) |
| 134 | 3-CN—Ph | CH2(2-(1,2,3-triazolyl)) |
| 135 | 3-CN—Ph | CH2(1-(1,2,4-triazolyl)) |
| 136 | 3-CN—Ph | CH2(1-pyrazolyl) |
| 137 | 3-OMe—Ph | CN |
| 138 | 3-OMe—Ph | F |
| 139 | 3-OMe—Ph | Cl |
| 140 | 3-OMe—Ph | CH2OH |
| 141 | 3-OMe—Ph | OH |
| 142 | 3-OMe—Ph | NH2 |
| 143 | 3-OMe—Ph | CO2Me |
| 144 | 3-OMe—Ph | CO2Et |
| 145 | 3-OMe—Ph | CONH2 |
| 146 | 3-OMe—Ph | NHPh |
| 147 | 3-OMe—Ph | NHMe |
| 148 | 3-OMe—Ph | OMe |
| 149 | 3-OMe—Ph | C(O)(2-imidazolyl) |
| 150 | 3-OMe—Ph | C(O)(4-imidazolyl) |
| 151 | 3-OMe—Ph | C(O)(2-thiazolyl) |
| 152 | 3-OMe—Ph | C(O)(4-thiazolyl) |
| 153 | 3-OMe—Ph | C(O)(2-oxazolyl) |
| 154 | 3-OMe—Ph | C(O)(4-oxazolyl) |
| 155 | 3-OMe—Ph | C(O)(3-pyrazolyl) |
| 156 | 3-OMe—Ph | C(O)(4-pyrazolyl) |
| 157 | 3-OMe—Ph | C(O)(5-tetrazolyl) |
| 158 | 3-OMe—Ph | C(O)(2-pyridyl) |
| 159 | 3-OMe—Ph | C(O)(3-pyridyl) |
| 160 | 3-OMe—Ph | C(O)(4-pyridyl) |
| 161 | 3-OMe—Ph | C(O)(2-thienyl) |
| 162 | 3-OMe—Ph | C(O)(3-thienyl) |
| 163 | 3-OMe—Ph | C(O)(2-furanyl) |
| 164 | 3-OMe—Ph | C(O)(3-furanyl) |
| 165 | 3-OMe—Ph | 2-thienyl |
| 166 | 3-OMe—Ph | 3-thienyl |
| 167 | 3-OMe—Ph | 2-furanyl |
| 168 | 3-OMe—Ph | 3-furanyl |
| 169 | 3-OMe—Ph | 2-pyridyl |
| 170 | 3-OMe—Ph | 3-pyridyl |
| 171 | 3-OMe—Ph | 4-pyridyl |
| 172 | 3-OMe—Ph | 1-imidazolyl |
| 173 | 3-OMe—Ph | 2-imidazolyl |
| 174 | 3-OMe—Ph | 4-imidazolyl |
| 175 | 3-OMe—Ph | 1-pyrazolyl |
| 176 | 3-OMe—Ph | 3-pyrazolyl |
| 177 | 3-OMe—Ph | 4-pyrazolyl |
| 178 | 3-OMe—Ph | 2-thiazolyl |
| 179 | 3-OMe—Ph | 4-thiazolyl |
| 180 | 3-OMe—Ph | 5-tetrazolyl |
| 181 | 3-OMe—Ph | 2-oxazolyl |
| 182 | 3-OMe—Ph | 4-oxazolyl |
| 183 | 3-OMe—Ph | C(O)N(2-imidazolyl) |
| 184 | 3-OMe—Ph | C(O)N(4-imidazolyl) |
| 185 | 3-OMe—Ph | C(O)N(2-thiazolyl) |
| 186 | 3-OMe—Ph | C(O)N(4-thiazolyl) |
| 187 | 3-OMe—Ph | C(O)N(2-oxazolyl) |
| 188 | 3-OMe—Ph | C(O)N(4-oxazolyl) |
| 189 | 3-OMe—Ph | C(O)N(3-pyrazolyl) |
| 190 | 3-OMe—Ph | C(O)N(4-pyrazolyl) |
| 191 | 3-OMe—Ph | C(O)N(2-pyridyl) |
| 192 | 3-OMe—Ph | C(O)N(3-pyridyl) |
| 193 | 3-OMe—Ph | C(O)N(4-pyridyl) |
| 194 | 3-OMe—Ph | C(O)N(2-thienyl) |
| 195 | 3-OMe—Ph | C(O)N(3-thienyl) |
| 196 | 3-OMe—Ph | C(O)N(2-furanyl) |
| 197 | 3-OMe—Ph | C(O)N(3-furanyl) |
| 198 | 3-OMe—Ph | C(O)N(2-pyrrolyl) |
| 199 | 3-OMe—Ph | C(O)N(3-pyrrolyl) |

TABLE 6*-continued

| | | |
|---|---|---|
| 200 | 3-OMe—Ph | CH2(1-imidazolyl) |
| 201 | 3-OMe—Ph | CH2(1-(1,2,3-triazolyl)) |
| 202 | 3-OMe—Ph | CH2(2-(1,2,3-triazolyl)) |
| 203 | 3-OMe—Ph | CH2(1-(1,2,4-triazolyl)) |
| 204 | 3-OMe—Ph | CH2(1-pyrazolyl) |
| 205 | 3-C(O)Me—Ph | CN |
| 206 | 3-C(O)Me—Ph | F |
| 207 | 3-C(O)Me—Ph | Cl |
| 208 | 3-C(O)Me—Ph | CH2OH |
| 209 | 3-C(O)Me—Ph | OH |
| 210 | 3-C(O)Me—Ph | NH2 |
| 211 | 3-C(O)Me—Ph | CO2Me |
| 212 | 3-C(O)Me—Ph | CO2Et |
| 213 | 3-C(O)Me—Ph | CONH2 |
| 214 | 3-C(O)Me—Ph | NHPh |
| 215 | 3-C(O)Me—Ph | NHMe |
| 216 | 3-C(O)Me—Ph | OMe |
| 217 | 3-C(O)Me—Ph | C(O)(2-imidazolyl) |
| 218 | 3-C(O)Me—Ph | C(O)(4-imidazolyl) |
| 219 | 3-C(O)Me—Ph | C(O)(2-thiazolyl) |
| 220 | 3-C(O)Me—Ph | C(O)(4-thiazolyl) |
| 221 | 3-C(O)Me—Ph | C(O)(2-oxazolyl) |
| 222 | 3-C(O)Me—Ph | C(O)(4-oxazolyl) |
| 223 | 3-C(O)Me—Ph | C(O)(3-pyrazolyl) |
| 224 | 3-C(O)Me—Ph | C(O)(4-pyrazolyl) |
| 225 | 3-C(O)Me—Ph | C(O)(5-tetrazolyl) |
| 226 | 3-C(O)Me—Ph | C(O)(2-pyridyl) |
| 227 | 3-C(O)Me—Ph | C(O)(3-pyridyl) |
| 228 | 3-C(O)Me—Ph | C(O)(4-pyridyl) |
| 229 | 3-C(O)Me—Ph | C(O)(2-thienyl) |
| 230 | 3-C(O)Me—Ph | C(O)(3-thienyl) |
| 231 | 3-C(O)Me—Ph | C(O)(2-furanyl) |
| 232 | 3-C(O)Me—Ph | C(O)(3-furanyl) |
| 233 | 3-C(O)Me—Ph | 2-thienyl |
| 234 | 3-C(O)Me—Ph | 3-thienyl |
| 235 | 3-C(O)Me—Ph | 2-furanyl |
| 236 | 3-C(O)Me—Ph | 3-furanyl |
| 237 | 3-C(O)Me—Ph | 2-pyridyl |
| 238 | 3-C(O)Me—Ph | 3-pyridyl |
| 239 | 3-C(O)Me—Ph | 4-pyridyl |
| 240 | 3-C(O)Me—Ph | 1-imidazolyl |
| 241 | 3-C(O)Me—Ph | 2-imidazolyl |
| 242 | 3-C(O)Me—Ph | 4-imidazolyl |
| 243 | 3-C(O)Me—Ph | 1-pyrazolyl |
| 244 | 3-C(O)Me—Ph | 3-pyrazolyl |
| 245 | 3-C(O)Me—Ph | 4-pyrazolyl |
| 246 | 3-C(O)Me—Ph | 2-thiazolyl |
| 247 | 3-C(O)Me—Ph | 4-thiazolyl |
| 248 | 3-C(O)Me—Ph | 5-tetrazolyl |
| 249 | 3-C(O)Me—Ph | 2-oxazolyl |
| 250 | 3-C(O)Me—Ph | 4-oxazolyl |
| 251 | 3-C(O)He—Ph | C(O)N(2-imidazolyl) |
| 252 | 3-C(O)Me—Ph | C(O)N(4-imidazolyl) |
| 253 | 3-C(O)Me—Ph | C(O)N(2-thiazolyl) |
| 254 | 3-C(O)Me—Ph | C(O)N(4-thiazolyl) |
| 255 | 3-C(O)Me—Ph | C(O)N(2-oxazolyl) |
| 256 | 3-C(O)Me—Ph | C(O)N(4-oxazolyl) |
| 257 | 3-C(O)Me—Ph | C(O)N(3-pyrazolyl) |
| 258 | 3-C(O)Me—Ph | C(O)N(4-pyrazolyl) |
| 259 | 3-C(O)Me—Ph | C(O)N(2-pyridyl) |
| 260 | 3-C(O)Me—Ph | C(O)N(3-pyridyl) |
| 261 | 3-C(O)Me—Ph | C(O)N(4-pyridyl) |
| 262 | 3-C(O)Me—Ph | C(O)N(2-thienyl) |
| 263 | 3-C(O)Me—Ph | C(O)N(3-thienyl) |
| 264 | 3-C(O)Me—Ph | C(O)N(2-furanyl) |
| 265 | 3-C(O)Me—Ph | C(O)N(3-furanyl) |
| 266 | 3-C(O)Me—Ph | C(O)N(2-pyrrolyl) |
| 267 | 3-C(O)Me—Ph | C(O)N(3-pyrrolyl) |
| 268 | 3-C(O)Me—Ph | CH2(1-imidazolyl) |
| 269 | 3-C(O)Me—Ph | CH2(1-(1,2,3-triazolyl)) |
| 270 | 3-C(O)Me—Ph | CH2(2-(1,2,3-triazolyl)) |
| 271 | 3-C(O)Me—Ph | CH2(1-(1,2,4-triazolyl)) |
| 272 | 3-C(O)Me—Ph | CH2(1-pyrazolyl) |
| 273 | 4-F—Ph | CN |
| 274 | 4-F—Ph | F |
| 275 | 4-F—Ph | Cl |
| 276 | 4-F—Ph | CH2OH |
| 277 | 4-F—Ph | OH |
| 278 | 4-F—Ph | NH2 |
| 279 | 4-F—Ph | CO2Me |
| 280 | 4-F—Ph | CO2Et |
| 281 | 4-F—Ph | CONH2 |
| 282 | 4-F—Ph | NHPh |
| 283 | 4-F—Ph | NHMe |
| 284 | 4-F—Ph | OMe |
| 285 | 4-F—Ph | C(O)(2-imidazolyl) |
| 286 | 4-F—Ph | C(O)(4-imidazolyl) |
| 287 | 4-F—Ph | C(O)(2-thiazolyl) |
| 288 | 4-F—Ph | C(O)(4-thiazolyl) |
| 289 | 4-F—Ph | C(O)(2-oxazolyl) |
| 290 | 4-F—Ph | C(O)(4-oxazolyl) |
| 291 | 4-F—Ph | C(O)(3-pyrazolyl) |
| 292 | 4-F—Ph | C(O)(4-pyrazolyl) |
| 293 | 4-F—Ph | C(O)(5-tetrazolyl) |
| 294 | 4-F—Ph | C(O)(2-pyridyl) |
| 295 | 4-F—Ph | C(O)(3-pyridyl) |
| 296 | 4-F—Ph | C(O)(4-pyridyl) |
| 297 | 4-F—Ph | C(O)(2-thienyl) |
| 298 | 4-F—Ph | C(O)(3-thienyl) |
| 299 | 4-F—Ph | C(O)(2-furanyl) |
| 300 | 4-F—Ph | C(O)(3-furanyl) |
| 301 | 4-F—Ph | 2-thienyl |
| 302 | 4-F—Ph | 3-thienyl |
| 303 | 4-F—Ph | 2-furanyl |
| 304 | 4-F—Ph | 3-furanyl |
| 305 | 4-F—Ph | 2-pyridyl |
| 306 | 4-F—Ph | 3-pyridyl |
| 307 | 4-F—Ph | 4-pyridyl |
| 308 | 4-F—Ph | 1-imidazolyl |
| 309 | 4-F—Ph | 2-imidazolyl |
| 310 | 4-F—Ph | 4-imidazolyl |
| 311 | 4-F—Ph | 1-pyrazolyl |
| 312 | 4-F—Ph | 3-pyrazolyl |
| 313 | 4-F—Ph | 4-pyrazolyl |
| 314 | 4-F—Ph | 2-thiazolyl |
| 315 | 4-F—Ph | 4-thiazolyl |
| 316 | 4-F—Ph | 5-tetrazolyl |
| 317 | 4-F—Ph | 2-oxazolyl |
| 318 | 4-F—Ph | 4-oxazolyl |
| 319 | 4-F—Ph | C(O)N(2-imidazolyl) |
| 320 | 4-F—Ph | C(O)N(4-imidazolyl) |
| 321 | 4-F—Ph | C(O)N(2-thiazolyl) |
| 322 | 4-F—Ph | C(O)N(4-thiazolyl) |
| 323 | 4-F—Ph | C(O)N(2-oxazolyl) |
| 324 | 4-F—Ph | C(O)N(4-oxazolyl) |
| 325 | 4-F—Ph | C(O)N(3-pyrazolyl) |
| 326 | 4-F—Ph | C(O)N(4-pyrazolyl) |
| 327 | 4-F—Ph | C(O)N(2-pyridyl) |
| 328 | 4-F—Ph | C(O)N(3-pyridyl) |
| 329 | 4-F—Ph | C(O)N(4-pyridyl) |
| 330 | 4-F—Ph | C(O)N(2-thienyl) |
| 331 | 4-F—Ph | C(O)N(3-thienyl) |
| 332 | 4-F—Ph | C(O)N(2-furanyl) |
| 333 | 4-F—Ph | C(O)N(3-furanyl) |
| 334 | 4-F—Ph | C(O)N(2-pyrrolyl) |
| 335 | 4-F—Ph | C(O)N(3-pyrrolyl) |
| 336 | 4-F—Ph | CH2(1-imidazolyl) |
| 337 | 4-F—Ph | CH2(1-(1,2,3-triazolyl)) |
| 338 | 4-F—Ph | CH2(2-(1,2,3-triazolyl)) |
| 339 | 4-F—Ph | CH2(1-(1,2,4-triazolyl)) |
| 340 | 4-F—Ph | CH2(1-pyrazolyl) |

TABLE 7
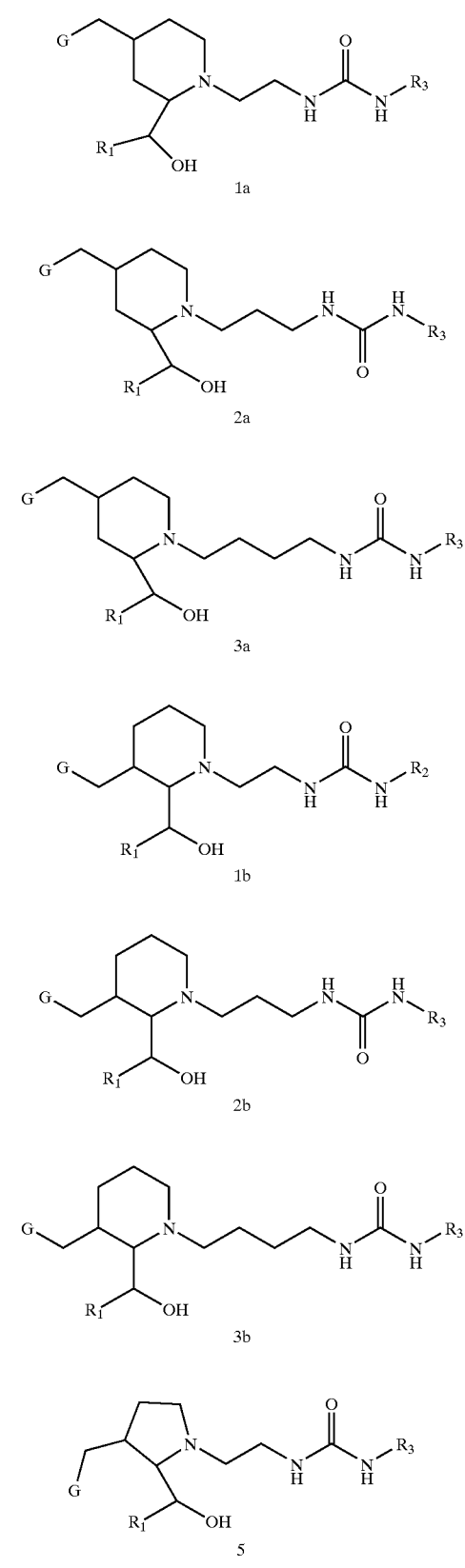
TABLE 7-continued
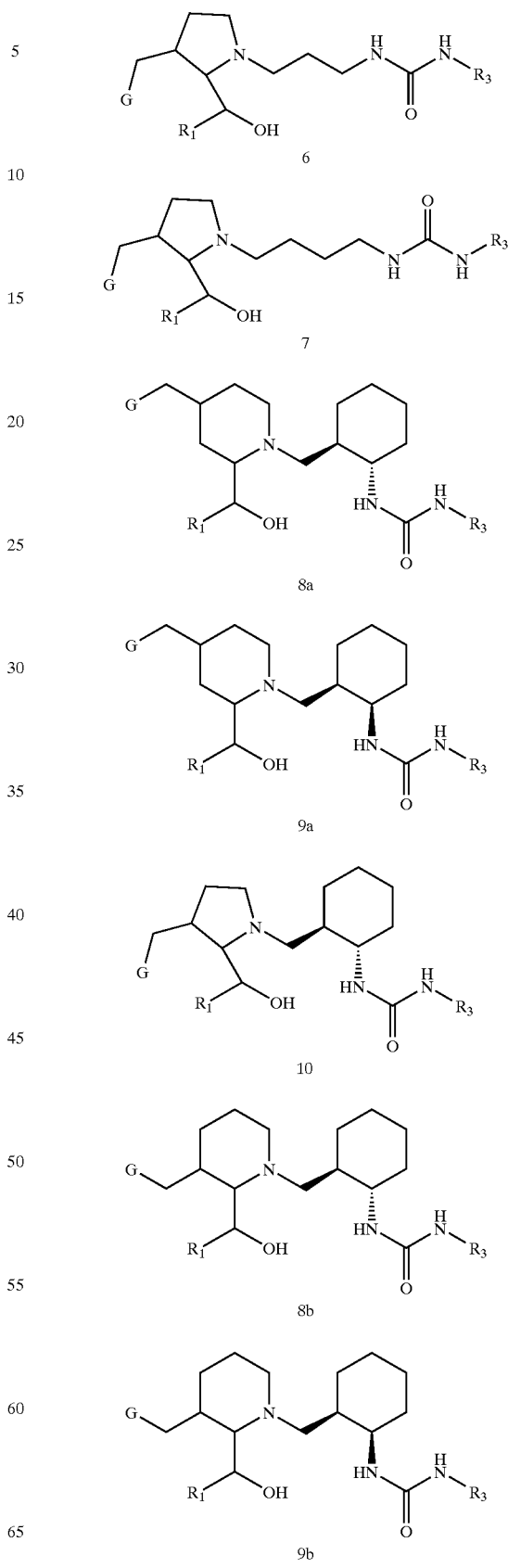

TABLE 7-continued
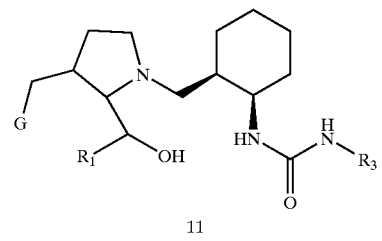
11
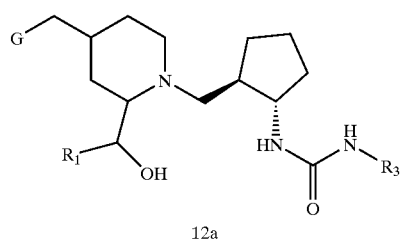
12a
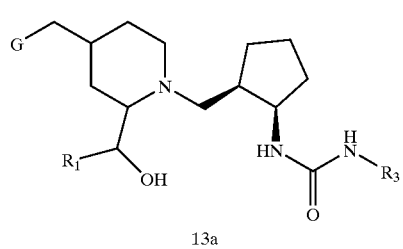
13a
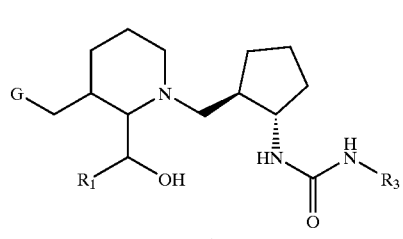
12b
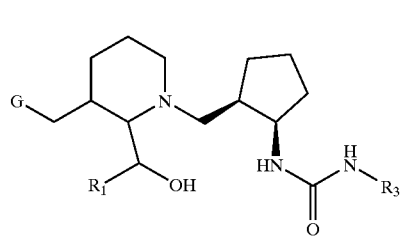
13b
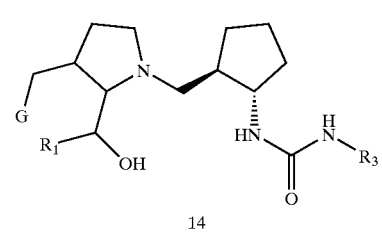
14
TABLE 7-continued
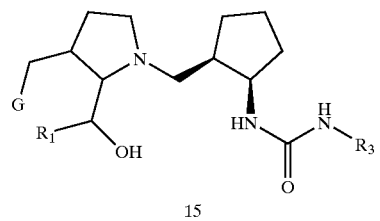
15
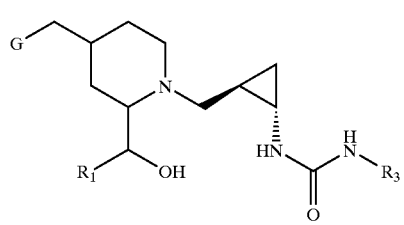
16a
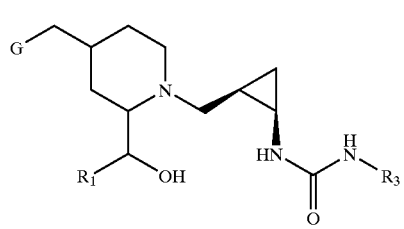
17a
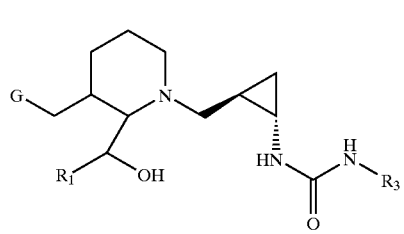
16b
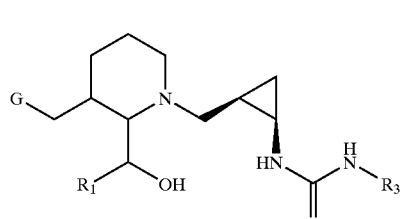
17b
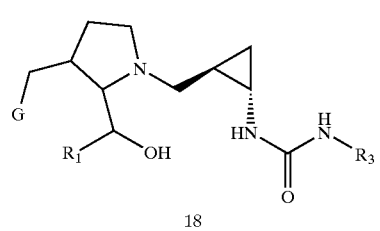
18

TABLE 7-continued
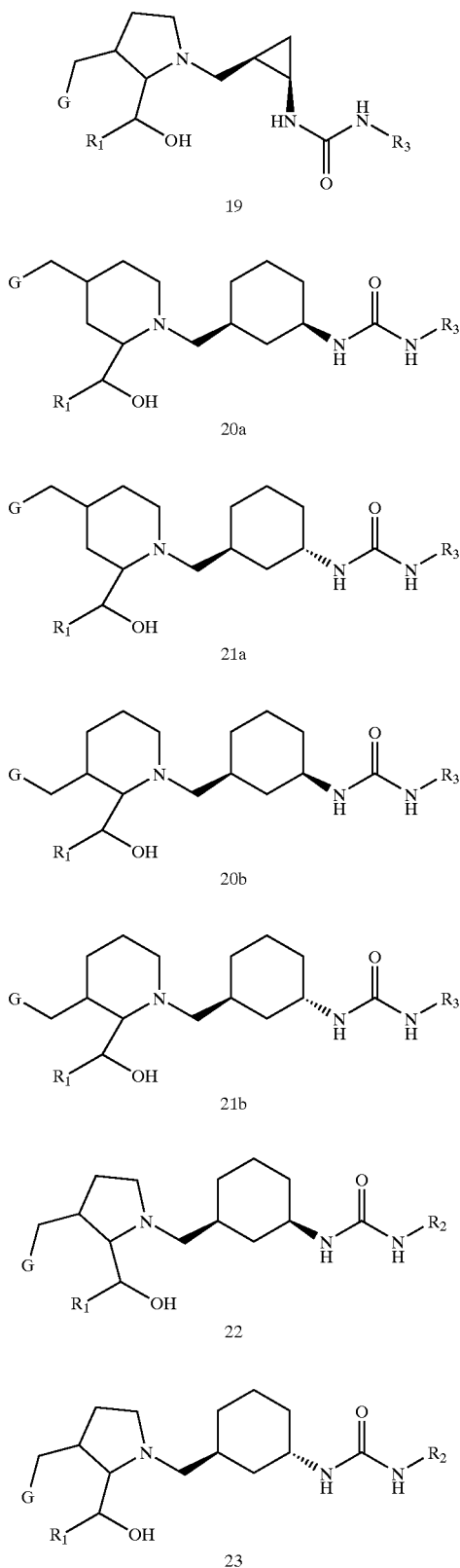
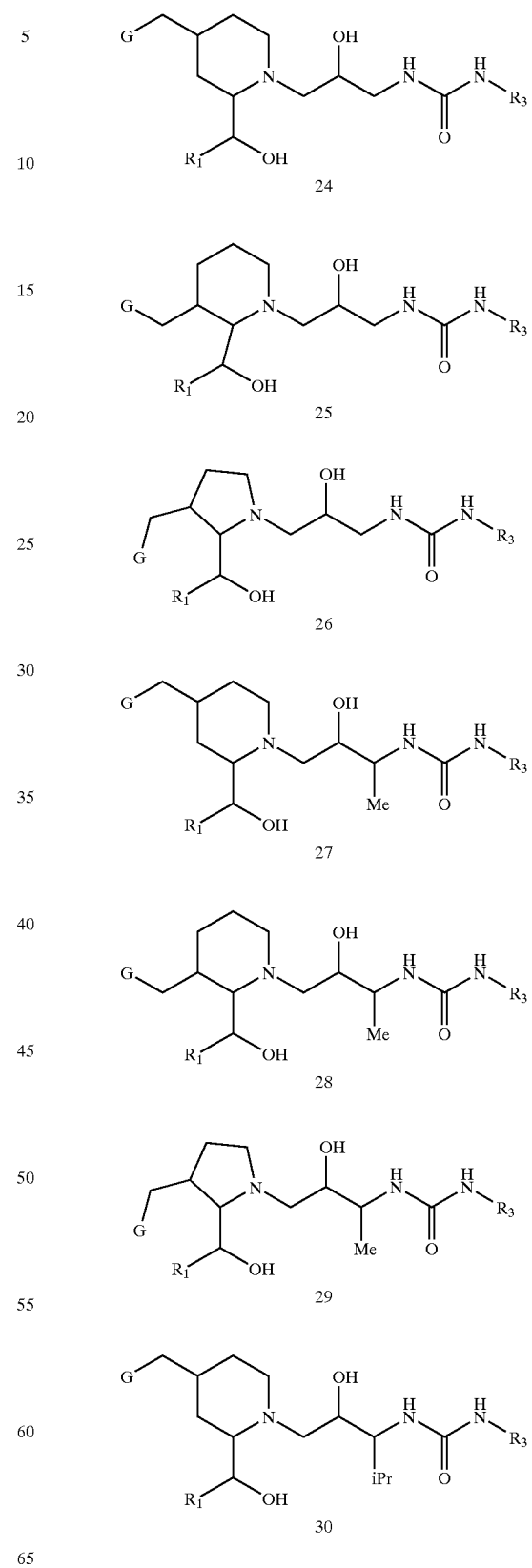

TABLE 7-continued
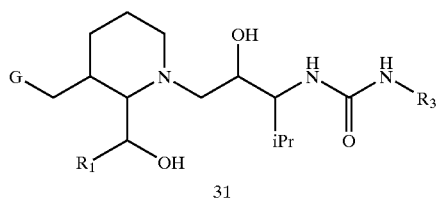
31
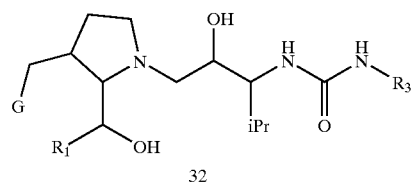
32
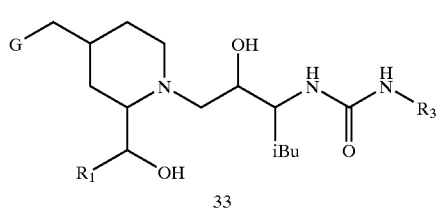
33
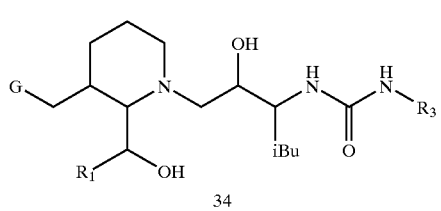
34
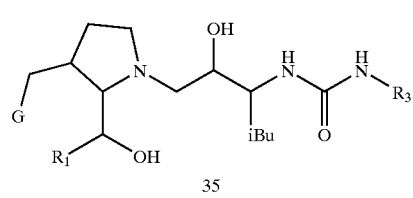
35
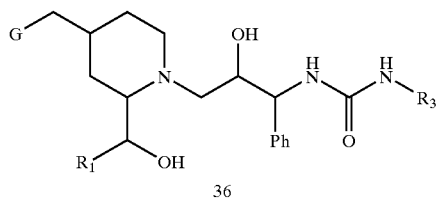
36
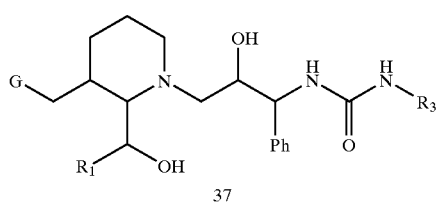
37
TABLE 7-continued
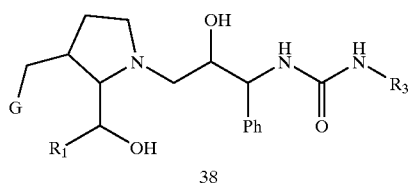
38
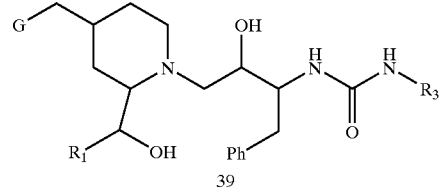
39
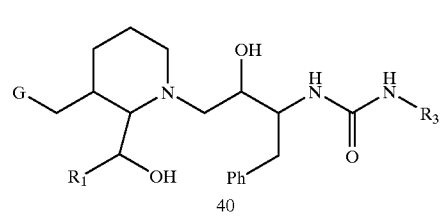
40
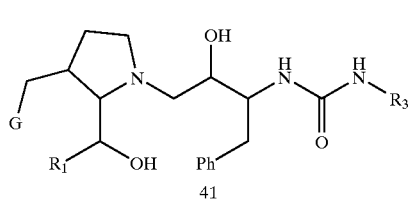
41
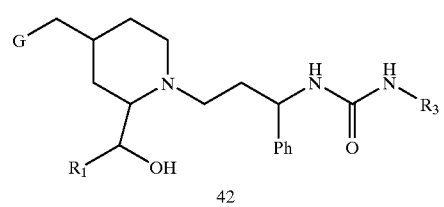
42
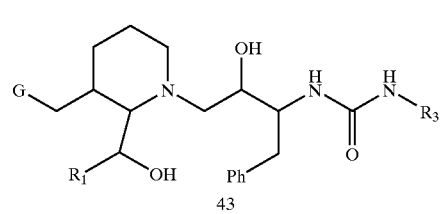
43
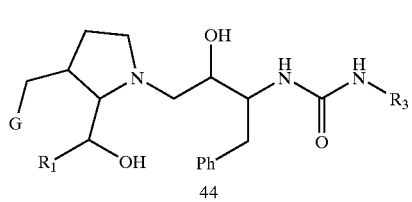
44

TABLE 7-continued

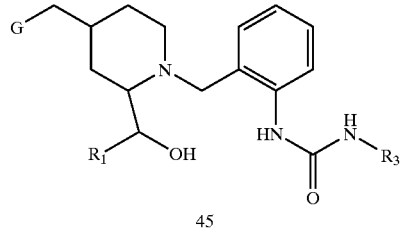

45

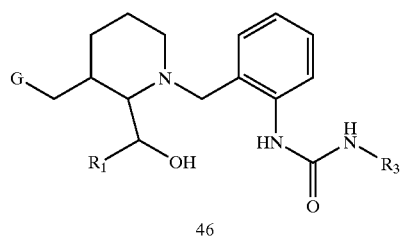

46

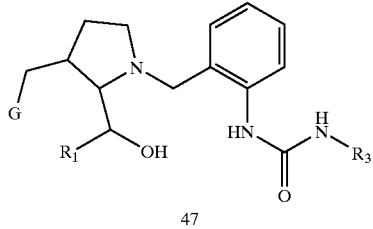

47

R1 = a) H, b) methyl, c) ethyl, d) n-propyl, e) allyl, f) n-butyl, g) n-pentyl, and h) n-hexyl.

| Entry | G | R3 |
|---|---|---|
| 1 | 4-F—Ph | Ph |
| 2 | 4-F—Ph | 3-CN—Ph |
| 3 | 4-F—Ph | 3-COCH3—Ph |
| 4 | 4-F—Ph | 3-CO2Me—Ph |
| 5 | 4-F—Ph | 3-CO2Et—Ph |
| 6 | 4-F—Ph | 3-CO2H—Ph |
| 7 | 4-F—Ph | 3-CONH2—Ph |
| 8 | 4-F—Ph | 3-CONHMe—Ph |
| 9 | 4-F—Ph | 3-F—Ph |
| 10 | 4-F—Ph | 3-Cl—Ph |
| 11 | 4-F—Ph | 3-Br—Ph |
| 12 | 4-F—Ph | 3-NO2—Ph |
| 13 | 4-F—Ph | 3-NH2—Ph |
| 14 | 4-F—Ph | 3-NHMe—Ph |
| 15 | 4-F—Ph | 3-NMe2—Ph |
| 16 | 4-F—Ph | 3-NHCOCH3—Ph |
| 17 | 4-F—Ph | 3-SO2NH2—Ph |
| 18 | 4-F—Ph | 3-SO2NHMe—Ph |
| 19 | 4-F—Ph | 3-CF3—Ph |
| 20 | 4-F—Ph | 3-OCH3—Ph |
| 21 | 4-F—Ph | 3-OPh—Ph |
| 22 | 4-F—Ph | 3-OCF3—Ph |
| 23 | 4-F—Ph | 3-SCH3—Ph |
| 24 | 4-F—Ph | 3-SOCH3—Ph |
| 25 | 4-F—Ph | 3-SO2CH3—Ph |
| 26 | 4-F—Ph | 3-OH—Ph |
| 27 | 4-F—Ph | 3-CH2OH—Ph |
| 28 | 4-F—Ph | 3-CHOHCH3—Ph |
| 29 | 4-F—Ph | 3-COH(CH3)2—Ph |
| 30 | 4-F—Ph | 3-CHOHPh—Ph |
| 31 | 4-F—Ph | 3-CH3—Ph |
| 32 | 4-F—Ph | 3-C2H5—Ph |
| 33 | 4-F—Ph | 3-iPr-Ph |
| 34 | 4-F—Ph | 3-tBu-Ph |
| 35 | 4-F—Ph | 3-Ph—Ph |
| 36 | 4-F—Ph | 3-CH2Ph—Ph |
| 37 | 4-F—Ph | 3-CH2CO2Me—Ph |
| 38 | 4-F—Ph | 3-(1-piperidinyl)-Ph |
| 39 | 4-F—Ph | 3-(1-pyrrolidinyl)-Ph |
| 40 | 4-F—Ph | 3-(2-imidazolyl)-Ph |
| 41 | 4-F—Ph | 3-(1-imidazolyl)-Ph |
| 42 | 4-F—Ph | 3-(2-thiazolyl)-Ph |
| 43 | 4-F—Ph | 3-(3-pyrazolyl)-Ph |
| 44 | 4-F—Ph | 3-(1-pyrazolyl)-Ph |
| 45 | 4-F—Ph | 3-(1-tetrazol)-Ph |
| 46 | 4-F—Ph | 3-(5-tetrazolyl)-Ph |
| 47 | 4-F—Ph | 3-(2-pyridyl)-Ph |
| 48 | 4-F—Ph | 3-(2-thienyl)-Ph |
| 49 | 4-F—Ph | 3-(2-furanyl)-Ph |
| 50 | 4-F—Ph | 4-CN—Ph |
| 51 | 4-F—Ph | 4-COCH3—Ph |
| 52 | 4-F—Ph | 4-CO2Me—Ph |
| 53 | 4-F—Ph | 4-CO2Et—Ph |
| 54 | 4-F—Ph | 4-CO2H—Ph |
| 55 | 4-F—Ph | 4-CONH2—Ph |
| 56 | 4-F—Ph | 4-CONHMe—Ph |
| 57 | 4-F—Ph | 4-CONHPh—Ph |
| 58 | 4-F—Ph | 4-NHCONH2—Ph |
| 59 | 4-F—Ph | 4-F—Ph |
| 60 | 4-F—Ph | 4-Cl—Ph |
| 61 | 4-F—Ph | 4-Br—Ph |
| 62 | 4-F—Ph | 4-NO2—Ph |
| 63 | 4-F—Ph | 4-NH2—Ph |
| 64 | 4-F—Ph | 4-NHMe—Ph |
| 65 | 4-F—Ph | 4-NMe2—Ph |
| 66 | 4-F—Ph | 4-NHCOCH3—Ph |
| 67 | 4-F—Ph | 4-SO2NH2—Ph |
| 68 | 4-F—Ph | 4-SO2NHMe—Ph |
| 69 | 4-F—Ph | 4-CF3—Ph |
| 70 | 4-F—Ph | 4-OCH3—Ph |
| 71 | 4-F—Ph | 4-OPh—Ph |
| 72 | 4-F—Ph | 4-OCF3—Ph |
| 73 | 4-F—Ph | 4-SCH3—Ph |
| 74 | 4-F—Ph | 4-SOCH3—Ph |
| 75 | 4-F—Ph | 4-SO2CH3—Ph |
| 76 | 4-F—Ph | 4-OH—Ph |
| 77 | 4-F—Ph | 4-CH2OH—Ph |
| 78 | 4-F—Ph | 4-CHOHCH3—Ph |
| 79 | 4-F—Ph | 4-COH(CH3)2—Ph |
| 80 | 4-F—Ph | 4-CH3—Ph |
| 81 | 4-F—Ph | 4-C2H5—Ph |
| 82 | 4-F—Ph | 4-iPr-Ph |
| 83 | 4-F—Ph | 4-tBu-Ph |
| 84 | 4-F—Ph | 4-Ph—Ph |
| 85 | 4-F—Ph | 4-CH2Ph—Ph |
| 86 | 4-F—Ph | 4-CH2CO2Me—Ph |
| 87 | 4-F—Ph | 4-(1-piperidinyl)-Ph |
| 88 | 4-F—Ph | 4-(1-pyrrolidinyl)-Ph |
| 89 | 4-F—Ph | 4-(2-imidazolyl)-Ph |
| 90 | 4-F—Ph | 4-(1-imidazolyl)-Ph |
| 91 | 4-F—Ph | 4-(2-thiazolyl)-Ph |
| 92 | 4-F—Ph | 4-(3-pyrazolyl)-Ph |
| 93 | 4-F—Ph | 4-(1-pyrazolyl)-Ph |
| 94 | 4-F—Ph | 4-(1-tetrazolyl)-Ph |
| 95 | 4-F—Ph | 4-(5-tetrazolyl)-Ph |
| 96 | 4-F—Ph | 4-(2-pyridyl)-Ph |
| 97 | 4-F—Ph | 4-(2-thienyl)-Ph |
| 98 | 4-F—Ph | 4-(2-furanyl)-Ph |
| 99 | 4-F—Ph | 2-CN—Ph |
| 100 | 4-F—Ph | 2-COCH3—Ph |
| 101 | 4-F—Ph | 2-CO2Me—Ph |
| 102 | 4-F—Ph | 2-CO2Et—Ph |
| 103 | 4-F—Ph | 2-CO2H—Ph |
| 104 | 4-F—Ph | 2-CONH2—Ph |
| 105 | 4-F—Ph | 2-CONHMe—Ph |
| 106 | 4-F—Ph | 2-F—Ph |
| 107 | 4-F—Ph | 2-Cl—Ph |
| 108 | 4-F—Ph | 2-Br—Ph |
| 109 | 4-F—Ph | 2-NO2—Ph |
| 110 | 4-F—Ph | 2-NH2—Ph |
| 111 | 4-F—Ph | 2-NHMe—Ph |
| 112 | 4-F—Ph | 2-NMe2—Ph |
| 113 | 4-F—Ph | 2-NHCOCH3—Ph |
| 114 | 4-F—Ph | 2-SO2NH2—Ph |
| 115 | 4-F—Ph | 2-SO2NHMe—Ph |
| 116 | 4-F—Ph | 2-CF3—Ph |

TABLE 7-continued

| | | |
|---|---|---|
| 117 | 4-F—Ph | 2-OCH3—Ph |
| 118 | 4-F—Ph | 2-OPh—Ph |
| 119 | 4-F—Ph | 2-OCF3—Ph |
| 120 | 4-F—Ph | 2-SCH3—Ph |
| 121 | 4-F—Ph | 2-SOCH3—Ph |
| 122 | 4-F—Ph | 2-SO2CH3—Ph |
| 123 | 4-F—Ph | 2-OH—Ph |
| 124 | 4-F—Ph | 2-CH2OH—Ph |
| 125 | 4-F—Ph | 2-CHOHCH3—Ph |
| 126 | 4-F—Ph | 2-COH(CH3)2—Ph |
| 127 | 4-F—Ph | 2-CHOHPh—Ph |
| 128 | 4-F—Ph | 2-CH3—Ph |
| 129 | 4-F—Ph | 2-C2H5—Ph |
| 130 | 4-F—Ph | 2-iPr-Ph |
| 131 | 4-F—Ph | 2-tBu-Ph |
| 132 | 4-F—Ph | 2-Ph—Ph |
| 133 | 4-F—Ph | 2-CH2Ph—Ph |
| 134 | 4-F—Ph | 2-CH2CO2Me—Ph |
| 135 | 4-F—Ph | 2-(1-piperidinyl)-Ph |
| 136 | 4-F—Ph | 2-(1-pyrrolidinyl)-Ph |
| 137 | 4-F—Ph | 2-(2-imidazolyl)-Ph |
| 138 | 4-F—Ph | 2-(1-imidazolyl)-Ph |
| 139 | 4-F—Ph | 2-(2-thiazolyl)-Ph |
| 140 | 4-F—Ph | 2-(3-pyrazolyl)-Ph |
| 141 | 4-F—Ph | 2-(1-pyrazolyl)-Ph |
| 142 | 4-F—Ph | 2-(1-tetrazolyl)-Ph |
| 143 | 4-F—Ph | 2-(5-tetrazolyl)-Ph |
| 144 | 4-F—Ph | 2-(2-pyridyl)-Ph |
| 145 | 4-F—Ph | 2-(2-thienyl)-Ph |
| 146 | 4-F—Ph | 2-(2-furanyl)-Ph |
| 147 | 4-F—Ph | 2,4-diF—Ph |
| 148 | 4-F—Ph | 2,5-diF—Ph |
| 149 | 4-F—Ph | 2,6-diF—Ph |
| 150 | 4-F—Ph | 3,4-diF—Ph |
| 151 | 4-F—Ph | 3,5-diF—Ph |
| 152 | 4-F—Ph | 2,4-diCl—Ph |
| 153 | 4-F—Ph | 2,5-diCl—Ph |
| 154 | 4-F—Ph | 2,6-diCl—Ph |
| 155 | 4-F—Ph | 3,4-diCl—Ph |
| 156 | 4-F—Ph | 3,5-diCl—Ph |
| 157 | 4-F—Ph | 3,4-diCF3—Ph |
| 158 | 4-F—Ph | 3,5-diCF3—Ph |
| 159 | 4-F—Ph | 5-Cl-2-MeO—Ph |
| 160 | 4-F—Ph | 5-Cl-2-Me—Ph |
| 161 | 4-F—Ph | 2-F-5-Me—Ph |
| 162 | 4-F—Ph | 2-F-5-NO2—Ph |
| 163 | 4-F—Ph | 3,4-OCH2O—Ph |
| 164 | 4-F—Ph | 3,4-OCH2CH2O—Ph |
| 165 | 4-F—Ph | 2-MeO-4-Me—Ph |
| 166 | 4-F—Ph | 2-MeO-5-Me—Ph |
| 167 | 4-F—Ph | 1-naphthyl |
| 168 | 4-F—Ph | 2-naphthyl |
| 169 | 4-F—Ph | 2-thienyl |
| 170 | 4-F—Ph | 3-thienyl |
| 171 | 4-F—Ph | 2-furanyl |
| 172 | 4-F—Ph | 3-furanyl |
| 173 | 4-F—Ph | 2-pyridyl |
| 174 | 4-F—Ph | 3-pyridyl |
| 175 | 4-F—Ph | 4-pyridyl |
| 176 | 4-F—Ph | 2-indolyl |
| 177 | 4-F—Ph | 3-indolyl |
| 178 | 4-F—Ph | 5-indolyl |
| 179 | 4-F—Ph | 6-indolyl |
| 180 | 4-F—Ph | 3-indazolyl |
| 181 | 4-F—Ph | 5-indazolyl |
| 182 | 4-F—Ph | 6-indazolyl |
| 183 | 4-F—Ph | 2-imidazolyl |
| 184 | 4-F—Ph | 3-pyrazolyl |
| 185 | 4-F—Ph | 2-thiazolyl |
| 186 | 4-F—Ph | 5-tetrazolyl |
| 187 | 4-F—Ph | 2-benzimidazolyl |
| 188 | 4-F—Ph | 5-benzimidazolyl |
| 189 | 4-F—Ph | 2-benzothiazolyl |
| 190 | 4-F—Ph | 5-benzothiazolyl |
| 191 | 4-F—Ph | 2-benzoxazolyl |
| 192 | 4-F—Ph | 5-benzoxazolyl |
| 193 | 4-F—Ph | 1-adamantyl |
| 194 | 4-F—Ph | 2-adamantyl |
| 195 | 4-F—Ph | t-Bu |
| 196 | 2-F—Ph | 3-CN—Ph |
| 197 | 2-F—Ph | 3-COCH3—Ph |
| 198 | 2-F—Ph | 3-CO2Me—Ph |
| 199 | 2-F—Ph | 3-CO2Et—Ph |
| 200 | 2-F—Ph | 3-CO2H—Ph |
| 201 | 2-F—Ph | 3-CONH2—Ph |
| 202 | 2-F—Ph | 3-F—Ph |
| 203 | 2-F—Ph | 3-Cl—Ph |
| 204 | 2-F—Ph | 3-NH2—Ph |
| 205 | 2-F—Ph | 3-SO2NH2—Ph |
| 206 | 2-F—Ph | 3-CF3—Ph |
| 207 | 2-F—Ph | 3-OCH3—Ph |
| 208 | 2-F—Ph | 3-OEt—Ph |
| 209 | 2-F—Ph | 3-OCF3—Ph |
| 210 | 2-F—Ph | 3-SO2CH3—Ph |
| 211 | 2-F—Ph | 3-OH—Ph |
| 212 | 2-F—Ph | 3-CH3—Ph |
| 213 | 2-F—Ph | 3-C2H5—Ph |
| 214 | 2-F—Ph | 4-CN—Ph |
| 215 | 2-F—Ph | 4-COCH3—Ph |
| 216 | 2-F—Ph | 4-CO2Me—Ph |
| 217 | 2-F—Ph | 4-CO2Et—Ph |
| 218 | 2-F—Ph | 4-CO2H—Ph |
| 219 | 2-F—Ph | 4-CONH2—Ph |
| 220 | 2-F—Ph | 4-F—Ph |
| 221 | 2-F—Ph | 4-Cl—Ph |
| 222 | 2-F—Ph | 4-NH2—Ph |
| 223 | 2-F—Ph | 4-SO2NH2—Ph |
| 224 | 2-F—Ph | 4-CF3—Ph |
| 225 | 2-F—Ph | 4-OCH3—Ph |
| 226 | 2-F—Ph | 4-OEt—Ph |
| 227 | 2-F—Ph | 4-OCF3—Ph |
| 228 | 2-F—Ph | 4-SO2CH3—Ph |
| 229 | 2-F—Ph | 4-OH—Ph |
| 230 | 2-F—Ph | 4-CH3—Ph |
| 231 | 2-F—Ph | 4-C2H5—Ph |
| 232 | 2-F—Ph | 2,4-diF—Ph |
| 233 | 2-F—Ph | 2,5-diF—Ph |
| 234 | 2-F—Ph | 3,4-diF—Ph |
| 235 | 2-F—Ph | 3,5-diF—Ph |
| 236 | 2-F—Ph | 2,4-diCl—Ph |
| 237 | 2-F—Ph | 2,5-diCl—Ph |
| 238 | 2-F—Ph | 3,4-diCl—Ph |
| 239 | 2-F—Ph | 3,5-diCl—Ph |
| 240 | 2-F—Ph | 3,4-OCH2O—Ph |
| 241 | 2-F—Ph | 3,4-OCH2CH2O—Ph |
| 242 | 2-F—Ph | 2-thienyl |
| 243 | 2-F—Ph | 2-furanyl |
| 244 | 2-F—Ph | 2-pyridyl |
| 245 | 2-F—Ph | 4-pyridyl |
| 246 | 2-F—Ph | 2-imidazolyl |
| 247 | 2-F—Ph | 3-pyrazolyl |
| 248 | 2-F—Ph | 2-thiazolyl |
| 249 | 2-F—Ph | 5-tetrazolyl |
| 250 | 2-F—Ph | 1-adamantyl |
| 251 | 2,4-diF—Ph | 3-CN—Ph |
| 252 | 2,4-diF—Ph | 3-COCH3—Ph |
| 253 | 2,4-diF—Ph | 3-CO2Me—Ph |
| 254 | 2,4-diF—Ph | 3-CO2Et—Ph |
| 255 | 2,4-diF—Ph | 3-CO2H—Ph |
| 256 | 2,4-diF—Ph | 3-CONH2—Ph |
| 257 | 2,4-diF—Ph | 3-F—Ph |
| 258 | 2,4-diF—Ph | 3-Cl—Ph |
| 259 | 2,4-diF—Ph | 3-NH2—Ph |
| 260 | 2,4-diF—Ph | 3-SO2NH2—Ph |
| 261 | 2,4-diF—Ph | 3-CF3—Ph |
| 262 | 2,4-diF—Ph | 3-OCH3—Ph |
| 263 | 2,4-diF—Ph | 3-OEt—Ph |
| 264 | 2,4-diF—Ph | 3-OCF3—Ph |
| 265 | 2,4-diF—Ph | 3-SO2CH3—Ph |
| 266 | 2,4-diF—Ph | 3-OH—Ph |
| 267 | 2,4-diF—Ph | 3-CH3—Ph |
| 268 | 2,4-diF—Ph | 3-C2H5—Ph |
| 269 | 2,4-diF—Ph | 4-CN—Ph |
| 270 | 2,4-diF—Ph | 4-COCH3—Ph |
| 271 | 2,4-diF—Ph | 4-CO2Me—Ph |
| 272 | 2,4-diF—Ph | 4-CO2Et—Ph |
| 273 | 2,4-diF—Ph | 4-CO2H—Ph |
| 274 | 2,4-diF—Ph | 4-CONH2—Ph |

TABLE 7-continued

| | | |
|---|---|---|
| 275 | 2,4-diF—Ph | 4-F—Ph |
| 276 | 2,4-diF—Ph | 4-Cl—Ph |
| 277 | 2,4-diF—Ph | 4-NH2—Ph |
| 278 | 2,4-diF—Ph | 4-SO2NH2—Ph |
| 279 | 2,4-diF—Ph | 4-CF3—Ph |
| 280 | 2,4-diF—Ph | 4-OCH3—Ph |
| 281 | 2,4-diF—Ph | 4-OEt—Ph |
| 282 | 2,4-diF—Ph | 4-OCF3—Ph |
| 283 | 2,4-diF—Ph | 4-SO2CH3—Ph |
| 284 | 2,4-diF—Ph | 4-OH—Ph |
| 285 | 2,4-diF—Ph | 4-CH3—Ph |
| 286 | 2,4-diF—Ph | 4-C2H5—Ph |
| 287 | 2,4-diF—Ph | 2,4-diF—Ph |
| 288 | 2,4-diF—Ph | 2,5-diF—Ph |
| 289 | 2,4-diF—Ph | 3,4-diF—Ph |
| 290 | 2,4-diF—Ph | 3,5-diF—Ph |
| 291 | 2,4-diF—Ph | 2,4-diCl—Ph |
| 292 | 2,4-diF—Ph | 2,5-diCl—Ph |
| 293 | 2,4-diF—Ph | 3,4-diCl—Ph |
| 294 | 2,4-diF—Ph | 3,5-diCl—Ph |
| 295 | 2,4-diF—Ph | 3,4-OCH2O—Ph |
| 296 | 2,4-diF—Ph | 3,4-OCH2CH2O—Ph |
| 297 | 2,4-diF—Ph | 2-thienyl |
| 298 | 2,4-diF—Ph | 2-furanyl |
| 299 | 2,4-diF—Ph | 2-pyridyl |
| 300 | 2,4-diF—Ph | 4-pyridyl |
| 301 | 2,4-diF—Ph | 2-imidazolyl |
| 302 | 2,4-diF—Ph | 3-pyrazolyl |
| 303 | 2,4-diF—Ph | 2-thiazolyl |
| 304 | 2,4-diF—Ph | 5-tetrazolyl |
| 305 | 2,4-diF—Ph | 1-adamantyl |
| 306 | 4-Cl—Ph | Ph |
| 307 | 4-Cl—Ph | 3-CN—Ph |
| 308 | 4-Cl—Ph | 3-COCH3—Ph |
| 309 | 4-Cl—Ph | 3-CO2Me—Ph |
| 310 | 4-Cl—Ph | 3-CO2Et—Ph |
| 311 | 4-Cl—Ph | 3-CO2H—Ph |
| 312 | 4-Cl—Ph | 3-CONH2—Ph |
| 313 | 4-Cl—Ph | 3-CONHMe—Ph |
| 314 | 4-Cl—Ph | 3-F—Ph |
| 315 | 4-Cl—Ph | 3-Cl—Ph |
| 316 | 4-Cl—Ph | 3-Br—Ph |
| 317 | 4-Cl—Ph | 3-NO2—Ph |
| 318 | 4-Cl—Ph | 3-NH2—Ph |
| 319 | 4-Cl—Ph | 3-NHMe—Ph |
| 320 | 4-Cl—Ph | 3-NMe2—Ph |
| 321 | 4-Cl—Ph | 3-NHCOCH3—Ph |
| 322 | 4-Cl—Ph | 3-SO2NH2—Ph |
| 323 | 4-Cl—Ph | 3-SO2NHMe—Ph |
| 324 | 4-Cl—Ph | 3-CF3—Ph |
| 325 | 4-Cl—Ph | 3-OCH3—Ph |
| 326 | 4-Cl—Ph | 3-OPh—Ph |
| 327 | 4-Cl—Ph | 3-OCF3—Ph |
| 328 | 4-Cl—Ph | 3-SCH3—Ph |
| 329 | 4-Cl—Ph | 3-SOCH3—Ph |
| 330 | 4-Cl—Ph | 3-SO2CH3—Ph |
| 331 | 4-Cl—Ph | 3-OH—Ph |
| 332 | 4-Cl—Ph | 3-CH2OH—Ph |
| 333 | 4-Cl—Ph | 3-CHOHCH3—Ph |
| 334 | 4-Cl—Ph | 3-COH(CH3)2—Ph |
| 335 | 4-Cl—Ph | 3-CHOHPh—Ph |
| 336 | 4-Cl—Ph | 3-CH3—Ph |
| 337 | 4-Cl—Ph | 3-C2H5—Ph |
| 338 | 4-Cl—Ph | 3-iPr-Ph |
| 339 | 4-Cl—Ph | 3-tBu-Ph |
| 340 | 4-Cl—Ph | 3-Ph—Ph |
| 341 | 4-Cl—Ph | 3-CH2Ph—Ph |
| 342 | 4-Cl—Ph | 3-CH2CO2Me—Ph |
| 343 | 4-Cl—Ph | 3-(1-piperidinyl)-Ph |
| 344 | 4-Cl—Ph | 3-(1-pyrrolidinyl)-Ph |
| 345 | 4-Cl—Ph | 3-(2-imidazolyl)-Ph |
| 346 | 4-Cl—Ph | 3-(1-imidazolyl)-Ph |
| 347 | 4-Cl—Ph | 3-(2-thiazolyl)-Ph |
| 348 | 4-Cl—Ph | 3-(3-pyrazolyl)-Ph |
| 349 | 4-Cl—Ph | 3-(1-pyrazolyl)-Ph |
| 350 | 4-Cl—Ph | 3-(1-tetrazolyl)-Ph |
| 351 | 4-Cl—Ph | 3-(5-tetrazolyl)-Ph |
| 352 | 4-Cl—Ph | 3-(2-pyridyl)-Ph |
| 353 | 4-Cl—Ph | 3-(2-thienyl)-Ph |
| 354 | 4-Cl—Ph | 3-(2-furanyl)-Ph |
| 355 | 4-Cl—Ph | 4-CN—Ph |
| 356 | 4-Cl—Ph | 4-COCH3—Ph |
| 357 | 4-Cl—Ph | 4-CO2Me—Ph |
| 358 | 4-Cl—Ph | 4-CO2Et—Ph |
| 359 | 4-Cl—Ph | 4-CO2H—Ph |
| 360 | 4-Cl—Ph | 4-CONH2—Ph |
| 361 | 4-Cl—Ph | 4-CONHMe—Ph |
| 362 | 4-Cl—Ph | 4-CONHPh—Ph |
| 363 | 4-Cl—Ph | 4-NHCONH2—Ph |
| 364 | 4-Cl—Ph | 4-F—Ph |
| 365 | 4-Cl—Ph | 4-Cl—Ph |
| 366 | 4-Cl—Ph | 4-Br—Ph |
| 367 | 4-Cl—Ph | 4-NO2—Ph |
| 368 | 4-Cl—Ph | 4-NH2—Ph |
| 369 | 4-Cl—Ph | 4-NHMe—Ph |
| 370 | 4-Cl—Ph | 4-NMe2—Ph |
| 371 | 4-Cl—Ph | 4-NHCOCH3—Ph |
| 372 | 4-Cl—Ph | 4-SO2NH2—Ph |
| 373 | 4-Cl—Ph | 4-SO2NHMe—Ph |
| 374 | 4-Cl—Ph | 4-CF3—Ph |
| 375 | 4-Cl—Ph | 4-OCH3—Ph |
| 376 | 4-Cl—Ph | 4-OPh—Ph |
| 377 | 4-Cl—Ph | 4-OCF3—Ph |
| 378 | 4-Cl—Ph | 4-SCH3—Ph |
| 379 | 4-Cl—Ph | 4-SOCH3—Ph |
| 380 | 4-Cl—Ph | 4-SO2CH3—Ph |
| 381 | 4-Cl—Ph | 4-OH—Ph |
| 382 | 4-Cl—Ph | 4-CH2OH—Ph |
| 383 | 4-Cl—Ph | 4-CHOHCH3—Ph |
| 384 | 4-Cl—Ph | 4-COH(CH3)2—Ph |
| 385 | 4-Cl—Ph | 4-CH3—Ph |
| 386 | 4-Cl—Ph | 4-C2H5—Ph |
| 387 | 4-Cl—Ph | 4-iPr-Ph |
| 388 | 4-Cl—Ph | 4-tBu-Ph |
| 389 | 4-Cl—Ph | 4-Ph—Ph |
| 390 | 4-Cl—Ph | 4-CH2Ph—Ph |
| 391 | 4-Cl—Ph | 4-CH2CO2Me—Ph |
| 392 | 4-Cl—Ph | 4-(1-piperidinyl)-Ph |
| 393 | 4-Cl—Ph | 4-(1-pyrrolidinyl)-Ph |
| 394 | 4-Cl—Ph | 4-(2-imidazolyl)-Ph |
| 395 | 4-Cl—Ph | 4-(1-imidazolyl)-Ph |
| 396 | 4-Cl—Ph | 4-(2-thiazolyl)-Ph |
| 397 | 4-Cl—Ph | 4-(3-pyrazolyl)-Ph |
| 398 | 4-Cl—Ph | 4-(1-pyrazolyl)-Ph |
| 399 | 4-Cl—Ph | 4-(1-tetrazolyl)-Ph |
| 400 | 4-Cl—Ph | 4-(5-tetrazolyl)-Ph |
| 401 | 4-Cl—Ph | 4-(2-pyridyl)-Ph |
| 402 | 4-Cl—Ph | 4-(2-thienyl)-Ph |
| 403 | 4-Cl—Ph | 4-(2-furanyl)-Ph |
| 404 | 4-Cl—Ph | 2-CN—Ph |
| 405 | 4-Cl—Ph | 2-COCH3—Ph |
| 406 | 4-Cl—Ph | 2-CO2Me—Ph |
| 407 | 4-Cl—Ph | 2-CO2Et—Ph |
| 408 | 4-Cl—Ph | 2-CO2H—Ph |
| 409 | 4-Cl—Ph | 2-CONH2—Ph |
| 410 | 4-Cl—Ph | 2-CONHMe—Ph |
| 411 | 4-Cl—Ph | 2-F—Ph |
| 412 | 4-Cl—Ph | 2-Cl—Ph |
| 413 | 4-Cl—Ph | 2-Br—Ph |
| 414 | 4-Cl—Ph | 2-NO2—Ph |
| 415 | 4-Cl—Ph | 2-NH2—Ph |
| 416 | 4-Cl—Ph | 2-NHMe—Ph |
| 417 | 4-Cl—Ph | 2-NMe2—Ph |
| 418 | 4-Cl—Ph | 2-NHCOCH3—Ph |
| 419 | 4-Cl—Ph | 2-SO2NH2—Ph |
| 420 | 4-Cl—Ph | 2-SO2NHMe—Ph |
| 421 | 4-Cl—Ph | 2-CF3—Ph |
| 422 | 4-Cl—Ph | 2-OCH3—Ph |
| 423 | 4-Cl—Ph | 2-OPh—Ph |
| 424 | 4-Cl—Ph | 2-OCF3—Ph |
| 425 | 4-Cl—Ph | 2-SCH3—Ph |
| 426 | 4-Cl—Ph | 2-SOCH3—Ph |
| 427 | 4-Cl—Ph | 2-SO2CH3—Ph |
| 428 | 4-Cl—Ph | 2-OH—Ph |
| 429 | 4-Cl—Ph | 2-CH2OH—Ph |
| 430 | 4-Cl—Ph | 2-CHOHCH3—Ph |
| 431 | 4-Cl—Ph | 2-COH(CH3)2—Ph |
| 432 | 4-Cl—Ph | 2-CHOHPh—Ph |

TABLE 7-continued

| | | |
|---|---|---|
| 433 | 4-Cl—Ph | 2-CH3—Ph |
| 434 | 4-Cl—Ph | 2-C2H5—Ph |
| 435 | 4-Cl—Ph | 2-iPr-Ph |
| 436 | 4-Cl—Ph | 2-tBu-Ph |
| 437 | 4-Cl—Ph | 2-Ph—Ph |
| 438 | 4-Cl—Ph | 2-CH2Ph—Ph |
| 439 | 4-Cl—Ph | 2-CH2CO2Me—Ph |
| 440 | 4-Cl—Ph | 2-(1-piperidinyl)-Ph |
| 441 | 4-Cl—Ph | 2-(1-pyrrolidinyl)-Ph |
| 442 | 4-Cl—Ph | 2-(2-imidazolyl)-Ph |
| 443 | 4-Cl—Ph | 2-(1-imidazolyl)-Ph |
| 444 | 4-Cl—Ph | 2-(2-thiazolyl)-Ph |
| 445 | 4-Cl—Ph | 2-(3-pyrazolyl)-Ph |
| 446 | 4-Cl—Ph | 2-(1-pyrazolyl)-Ph |
| 447 | 4-Cl—Ph | 2-(1-tetrazolyl)-Ph |
| 448 | 4-Cl—Ph | 2-(5-tetrazolyl)-Ph |
| 449 | 4-Cl—Ph | 2-(2-pyridyl)-Ph |
| 450 | 4-Cl—Ph | 2-(2-thienyl)-Ph |
| 451 | 4-Cl—Ph | 2-(2-furanyl)-Ph |
| 452 | 4-Cl—Ph | 2,4-diF—Ph |
| 453 | 4-Cl—Ph | 2,5-diF—Ph |
| 454 | 4-Cl—Ph | 2,6-diF—Ph |
| 455 | 4-Cl—Ph | 3,4-diF—Ph |
| 456 | 4-Cl—Ph | 3,5-diF—Ph |
| 457 | 4-Cl—Ph | 2,4-diCl—Ph |
| 458 | 4-Cl—Ph | 2,5-diCl—Ph |
| 459 | 4-Cl—Ph | 2,6-diCl—Ph |
| 460 | 4-Cl—Ph | 3,4-diCl—Ph |
| 461 | 4-Cl—Ph | 3,5-diCl—Ph |
| 462 | 4-Cl—Ph | 3,4-diCF3—Ph |
| 463 | 4-Cl—Ph | 3,5-diCF3—Ph |
| 464 | 4-Cl—Ph | 5-Cl-2-MeO—Ph |
| 465 | 4-Cl—Ph | 5-Cl-2-Me—Ph |
| 466 | 4-Cl—Ph | 2-F-5-Me—Ph |
| 467 | 4-Cl—Ph | 2-F-5-NO2—Ph |
| 468 | 4-Cl—Ph | 3,4-OCH2O—Ph |
| 469 | 4-Cl—Ph | 3,4-OCH2CH2O—Ph |
| 470 | 4-Cl—Ph | 2-MeO-4-Me—Ph |
| 471 | 4-Cl—Ph | 2-MeO-5-Me—Ph |
| 472 | 4-Cl—Ph | 1-naphthyl |
| 473 | 4-Cl—Ph | 2-naphthyl |
| 474 | 4-Cl—Ph | 2-thienyl |
| 475 | 4-Cl—Ph | 3-thienyl |
| 476 | 4-Cl—Ph | 2-furanyl |
| 477 | 4-Cl—Ph | 3-furanyl |
| 478 | 4-Cl—Ph | 2-pyridyl |
| 479 | 4-Cl—Ph | 3-pyridyl |
| 480 | 4-Cl—Ph | 4-pyridyl |
| 481 | 4-Cl—Ph | 2-indolyl |
| 482 | 4-Cl—Ph | 3-indolyl |
| 483 | 4-Cl—Ph | 5-indolyl |
| 484 | 4-Cl—Ph | 6-indolyl |
| 485 | 4-Cl—Ph | 3-indazolyl |
| 486 | 4-Cl—Ph | 5-indazolyl |
| 487 | 4-Cl—Ph | 6-indazolyl |
| 488 | 4-Cl—Ph | 2-imidazolyl |
| 489 | 4-Cl—Ph | 3-pyrazolyl |
| 490 | 4-Cl—Ph | 2-thiazolyl |
| 491 | 4-Cl—Ph | 5-tetrazolyl |
| 492 | 4-Cl—Ph | 2-benzimidazolyl |
| 493 | 4-Cl—Ph | 5-benzimidazolyl |
| 494 | 4-Cl—Ph | 2-benzothiazolyl |
| 495 | 4-Cl—Ph | 5-benzothiazolyl |
| 496 | 4-Cl—Ph | 2-benzoxazolyl |
| 497 | 4-Cl—Ph | 5-benzoxazolyl |
| 498 | 4-Cl—Ph | 1-adamantyl |
| 499 | 4-Cl—Ph | 2-adamantyl |
| 500 | 4-Cl—Ph | t-Bu |
| 501 | 2-Cl—Ph | 3-CN—Ph |
| 502 | 2-Cl—Ph | 3-COCH3—Ph |
| 503 | 2-Cl—Ph | 3-CO2Me—Ph |
| 504 | 2-Cl—Ph | 3-CO2Et—Ph |
| 505 | 2-Cl—Ph | 3-CO2H—Ph |
| 506 | 2-Cl—Ph | 3-CONH2—Ph |
| 507 | 2-Cl—Ph | 3-F—Ph |
| 508 | 2-Cl—Ph | 3-Cl—Ph |
| 509 | 2-Cl—Ph | 3-NH2—Ph |
| 510 | 2-Cl—Ph | 3-SO2NH2—Ph |
| 511 | 2-Cl—Ph | 3-CF3—Ph |
| 512 | 2-Cl—Ph | 3-OCH3—Ph |
| 513 | 2-Cl—Ph | 3-OEt—Ph |
| 514 | 2-Cl—Ph | 3-OCF3—Ph |
| 515 | 2-Cl—Ph | 3-SO2CH3—Ph |
| 516 | 2-Cl—Ph | 3-OH—Ph |
| 517 | 2-Cl—Ph | 3-CH3—Ph |
| 518 | 2-Cl—Ph | 3-C2H5—Ph |
| 519 | 2-Cl—Ph | 4-CN—Ph |
| 520 | 2-Cl—Ph | 4-COCH3—Ph |
| 521 | 2-Cl—Ph | 4-CO2Me—Ph |
| 522 | 2-Cl—Ph | 4-CO2Et—Ph |
| 523 | 2-Cl—Ph | 4-CO2H—Ph |
| 524 | 2-Cl—Ph | 4-CONH2—Ph |
| 525 | 2-Cl—Ph | 4-F—Ph |
| 526 | 2-Cl—Ph | 4-Cl—Ph |
| 527 | 2-Cl—Ph | 4-NH2—Ph |
| 528 | 2-Cl—Ph | 4-SO2NH2—Ph |
| 529 | 2-Cl—Ph | 4-CF3—Ph |
| 530 | 2-Cl—Ph | 4-OCH3—Ph |
| 531 | 2-Cl—Ph | 4-OEt—Ph |
| 532 | 2-Cl—Ph | 4-OCF3—Ph |
| 533 | 2-Cl—Ph | 4-SO2CH3—Ph |
| 534 | 2-Cl—Ph | 4-OH—Ph |
| 535 | 2-Cl—Ph | 4-CH3—Ph |
| 536 | 2-Cl—Ph | 4-C2H5—Ph |
| 537 | 2-Cl—Ph | 2,4-diF—Ph |
| 538 | 2-Cl—Ph | 2,5-diF—Ph |
| 539 | 2-Cl—Ph | 3,4-diF—Ph |
| 540 | 2-Cl—Ph | 3,5-diF—Ph |
| 541 | 2-Cl—Ph | 2,4-diCl—Ph |
| 542 | 2-Cl—Ph | 2,5-diCl—Ph |
| 543 | 2-Cl—Ph | 3,4-diCl—Ph |
| 544 | 2-Cl—Ph | 3,5-diCl—Ph |
| 545 | 2-Cl—Ph | 3,4-OCH2O—Ph |
| 546 | 2-Cl—Ph | 3,4-OCH2CH2O—Ph |
| 547 | 2-Cl—Ph | 2-thienyl |
| 548 | 2-Cl—Ph | 2-furanyl |
| 549 | 2-Cl—Ph | 2-pyridyl |
| 550 | 2-Cl—Ph | 4-pyridyl |
| 551 | 2-Cl—Ph | 2-imidazolyl |
| 552 | 2-Cl—Ph | 3-pyrazolyl |
| 553 | 2-Cl—Ph | 2-thiazolyl |
| 554 | 2-Cl—Ph | 5-tetrazolyl |
| 555 | 2-Cl—Ph | 1-adamantyl |
| 556 | 2,4-diCl—Ph | 3-CN—Ph |
| 557 | 2,4-diCl—Ph | 3-COCH3—Ph |
| 558 | 2,4-diCl—Ph | 3-CO2Me—Ph |
| 559 | 2,4-diCl—Ph | 3-CO2Et—Ph |
| 560 | 2,4-diCl—Ph | 3-CO2H—Ph |
| 561 | 2,4-diCl—Ph | 3-CONH2—Ph |
| 562 | 2,4-diCl—Ph | 3-F—Ph |
| 563 | 2,4-diCl—Ph | 3-Cl—Ph |
| 564 | 2,4-diCl—Ph | 3-NH2—Ph |
| 565 | 2,4-diCl—Ph | 3-SO2NH2—Ph |
| 566 | 2,4-diCl—Ph | 3-CF3—Ph |
| 567 | 2,4-diCl—Ph | 3-OCH3—Ph |
| 568 | 2,4-diCl—Ph | 3-OEt—Ph |
| 569 | 2,4-diCl—Ph | 3-OCF3—Ph |
| 570 | 2,4-diCl—Ph | 3-SO2CH3—Ph |
| 571 | 2,4-diCl—Ph | 3-OH—Ph |
| 572 | 2,4-diCl—Ph | 3-CH3—Ph |
| 573 | 2,4-diCl—Ph | 3-C2H5—Ph |
| 574 | 2,4-diCl—Ph | 4-CN—Ph |
| 575 | 2,4-diCl—Ph | 4-COCH3—Ph |
| 576 | 2,4-diCl—Ph | 4-CO2Me—Ph |
| 577 | 2,4-diCl—Ph | 4-CO2Et—Ph |
| 578 | 2,4-diCl—Ph | 4-CO2H—Ph |
| 579 | 2,4-diCl—Ph | 4-CONH2—Ph |
| 580 | 2,4-diCl—Ph | 4-F—Ph |
| 581 | 2,4-diCl—Ph | 4-Cl—Ph |
| 582 | 2,4-diCl—Ph | 4-NH2—Ph |
| 583 | 2,4-diCl—Ph | 4-SO2NH2—Ph |
| 584 | 2,4-diCl—Ph | 4-CF3—Ph |
| 585 | 2,4-diCl—Ph | 4-OCH3—Ph |
| 586 | 2,4-diCl—Ph | 4-OEt—Ph |
| 587 | 2,4-diCl—Ph | 4-OCF3—Ph |
| 588 | 2,4-diCl—Ph | 4-SO2CH3—Ph |
| 589 | 2,4-diCl—Ph | 4-OH—Ph |
| 590 | 2,4-diCl—Ph | 4-CH3—Ph |

TABLE 7-continued

| | | |
|---|---|---|
| 591 | 2,4-diCl—Ph | 4-C2H5—Ph |
| 592 | 2,4-diCl—Ph | 2,4-diF—Ph |
| 593 | 2,4-diCl—Ph | 2,5-diF—Ph |
| 594 | 2,4-diCl—Ph | 3,4-diF—Ph |
| 595 | 2,4-diCl—Ph | 3,5-diF—Ph |
| 596 | 2,4-diCl—Ph | 2,4-diCl—Ph |
| 597 | 2,4-diCl—Ph | 2,5-diCl—Ph |
| 598 | 2,4-diCl—Ph | 3,4-diCl—Ph |
| 599 | 2,4-diCl—Ph | 3,5-diCl—Ph |
| 600 | 2,4-diCl—Ph | 3,4-OCH2O—Ph |
| 601 | 2,4-diCl—Ph | 3,4-OCH2CH2O—Ph |
| 602 | 2,4-diCl—Ph | 2-thienyl |
| 603 | 2,4-diCl—Ph | 2-furanyl |
| 604 | 2,4-diCl—Ph | 2-pyridyl |
| 605 | 2,4-diCl—Ph | 4-pyridyl |
| 606 | 2,4-diCl—Ph | 2-imidazolyl |
| 607 | 2,4-diCl—Ph | 3-pyrazolyl |
| 608 | 2,4-diCl—Ph | 2-thiazolyl |
| 609 | 2,4-diCl—Ph | 5-tetrazolyl |
| 610 | 2,4-diCl—Ph | 1-adamantyl |
| 611 | 3-OCH3—Ph | 3-CN—Ph |
| 612 | 3-OCH3—Ph | 3-COCH3—Ph |
| 613 | 3-OCH3—Ph | 3-CO2Me—Ph |
| 614 | 3-OCH3—Ph | 3-CO2Et—Ph |
| 615 | 3-OCH3—Ph | 3-CO2H—Ph |
| 616 | 3-OCH3—Ph | 3-CONH2—Ph |
| 617 | 3-OCH3—Ph | 3-F—Ph |
| 618 | 3-OCH3—Ph | 3-Cl—Ph |
| 619 | 3-OCH3—Ph | 3-NH2—Ph |
| 620 | 3-OCH3—Ph | 3-SO2NH2—Ph |
| 621 | 3-OCH3—Ph | 3-CF3—Ph |
| 622 | 3-OCH3—Ph | 3-OCH3—Ph |
| 623 | 3-OCH3—Ph | 3-OEt—Ph |
| 624 | 3-OCH3—Ph | 3-OCF3—Ph |
| 625 | 3-OCH3—Ph | 3-SO2CH3—Ph |
| 626 | 3-OCH3—Ph | 3-OH—Ph |
| 627 | 3-OCH3—Ph | 3-CH3—Ph |
| 628 | 3-OCH3—Ph | 3-C2H5—Ph |
| 629 | 3-OCH3—Ph | 4-CN—Ph |
| 630 | 3-OCH3—Ph | 4-COCH3—Ph |
| 631 | 3-OCH3—Ph | 4-CO2Me—Ph |
| 632 | 3-OCH3—Ph | 4-CO2Et—Ph |
| 633 | 3-OCH3—Ph | 4-CO2H—Ph |
| 634 | 3-OCH3—Ph | 4-CONH2—Ph |
| 635 | 3-OCH3—Ph | 4-F—Ph |
| 636 | 3-OCH3—Ph | 4-Cl—Ph |
| 637 | 3-OCH3—Ph | 4-NH2—Ph |
| 638 | 3-OCH3—Ph | 4-SO2NH2—Ph |
| 639 | 3-OCH3—Ph | 4-CF3—Ph |
| 640 | 3-OCH3—Ph | 4-OCH3—Ph |
| 641 | 3-OCH3—Ph | 4-OEt—Ph |
| 642 | 3-OCH3—Ph | 4-OCF3—Ph |
| 643 | 3-OCH3—Ph | 4-SO2CH3—Ph |
| 644 | 3-OCH3—Ph | 4-OH—Ph |
| 645 | 3-OCH3—Ph | 4-CH3—Ph |
| 646 | 3-OCH3—Ph | 4-C2H5—Ph |
| 647 | 3-OCH3—Ph | 2,4-diF—Ph |
| 648 | 3-OCH3—Ph | 2,5-diF—Ph |
| 649 | 3-OCH3—Ph | 3,4-diF—Ph |
| 650 | 3-OCH3—Ph | 3,5-diF—Ph |
| 651 | 3-OCH3—Ph | 2,4-diCl—Ph |
| 652 | 3-OCH3—Ph | 2,5-diCl—Ph |
| 653 | 3-OCH3—Ph | 3,4-diCl—Ph |
| 654 | 3-OCH3—Ph | 3,5-diCl—Ph |
| 655 | 3-OCH3—Ph | 3,4-OCH2O—Ph |
| 656 | 3-OCH3—Ph | 3,4-OCH2CH2O—Ph |
| 657 | 3-OCH3—Ph | 2-thienyl |
| 658 | 3-OCH3—Ph | 2-furanyl |
| 659 | 3-OCH3—Ph | 2-pyridyl |
| 660 | 3-OCH3—Ph | 4-pyridyl |
| 661 | 3-OCH3—Ph | 2-imidazolyl |
| 662 | 3-OCH3—Ph | 3-pyrazolyl |
| 663 | 3-OCH3—Ph | 2-thiazolyl |
| 664 | 3-OCH3—Ph | 5-tetrazolyl |
| 665 | 3-OCH3—Ph | 1-adamantyl |
| 666 | 2-thienyl | 3-CN—Ph |
| 667 | 2-thienyl | 3-COCH3—Ph |
| 668 | 2-thienyl | 3-F—Ph |
| 669 | 2-thienyl | 3-Cl—Ph |
| 670 | 2-thienyl | 3-NH2—Ph |
| 671 | 2-thienyl | 3-OCH3—Ph |
| 672 | 2-thienyl | 3-OH—Ph |
| 673 | 2-thienyl | 4-CN—Ph |
| 674 | 2-thienyl | 4-COCH3—Ph |
| 675 | 2-thienyl | 4-F—Ph |
| 676 | 2-thienyl | 4-Cl—Ph |
| 677 | 2-thienyl | 4-NH2—Ph |
| 678 | 2-thienyl | 4-OCH3—Ph |
| 679 | 2-thienyl | 4-OH—Ph |
| 680 | 2-thienyl | 3,4-diF—Ph |
| 681 | 2-thienyl | 3,5-diF—Ph |
| 682 | 2-thienyl | 3,4-diCl—Ph |
| 683 | 2-thienyl | 3,5-diCl—Ph |
| 684 | 2-thienyl | 3,4-OCH2O—Ph |
| 685 | 2-thienyl | 3,4-OCH2CH2O—Ph |
| 686 | 3-thienyl | 3-CN—Ph |
| 687 | 3-thienyl | 3-COCH3—Ph |
| 688 | 3-thienyl | 3-F—Ph |
| 689 | 3-thienyl | 3-Cl—Ph |
| 690 | 3-thienyl | 3-NH2—Ph |
| 691 | 3-thienyl | 3-OCH3—Ph |
| 692 | 3-thienyl | 3-OH-Ph |
| 693 | 3-thienyl | 4-CN—Ph |
| 694 | 3-thienyl | 4-COCH3—Ph |
| 695 | 3-thienyl | 4-F—Ph |
| 696 | 3-thienyl | 4-Cl—Ph |
| 697 | 3-thienyl | 4-NH2—Ph |
| 698 | 3-thienyl | 4-OCH3—Ph |
| 699 | 3-thienyl | 4-OH—Ph |
| 700 | 3-thienyl | 3,4-diF—Ph |
| 701 | 3-thienyl | 3,5-diF—Ph |
| 702 | 3-thienyl | 3,4-diCl—Ph |
| 703 | 3-thienyl | 3,5-diCl—Ph |
| 704 | 3-thienyl | 3,4-OCH2O—Ph |
| 705 | 3-thienyl | 3,4-OCH2CH2O—Ph |
| 706 | 2-furanyl | 3-CN—Ph |
| 707 | 2-furanyl | 3-COCH3—Ph |
| 708 | 2-furanyl | 3-F—Ph |
| 709 | 2-furanyl | 3-Cl—Ph |
| 710 | 2-furanyl | 3-NH2—Ph |
| 711 | 2-furanyl | 3-OCH3—Ph |
| 712 | 2-furanyl | 3-OH—Ph |
| 713 | 2-furanyl | 4-CN—Ph |
| 714 | 2-furanyl | 4-COCH3—Ph |
| 715 | 2-furanyl | 4-F—Ph |
| 716 | 2-furanyl | 4-Cl—Ph |
| 717 | 2-furanyl | 4-NH2—Ph |
| 718 | 2-furanyl | 4-OCH3—Ph |
| 719 | 2-furanyl | 4-OH—Ph |
| 720 | 2-furanyl | 3,4-diF—Ph |
| 721 | 2-furanyl | 3,5-diF—Ph |
| 722 | 2-furanyl | 3,4-diCl—Ph |
| 723 | 2-furanyl | 3,5-diCl—Ph |
| 724 | 2-furanyl | 3,4-OCH2O—Ph |
| 725 | 2-furanyl | 3,4-OCH2CH2O—Ph |
| 726 | 3-furanyl | 3-CN—Ph |
| 727 | 3-furanyl | 3-COCH3—Ph |
| 728 | 3-furanyl | 3-F—Ph |
| 729 | 3-furanyl | 3-Cl—Ph |
| 730 | 3-furanyl | 3-NH2—Ph |
| 731 | 3-furanyl | 3-OCH3—Ph |
| 732 | 3-furanyl | 3-OH—Ph |
| 733 | 3-furanyl | 4-CN—Ph |
| 734 | 3-furanyl | 4-COCH3—Ph |
| 735 | 3-furanyl | 4-F—Ph |
| 736 | 3-furanyl | 4-Cl—Ph |
| 737 | 3-furanyl | 4-NH2—Ph |
| 738 | 3-furanyl | 4-OCH3—Ph |
| 739 | 3-furanyl | 4-OH—Ph |
| 740 | 3-furanyl | 3,4-diF—Ph |
| 741 | 3-furanyl | 3,5-diF—Ph |
| 742 | 3-furanyl | 3,4-diCl—Ph |
| 743 | 3-furanyl | 3,5-diCl—Ph |
| 744 | 3-furanyl | 3,4-OCH2O—Ph |
| 745 | 3-furanyl | 3,4-OCH2CH2O—Ph |
| 746 | 2-pyridyl | 3-CN—Ph |
| 747 | 2-pyridyl | 3-COCH3—Ph |
| 748 | 2-pyridyl | 3-F—Ph |

TABLE 7-continued

| | | |
|---|---|---|
| 749 | 2-pyridyl | 3-Cl—Ph |
| 750 | 2-pyridyl | 3-NH2—Ph |
| 751 | 2-pyridyl | 3-OCH3—Ph |
| 752 | 2-pyridyl | 3-OH—Ph |
| 753 | 2-pyridyl | 4-CN—Ph |
| 754 | 2-pyridyl | 4-COCH3—Ph |
| 755 | 2-pyridyl | 4-F—Ph |
| 756 | 2-pyridyl | 4-Cl—Ph |
| 757 | 2-pyridyl | 4-NH2—Ph |
| 758 | 2-pyridyl | 4-OCH3—Ph |
| 759 | 2-pyridyl | 4-OH—Ph |
| 760 | 2-pyridyl | 3,4-diF—Ph |
| 761 | 2-pyridyl | 3,5-diF—Ph |
| 762 | 2-pyridyl | 3,4-diCl—Ph |
| 763 | 2-pyridyl | 3,5-diCl—Ph |
| 764 | 2-pyridyl | 3,4-OCH2O—Ph |
| 765 | 2-pyridyl | 3,4-OCH2CH2O—Ph |
| 766 | 3-pyridyl | 3-CN—Ph |
| 767 | 3-pyridyl | 3-COCH3—Ph |
| 768 | 3-pyridyl | 3-F—Ph |
| 769 | 3-pyridyl | 3-Cl—Ph |
| 770 | 3-pyridyl | 3-NH2—Ph |
| 771 | 3-pyridyl | 3-OCH3—Ph |
| 772 | 3-pyridyl | 3-OH—Ph |
| 773 | 3-pyridyl | 4-CN—Ph |
| 774 | 3-pyridyl | 4-COCH3—Ph |
| 775 | 3-pyridyl | 4-F—Ph |
| 776 | 3-pyridyl | 4-Cl—Ph |
| 777 | 3-pyridyl | 4-NH2—Ph |
| 778 | 3-pyridyl | 4-OCH3—Ph |
| 779 | 3-pyridyl | 4-OH—Ph |
| 780 | 3-pyridyl | 3,4-diF—Ph |
| 781 | 3-pyridyl | 3,5-diF—Ph |
| 782 | 3-pyridyl | 3,4-diCl—Ph |
| 783 | 3-pyridyl | 3,5-diCl—Ph |
| 784 | 3-pyridyl | 3,4-OCH2O—Ph |
| 785 | 3-pyridyl | 3,4-OCH2CH2O—Ph |
| 786 | 4-pyridyl | 3-CN—Ph |
| 787 | 4-pyridyl | 3-COCH3—Ph |
| 788 | 4-pyridyl | 3-F—Ph |
| 789 | 4-pyridyl | 3-Cl—Ph |
| 790 | 4-pyridyl | 3-NH2—Ph |
| 791 | 4-pyridyl | 3-OCH3—Ph |
| 792 | 4-pyridyl | 3-OH—Ph |
| 793 | 4-pyridyl | 4-CN—Ph |
| 794 | 4-pyridyl | 4-COCH3—Ph |
| 795 | 4-pyridyl | 4-F—Ph |
| 796 | 4-pyridyl | 4-Cl—Ph |
| 797 | 4-pyridyl | 4-NH2—Ph |
| 798 | 4-pyridyl | 4-OCH3—Ph |
| 799 | 4-pyridyl | 4-OH—Ph |
| 800 | 4-pyridyl | 3,4-diF—Ph |
| 801 | 4-pyridyl | 3,5-diF—Ph |
| 802 | 4-pyridyl | 3,4-diCl—Ph |
| 803 | 4-pyridyl | 3,5-diCl—Ph |
| 804 | 4-pyridyl | 3,4-OCH2O—Ph |
| 805 | 4-pyridyl | 3,4-OCH2CH2O—Ph |
| 806 | 3-indolyl | 3-CN—Ph |
| 807 | 3-indolyl | 3-COCH3—Ph |
| 808 | 3-indolyl | 3-F—Ph |
| 809 | 3-indolyl | 3-Cl—Ph |
| 810 | 3-indolyl | 3-NH2—Ph |
| 811 | 3-indolyl | 3-OCH3—Ph |
| 812 | 3-indolyl | 3-OH—Ph |
| 813 | 3-indolyl | 4-CN—Ph |
| 814 | 3-indolyl | 4-COCH3—Ph |
| 815 | 3-indolyl | 4-F—Ph |
| 816 | 3-indolyl | 4-Cl—Ph |
| 817 | 3-indolyl | 4-NH2—Ph |
| 818 | 3-indolyl | 4-OCH3—Ph |
| 819 | 3-indolyl | 4-OH—Ph |
| 820 | 3-indolyl | 3,4-diF—Ph |
| 821 | 3-indolyl | 3,5-diF—Ph |
| 822 | 3-indolyl | 3,4-diCl—Ph |
| 823 | 3-indolyl | 3,5-diCl—Ph |
| 824 | 3-indolyl | 3,4-OCH2O—Ph |
| 825 | 3-indolyl | 3,4-OCH2CH2O—Ph |
| 826 | 5-indolyl | 3-CN—Ph |
| 827 | 5-indolyl | 3-COCH3—Ph |
| 828 | 5-indolyl | 3-F—Ph |
| 829 | 5-indolyl | 3-Cl—Ph |
| 830 | 5-indolyl | 3-NH2—Ph |
| 831 | 5-indolyl | 3-OCH3—Ph |
| 832 | 5-indolyl | 3-OH—Ph |
| 833 | 5-indolyl | 4-CN—Ph |
| 834 | 5-indolyl | 4-COCH3—Ph |
| 835 | 5-indolyl | 4-F—Ph |
| 836 | 5-indolyl | 4-Cl—Ph |
| 837 | 5-indolyl | 4-NH2—Ph |
| 838 | 5-indolyl | 4-OCH3—Ph |
| 839 | 5-indolyl | 4-OH—Ph |
| 840 | 5-indolyl | 3,4-diF—Ph |
| 841 | 5-indolyl | 3,5-diF—Ph |
| 842 | 5-indolyl | 3,4-diCl—Ph |
| 843 | 5-indolyl | 3,5-diCl—Ph |
| 844 | 5-indolyl | 3,4-OCH2O—Ph |
| 845 | 5-indolyl | 3,4-OCH2CH2O—Ph |
| 846 | 5-indazolyl | 3-CN—Ph |
| 847 | 5-indazolyl | 3-COCH3—Ph |
| 848 | 5-indazolyl | 3-F—Ph |
| 849 | 5-indazolyl | 3-Cl—Ph |
| 850 | 5-indazolyl | 3-NH2—Ph |
| 851 | 5-indazolyl | 3-OCH3—Ph |
| 852 | 5-indazolyl | 3-OH—Ph |
| 853 | 5-indazolyl | 4-CN—Ph |
| 854 | 5-indazolyl | 4-COCH3—Ph |
| 855 | 5-indazolyl | 4-F—Ph |
| 856 | 5-indazolyl | 4-Cl—Ph |
| 857 | 5-indazolyl | 4-NH2—Ph |
| 858 | 5-indazolyl | 4-OCH3—Ph |
| 859 | 5-indazolyl | 4-OH—Ph |
| 860 | 5-indazolyl | 3,4-diF—Ph |
| 861 | 5-indazolyl | 3,5-diF—Ph |
| 862 | 5-indazolyl | 3,4-diCl—Ph |
| 863 | 5-indazolyl | 3,5-diCl—Ph |
| 864 | 5-indazolyl | 3,4-OCH2O—Ph |
| 865 | 5-indazolyl | 3,4-OCH2CH2O—Ph |
| 866 | 5-benzimidazolyl | 3-CN—Ph |
| 867 | 5-benzimidazolyl | 3-COCH3—Ph |
| 868 | 5-benzimidazolyl | 3-F—Ph |
| 869 | 5-benzimidazolyl | 3-Cl—Ph |
| 870 | 5-benzimidazolyl | 3-NH2—Ph |
| 871 | 5-benzimidazolyl | 3-OCH3—Ph |
| 872 | 5-benzimidazolyl | 3-OH—Ph |
| 873 | 5-benzimidazolyl | 4-CN—Ph |
| 874 | 5-benzimidazolyl | 4-COCH3—Ph |
| 875 | 5-benzimidazolyl | 4-F—Ph |
| 876 | 5-benzimidazolyl | 4-Cl—Ph |
| 877 | 5-benzimidazolyl | 4-NH2—Ph |
| 878 | 5-benzimidazolyl | 4-OCH3—Ph |
| 879 | 5-benzimidazolyl | 4-OH—Ph |
| 880 | 5-benzimidazolyl | 3,4-diF—Ph |
| 881 | 5-benzimidazolyl | 3,5-diF—Ph |
| 882 | 5-benzimidazolyl | 3,4-diCl—Ph |
| 883 | 5-benzimidazolyl | 3,5-diCl—Ph |
| 884 | 5-benzimidazolyl | 3,4-OCH2O—Ph |
| 885 | 5-benzimidazolyl | 3,4-OCH2CH2O—Ph |
| 886 | 5-benzothiazolyl | 3-CN—Ph |
| 887 | 5-benzothiazolyl | 3-COCH3—Ph |
| 888 | 5-benzothiazolyl | 3-F—Ph |
| 889 | 5-benzothiazolyl | 3-Cl—Ph |
| 890 | 5-benzothiazolyl | 3-NH2—Ph |
| 891 | 5-benzothiazolyl | 3-OCH3—Ph |
| 892 | 5-benzothiazolyl | 3-OH—Ph |
| 893 | 5-benzothiazolyl | 4-CN—Ph |
| 894 | 5-benzothiazolyl | 4-COCH3—Ph |
| 895 | 5-benzothiazolyl | 4-F—Ph |
| 896 | 5-benzothiazolyl | 4-Cl—Ph |
| 897 | 5-benzothiazolyl | 4-NH2—Ph |
| 898 | 5-benzothiazolyl | 4-OCH3—Ph |
| 899 | 5-benzothiazolyl | 4-OH—Ph |
| 900 | 5-benzothiazolyl | 3,4-diF—Ph |
| 901 | 5-benzothiazolyl | 3,5-diF—Ph |
| 902 | 5-benzothiazolyl | 3,4-diCl—Ph |
| 903 | 5-benzothiazolyl | 3,5-diCl—Ph |
| 904 | 5-benzothiazolyl | 3,4-OCH2O—Ph |
| 905 | 5-benzothiazolyl | 3,4-OCH2CH2O—Ph |
| 906 | 5-benzoxazolyl | 3-CN—Ph |

TABLE 7-continued

| 907 | 5-benzoxazolyl | 3-COCH3—Ph |
| 908 | 5-benzoxazolyl | 3-F—Ph |
| 909 | 5-benzoxazolyl | 3-Cl—Ph |
| 910 | 5-benzoxazolyl | 3-NH2—Ph |
| 911 | 5-benzoxazolyl | 3-OCH3—Ph |
| 912 | 5-benzoxazolyl | 3-OH—Ph |
| 913 | 5-benzoxazolyl | 4-CN—Ph |
| 914 | 5-benzoxazolyl | 4-COCH3—Ph |
| 915 | 5-benzoxazolyl | 4-F—Ph |
| 916 | 5-benzoxazolyl | 4-Cl—Ph |
| 917 | 5-benzoxazolyl | 4-NH2—Ph |
| 918 | 5-benzoxazolyl | 4-OCH3—Ph |
| 919 | 5-benzoxazolyl | 4-OH—Ph |
| 920 | 5-benzoxazolyl | 3,4-diF—Ph |
| 921 | 5-benzoxazolyl | 3,5-diF—Ph |
| 922 | 5-benzoxazolyl | 3,4-diCl—Ph |
| 923 | 5-benzoxazolyl | 3,5-diCl—Ph |
| 924 | 5-benzoxazolyl | 3,4-OCH2O—Ph |
| 925 | 5-benzoxazolyl | 3,4-OCH2CH2O—Ph |

Utility

The utility of the compounds in accordance with the present invention as modulators of chemokine receptor activity may be demonstrated by methodology known in the art, such as the assays for CCR-2 and CCR-3 ligand binding, as disclosed by Ponath et al., J. Exp. Med., 183, 2437–2448 (1996) and Uguccioni et al., J. Clin. Invest., 100, 1137–1143 (1997). Cell lines for expressing the receptor of interest include those naturally expressing the chemokine receptor, such as EOL-3 or THP-1, those induced to express the chemokine receptor by the addition of chemical or protein agents, such as HL-60 or AML14.3D10 cells treated with, for example, butyric acid with interleukin-S present, or a cell engineered to express a recombinant chemokine receptor, such as CHO or HEK-293. Finally, blood or tissue cells, for example human peripheral blood eosinophils, isolated using methods as described by Hansel et al., J. Immunol. Methods, 145, 105–110 (1991), can be utilized in such assays. In particular, the compound of the present invention have activity in binding to the CCR-3 receptor in the aforementioned assays. As used herein, "activity" is intended to mean a compound demonstrating an IC50 of 10 $\mu$M or lower in concentration when measured in the aforementioned assays. Such a result is indicative of the intrinsic activity of the compounds as modulators of chemokine receptor activity. A general binding protocol is described below.

CCR3-Receptor Binding Protocol

Millipore filter plates (#MABVN1250) are treated with 5 $\mu$g/ml protamine in phosphate buffered saline, pH 7.2, for ten minutes at room temperature. Plates are washed three times with phosphate buffered saline and incubated with phosphate buffered saline for thirty minutes at room temperature. For binding, 50 $\mu$l of binding buffer (0.5% bovine serum albumen, 20 mM HEPES buffer and 5 mM magnesium chloride in RPMI 1640 media) with or without a test concentration of a compound present at a known concentration is combined with 50 $\mu$l of 125-I labeled human eotaxin (to give a final concentration of 150 pM radioligand) and 50 $\mu$l of cell suspension in binding buffer containing $5\times10^5$ total cells. Cells used for such binding assays can include cell lines transfected with a gene expressing CCR3 such as that described by Daugherty et al. (1996), isolated human eosinophils such as described by Hansel et al. (1991) or the AML14.3D10 cell line after differentiation with butyric acid as described by Tiffany et al. (1998). The mixture of compound, cells and radioligand are incubated at room temperature for thirty minutes. Plates are placed onto a vacuum manifold, vacuum applied, and plates washed three times with binding buffer with 0.5M NaCl added. The plastic skirt is removed from the plate, the plate allowed to air dry, the wells punch out and CPM counted. The percent inhibition of binding is calculated using the total count obtained in the absence of any competing compound or chemokine ligand and the background binding determined by addition of 100 nM eotaxin in place of the test compound.

The utility of the compounds in accordance with the present invention as inhibitors of the migration of eosinophils or cell lines expressing the chemokine receptors may be demonstrated-by methodology known in the art, such as the chemotaxis assay disclosed by Bacon et al., Brit. J. Pharmacol., 95, 966–974 (1988). In particular, the compound of the present invention have activity in inhibition of the migration of eosinophils in the aforementioned assays. As used herein, "activity" is intended to mean a compound demonstrating an IC50 of 10 $\mu$M or lower in concentration when measured in the aforementioned assays. Such a result is indicative of the intrinsic activity of the compounds as modulators of chemokine receptor activity. A human eosinophil chemotaxis assay protocol is described below.

Human Eosinophil Chemotaxis Assay

Neuroprobe MBA96 96-well chemotaxis chambers with Neuroprobe polyvinylpyrrolidone-free polycarbonate PFD5 5-micron filters in place are warmed in a 37° C. incubator prior to assay. Freshly isolated human eosinophils, isolated according to a method such as that described by Hansel et al. (1991), are suspended in RPMI 1640 with 0.1% bovine serum albumin at $1\times10^6$ cells/ml and warmed in a 37° C. incubator prior to assay. A 20 nM solution of human eotaxin in RPMI 1640 with 0.1% bovine serum albumin is warmed in a 37° C. incubator prior to assay. The eosinophil suspension and the 20 nM eotaxin solution are each mixed 1:1 with prewarmed RPMI 1640 with 0.1% bovine serum albumin with or without a dilution of a test compound that is at two fold the desired final concentration. These mixtures are warmed in a 37° C. incubator prior to assay. The filter is separated from the prewarmed Neuroprobe chemotaxis chamber and the eotaxin/compound mixture is placed into a Polyfiltronics MPC 96 well plate that has been placed in the bottom part of the Neuro Probe chemotaxis chamber. The approximate volume is 370 microliters and there should be a positive meniscus after dispensing. The filter is replaced above the 96 well plate, the rubber gasket is attached to the bottom of the upper chamber, and the chamber assembled. A 200 $\mu$l volume of the cell suspension/compound mixture is added to the appropriate wells of the upper chamber. The upper chamber is covered with a plate sealer, and the assembled unit placed in a 37° C. incubator for 45 minutes. After incubation, the plate sealer is removed and all remaining cell suspension is aspirated off. The chamber is disassembled and, while holding the filter by the sides at a 90-degree angle, unmigrated cells are washed away using a gentle stream of phosphate buffered saline dispensed from a squirt bottle and then the filter wiped with a rubber tipped squeegee. The filter is allowed to completely dry and immersed completely in Wright Giemsa stain for 30–45 seconds. The filter is rinsed with distilled water for 7 minutes, rinsed once with water briefly, and allowed to dry. Migrated cells are enumerated by microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays. As used herein, "activity" is intended to mean a compound demonstrating an IC50 of 10 $\mu$M or lower in concentration when measured in the aforementioned assays. Such a result is also indicative of the intrinsic activity of the compounds as modulators of chemokine receptor activity.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., Toxocara), eosinophilic gastroenteritis (e.g., Anisaki sp., Phocanema sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102,203), leukotriene biosynthesis inhibitors (zileuton, BAY-1005); (f) non-steroidal antiinflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate; stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contract between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed is:

1. A compound of formula (I):

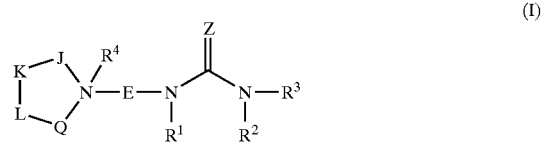

or stereoisomers or pharmaceutically acceptable salts thereof, wherein:

Q is selected from $CH_2$, $CHR^5$, $CHR^{13}$, $CR^{13}R^{13}$, and $CR^5R^{13}$;

K, and L are independently selected from $CH_2$, $CHR^5$, $CHR^6$, $CR^6R^6$ and $CR^5R^6$;

with the proviso:

at least one of J, K, L, or Q contains an $R^5$;

J is selected from $CH_2$, $CHR^5$, $CHR^{13}$, and $CR^5R^{13}$;

Z is selected from O and S;

E is selected from:

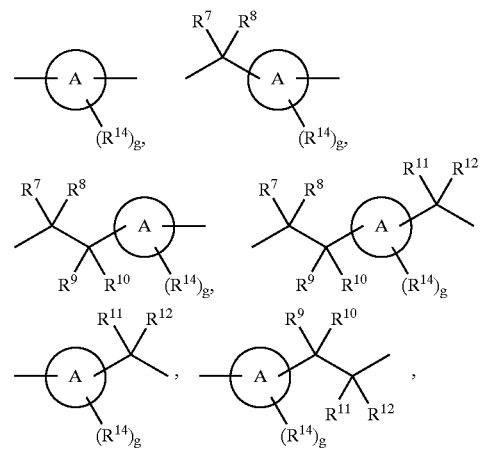

-continued

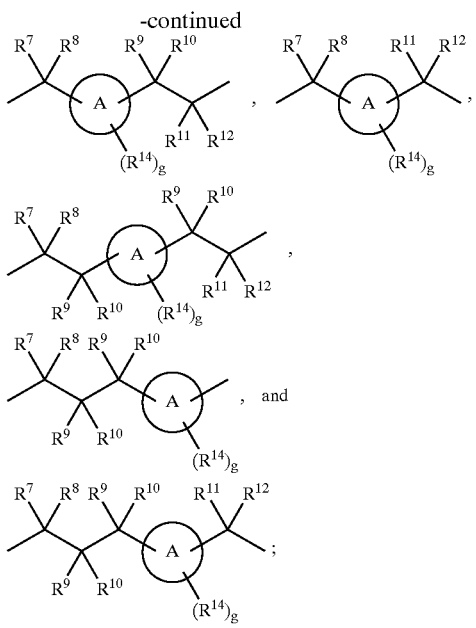

ring A is phenyl or naphthyl;

$R^1$ and $R^2$ are independently selected from H, $C_{1-6}$ alkyl, $C_{2-8}$ alkenyl, $C_{2-8}$ alkynyl, $(CH_2)_rC_{3-6}$ cycloalkyl, and a $(CH_2)_r$—$C_{3-10}$ carbocyclic residue substituted with 0–5 $R^a$;

$R^a$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^bR^b$, $(CH_2)_rOH$, $(CH_2)_rOR^c$, $(CH_2)_rSH$, $(CH_2)_rSR^c$, $(CH_2)_rC(O)R^b$, $(CH_2)_rC(O)NR^bR^b$, $(CH_2)_rNR^bC(O)R^b$, $(CH_2)_rC(O)OR^b$, $(CH_2)_rOC(O)R^c$, $(CH_2)_rCH(=NR^b)NR^bR^b$, $(CH_2)_rNHC(=NR^b)NR^bR^b$, $(CH_2)_rS(O)_pR^c$, $(CH_2)_rS(O)_2NR^bR^b$, $(CH_2)_rNR^bS(O)_2R^c$, and $(CH_2)_r$phenyl;

$R^b$, at each occurrence, is selected from H, $C_{1-6}$ alkyl, $C_{3-6}$ cycloalkyl, and phenyl;

$R^c$, at each occurrence, is selected from $C_{1-6}$ alkyl, $C_{3-6}$ cycloalkyl, and phenyl;

alternatively; $R^2$ and $R^3$ join to form a 5, 6, or 7-membered ring substituted with 0–3 $R^a$;

$R^3$ is selected from a $(CR^{3'}R^{3''})_r$—$C_{3-8}$ carbocyclic residue substituted with 1 $R^{15'}$ and 0–4 $R^{15}$; a $(CR^{3'}R^{3''})_r$—$C_{9-10}$ carbocyclic residue substituted with 0–4 $R^{15}$; and a $(CR^{3'}R^{3''})_r$-5–10 membered heterocyclic system containing 1–4 heteroatoms selected from N, O, and S, substituted with 0–3 $R^{15}$;

$R^{3'}$ and $R^{3''}$, at each occurrence, are selected from H, $C_{1-6}$ alkyl, $(CH_2)_rC_{3-6}$ cycloalkyl, and phenyl;

$R^4$ is absent, taken with the nitrogen to which it is attached to form an N-oxide, or selected from $C_{1-6}$ alkyl, $C_{2-8}$ alkenyl, $C_{2-8}$ alkynyl, $(CH_2)_rC_{3-6}$ cycloalkyl, $(CH_2)_qC(O)R^{4b}$, $(CH_2)_qC(O)NR^{4a}R^{4a'}$, $(CH_2)_qC(O)OR^{4b}$, and a $(CH_2)_r$—$C_{3-10}$ carbocyclic residue substituted with 0–3 $R^{4c}$;

$R^{4a}$ and $R^{4a'}$, at each occurrence, are selected from H, $C_{1-6}$ alkyl, $(CH_2)_rC_{3-6}$ cycloalkyl, and phenyl;

$R^{4b}$, at each occurrence, is selected from $C_{1-6}$ alkyl, $C_{2-8}$ alkenyl, $C_{2-8}$ alkynyl, $C_{3-6}$ cycloalkyl, and phenyl;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_r$ $SC_{1-5}$ alkyl, $(CH_2)_rNR^{4a}R^{4a'}$, and $(CH_2)_r$ phenyl;

alternatively, $R^4$ joins with $R^7$, $R^9$, $R^{11}$, or $R^{14}$ to form a 5, 6 or 7 membered piperidinium spirocycle or pyrrolidinium spirocycle substituted with 0–3 $R^a$;

$R^5$ is selected from a $(CR^{5'}R^{5''})_t$-$C_{3-10}$ carbocyclic residue substituted with 0–5 $R^{16}$ and a $(CR^{5'}R^{5''})_t$-5–10 membered heterocyclic system containing 1–4 heteroatoms selected from N, O, and S, substituted with 0–3 $R^{16}$;

$R^{5'}$ and $R^{5''}$, at each occurrence, are selected from H, $C_{1-6}$ alkyl, $(CH_2)_rC_{3-6}$ cycloalkyl, and phenyl;

$R^6$, at each occurrence, is selected from $C_{1-6}$ alkyl, $C_{2-8}$ alkenyl, $C_{2-8}$ alkynyl, $(CH_2)_rC_{3-6}$ cycloalkyl, $(CF_2)_r$ $CF_3$, CN, $(CH_2)_rNR^{6a}R^{6a'}$, $(CH_2)_rOH$, $(CH_2)_rOR^{6b}$, $(CH_2)_rSH$, $(CH_2)_rSR^{6b}$, $(CH_2)_rC(O)OH$, $(CH_2)_rC(O)$ $R^{6b}$, $(CH_2)_rC(O)NR^{6a}R^{6a'}$, $(CH_2)_rNR^{6d}C(O)R^{6a}$, $(CH_2)_rC(O)OR^{6b}$, $(CH_2)_rOC(O)R^{6b}$, $(CH_2)_rS(O)_pR^{6b}$, $(CH_2)_rS(O)_2NR^{6a}R^{6a'}$, $(CH_2)_rNR^{6d}S(O)_2R^{6b}$, and $(CH_2)_r$phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_r$ $OC_{1-5}$ alkyl, $(CH_2)_rOH$, $(CH_2)_rSC_{1-5}$ alkyl, and $(CH_2)_r$ $NR^{6d}R^{6d}$;

$R^{6d}$, at each occurrence, is selected from H, $C_{1-6}$ alkyl, and $C_{3-6}$ cycloalkyl;

with the proviso that when any of J, K, or L is $CR^6R^6$ and $R^6$ is halogen, cyano, nitro, or bonded to the carbon to which it is attached through a heteroatom, the other $R^6$ is not halogen, cyano, or bonded to the carbon to which it is attached through a heteroatom;

$R^7$, is selected from H, $C_{1-6}$ alkyl, $C_{2-8}$ alkenyl, $C_{2-8}$ alkynyl, $(CH_2)_qOH$, $(CH_2)_qSH$, $(CH_2)_qOR^{7d}$, $(CH_2)_q$ $SR^{7d}$, $(CH_2)_qNR^{7a}R^{7a'}$, $(CH_2)_rC(O)OH$, $(CH_2)_qC(O)$ $R^{7b}$, $(CH_2)_qC(O)NR^{7a}R^{7a'}$, $(CH_2)_qNR^{7a}C(O)R^{7a}$, $(CH_2)_qNR^{7a}C(O)H$, $(CH_2)_qC(O)OR^{7b}$, $(CH_2)_qOC(O)$ $R^{7b}$, $(CH_2)_qS(O)_pR^{7b}$, $(CH_2)_qS(O)_2NR^{7a}R^{7a'}$, $(CH_2)_q$ $NR^{7a}S(O)_2R^{7b}$, $C_{1-6}$ haloalkyl, a $(CH_2)_r$—$C_{3-10}$ carbocyclic residue substituted with 0–3 $R^{7c}$, and a $(CH_2)_r$-5–10 membered heterocyclic system containing 1–4 heteroatoms selected from N, O, and S, substituted with 0–2 $R^{7c}$;

$R^{7a}$ and $R^{7a'}$, at each occurrence, are selected from H, $C_{1-6}$ alkyl, $C_{2-8}$ alkenyl, $C_{2-8}$ alkynyl, $(CH_2)_rC_{3-6}$ cycloalkyl, a $(CH_2)_r$—$C_{3-10}$ carbocyclic residue substituted with 0–5 $R^{7e}$, and a $(CH_2)_r$-5–10 membered heterocyclic system containing 1–4 heteroatoms selected from N, O, and S, substituted with 0–3 $R^{7e}$;

$R^{7b}$, at each occurrence, is selected from $C_{1-6}$ alkyl, $C_{2-8}$ alkenyl, $C_{2-8}$ alkynyl, a $(CH_2)_rC_{3-6}$ carbocyclic residue substituted with 0–2 $R^{7e}$, and a $(CH_2)_r$-5–6 membered heterocyclic system containing 1–4 heteroatoms selected from N, O, and S, substituted with 0–3 $R^{7e}$;

$R^{7c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{7f}R^{7f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{7b}$, $(CH_2)_rC(O)NR^{7f}R^{7f}$, $(CH_2)_rNR^{7f}C$ $(O)R^{7a}$, $(CH_2)_rC(O)OC_{1-4}$ alkyl, $(CH_2)_rOC(O)R^{7b}$, $(CH_2)_rC(=NR^{7f})NR^{7f}R^{7f}$, $(CH_2)_rS(O)_pR^{7b}$, $(CH_2)_r$ $NHC(NR^{7f})NR^{7f}R^{7f}$, $(CH_2)_rS(O)_2NR^{7f}R^{7f}$, $(CH_2)_r$ $NR^{7f}S(O)_2R^{7b}$, and $(CH_2)_r$phenyl substituted with 0–3 $R^{7e}$;

$R^{7d}$, at each occurrence, is selected from $C_{1-6}$ alkyl substituted with 0–3 $R^{7e}$, alkenyl, alkynyl, and a $C_{3-10}$ carbocyclic residue substituted with 0–3 $R^{7c}$;

$R^{7e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r SC_{1-5}$ alkyl, $(CH_2)_rNR^{7f}R^{7f}$, and $(CH_2)_r$phenyl;

$R^{7f}$, at each occurrence, is selected from H, $C_{1-6}$ alkyl, and $C_{3-6}$ cycloalkyl;

$R^8$ is selected from H, $C_{1-6}$ alkyl, $C_{3-6}$ cycloalkyl, and $(CH_2)_r$phenyl substituted with 0–3 $R^{8a}$;

$R^{8a}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r SC_{1-5}$ alkyl, $(CH_2)_rNR^{7f}R^{7f}$, and $(CH_2)_r$phenyl;

alternatively, $R^7$ and $R^8$ join to form $C_{3-7}$ cycloalkyl, or =$NR^{8b}$;

$R^{8b}$ is selected from H, $C_{1-6}$ alkyl, $C_{3-6}$ cycloalkyl, OH, CN, and $(CH_2)_r$-phenyl;

$R^9$, is selected from H, $C_{1-6}$ alkyl, $C_{2-8}$ alkenyl, $C_{2-8}$ alkynyl, F, Cl, Br, I, $NO_2$, CN, $(CH_2)_rOH$, $(CH_2)_rSH$, $(CH_2)_rOR^{9d}$, $(CH_2)_rSR^{9d}$, $(CH_2)_rNR^{9a}R^{9a'}$, $(CH_2)_rC(O)OH$, $(CH_2)_rC(O)R^{9b}$, $(CH_2)_rC(O)NR^{9a}R^{9a'}$, $(CH_2)_rNR^{9a}C(O)R^{9a}$, $(CH_2)_rNR^{9a}C(O)H$, $(CH_2)_rNR^{9a}C(O)NHR^{9a}$, $(CH_2)_rC(O)OR^{9b}$, $(CH_2)_rOC(O)R^{9b}$, $(CH_2)_rOC(O)NHR^{9a}$, $(CH_2)_rS(O)_pR^{9b}$, $(CH_2)_rS(O)_2NR^{9a}R^{9a'}$, $(CH_2)_rNR^{9a}S(O)_2R^{9b}$, $C_{1-6}$ haloalkyl, a $(CH_2)_r$—$C_{3-10}$ carbocyclic residue substituted with 0–5 $R^{9c}$, and a $(CH_2)_r$-5–10 membered heterocyclic system containing 1–4 heteroatoms selected from N, O, and S, substituted with 0–3 $R^{9c}$;

$R^{9a}$ and $R^{9a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{9e}$, and a $(CH_2)_r$-5–10 menibered heterocyclic system containing 1–4 heteroatoms selected from N, O, and S, substituted with 0–3 $R^{9e}$;

$R^{9b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–2 $R^{9e}$, and a $(CH_2)_r$-5–6 membered heterocyclic system containing 1–4 heteroatoms selected from N, O, and S, substituted with 0–3 $R^{9e}$;

$R^{9c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{9f}R^{9f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{9b}$, $(CH_2)_rC(O)NR^{9f}R^{9f}$, $(CH_2)_rNR^{9f}C(O)R^{9a}$, $(CH_2)_rC(O)OC_{1-4}$ alkyl, $(CH_2)_rOC(O)R^{9b}$, $(CH_2)_rC(=NR^{9f})NR^{9f}R^{9f}$, $(CH_2)_rS(O)_pR^{9b}$, $(CH_2)_rNHC(=NR^{9f})NR^{9f}R^{9f}$, $(CH_2)_rS(O)_2NR^{9f}R^{9f}$, $(CH_2)_rNR^{9f}S(O)_2R^{9b}$, and $(CH_2)_r$phenyl substituted with 0–3 $R^{9e}$;

$R^{9d}$, at each occurrence, is selected from $C_{1-6}$ alkyl, $C_{2-6}$ alkenyl, $C_{2-6}$ alkynyl, a $C_{3-10}$ carbocyclic residue substituted with 0–3 $R^{9c}$, and a 5–6 membered heterocyclic system containing 1–4 heteroatoms selected from the group consisting of N, O, and S substituted with 0–3 $R^{9c}$;

$R^{9e}$, at each occurrence, is selected from $C_{1-6}$ alkyl, $C_{2-8}$ alkenyl, $C_{2-8}$ alkynyl, $(CH_2)_rC_{3-6}$ Cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{9f}R^{9f}$, and $(CH_2)_r$phenyl;

$R^{9f}$, at each occurrence, is selected from H, $C_{1-6}$ alkyl, and $C_{3-6}$ cycloalkyl;

$R^{10}$, is selected from H, $C_{1-6}$ alkyl, $C_{2-8}$ alkenyl, $C_{2-8}$ alkynyl, F, Cl, Br, I, $NO_2$, CN, $(CH_2)_rOH$, $(CH_2)_rOR^{10d}$, $(CH_2)_rSR^{10d}$, $(CH_2)_rNR^{10a}R^{10a'}$, $(CH_2)_rC(O)OH$, $(CH_2)_rC(O)R^{10b}$, $(CH_2)_rC(O)NR^{10a}R^{10a'}$, $(CH_2)_rNR^{10a}C(O)R^{10a}$, $(CH_2)_rNR^{10a}C(O)H$, $(CH_2)_rC(O)OR^{10b}$, $(CH_2)_rOC(O)R^{10b}$, $(CH_2)_rS(O)_pR^{10b}$, $(CH_2)_rS(O)_2NR^{10a}R^{10a'}$, $(CH_2)_rNR^{10a}S(O)_2R^{10b}$, $C_{1-6}$ haloalkyl, a $(CH_2)_r$—$C_{3-10}$ carbocyclic residue substituted with 0–5 $R^{10c}$, and a $(CH_2)_r$-5–10 membered heterocyclic system containing 1–4 heteroatoms selected from N, O, and S, substituted with 0–3 $R^{10c}$;

$R^{10a}$ and $R^{10a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{10e}$, and a $(CH_2)_r$-5–10 membered heterocyclic system containing 1–4 heteroatoms selected from N, O, and S, substituted with 0–3 $R^{10e}$;

$R^{10b}$, at each occurrence, is selected from $C_{1-6}$ alkyl, $C_{2-8}$ alkenyl, $C_{2-8}$ alkynyl, a $(CH_2)_rC_{3-6}$ carbocyclic residue substituted with 0–2 $R^{10e}$, and a $(CH_2)_r$-5–6 membered heterocyclic system containing 1–4 heteroatoms selected from N, O, and S, substituted with 0–3 $R^{10e}$;

$R^{10c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{10f}R^{10f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{10b}$, $(CH_2)_rC(O)NR^{10f}R^{10f}$, $(CH_2)_rNR^{10f}C(O)R^{10a}$, $(CH_2)_rC(O)OC_{1-4}$ alkyl, $(CH_2)_rOC(O)R^{10b}$, $(CH_2)_rC(=NR^{10f})NR^{10f}R^{10f}$, $(CH_2)_rS(O)_pR^{10b}$, $(CH_2)_rNHC(=NR^{10f})NR^{10f}R^{10f}$, $(CH_2)_rS(O)_2NR^{10f}R^{10f}$, $(CH_2)_rNR^{10f}S(O)_2R^{10b}$, and $(CH_2)_r$phenyl substituted with 0–3 $R^{10e}$;

$R^{10d}$, at each occurrence, is selected from $C_{1-6}$ alkyl, $C_{2-6}$ alkenyl, $C_{2-6}$ alkynyl, a $C_{3-10}$ carbocyclic residue substituted with 0–3 $R^{10c}$, and a 5–6 membered heterocyclic system containing 1–4 heteroatoms selected from the group consisting of N, O, and S substituted with 0–3 $R^{10c}$;

$R^{10e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{10f}R^{10f}$, and $(CH_2)_r$ phenyl;

$R^{10f}$, at each occurrence, is selected from H, $C_{1-5}$ alkyl, and $C_{3-6}$ cycloalkyl;

alternatively, $R^9$ and $R^{10}$ join to form $C_{3-7}$ cycloalkyl, 5–6-membered cyclic ketal or =O;

with the proviso that when $R^{10}$ is halogen, cyano, nitro, or bonded to the carbon to which it is attached through a heteroatom, $R^9$ is not halogen, cyano, or bonded to the carbon to which it is attached through a heteroatom;

$R^{11}$, is selected from H, $C_{1-6}$ alkyl, $C_{2-8}$ alkenyl, $C_{2-8}$ alkynyl, $(CH_2)_qOH$, $(CH_2)_qSH$, $(CH_2)_qOR^{11d}$, $(CH_2)_qSR^{11d}$, $(CH_2)_qNR^{11a}R^{11a'}$, $(CH_2)_rC(O)OH$, $(CH_2)_rC(O)R^{11b}$, $(CH_2)_rC(O)NR^{11a}R^{11a'}$, $(CH_2)_qNR^{11a}C(O)R^{11a}$, $(CH_2)_qNR^{11a}C(O)NHR^{11a}$, $(CH_2)_rC(O)OR^{11b}$, $(CH_2)_qOC(O)R^{11b}$, $(CH_2)_qS(O)_pR^{11b}$, $(CH_2)_qS(O)_2NR^{11a}R^{11a'}$, $(CH_2)_qNR^{11a}S(O)_2R^{11b}$, $C_{1-6}$ haloalkyl, a $(CH_2)_r$—$C_{3-10}$ carbocyclic residue substituted with 0–5 $R^{11c}$, and a $(CH_2)_r$-5–10 membered heterocyclic system containing 1–4 heteroatoms selected from N, O, and S, substituted with 0–3 $R^{11c}$;

$R^{11a}$ and $R^{11a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{11e}$, and a $(CH_2)_r$-5–10 membered heterocyclic system containing 1–4 heteroatoms selected from N, O, and S, substituted with 0–3 $R^{11e}$;

241

$R^{11b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–2 $R^{11e}$, and a $(CH_2)_r$-5–6 membered heterocyclic system containing 1–4 heteroatoms selected from N, O, and S, substituted with 0–3 $R^{11e}$;

$R^{11c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{11f}R^{11f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{11b}$, $(CH_2)_rC(O)NR^{11f}R^{11f}$, $(CH_2)_r$ $NR^{11f}C(O)R^{11a}$, $(CH_2)_rC(O)OC_{1-4}$ alkyl, $(CH_2)_rOC(O)R^{11b}$, $(CH_2)_rC(=NR^{11f})R^{11f}$, $(CH_2)_rNHC(=NR^{11f})$ $NR^{11f}R^{11f}$, $(CH_2)_rS(O)_pR^{11b}$, $(CH_2)_rS(O)_2NR^{11f}R^{11f}$, $(CH_2)_rNR^{11f}S(O)_2R^{11b}$, and $(CH_2)_r$phenyl substituted with 0–3 $R^{11e}$;

$R^{11d}$, at each occurrence, is selected from $C_{1-6}$ alkyl substituted with 0–3 $R^{11e}$, $C_{2-6}$ alkenyl, $C_{2-6}$ alkynyl, and a $C_{3-10}$ carbocyclic residue substituted with 0–3 $R^{11c}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{11f}R^{11f}$, and $(CH_2)_r$phenyl;

$R^{11f}$, at each occurrence, is selected from H, $C_{1-6}$ alkyl, and $C_{3-6}$ cycloalkyl;

$R^{12}$ is selected from H, $C_{1-6}$ alkyl, $(CH_2)_qOH$, $(CH_2)_rC_{3-6}$ cycloalkyl, and $(CH_2)$tphenyl substituted with 0–3 $R^{12a}$;

$R^{12a}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{9f}R^{9f}$, and $(CH_2)_r$phenyl;

alternatively, $R^{11}$ and $R^{12}$ join to form $C_{3-7}$ cycloalkyl;

$R^{13}$, at each occurrence, is selected from $C_{1-6}$ alkyl, $C_{2-8}$ alkenyl, $C_{2-8}$ alkynyl, $C_{3-6}$ cycloalkyl, $(CF_2)_wCF_3$, $(CH_2)_rNR^{13a}R^{13a'}$, $(CH_2)_rOH$, $(CH_2)_rOR^{13b}$, $(CH_2)_rSH$, $(CH_2)_rSR^{13b}$, $(CH_2)_wC(O)OH$, $(CH_2)_wC(O)R^{13b}$, $(CH_2)_wC(O)NR^{13a}R^{13a'}$, $(CH_2)_rNR^{13d}C(O)R^{13a}$, $(CH_2)_wC(O)OR^{13b}$, $(CH_2)_rOC(O)R^{13b}$, $(CH_2)_wS(O)_pR^{13b}$, $(CH_2)_wS(O)_2NR^{13a}R^{13a'}$, $(CH_2)_rR^{13d}S(O)_2R^{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_r$ $OC_{1-5}$ alkyl, $(CH_2)_rOH$, $(CH_2)_rSC_{1-5}$ alkyl, and $(CH_2)_rNR^{13d}R^{13d}$;

$R^{13d}$, at each occurrence, is selected from H, $C_{1-6}$ alkyl, and $C_{3-6}$ cycloalkyl;

$R^{14}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{14a}R^{14a'}$, $(CHR')_rOH$, $(CHR')_rO(CHR')_rR^{14d}$, $(CHR')_rSH$, $(CHR')_rC(O)H$, $(CHR')_rS(CHR')_rR^{14d}$, $(CHR')_rC(O)OH$, $(CHR')_rC(O)(CHR')_rR^{14b}$, $(CHR')_rC(O)NR^{14a}R^{14a'}$, $(CHR')_rNR^{14f}C(O)(CHR')_rR^{14b}$, $(CHR')_rC(O)O(CHR')_rR^{14d}$, $(CHR')_rOC(O)(CHR')_rR^{14b}$, $(CHR')_rC(=NR^{14f})NR^{14a}R^{14a'}$, $(CHR')_rNHC(=NR^{14f})NR^{14f}R^{14f}$, $(CHR')_rS(O)_p(CHR')_rR^{14b}$, $(CHR')_rS(O)_2NR^{14a}R^{14a'}$, $(CHR')_rNR^{14f}S(O)_2(CHR')_rR^{4b}$, $C_{1-6}$ haloalkyl, $C_{2-8}$ alkenyl substituted with 0–3 R', $C_{2-8}$ alkynyl substituted with 0–3 R', $(CHR')_r$phenyl substituted with 0–3 $R^{14e}$, and a

242

$(CH_2)_r$-5–10 membered heterocyclic system containing 1–4 heteroatoms selected from N, O, and S, substituted with 0–2 $R^{15e}$, or two $R^{14}$ substituents on adjacent atoms on ring A form to join a 5–6 membered heterocyclic system containing 1–3 heteroatoms selected from N, O, and S substituted with 0–2 $R^{15e}$;

alternatively, $R^{14}$ joins with $R^4$ to form a 5, 6 or 7 membered piperidinium spirocycle or pyrrolidinium spirocycle fused to ring A, the spirocycle substituted with 0–3 $R^a$;

R', at each occurrence, is selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with $R^{14e}$;

$R^{14a}$ and $R^{14a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{14e}$, and a $(CH_2)_r$-5–10 membered heterocyclic system containing 1–4 heteroatoms selected from N, O, and S, substituted with 0–2 $R^{14e}$;

$R^{14b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{14e}$, and $(CH_2)_r$-5–6 membered heterocyclic system containing 1–4 heteroatoms selected from N, O, and S, substituted with 0–2 $R^{14e}$;

$R^{14d}$, at each occurrence, is selected from $C_{2-8}$ alkenyl, $C_{2-8}$ alkynyl, $C_{1-6}$ alkyl substituted with 0–3 $R^{14e}$, a $(CH_2)_r$—$C_{3-10}$ carbocyclic residue substituted with 0–3 $R^{14e}$, and a $(CH_2)_r$-5–6 membered heterocyclic system containing 1–4 heteroatoms selected from N, O, and S, substituted with 0–3 $R^{14e}$;

$R^{14e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{14f}R^{14f}$, and $(CH_2)_r$ phenyl;

$R^{14f}$, at each occurrence, is selected from H, $C_{1-6}$ alkyl, $C_{3-6}$ cycloalkyl, and phenyl;

$R^{15}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{15a}R^{15a'}$, $(CHR')_rOH$, $(CHR')_rO(CHR')_rR^{15d}$, $(CHR')_rSH$, $(CHR')_rC(O)H$, $(CHR')_rS(CHR')_rR^{15d}$, $(CHR')_rC(O)OH$, $(CHR')_rC(O)(CHR')_rR^{15b}$, $(CHR')_rC(O)NR^{15a}R^{15a'}$, $(CHR')_rNR^{15f}C(O)(CHR')_rR^{15b}$, $(CHR')_rC(O)O(CHR')_rR^{15d}$, $(CHR')_rOC(O)(CHR')_rR^{15b}$, $(CHR')_rC(=NR^{15f})NR^{15a}R^{15a'}$, $(CHR')_rNHC(=NR^{15f})NR^{15f}R^{15f}$, $(CHR')_rS(O)_p(CHR')_rR^{15b}$, $(CHR')_rS(O)_2NR^{15a}R^{15a'}$, $(CHR')_rNR^{15f}S(O)_2(CHR')_rR^{15b}$, $C_{1-6}$ haloalkyl, $C_{2-8}$ alkenyl substituted with 0–3 R', $C_{2-8}$ alkynyl substituted with 0–3 R', $(CHR')_r$phenyl substituted with 0–3 $R^{15e}$, and a $(CH_2)_r$-5–10 membered heterocyclic system containing 1–4 heteroatoms selected from N, O, and S, substituted with 0–2 $R^{15e}$;

$R^{15'}$, at each occurrence, is selected from $C_{2-8}$ alkenyl, $C_{2-8}$ alkynyl, $(CH_2)_rC_{3-6}$ cycloalkyl, $(CHR')_rNR^{15a}R^{15a'}$, $(CHR')_rO(CHR')_rR^{15d}$, $(CHR')_rSH$, $(CHR')_{3-5}C(O)H$, $(CHR')_rS(CHR')_rR^{15d}$, $(CHR')_qC(O)OH$, $(CHR')_qC(O)(CHR')_qR^{15b}$, $(CHR')_rC(O)NR^{15a}R^{15a'}$, $(CHR')_rNR^{15f}C(O)(CHR')_rR^{15b}$, $(CHR')_rC(O)O(CHR')_rR^{15d}$, $(CHR')_rOC(O)(CHR')_rR^{15b}$, $(CHR')_rC(=NR^{15f})NR^{15a}R^{15a'}$, $(CHR')_rNHC(=NR^{15f})NR^{15f}R^{15f}$, $(CHR')_rS(O)_p(CHR')_rR^{15b}$, $(CHR')_rS(O)_2NR^{15a}R^{15a'}$, $(CHR')_rNR^{15f}S(O)_2(CHR')_rR^{15b}$, $C_{2-8}$ alkenyl substituted with 0–3 R', $C_{2-8}$ alkynyl substituted with 0–3 R', $(CHR')_r$phenyl substituted with 0–3 $R^{15e}$, and a $(CH_2)_r$-5–10 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{5e}$, and a $(CH_2)_r$-5–10 membered heterocyclic system containing 1–4 heteroatoms selected from N, O, and S, substituted with 0–2 $R^{15e}$;

$R^{15b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–3 $R^{15e}$, and $(CH_2)_r$-5–6 membered heterocyclic system containing 1–4 heteroatoms selected from N, O, and S, substituted with 0–2 $R^{15e}$;

$R^{15d}$, at each occurrence, is selected from $C_{2-8}$ alkenyl, $C_{2-8}$ a alkynyl, $C_{1-6}$ alkyl substituted with 0–3 $R^{15e}$, a $(CH_2)_r$—$C_{3-10}$ carbocyclic residue substituted with 0–3 $R^{15e}$, and a $(CH_2)_r$5–6 membered heterocyclic system containing 1–4 heteroatoms selected from N, O, and S, substituted with 0–3 $R^{15e}$;

$R^{15e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{15f}R^{15f}$, and $(CH_2)_r$ phenyl;

$R^{15f}$, at each occurrence, is selected from H, $C_{1-6}$ alkyl, $C_{3-6}$ cycloalkyl, and phenyl;

$R^{16}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a'}$, $(CHR')_rOH$, $(CHR')_rO(CHR')_rR^{16d}$, $(CHR')_rSH$, $(CHR')_rC(O)H$, $(CHR')_rS(CHR')_rR^{16d}$, $(CHR')_rC(O)OH$, $(CHR')_rC(O)(CHR')_rR^{16b}$, $(CHR')_rC(O)NR^{16a}R^{16a'}$, $(CHR')_rNR^{16f}C(O)(CHR')_rR^{16b}$, $(CHR')_rC(O)O(CHR')_rR^{16d}$, $(CHR')_rOC(O)(CHR')_rR^{16b}$, $(CHR')_rC(=NR^{16f})NR^{16a}R^{16a'}$, $(CHR')_rNHC(=NR^{16f})NR^{16f}R^{16f}$, $(CHR')_rS(O)_p(CHR')_rR^{16b}$, $(CHR')_rS(O)_2NR^{16a}R^{16a'}$, $(CHR')_rNR^{16f}S(O)_2(CHR')_rR^{16b}$, $C_{1-6}$ haloalkyl, $C_{2-8}$ alkenyl substituted with 0–3 R', $C_{2-8}$ alkynyl substituted with 0–3 R', and $(CHR')_r$phenyl substituted with 0–3 $R^{16e}$;

$R^{16a}$ and $R^{16a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{16e}$, and a $(CH_2)_r$-5–10 membered heterocyclic system containing 1–4 heteroatoms selected from N, O, and S, substituted with 0–2 $R^{16e}$;

$R^{16b}$, at each occurrence, is selected from $C_{1-6}$ alkyl, $C_{2-8}$ alkenyl, $C_{2-8}$ alkynyl, a $(CH_2)_rC_{3-6}$ carbocyclic residue substituted with 0–3 $R^{16e}$, and a $(CH_2)_r$-5–6 membered heterocyclic system containing 1–4 heteroatoms selected from N, O, and S, substituted with 0–2 $R^{16e}$;

$R^{16d}$, at each occurrence, is selected from $C_{2-8}$ alkenyl, $C_{2-8}$ alkynyl, $C_{1-6}$ alkyl substituted with 0–3 $R^{16e}$, a $(CH_2)_r$—$C_{3-10}$ carbocyclic residue substituted with 0–3 $R^{16e}$, and a $(CH_2)_r$-5–6 membered heterocyclic system containing 1–4 heteroatoms selected from N, O, and S, substituted with 0–3 $R^{16e}$;

$R^{16e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{16f}R^{16f}$, and $(CH_2)_r$ phenyl;

$R^{16f}$, at each occurrence, is selected from H, $C_{1-6}$ alkyl, and $C_{3-6}$ cycloalkyl, and phenyl;

g is selected from 0, 1, 2, 3, and 4;

t is selected from 1 and 2;

w is selected from 0 and 1;

r is selected from 0, 1, 2, 3, 4, and 5;

q is selected from 1, 2, 3, 4, and 5; and p is selected from 0, 1, 2, and 3.

2. The compound of claim 1, wherein:

Z is selected from O and S;

E is selected from:

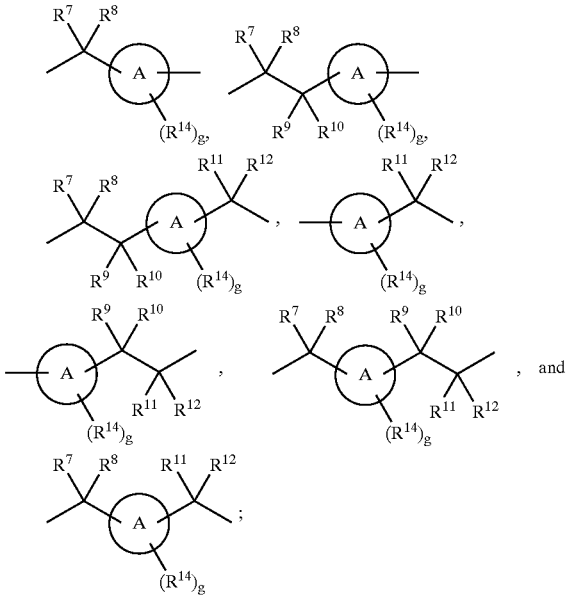

$R^4$ is absent, taken with the nitrogen to which it is attached to form an N-oxide, or selected from $C_{1-8}$ alkyl, $(CH_2)_r C_{3-6}$ cycloalkyl, and $(CH_2)_r$-phenyl substituted with 0–3 $R^{4c}$;

$R^{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_r SC_{1-5}$ alkyl, $(CH_2)_rNR^{4a}R^{4a'}$, and $(CH_2)_r$ phenyl;

alternatively, $R^4$ joins with $R^7$ $R^9$, or $R^{14}$ to form a 5, 6 or 7 membered piperidinium spirocycle substituted with 0–3 $R^a$;

$R^1$ and $R^2$ are independently selected from H and $C_{1-4}$ alkyl;

$R^6$, at each occurrence, is selected from $C_{1-4}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rOH$, $(CH_2)_rOH^{6b}$, $(CH_2)_rC(O)R^{6b}$, $(CH_2)_rC(O)NR^{6a}R^{6a'}$, $(CH_2)_rNR^{6d}C(O)R^{6a}$, and $(CH_2)_r$ phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR^{6d}R^{6d}$;

$R^{6d}$, at each occurrence, is selected from H, $C_{1-6}$ alkyl, and $C_{3-6}$ cycloalkyl;

$R^7$, is selected from H, $C_{1-3}$ alkyl, $(CH_2)_rC_{3-6}$ cycloalkyl, $(CH_2)_qOH$, $(CH_2)_qOR^{7d}$, $(CH_2)_qNR^{7a}R^{7a'}$, $(CH_2)_qC(O)R^{7b}$, $(CH_2)_rC(O)NR^{7a}R^{7a'}$, $(CH_2)_qNR^{7a}C(O)R^{7a}$, $C_{1-6}$ haloalkyl, $(CH_2)_r$phenyl with 0–2 $R^{7c}$;

$R^{7a}$ and $R^{7a'}$, at each occurrence, are selected from H, $C_{1-6}$ alkyl, $(CH_2)_rC_{3-6}$ cycloalkyl, a $(CH_2)_r$phenyl substituted with 0–3 $R^{7e}$;

$R^{7b}$, at each occurrence, is selected from $C_{1-6}$ alkyl, $C_{2-8}$ alkenyl, $C_{2-8}$ alkynyl, $(CH_2)_rC_{3-6}$ cycloalkyl, $(CH_2)_r$phenyl substituted with 0–3 $R^{7e}$;

$R^{7c}$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{7f}R^{7f}$, $(CH_2)_rOH$, $(CH_2)_rOC_{1-4}$ alkyl, $(CH_2)_rC(O)R^{7b}$, $(CH_2)_rC(O)NR^{7f}R^{7f}$, $(CH_2)_rNR^{7f}C(O)R^{7a}$, $(CH_2)_rS(O)_pR^{7b}$, $(CH_2)_r S(O)_2NR^{7f}R^{7f}$, $(CH_2)_rNR^{7f}S(O)_2R^{7b}$, and $(CH_2)_r$ phenyl substituted with 0–2 $R^{7e}$;

$R^{7d}$, at each occurrence, is selected from $C_{1-6}$ alkyl, $(CH_2)_rC_{3-6}$ cycloalkyl, $(CH_2)_r$phenyl substituted with 0–3 $R^{7e}$;

$R^{7e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r SC_{1-5}$ alkyl, $(CH_2)_rNR^{7f}R^{7f}$, and $(CH_2)_r$phenyl;

$R^{7f}$, at each occurrence, is selected from H, $C_{1-5}$ alkyl, and $C_{3-6}$ cycloalkyl; p1 $R^8$ is H or joins with $R^7$ to form $C_{3-7}$ cycloalkyl or $=NR^{8b}$;

$R^{11}$, is selected from H, $C_{1-6}$ alkyl, $(CH_2)_rC_{3-6}$ cycloalkyl, $(CH_2)_qOH$, $(CH_2)_qOR^{11d}$, $(CH_2)_qNR^{11a}R^{11a'}$, $(CH_2)_rC(O)R^{11b}$, $(CH_2)_rC(O)NR^{11a}R^{11a'}$, $(CH_2)_qNR^{11a}C(O)R^{11a}$, $C_{1-6}$ haloalkyl, $(CH_2)_r$phenyl with 0–2 $R^{11c}$, $(CH_2)_r$-5–10 membered heterocyclic system containing 1–4 heteroatoms selected from N, O, and S, substituted with 0–3 $R^{15}$;

$R^{11a}$ and $R^{11a'}$, at each occurrence, are selected from H, $C_{1-6}$ alkyl, $(CH_2)_rC_{3-6}$ cycloalkyl, a $(CH_2)_r$phenyl substituted with 0–3 $R^{11e}$;

$R^{11b}$, at each occurrence, is selected from $C_{1-6}$ alkyl, $C_{2-8}$ alkenyl, $C_{2-8}$ alkynyl, $(CH_2)_rC_{3-6}$ cycloalkyl, $(CH_2)_r$phenyl substituted with 0–3 $R^{11e}$;

$R^{11c}$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{11f}R^{11f}$, $(CH_2)_rOH$, $(CH_2)_rOC_{1-4}$ alkyl, $(CH_2)_rC(O)R^{11b}$, $(CH_2)_rC(O)NR^{11f}R^{11f}$, $(CH_2)_rNR^{11f}C(O)R^{11a}$, $(CH_2)_rS(O)_pR^{11b}$, $(CH_2)_rS(O)_2NR^{11f}R^{11f}$, $(CH_2)_rNR^{11f}S(O)_2R^{11b}$, and $(CH_2)_r$phenyl substituted with 0–2 $R^{11e}$;

$R^{11d}$, at each occurrence, is selected from $c_{1-6}$ alkyl, $(CH_2)_rC_{3-6}$ cycloalkyl, $(CH_2)_r$phenyl substituted with 0–3 $R^{11e}$;

$R^{11e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r SC_{1-5}$ alkyl, $(CH_2)_rNR^{11f}R^{11f}$, and $(CH_2)_r$phenyl;

$R^{11f}$, at each occurrence, is selected from H, $C_{1-5}$ alkyl and $C_{3-6}$ cycloalkyl;

$R^{12}$ is H or joins with $R^{11}$ to form $C_{3-7}$ cycloalkyl;

$R^{13}$, at each occurrence, is selected from $C_{1-4}$ alkyl, $C_{3-6}$ cycloalkyl, $(CH_2)_rNR^{13a}R^{13a'}$, $(CH_2)_rOH$, $(CH_2)_rOR^{13b}$, $(CH_2)_wC(O)R^{13b}$, $(CH_2)_wC(O)NR^{13a}R^{13a'}$, $(CH_2)_rNR^{13d}C(O)R^{13a}$, $(CH_2)_wS(O)_2NR^{13a}R^{13a'}$, $(CH_2)_r NR^{13d}S(O)_2R^{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_r OC_{1-5}$ alkyl, $(CH_2)_rOH$, and $(CH_2)_rNR^{13d}R^{13d'}$;

$R^{13d}$, at each occurrence, is selected from H, $C_{1-6}$ alkyl, and $C_{3-6}$ cycloalkyl;

q is selected from 1, 2, and 3; and r is selected from 0, 1, 2, and 3.

3. The compound of claim 2, wherein: ring A is selected from:

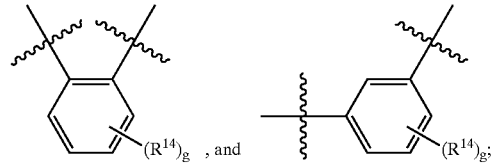

$R^3$ is selected from a $(CR^3{}'H)_r$—$C_{3-8}$ carbocyclic residue substituted with 1 $R^{15'}$ and 0–4 $R^{15}$, wherein the $C_{3-8}$ carbocyclic residue is selected from phenyl, $C_{3-6}$ cycloalkyl; a $(CR_3{}'H)_r$—$C_{9-10}$ carbocyclic residue substituted with 0–4 $R^{15}$, wherein the $C_{9-10}$ carbocyclic residue is selected from naphthyl and adamantyl; and a $(CR^3{}'H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^5$ is selected from $(CR^5{}'H)_r$-phenyl substituted with 0–5 $R^{16}$; and a $(CR_5{}'H)_r$-heterocyclic system substituted with 0–3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl.

4. The compound of claim 3, wherein formula (I) is:

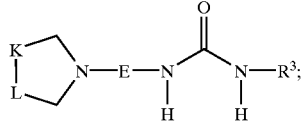

with the proviso that at least one of K or L contains an $R^5$;

$R^{16}$, at each occurrence, is selected from $C_{1-8}$ alkyl, $(CH_2)_rC_{3-6}$ cycloalkyl, $CF_3$, Cl, Br, I, F, $(CH_2)_r NR^{16a}R^{16a'}$, $NO_2$, CN, OH, $(CH_2)_rOR^{16d}$, $(CH_2)_rC(O)R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_r NR^{16f}S(O)_2R^{16b}$, and $(CH_2)_r$phenyl substituted with 0–3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl;

$R^{16e}$, at each occurrence, is selected from $C_{2-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

5. The compound of claim 4, wherein:

$R^5$ is $CH_2$phenyl substituted with 0–3 $R^{16}$;

$R^9$, is selected from H, $C_{1-6}$ alkyl, $(CH_2)_rC_{3-6}$ cycloalkyl, F, Cl, CN, $(CH_2)_rOH$, $(CH_2)_rOR^{9d}$, $(CH_2)_rNR^{9a}R^{9a'}$, $(CH_2)_rOC(O)NHR^{9a}$, $(CH_2)_r$phenyl substituted with 0–5 $R^{9e}$, and a heterocyclic system substituted with 0–2 $R^{9e}$, wherein the heterocyclic system is selected from pyridyl, thiophenyl, furanyl, oxazolyl, and thiazolyl;

$R^{9a}$ and $R^{9'}$, at each occurrence, are selected from H, $C_{1-6}$ alkyl, $C_{3-6}$ cycloalkyl, and $(CH_2)_r$phenyl substituted with 0–3 $R^{9e}$;

$R^{9d}$, at each occurrence, is selected from $C_{1-6}$ alkyl and phenyl;

$R^{9e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{10}$ is selected from H, $C_{1-8}$ alkyl, OH, and $CH_2OH$;

alternatively, $R^9$ and $R^{10}$ join to form $C_{3-7}$ cycloalkyl, 5–6-membered cyclic ketal or =O;

with the proviso that when $R^{10}$ is halogen, cyano, nitro, or bonded to the carbon to which it is attached through a heteroatom, $R^9$ is not halogen, cyano, or bonded to the carbon to which it is attached through a heteroatom;

$R^{11}$ is selected from H, $C_{1-8}$ alkyl, $(CH_2)_r$phenyl substituted with 0–5 $R^{11e}$, and a $(CH_2)_r$-heterocyclic system substituted with 0–2 $R^{11e}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl; and $R^{11e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{12}$ is H;

alternatively, $R^{11}$ and $R^{12}$ join to form $C_{3-7}$ cycloalkyl;

$R^{14}$, at each occurrence, is selected from $C_{1-8}$ alkyl, $(CH_2)_rC_{3-6}$ cycloalkyl, $CF_3$, Cl, Br, I, F, $(CH_2)_rNR^{14a}R^{14a'}$, $NO_2$, CN, OH, $(CH_2)_rOR^{14d}$, $(CH_2)_rC(O)R^{14b}$, $(CH_2)_rC(O)NR^{14a}R^{14a'}$, $(CH_2)_rNR^{14f}C(O)R^{14b}$, $(CH_2)_rS(O)_pR^{14b}$, $(CH_2)_rS(O)_2NR^{14a}R^{14a'}$, $(CH_2)_rNR^{14f}S(O)_2R^{14b}$, $(CH_2)_r$phenyl substituted with 0–3 $R^{14e}$, and a $(CH_2)_r$-5–6 membered heterocyclic system containing 1–4 heteroatoms selected from N, O, and S, substituted with 0–2 $R^{15e}$, or two $R^{14}$ substituents on adjacent atoms on ring A form to join a 5–6 membered heterocyclic system containing 1–3 heteroatoms selected from N, O, and S substituted with 0–2 $R^{15e}$;

$R^{14a}$ and $R^{14a'}$, at each occurrence, are selected from H, $C_{1-6}$ alkyl, $C_{3-6}$ cycloalkyl, and $(CH_2)_r$phenyl substituted with 0–3 $R^{14e}$;

$R^{14b}$, at each occurrence, is selected from H, $C_{1-6}$ alkyl, $C_{3-6}$ cycloalkyl, and $(CH_2)_r$phenyl substituted with 0–3 $R^{14e}$;

$R^{14d}$, at each occurrence, is selected from $C_{1-6}$ alkyl and phenyl;

$R^{14e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{14f}$, at each occurrence, is selected from H, and $C_{1-5}$ alkyl; and r is selected from 0, 1, and 2.

6. The compound of claim 5, wherein:

L is selected from $CH_2$ and $CHR^5$;

$R^3$ is selected from a $C_{3-8}$ carbocyclic residue substituted with 1 $R^{15'}$ and 0–3 $R^{15}$, wherein the $C_{3-8}$ carbocyclic residue is selected from cyclopropyl, cyclopentyl, cyclohexyl, and phenyl; a $C_{9-10}$ carbocyclic residue substituted with 0–3 $R^{15}$, wherein the $C_{9-10}$ carbocyclic residue is selected from naphthyl and adamantyl; and a $(CR_3'H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{15}$, at each occurrence, is selected from $C_{1-8}$ alkyl, $(CH_2)_rC_{3-6}$ cycloalkyl, $CF_3$, Cl, Br, I, F, $(CH_2)_rNR^{15a}R^{15a'}$, $NO_2$, CN, OH, $(CH_2)_rOR^{15d}$, $(CH_2)_rC(O)R^{15b}$, $(CH_2)_rC(O)NR^{15a}R^{15a'}$, $(CH_2)_rNR^{15f}C(O)R^{15b}$, $(CH_2)_rS(O)_pR^{15b}$, $(CH_2)_rS(O)_2NR^{15a}R^{15a'}$, $(CH_2)_rNR^{15f}S(O)_2R^{15b}$, and $(CH_2)_r$phenyl substituted with 0–3 $R^{15e}$, and a $(CH_2)_r$-5–6 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{3-6}$ cycloalkyl, and $(CH_2)_r$phenyl substituted with 0–3 $R^{15e}$;

$R^{15b}$, at each occurrence, is selected from H, $C_{1-6}$ alkyl, $C_{3-6}$ cycloalkyl, and $(CH_2)_r$phenyl substituted with 0–3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H and $C_{1-5}$ alkyl.

7. A pharmaceutical composition, comprising a pharmaceutically acceptable carrier and a therapeutically effective amount of a compound of claim 6.

8. A method for modulation of chemokine receptor activity comprising administering to a patient in need thereof a therapeutically effective amount of a compound of claim 6.

9. A method for treating inflammatory diseases, comprising administering to a patient in need thereof a therapeutically effective amount of a compound of claim 6.

10. A method for treating asthma, comprising administering to a patient in need thereof a therapeutically effective amount of a compound of claim 6.

11. A method for treating disorders comprising administering to a patient in need thereof a therapeutically effective amount of a compound of claim 6, wherein the disorder is selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

12. The method of claim 11 for treating disorders selected from asthma, allergic rhinitis, atopic dermatitis, and inflammatory bowel diseases.

13. A pharmaceutical composition, comprising a pharmaceutically acceptable carrier and a therapeutically effective amount of a compound of claim 1.

14. A method for modulation of chetnokine receptor activity comprising administering to a patient in need thereof a therapeutically effective amount of a compound of claim 1.

15. A method for treating inflammatory diseases, comprising administering to a patient in need thereof a therapeutically effective amount of a compound of claim 1.

16. A method for treating asthma, comprising administering to a patient in need thereof a therapeutically effective amount of a compound of claim 1.

17. A method for modulation of chemokine receptor activity comprising administering to a patient in need thereof a therapeutically effective amount of a compound of claim 1.

18. A method for modulation of chemokine receptor activity comprising contacting a CCR3 receptor with an effective inhibitory amount of a compound of claim 1.

19. A method for treating inflammatory disorders comprising administering to a patient in need thereof a therapeutically effective amount of a compound of claim 1.

20. A method for treating disorders comprising administering to a patient in need thereof a therapeutically effective amount of a compound of claim 1, wherein the disorder is selected from asthma, allergic rhinitis, atopic dermatitis, inflammatory bowel diseases, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, HIV infection, cystic fibrosis, Churg-Strauss syndrome, lymphoma, Hodgkin's disease, and colonic carcinoma.

21. The method of claim 20 for treating disorders selected from asthma, allergic rhinitis, atopic dermatitis, and inflammatory bowel diseases.

22. A method for the modulation of the chemokine receptor CCR-3 comprising the administration of an effective amount of a compound of formula (I)

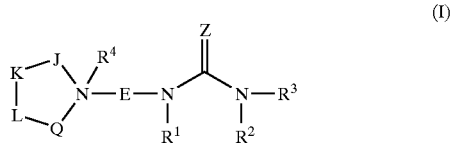

(I)

or stereoisomers or pharmaceutically acceptable salts thereof, wherein:

Q is selected from $CH_2$, $CHR^5$, $CHR^{13}$, $CR^{13}R^{13}$, and $CR^5R^{13}$;

K, and L are independently selected from $CH_2$, $CHR^5$, $CHR^6$, $CR^6R^6$ and $CR^5R^6$; with the proviso:
at least one of J, K, L, or Q contains an $R^5$;
is selected from $CH_2$, $CHR^5$, $CHR^{13}$, and $CR^5R^{13}$;

Z is selected from O and S;
E is selected from:

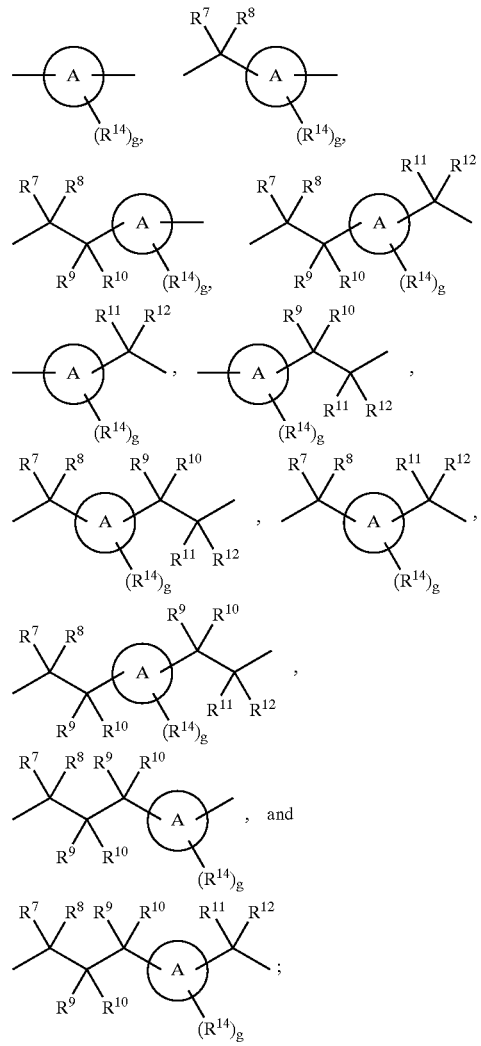

ring A is phenyl or naphthyl;

$R_1$ and $R_2$ are independently selected from H, $C_{1-6}$ alkyl, $C_{2-8}$ alkenyl, $C_{2-8}$ alkynyl, $(CH_2)_rC_{3-6}$ cycloalkyl, and a $(CH_2)_r$—$C_{3-10}$ carbocyclic residue substituted with 0–5 $R^a$;

$R^a$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^bR^b$, $(CH_2)_rOH$, $(CH_2)_rOR^c$, $(CH_2)_rSH$, $(CH_2)_rSR^c$, $(CH_2)_rC(O)R^b$, $(CH_2)_rC(O)NR^bR^b$, $(CH_2)_rNR^bC(O)R^b$, $(CH_2)_rC(O)OR^b$, $(CH_2)_rOC(O)R^c$, $(CH_2)_rCH(=NR^b)NR^bR^b$, $(CH_2)_rNHC(=NR^b)NR^bR^b$, $(CH_2)_rS(O)_pR^c$, $(CH_2)_rS(O)_2NR^bR^b$, $(CH_2)_rNR^bS(O)_2R^c$, and $(CH_2)_r$phenyl;

$R^b$, at each occurrence, is selected from H, $C_{1-6}$ alkyl, $C_{3-6}$ cycloalkyl, and phenyl;

$R^c$, at each occurrence, is selected from $C_{1-6}$ alkyl, $C_{3-6}$ cycloalkyl, and phenyl;

alternatively, $R_2$ and $R_3$ join to form a 5, 6, or 7-membered ring substituted with 0–3 $R^a$;

$R^3$ is selected from a $(CR^{3\prime}R^{3\prime\prime})_r$—$C_{3-10}$ carbocyclic residue substituted with 0–5 $R^{15}$, and a $(CR^{3\prime}R^{3\prime\prime})_r$-5–10 membered heterocyclic system containing 1–4 heteroatoms selected from N, O, and S, substituted with 0–3 $R^{15}$;

251

$R^{3'}$ and $R^{3''}$, at each occurrence, are selected from H, $C_{1-6}$ alkyl, $(CH_2)_rC_{3-6}$ cycloalkyl, and phenyl;

$R^4$ is absent, taken with the nitrogen to which it is attached to form an N-oxide, or selected from $C_{1-6}$ alkyl, $C_{2-8}$ alkenyl, $C_{2-8}$ alkynyl, $(CH_2)_rC_{3-6}$ cycloalkyl, $(CH_2)_qC(O)R^{4b}$, $(CH_2)_qC(O)NR_{4a}R_{4a}'$, $(CH_2)_qC(O)OR_{4b}$, and a $(CH_2)_r$—$C_{3-10}$ carbocyclic residue substituted with 0–3 $R^{4c}$;

$R^{4a}$ and $R^{4a'}$, at each occurrence, are selected from H, $C_{1-6}$ alkyl, $(CH_2)_rC_{3-6}$ cycloalkyl, and phenyl;

$R^{4b}$, at each occurrence, is selected from $C_{1-6}$ alkyl, $C_{2-8}$ alkenyl, $(CH_2)_rC_{3-6}$ cycloalkyl, $C_{2-8}$ alkynyl, and phenyl;

$R_{4c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_r SC_{1-5}$ alkyl, $(CH_2)_rNR_{4a}R_{4a}'$, and $(OH_2)_r$ Phenyl;

alternatively, $R^4$ joins with $R^7$, $R^9$, $R^{11}$ or $R^{14}$ to form a 5, 6 or 7 membered piperidinium spirocycle or pyrrolidinium spirocycle substituted with 0–3 $R^a$;

$R^5$ is selected from a $(CR^{5'}R^{5''})_t$—$C_{3-10}$ carbocyclic residue substituted with 0–5 $R^{16}$ and a $(CR_5'R_5'')_r$-5–10 membered heterocyclic system containing 1–4 heteroatoms selected from N, O, and S, substituted with 0–3 $R^{16}$;

$R^{5'}$ and $R_5''$, at each occurrence, are selected from H, $C_{1-6}$ alkyl, $(CH_2)_rC_{3-6}$ cycloalkyl, and phenyl;

$R^6$, at each occurrence, is selected from $C_{1-6}$ alkyl, $C_{2-8}$ alkenyl, $C_{2-8}$ alkynyl, $(CH_2)_rC_{3-6}$ cycloalkyl, $(CF_2)_rCF_3$, CN, $(CH_2)_rNR^{6a}R^{6a'}$, $(CH_2)_rOH$, $(CH_2)_rOR^{6b}$, $(CH_2)_rSH$, $(CH_2)_rSR^{6b}$, $(CH_2)_rC(O)OH$, $(CH_2)_rC(O)R^{6b}$, $(CH_2)_rC(O)NR^{6a}R^{6a'}$, $(CH_2)_rNR^{6d}C(O)R^{6a}$, $(CH_2)_rC(O)OR^{6b}$, $(CH_2)_rOC(O)R^{6b}$, $(CH_2)_rS(O)_pR^{6b}$, $(CH_2)_rS(O)_2NR^{6a}R^{6a'}$, $(CH_2)_rNR^{6d}S(O)_2R^{6b}$, and $(CH_2)_r$phenyl substituted with 0–3 $R^{6c}$;

$R_{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{6c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_rSC_{1-5}$ alkyl, and $(CH_2)_rNR_{6d}R^{6d}$;

$R^{6d}$, at each occurrence, is selected from H, $C_{1-6}$ alkyl, and $C_{3-6}$ cycloalkyl;

with the proviso that when any of J, K, or L is $CR^6R_6$ and $R_6$ is halogen, cyano, nitro, or bonded to the carbon to which it is attached through a heteroatom, the other $R^6$ is not halogen, cyano, or bonded to the carbon to which it is attached through a heteroatom;

$R^7$, is selected from H, $C_{1-6}$ alkyl, $C_{2-8}$ alkenyl, $C_{2-8}$ alkynyl, $(CH_2)_qOH$, $(CH_2)_qSH$, $(CH_2)_qOR^{7d}$, $(CH_2)_qSR^{7d}$, $(CH_2)_qNR^{7a}R^{7a'}$, $(CH_2)_rC(O)OH$, $(CH_2)_rC(O)R^{7b}$, $(CH_2)_rC(O)NR^{7a}R^{7a'}$, $(CH_2)_qNR^{7a}C(O)R^{7a}$, $(CH_2)_qNR_{7a}C(O)H$, $(CH_2)_rC(O)OR^{7b}$, $(CH_2)_qOC(O)R^{7b}$, $(CH_2)_qS(O)_pR^{7b}$, $(CH_2)_qS(O)_2NR^{7a}R^{7a'}$, $(CH_2)_qNR^{7a}S(O)_2R^{7b}$, $C_{1-6}$ haloalkyl, a $(CH_2)_r$—$C_{3-10}$ carbocyclic residue substituted with 0–3 $R^{7c}$, and a $(CH_2)_r$-5–10 membered heterocyclic system containing 1–4 heteroatoms selected from N, O, and S, substituted with 0–2 $R^{7c}$; p1 $R^{7a}$ and $R^{7a'}$, at each occurrence, are selected from H, $C_{1-6}$ alkyl, $C_{2-8}$ alkenyl, $C_{2-8}$ alkynyl, $(CH_2)_rC_{3-6}$ cycloalkyl, a $(CH_2)_r$—$C_{3-10}$ carbocyclic

252 residue substituted with 0–5 $R^{7e}$, and a $(CH_2)_r$-5–10 membered heterocyclic system containing 1–4 heteroatoms selected from N, O, and S, substituted with 0–3 $R^{7e}$;

$R^{7b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–2 $R^{7e}$, and a $(CH_2)_r$-5–6 membered heterocyclic system containing 1–4 heteroatoms selected from N, O, and S, substituted with 0–3 $R^{7e}$;

$R^{7c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{7f}R^{7f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{7b}$, $(CH_2)_rC(O)NR^{7f}R^{7f}$, $(CH_2)_rNR^{7f}C(O)R^{7a}$, $(CH_2)_rC(O)OC_{1-4}$ alkyl, $(CH_2)_rOC(O)R^{7b}$, $(CH_2)_rC(=NR^{7f})NR^{7f}R^{7f}$, $(CH_2)_rS(O)_pR^{7b}$, $(CH_2)_rNHC(=NR^{7f})NR^{7f}R^{7f}$, $(CH_2)_rS(O)_2NR^{7f}R^{7f}$, $(CH_2)_rNR^{7f}S(O)_2R^{7b}$, and $(CH_2)_r$phenyl substituted with 0–3 $R^{7e}$;

$R^{7d}$, at each occurrence, is selected from $C_{1-6}$ alkyl substituted with 0–3 $R^{7e}$, alkenyl, alkynyl, and a $c_{3-10}$ carbocyclic residue substituted with 0–3 $R^{7c}$;

$R^{7e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{7f}R^{7f}$, and $(CH_2)_r$phenyl;

$R^{7f}$, at each occurrence, is selected from H, $C_{1-6}$ alkyl, and $C_{3-6}$ cycloalkyl;

$R_8$ is selected from H, $C_{1-6}$ alkyl, $C_{3-6}$ cycloalkyl, and $(CH_2)_r$phenyl substituted with 0–3 $R^{8a}$;

$R_{8a}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl., $(CH_2)_rNR^{7f}R^{7f}$, and $(CH_2)_r$phenyl;

alternatively, $R^7$ and $R^8$ join to form $C_{3-7}$ cycloalkyl, or $=NR^{8b}$;

$R^{8b}$ is selected from H, $C_{1-6}$ alkyl, $C_{3-6}$ cycloalkyl, OH, CN, and $(CH_2)_r$-phefiyl;

$R^9$, is selected from H, $C_{1-6}$ alkyl, $C_{2-8}$ alkenyl, $C_{2-8}$ alkynyl, F, Cl, Br, I, $NO_2$, CN, $(CH_2)_rOH$, $(CH_2)_rSH$, $(CH_2)_rOR^{9d}$, $(CH_2)_rSR^{9d}$, $(CH_2)_rNR^{9a}R^{9a'}$, $(CH_2)_rC(O)OH$, $(CH_2)_rC(O)R^{9b}$, $(CH_2)_rC(O)NR^{9a}R^{9a'}$, $(CH_2)_rNR^{9a}C(O)R^{9a}$, $(CH_2)_rNR^{9a}C(O)H$, $(CH_2)_rNR^{9a}C(O)NHR^{9a}$, $(CH_2)_rC(O)OR^{9b}$, $(CH_2)_rOC(O)R^{9b}$, $(CH_2)_rOC(O)NHR^{9a}$, $(CH_2)_rS(O)_pR^{9b}$, $(CR_2)_rS(O)_2NR^{9a}R^{9a'}$, $(CR_2)_rNR^{9a}S(O)_2R^{9b}$, $C_{1-6}$ haloalkyl, a $(CH_2)_r$—$C_{3-10}$ carbocyclic residue substituted with 0–5 $R^{9c}$, and a $(CH_2)_r$-5–10 membered heterocyclic system containing 1–4 heteroatoms selected from N, O, and S, substituted with 0–3 $R^{9c}$;

$R^{9a}$ and $R^{9a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 $R^{9e}$, and a $(CH_2)_r$-5–10 membered heterocyclic system containing 1–4 heteroatoms selected from N, O, and S, substituted with 0–3 $R^{9e}$;

$R^{9b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–2 $R^{9e}$, and a $(CH_2)_r$-5–6 membered heterocyclic system containing 1–4 heteroatoms selected from N, O, and S, substituted with 0–3 $R^{9e}$;

$R^{9c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{9f}R^{9f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{9b}$, $(CH_2)_rC(O)NR^{9f}R^{9f}$, $(CH_2)_rNR^{9f}C$ (O)R$^{9a}$, (CH$_2$)$_r$C(O)OC$_{1-4}$ alkyl, (CH$_2$)$_r$OC(O)R$^{9b}$, (CH$_2$)$_r$C(=NR$^{9f}$)NR$^{9f}$R$^{9f}$, (CH$_2$)$_r$S(O)$_p$R$^{9b}$, (CH$_2$)$_r$NHC(=NR$^{9f}$)NR$^{9f}$R$^{9f}$, (CH$_2$)$_r$S(O)$_2$NR$^{9f}$R$^{9f}$, (CH$_2$)$_r$NR$^{9f}$S(O)$_2$R$^{9b}$, and (CH$_2$)$_r$phenyl substituted with 0–3 R$^{9e}$;

R$^{9d}$, at each occurrence, is selected from C$_{1-6}$ alkyl, C$_{2-6}$ alkenyl, C$_{2-6}$ alkynyl, a C$_{3-10}$ carbocyclic residue substituted with 0–3 R$^{9c}$, and a 5–6 membered heterocyclic system containing 1–4 heteroatoms selected from the group consisting of N, O, and S substituted with 0–3 R$^{9c}$;

R$^{9e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{9f}$R$^{9f}$, and (CH$_2$)$_r$phenyl;

R$^{9f}$, at each occurrence, is selected from H, C$_{1-6}$ alkyl, and C$_{3-6}$ cycloalkyl;

R$^{10}$, is selected from H, C$_{1-6}$ alkyl, C$_{2-8}$ alkenyl, C$_{2-8}$ alkynyl, F, Cl, Br, I, NO$_2$, CN, (CH$_2$)$_r$OH, (CH$_2$)$_r$OR$^{10d}$, (CH$_2$)$_r$SR$^{10d}$, (CH$_2$)$_r$NR$^{10a}$R$^{10'}$, (CH$_2$)$_r$C(O)OH, (CH$_2$)$_r$C(O)R$^{10b}$, (CH$_2$)$_r$C(O)NR$^{10a}$R$^{10a'}$, (CH$_2$)$_r$NR$^{10a}$C(O)R$^{10a}$, (CH$_2$)$_r$NR$^{10a}$C(O)H, (CH$_2$)$_r$C(O)OR$^{10b}$, (CH$_2$)$_r$OC(O)R$^{10b}$, (CH$_2$)$_r$S(O)$_p$R$^{10b}$, (CH$_2$)$_r$S(O)$_2$NR$^{10a}$R$^{10a'}$, (CH$_2$)$_r$NR$^{10a}$S(O)$_2$R$^{10b}$, C$_{1-6}$ haloalkyl, a (CH$_2$)$_r$—C$_{3-10}$ carbocyclic residue substituted with 0–5 R$^{10c}$, and a (CH$_2$)$_r$-5–10 membered heterocyclic system containing 1–4 heteroatoms selected from N, O, and S, substituted with 0–3 R$^{10c}$;

R$^{10a}$ and R$^{10a'}$, at each occurrence, are selected from H, C$_{1-6}$ alkyl, C$_{2-8}$ alkenyl, C$_{2-8}$ alkynyl, a (CH$_2$)$_r$—C$_{3-10}$ carbocyclic residue substituted with 0–5 R$^{10e}$, and a (CH$_2$)$_r$-5–10 membered heterocyclic system containing 1–4 heteroatoms selected from N, O, and S, substituted with 0–3 R$^{10e}$;

R$^{10b}$, at each occurrence, is selected from C$_{1-6}$ alkyl, C$_{2-8}$ alkenyl, C$_{2-8}$ alkynyl, a (CH$_2$)$_r$—C$_{3-6}$ carbocyclic residue substituted with 0–2 R$^{10e}$, and a (CH$_2$)$_r$-5–6 membered heterocyclic system containing 1–4 heteroatoms selected from N, O, and S, substituted with 0–3 R$^{10e}$;

R$^{10c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{10f}$R$^{10f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{10b}$, (CH$_2$)$_r$C(O)NR$^{10f}$R$^{10f}$, (CH$_2$)$_r$NR$^{10f}$C(O)R$^{10a}$, (CH$_2$)$_r$C(O)OC$_{1-4}$ alkyl, (CH$_2$)$_r$OC(O)R$^{10b}$, (CH$_2$)$_r$C(=NR$^{10f}$)NR$^{10f}$R$^{10f}$, (CH$_2$)$_r$S(O)$_p$R$^{10b}$, (CH$_2$)$_r$NHC(=NR$^{10f}$)NR$^{10f}$R$^{10f}$, (CH$_2$)$_r$S(O)$_2$NR$^{10f}$R$^{10f}$, (CH$_2$)$_r$NR$^{10f}$S(O)$_2$R$^{10b}$, and (CH$_2$)$_r$phenyl substituted with 0–3 R$^{10e}$;

R$^{10d}$, at each occurrence, is selected from C$_{1-6}$ alkyl, C$_{2-6}$ alkenyl, C$_{2-6}$ alkynyl, a C$_{3-10}$ carbocyclic residue substituted with 0–3 R$^{10c}$, and a 5–6 membered heterocyclic system containing 1–4 heteroatoms selected from the group consisting of N, O, and S substituted with 0–3 R$^{10c}$;

R$^{10e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{10f}$R$^{10f}$, and (CH$_2$)$_r$ phenyl;

R$^{10f}$, at each occurrence, is selected from H, C$_{1-5}$ alkyl, and C$_{3-6}$ cycloalkyl;

alternatively, R$^9$ and R$^{10}$ join to form C$_{3-7}$ cycloalkyl, 5–6-menibered cyclic ketal or =O;

with the proviso that when R$^{10}$ is halogen, cyano, nitro, or bonded to the carbon to which it is attached through a heteroatom, R$^9$ is not halogen, cyano, or bonded to the carbon to which it is attached through a heteroatom;

R$^{11}$, is selected from H, C$_{1-6}$ alkyl, C$_{2-8}$ alkenyl, C$_{2-8}$ alkynyl, (CH$_2$)$_q$OH, (CH$_2$)$_q$SH, (CH$_2$)$_q$OR$^{11d}$, (CH$_2$)$_q$SR$^{11d}$, (CH$_2$)$_q$NR$^{11a}$R$^{11a'}$, (CH$_2$)$_r$C(O)OH, (CH$_2$)$_r$C(O)R$^{11b}$, (CH$_2$)$_r$C(O)NR$^{11a}$R$^{11a'}$, (CH$_2$)$_q$NR$^{11a}$C(O)R$^{11a}$, (CH$_2$)$_q$NR$^{11a}$C(O)NHR$^{11a}$, (CH$_2$)$_r$C(O)OR$^{11b}$, (CH$_2$)$_q$OC(O)R$^{11b}$, (CH$_2$)$_q$S(O)$_p$R$^{11b}$, (CH$_2$)$_q$S(O)$_2$NR$^{11a}$R$^{11a'}$, (CH$_2$)$_q$NR$^{11a}$S(O)$_2$R$^{11b}$, C$_{1-6}$ haloalkyl, a (CH$_2$)$_r$—C$_{3-10}$ carbocyclic residue substituted with 0–5 R$^{11c}$, and a (CH$_2$)$_r$-5–10 membered heterocyclic system containing 1–4 heteroatoms selected from N, O, and S, substituted with 0–3 R$^{11c}$;

R$^{11a}$ and R$^{11a'}$, at each occurrence, are selected from H, C$_{1-6}$ alkyl, C$_{2-8}$ alkenyl, C$_{2-8}$ alkynyl, a (CH$_2$)$_r$—C$_{3-10}$ carbocyclic residue substituted with 0–5 R$^{11e}$, and a (CH$_2$)$_r$-5–10 membered heterocyclic system containing 1–4 heteroatoms selected from N, O, and S, substituted with 0–3 R$^{11e}$;

R$^{11b}$, at each occurrence, is selected from C$_{1-6}$ alkyl, C$_{2-8}$ alkenyl, C$_{2-8}$ alkynyl, a (CH$_2$)$_r$—C$_{3-6}$ carbocyclic residue substituted with 0–2 R$^{11e}$, and a (CH$_2$)$_r$-5–6 membered heterocyclic system containing 1–4 heteroatoms selected from N, O, and S, substituted with 0–3 R$^{11e}$;

R$^{11c}$, at each occurrence, is selected from C$_{1-4}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{11f}$R$^{11f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{11b}$, (CH$_2$)$_r$C(O)NR$^{11f}$R$^{11f}$, (CH$_2$)$_r$NR$^{11f}$C(O)R$^{11a}$, (CH$_2$)$_r$C(O)OC$_{1-4}$ alkyl, (CH$_2$)$_r$OC(O)R$^{11b}$, (CH$_2$)$_r$C(=NR$^{11f}$)NR$^{11f}$R$^{11f}$, (CH$_2$)$_r$NHC(=NR$^{11f}$)NR$^{11f}$R$^{11f}$, (CH$_2$)$_r$S(O)$_p$R$^{11b}$, (CH$_2$)$_r$S(O)$_2$NR$^{11f}$R$^{11f}$, (CH$_2$)$_r$NR$^{11f}$S(O)$_2$R$^{11b}$, and (CH$_2$)$_r$phenyl substituted with 0–3 R$^{11e}$;

R$^{11d}$, at each occurrence, is selected from C$_{1-6}$ alkyl substituted with 0–3 R$^{11e}$, C$_{2-6}$ alkenyl, C$_{2-6}$ alkynyl, and a C$_{3-10}$ carbocyclic residue substituted with 0–3 R$^{11c}$;

R$^{11e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{11f}$R$^{11f}$, and (CH$_2$)$_r$phenyl;

R$^{11f}$, at each occurrence, is selected from H, C$_{1-6}$ alkyl, and C$_{3-6}$ cycloalkyl;

R$^{12}$ is selected from H, C$_{1-6}$ alkyl, (CH$_2$)$_q$OH, (CH$_2$)$_r$C$_{3-6}$ cycloalkyl, and (CH$_2$)$_r$phenyl substituted with 0–3 R$^{12a}$;

R$^{12a}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{9f}$R$^{9f}$, and (CH$_2$)$_r$phenyl;

alternatively, R$^{11}$ and R$^{12}$ join to form C$_{3-7}$ cycloalkyl;

R$^{13}$, at each occurrence, is selected from C$_{1-6}$ alkyl, C$_{2-8}$ alkenyl, C$_{2-8}$ alkynyl, C$_{3-6}$ cycloalkyl, (CF$_2$)$_w$CF$_3$, (CH$_2$)$_r$NR$^{13a}$R$^{13a'}$, (CH$_2$)$_r$OH, (CH$_2$)$_r$OR$^{13b}$, (CH$_2$)$_r$SH, (CH$_2$)$_r$SR$^{13b}$, (CH$_2$)$_w$C(O)OH, (CH$_2$)$_w$C(O)R$^{13b}$, (CH$_2$)$_w$C(O)NR$^{13a}$R$^{13a'}$, (CH$_2$)$_r$NR$^{13d}$C(O)R$^{13a}$, (CH$_2$)$_w$C(O)OR$^{13b}$, (CH$_2$)$_r$OC(O)R$^{13b}$, (CH$_2$)$_w$S(O)$_p$R$^{13b}$, (CH$_2$)$_w$S(O)$_2$NR$^{13a}$R$^{13a'}$, (CH$_2$)$_r$NR$^{13d}$S(O)$_2$R$^{13b}$, and (CH$_2$)$_w$-phenyl substituted with 0–3 R$^{13c}$;

R$^{13a}$ and R$^{13a'}$, at each occurrence, are selected from H, C$_{1-6}$ alkyl, C$_{3-6}$ cycloalkyl, and phenyl substituted with 0–3 R$^{13c}$;

R$^{13b}$, at each occurrence, is selected from C$_{1-6}$ alkyl, C$_{3-6}$ cycloalkyl, and phenyl substituted with 0–3 R$^{13c}$, $R^{13c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_r$ $OC_{1-5}$ alkyl, $(CH_2)_r$OH, $(CH_2)_r$SC$_{1-5}$ alkyl, and $(CH_2)_r$ $NR^{13d}R^{13d}$;

$R^{13d}$, at each occurrence, is selected from H, $C_{1-6}$ alkyl, and $C_{3-6}$ cycloalkyl;

$R^{14}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{14a}R^{14a'}$, $(CHR')_r$OH, $(CHR')_r$ $O(CHR')_rR^{14d}$, $(CHR')_r$SH, $(CHR')_r$C(O)H, $(CHR')_r$S $(CHR')_rR^{14d}$, $(CHR')_r$C(O) OH, $(CHR')_r$C(O) $(CHR')_r$ $R^{14b}$, $(CHR')_r$C(O)NR$^{14a}$R$^{14a'}$, $(CHR')_r$NR$^{14f}$C(O) $(CHR')_rR^{14b}$, $(CHR')_r$C(O)O(CHR')$_r$R$^{14d}$, $(CHR')_r$OC (O) $(CHR')_rR^{14b}$, $(CHR')_r$C($=NR^{14f}$)NR$^{14a}$R$^{14a'}$, $(CHR')_r$NHC($=NR^{14f}$)NR$^{14f}R^{14f}$, $(CHR')_r$S(O)$_p$ $(CHR')_rR^{14b}$, $(CHR')_r$S(O)$_2$NR$^{14a}$R$^{14a'}$, $(CHR')_r$ $NR^{14f}S(O)_2(CHR')_rR^{14b}$, $C_{1-6}$ haloalkyl, $C_{2-8}$ alkenyl substituted with 0–3 R', $C_{2-8}$ alkynyl substituted with 0–3 R', $(CHR')_r$phenyl substituted with 0–3 R$^{14e}$, and a $(CH_2)_r$-5–10 meinbered heterocyclic system containing 1–4 heteroatoms selected from N, O, and S, substituted with 0–2 R$^{15e}$, or two R$^{14}$ substituents on adjacent atoms on ring A form to join a 5–6 rnembered heterocyclic system containing 1–3 heteroatoms selected from N, O, and S substituted with 0–2 R$^{15e}$;

alternatively, R$^{14}$ joins with R$_4$ to form a 5, 6 or 7 membered piperidinium spirocycle or pyrrolidinium spirocycle fused to ring A, the spirocycle substituted with 0–3 R$^a$;

R', at each occurrence, is selected from H, $C_{1-6}$ alkyl, $C_{2-8}$ alkenyl, $C_{2-8}$ alkynyl, $(CH_2)_rC_{3-6}$ cycloalkyl, and $(CH_2)_r$phenyl substituted with R$^{14e}$;

$R^{14a}$ and $R^{14a'}$, at each occurrence, are selected from H, $C_{1-6}$ alkyl, $C_{2-8}$ alkenyl, $C_{2-8}$ alkynyl, a $(CH_2)_r$–$C_{3-10}$ carbocyclic residue substituted with 0–5 R$^{14e}$, and a $(CH_2)_r$-5–10 membered heterocyclic system containing 1–4 heteroatoms selected from N, O, and S, substituted with 0–2 R$^{14e}$;

$R^{14b}$, at each occurrence, is selected from $C_{1-6}$ alkyl, $C_{2-8}$ alkenyl, $C_{2-8}$ alkynyl, a $(CH_2)_r$-$C_{2-6}$ carbocyclic residue substituted with 0–3 R$^{14e}$, and $(CH_2)_r$-5–6 membered heterocyclic system containing 1–4 heteroatoms selected from N, O, and S, substituted with 0–2 R$^{14e}$;

$R^{14d}$, at each occurrence, is selected from $C_{2-8}$ alkenyl, $C_{2-8}$ alkynyl, $C_{1-6}$ alkyl substituted with 0–3 R$^{14e}$, a $(CH_2)_r$-$C_{3-10}$ carbocyclic residue substituted with 0–3 R$^{14e}$, and a $(CH_2)_r$-5–6 membered heterocyclic system containing 1–4 heteroatoms selected from N, O, and S, substituted with 0–3 R$^{14e}$;

$R^{14e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$SC$_{1-5}$ alkyl, $(CH_2)_rNR^{14f}R^{14f}$, and $(CH_2)_r$ phenyl;

$R^{14f}$, at each occurrence, is selected from H, $C_{1-6}$ alkyl, $C_{3-6}$ cycloalkyl, and phenyl;

$R^{15}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{15a}R^{15a'}$, $(CHR')_r$OH, $(CHR')_r$ $O(CHR')_rR^{15d}$, $(CHR')_r$SH, $(CHR')_r$C(O)H, $(CHR')_r$S $(CHR')_rR^{15d}$, $(CHR')_r$C(O)OH, $(CHR')_r$C(O) $(CHR')_r$ $R^{15b}$, $(CHR')_r$C(O)NR$^{15a}$R$^{15a'}$, $(CHR')_r$NR$^{15f}$C (O) $(CHR')_rR^{15b}$, $(CHR')_r$C(O)O(CHR')$_r$R$^{15d}$, $(CHR')_r$OC (O) $(CHR')_rR^{15b}$, $(CHR')_r$C ($=NR^{15f}$)NR$^{15a}$R$^{15a'}$, $(CHR')_r$NHC($=NR^{15f}$)NR$^{15f}R^{15f}$, $(CHR')_r$S(O)$_p$ $(CHR')_rR^{15b}$, $(CHR')_r$S(O)$_2$NR$^{15a}$R$^{15a'}$, $(CHR')_r$ $NR^{15f}S(O)_2(CHR')_rR^{15b}$, $C_{1-6}$ haloalkyl, $C_{2-8}$ alkenyl substituted with 0–3 R', $C_{2-8}$ alkynyl substituted with 0–3 R', $(CHR')_r$phenyl substituted with 0–3 R$^{15e}$, and a $(CH_2)_r$-5–10 membered heterocyclic system containing 1–4 heteroatoms selected from N, O, and S, substituted with 0–2 R$^{15e}$;

$R^{15a}$ and $R^{15a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 R$^{15e}$, and a $(CH_2)_r$-5–10 menibered heterocyclic system containing 1–4 heteroatoms selected from N, O, and S, substituted with 0–2 R$^{15e}$;

$R^{15b}$, at each occurrence, is selected from $C_{1-6}$ alkyl, $C_{2-8}$ alkenyl, $C_{2-8}$ alkynyl, a $(CH_2)_rC_{3-6}$ carbocyclic residue substituted with 0–3 R$^{15e}$, and $(CH_2)_r$-5–6 membered heterocyclic system containing 1–4 heteroatoms selected from N, O, and S, substituted with 0–2 R$^{15e}$;

$R^{15d}$, at each occurrence, is selected from $C_{2-8}$ alkenyl, $C_{2-8}$ alkynyl, $C_{1-6}$ alkyl substituted with 0–3 R$^{15e}$, a $(CH_2)_rC_{3-}$ carbocyclic residue substituted with 0–3 R$^{15e}$, and a $(CN_2)_r$-5–6 membered heterocyclic system containing 1–4 heteroatoms selected from N, O, and S, substituted with 0–3 R$^{15e}$;

$R^{15e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, ON, $NO_2$, $(CF_2)_rCF_3$, $(CH_2)_rOC_{1-5}$ alkyl, OH, SH, $(CH_2)_r$SC$_{1-5}$ alkyl, $(CH_2)_rNR^{15f}R^{15f}$, and $(CH_2)_r$ phe- flyl;

$R^{15f}$, at each occurrence, is selected from H, $C_{1-6}$ alkyl, $C_{3-6}$ cycloalkyl, and phenyl;

$R^{16}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a'}$, $(CHR')_r$OH, $(CHR')_r$ $(CHR')_rR^{16d}$, $(CHR')_r$SH, $(CHR')_r$C(O)H, $(CHR')_r$S $(CHR')_rR^{16d}$, $(CHR')_r$C (O) OH, $(CHR')_r$C(O) $(CHR')_r$ $R^{16b}$, $(CHR')_r$C(O)NR$^{16a}$R$^{16a'}$, $(CHR')_r$NR$^{16f}$C (O) $(CHR')_rR^{16b}$, $(CHR')_r$C(O)O(CHR')$_r$R$^{16d}$, $(CHR')_r$OC (O) $(CHR')_rR^{16b}$, $(CHR')_r$C($=NR^{16f}$)NR$^{16a}$R$^{16a'}$, $(CHR')_r$NHC($=NR^{16f}$)NR$^{16f}R^{16f}$, $(CHR')_r$S(O)$_p$ $(CHR')_rR^{16b}$, $(CHR')_r$S(O)$_2$NR$^{16a}$R$^{16a'}$, $(CHR')_r$ $NR^{16f}S(O)_2(CHR')_rR^{16b}$, $C_{1-6}$ haloalkyl, $C_{2-8}$ alkenyl substituted with 0–3 R', $C_{2-8}$ alkynyl substituted with 0–3 R', and $(CHR')_r$phenyl substituted with 0–3 R$^{16e}$;

$R^{16a}$ and $R^{16a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0–5 R$^{16e}$, and a $(CH_2)_r$-5–10 membered heterocyclic system containing 1–4 heteroatoms selected from N, O, and S, substituted with 0–2 R$^{16e}$;

$R^{16b}$, at each occurrence, is selected from $C_{1-6}$ alkyl, $C_{2-8}$ alkenyl, $C_{2-8}$ alkynyl, a $(CH_2)_rC_{3-6}$ carbocyclic residue substituted with 0–3 R$^{16e}$, and a $(CH_2)_r$-5–6 membered heterocyclic system containing 1–4 heteroatoms selected from N, O, and S, substituted with 0–2 R$^{16e}$;

$R^{16d}$, at each occurrence, is selected from $C_{2-8}$ alkenyl, $C_{2-8}$ alkynyl, $C_{1-6}$ alkyl substituted with 0–3 R$^{16e}$, a $(CH_2)_rC_{3-10}$ carbocyclic residue substituted with 0–3 R$^{16e}$, and a $(CH_2)_r$-5–6 membered heterocyclic system containing 1–4 heteroatoms selected from N, O, and S, substituted with 0–3 R$^{16e}$;

$R^{16e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$SC$_{1-5}$ alkyl, $(CH_2)_rNR^{16f}R^{16f}$, and $(CH_2)_r$ phenyl;

$R^{16f}$, at each occurrence, is selected from H, $C_{1-6}$ alkyl, and $C_{3-6}$ cycloalkyl, and phenyl;

g is selected from 0, 1, 2, 3, and 4;

t is selected from 1 and 2;

w is selected from 0 and 1;

r is selected from 0, 1, 2, 3, 4, and 5;

q is selected from 1, 2, 3, 4, and 5; and p is selected from 0, 1, 2, and 3.

23. The method of claim 22, wherein:
E is selected from:

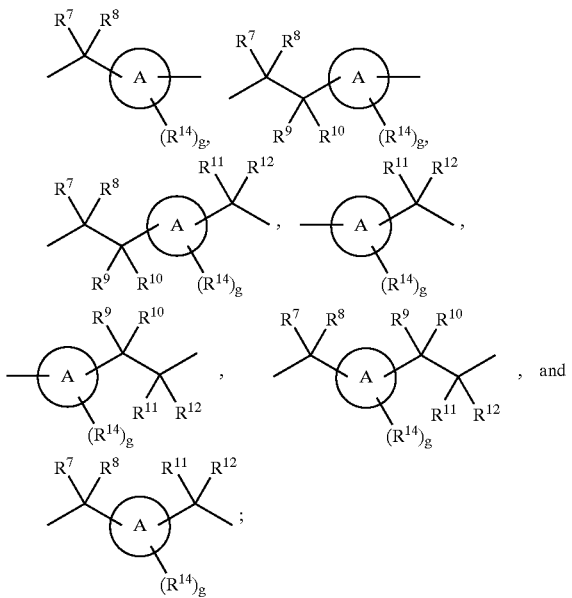

$R^4$ is absent, taken with the nitrogen to which it is attached to form an N-oxide, or selected from $C_{1-8}$ alkyl, $(CH_2)_r C_{3-6}$ cycloalkyl, and $(CH_2)_r$-phenyl substituted with 0–3 $R^{4c}$;

$R^{40c}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, $(CH_2)_rOH$, $(CH_2)_r$ $SC_{1-5}$ alkyl, $(CH_2)_rNR^{4a}R^{4a'}$, and $(CH_2)_r$ phenyl;

alternatively, $R^4$ joins with $R^7$, $R^9$ or $R^{14}$ to form a 5, 6 or 7 membered piperidinium spirocycle substituted with 0–3 $R^a$;

$R^1$ and $R^2$ are independently selected from H and $C_{1-4}$ alkyl;

$R^6$, at each occurrence, is selected from $C_{1-4}$ alkyl, $C_{2-8}$ alkenyl, $C_{2-8}$ alkynyl, $(CH_2)_rC_{3-6}$ cycloalkyl, $(CF_2)_r$ $CF_3$, CN, $(CH_2)_rOH$, $(CH_2)_rOR^{6b}$, $(CH_2)_rC(O)R^{6b}$, $(CH_2)_rC(O)NR^{6a}R^{6a'}$, $(CH_2)_rNR^{6d}C(O)R^{6a}$, and $(CH_2)_t$ phenyl substituted with 0–3 $R^{6c}$;

$R^{6a}$ and $R^{6a'}$, at each occurrence, are selected from H, $C_{1-6}$ alkyl, $C_{3-6}$ cycloalkyl, and phenyl substituted with 0–3 $R^{6c}$;

$R^{6b}$, at each occurrence, is selected from $C_{1-6}$ alkyl, $C_{3-6}$ cycloalkyl, and phenyl substituted with 0–3 $R^{5c}$;

$R^{6c}$, at each occurrence, is selected from $C_{1-6}$ alkyl, $C_{3-6}$ cycloalkyl, Cl, F, Br, I, CN, $NO_2$, $(CF_2)_rCF_3$, $(CH_2)_r$ $OC_{1-5}$ alkyl, $(CH_2)_rOH$, $(CH_2)_rSC_{1-5}$ alkyl, and $(CH_2)_r$ $NR^{6d}R^{6d'}$;

$R^{6d}$, at each occurrence, is selected from H, $C_{1-6}$ alkyl, and $C_{3-6}$ cycloalkyl;

$R^7$, is selected from H; $C_{1-3}$ alkyl, $(CH_2)_rC_{3-6}$ cycloalkyl, $(CH_2)_qOH$, $(CH_2)_qOR^{7d}$, $(CH_2)_qNR^{7a}R^{7a'}$, $(CH_2)_qC(O)R^{7b}$, $(CH_2)_rC(O)NR^{7a}R^{7a'}$, $(CH_2)_qNR^{7a}C(O)R^{7a}$, $C_{1-6}$ haloalkyl, $(CH_2)_r$phenyl with 0–2 $R^{7c}$;

$R^{7a}$ and $R^{7a'}$, at each occurrence, are selected from H, $C_{1-6}$ alkyl, $(CH_2)_rC_{3-6}$ cycloalkyl, a $(CH_2)_r$phenyl substituted with 0–3 $R^{7e}$;

$R^{7b}$, at each occurrence, is selected from $C_{1-6}$ alkyl, $C_{2-8}$ alkenyl, $C_{2-8}$ alkynyl, $(CH_2)_rC_{3-6}$ cycloalkyl, $(CH_2)_r$ phenyl substituted with 0–3 $R^{7e}$;

$R^{7c}$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{7f}R^{7f}$, $(CH_2)_rOH$, $(CH_2)_rOC_{1-4}$ alkyl, $(CH_2)_rC(O)R^{7b}$, $(CH_2)_rC(O)NR^{7f}R^{7f}$, $(CH_2)_rNR^{7f}C(O)R^{7a}$, $(CH_2)_rS(O)_pR^{7b}$, $(CH_2)_r$ $S(O)_2NR^{7f}R^{7f}$, $(CH_2)_rNR^{7f}S(O)_2R^{7b}$, and $(CH_2)_r$ phenyl substituted with 0–2 $R^{7e}$;

$R^7d$, at each occurrence, is selected from $C_{1-6}$ alkyl, $(CH_2)_rC_{3-6}$ cycloalkyl, $(CH_2)_r$phenyl substituted with 0–3 $R^{7e}$;

$R^{7e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{7f}R^{7f}$, and $(CM_2)_r$phenyl;

$R^{7f}$, at each occurrence, is selected from H, $C_{1-5}$ alkyl, and $C_{3-6}$ cycloalkyl;

$R^8$ is H or joins with $R^7$ to form $C_{3-7}$ cycloalkyl or $=NR^{ab}$;

$R^{11}$, is selected from H, $C_{1-6}$ alkyl, $(CH_2)_rC_{3-6}$ cycloalkyl, $(CH_2)_qOH$, $(CH_2)_qOR^{11d}$, $(CH_2)_qNR^{11a}R^{11a'}$, $(CH_2)_rC(O)R^{11b}$, $(CH_2)_rC(O)NR^{11a}R^{11a'}$, $(CH_2)_qNR^{11a}C(O)$ $R^{11a}$, $C_{1-6}$ haloalkyl, $(CH_2)_r$phenyl with 0–2 $R^{11c}$, $(CH_2)_r$-5–10 membered heterocyclic system containing 1–4 heteroatoms selected from N, O, and S, substituted with 0–3 $R^{15}$;

$R^{11a}$ and $R^{11a'}$, at each occurrence, are selected from H, $C_{1-6}$ alkyl, $(CH_2)_rC_{3-6}$ cycloalkyl, a $(CH_2)_r$phenyl substituted with 0–3 $R^{11e}$.

$R^{11b}$, at each occurrence, is selected from $C_{1-6}$ alkyl, $C_{2-8}$ alkenyl, $C_{2-8}$ alkynyl,. $(CH_2)_rC_{3-6}$ cycloalkyl, $(CH_2)_r$ phenyl substituted with 0–3 $R^{11e}$;

$R^{11c}$, at each occurrence, is selected from $C_{1-4}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{11f}R^{11f}$, $(CH_2)_rOH$, $(CH_2)_rOC_{1-4}$ alkyl, $(CH_2)_rC(O)R^{11b}$, $(CH_2)_rC(O)$ $NR^{11f}R^{11f}$, $(CH_2)_rNR^{11f}C(O)R^{11a}$, $(CH_2)_rS(O)_pR^{11b}$, $(CH_2)_rS(O)_2NR^{11f}R^{11f}$, $(CH_2)_rNR^{11f}S(O)_2R^{11b}$, and $(CH_2)_r$phenyl substituted with 0–2 $R^{11e}$;

$R^{11d}$, at each ocdurrence, is selected from $C_{1-6}$ alkyl, $(CH_2)_rC_{3-6}$ cycloalkyl, $(CH_2)_r$phenyl substituted with 0–3 $R^{11e}$;

$R^{11e}$, at each occurrence, is selected from $C_{1-6}$ alkyl, $C_{2-8}$ alkenyl, $C_{2-8}$alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{11f}R^{11f}$, and $(CH_2)_r$phenyl;

$R^{11f}$, at each occurrence, is selected from H, $C_{1-5}$ alkyl and $C_{3-6}$ cycloalkyl;

$R^{12}$ is H or joins with $R^{11}$ to form $C_{3-7}$ cycloalkyl;

$R^{13}$, at each occurrence, is selected from $C_{1-4}$ alkyl, $C_{3-6}$ cycloalkyl, $(CH_2)NR^{13a}R^{13a'}$, $(CH_2)OH$, $(CH_2)OR^{13b}$, $(CH_2)_wC(O)R^{13b}$, $(CH_2)_wC(O)NR^{13a}R^{13a'}$, $(CH_2)NR^{13d}C(O)R^{13a}$, $(CH_2)_wS(O)_2NR^{13a}R^{13a'}$, $(CH_2)NR^{13d}S(O)_2R^{13b}$, and $(CH_2)_w$-phenyl substituted with 0–3 $R^{13c}$;

$R^{13a}$ and $R^{13a'}$, at each occurrence, are selected from H, $C_{1-6}$ alkyl, $C_{3-6}$ cycloalkyl, and phenyl substituted with 0–3 $R^{13c}$;

$R^{13b}$, at each occurrence, is selected from $C_{1-6}$ alkyl, $C_{3-6}$ cycloalkyl, and phenyl substituted with 0–3 $R^{13c}$;

$R^{13c}$, at each occurrence, is selected from $C_{1-6}$ alkyl, $C_{31-6}$ cycloalkyl, Cl, F, Br, I, CN, $NO_2$, $(CF_2)_rCF_3$, $(CH_2)_r$ $OC_{1-5}$ alkyl, $(CH_2)_rOH$, and $(CH_2)_rNR^{13d}R^{13d}$;

$R^{13d}$, at each occurrence, is selected from H, $C_{1-6}$ alkyl, and $C_{3-6}$ cycloalkyl;

q is selected from 1, 2, and 3; and r is selected from 0, 1, 2, and 3.

24. The method of claim 23, wherein:

ring A is selected from:

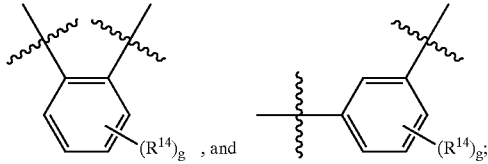

$R^3$ is selected from a $(CR^{3'}H)_r$-carbocyclic residue substituted with 0–5 $R^{15}$, wherein the carbocyclic residue is selected from phenyl, $C_{3-6}$ cycloalkyl, naphthyl, and adamantyl; and a $(CR^{3'}H)_r$-heterocyclic system substituted with 0–4 $R^{15}$, wherein the heterocyclic system is selected from pyridinyl, thiophenyl, furanyl, indazolyl, benzothiazolyl, benzimidazolyl, berizothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3- triazolyl, tetrazolyl, thiadiazolyl, thiazolyl, oxazolyl, pyrazinyl, and pyrimidinyl; and $R^5$ is selected from $(CR^{5'}H)_r$-phenyl substituted with 0–5 $R^{16}$; and a $(CR^{5'}H)_r$-heterocyclic system substituted with 0–3 $R^{16}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl.

25. The method of claim 24, wherein formula (I) is:

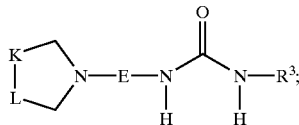

with the proviso that at least one of K or L contains an $R^5$;

$R^{16}$, at each occurrence, is selected from $C_{1-8}$ a alkyl, $(CH_2)_rC_{3-6}$ cycloalkyl, $CF_3$, Cl, Br, I, F, $(CH_2)_r$ $NR^{16a}R^{16a'}$, $NO_2$, CU, OH, $(CH_2)_rOR^{16d}$, $(CH_2)_rC(O)$ $R^{16b}$, $(CH_2)_rC(O)NR^{16a}R^{16a'}$, $(CH_2)_rNR^{16f}C(O)R^{16b}$, $(CH_2)_rS(O)_pR^{16b}$, $(CH_2)_rS(O)_2NR^{16a}R^{16a'}$, $(CH_2)_r$ $NR^{16f}S(O)_2R^{16b}$, and $(CH_2)_r$phenyl substituted with 0–3 $R^{16e}$;

$R^{16a}$ and $R^{16a'}$, at each occurrence, are selected from H, $C_{1-6}$ alkyl, $C_{3-6}$ cycloalkyl, and $(CH_2)_r$phenyl substituted with 0–3 $R^{16e}$;

$R^{16b}$, at each occurrence, is selected from H, $C_{1-6}$ alkyl, $C_{3-6}$ cycloalkyl, and $(CH_2)_r$phenyl substituted with 0–3 $R^{16e}$;

$R^{16d}$, at each occurrence, is selected from $C_{1-6}$ alkyl and phenyl;

$R^{16e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{16f}$, at each occurrence, is selected from H, and $C_{1-5}$ alkyl.

26. The method of claim 25, wherein:

$R^5$ is $CH_2$phenyl substituted with 0–3 $R^{16}$;

$R^9$, is selected from H, $C_{1-6}$ alkyl, $(CH_2)_rC_{3-6}$ cycloalkyl, F, Cl, CN, $(CH_2)_rOH$, $(CH_2)_rOR^{9d}$, $(CR^2)_rNR^{9a}R^{9a'}$, $(CH_2)_rOC(O)NR^{9a}$, $(CH^2)_r$phenyl substituted with 0–5 $R^{9e}$, and a heterocyclic system substituted with 0–2 $R^{9e}$, wherein the heterocyclic system is selected from pyridyl, thiophenyl, furanyl, oxazolyl, and thiazolyl;

$R^{9a}$ and $R^{9a'}$, at each occurrence, are selected from H, $C_{1-6}$ alkyl, $C_{3-6}$ cycloalkyl, and $(CH_2)_r$phenyl substituted with 0–3 $R^{9e}$;

$R^{9d}$, at each occurrence, is selected from $C_{1-6}$ alkyl and phenyl;

$R^{9e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{10}$ is selected from H, $C_{1-8}$ alkyl, OH, and CH2OH;

alternatively, $R^9$ and $R^{10}$ join to form $C_{3-7}$ cycloalkyl, 5–6-membered cyclic ketal or =O;

with the proviso that when $R^{10}$ is halogen, cyano, nitro, or bonded to the carbon to which it is attached through a heteroatom, $R^9$ is not halogen, cyano, or bonded to the carbon to which it is attached through a heteroatom;

$R^{11}$ is selected from H, $C_{1-8}$ alkyl, $(CH_2)_r$phenyl substituted with 0–5 $R^{11e}$, and a $(CH_2)_r$-heterocyclic system substituted with 0–2 $R^{11e}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, isoindolyl, piperidinyl, pyrrazolyl, 1,2,4-triazolyl, 1,2,3-triazolyl, tetrazolyl, thiazolyl, oxazolyl, pyrazinyl, and pyrimidinyl; and $R^{11e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{12}$ is H;

alternatively, $R^{11}$ and $R^{12}$ join to form $C_{3-7}$ cycloalkyl;

$R^{14}$, at each occurrence, is selected from $C_{1-8}$ alkyl, $(CH_2)_rC_{3-6}$ cycloalkyl, $CF_3$, Cl, Br, I, F, $(CH_2)_r$ $NR^{14a}R^{14a'}$, $NO_2$, CN, OH, $(CH_2)_rOR^{14d}$, $(CH_2)_rC(O)$ $R^{14b}$, $(CH_2)_rC(O)NR^{14a}R^{14a'}$, $(CH_2)_rNR^{14f}C(O)R^{14b}$, $(CH_2)_rS(O)_pR^{14b}$, $(CH_2)_rS(O)_2NR^{14a}R^{14a'}$, $(CH_2)_r$ $NR^{14f}S(O)_2R^{14b}$, $(CH_2)_r$phenyl substituted with 0–3 $R^{14e}$, and a $(CH_2)_r$-5–6 membered heterocyclic system containing 1–4 heteroatoms selected from N, O, and S, substituted with 0–2 $R^{15e}$, or two $R^{14}$ substituents on adjacent atoms on ring A form to join a 5–6 membered heterocyclic system containing 1–3 heteroatoms selected from N, O, and S substituted with 0–2 $R^{15e}$;

$R^{14a}$ and $R^{14a'}$, at each occurrence, are selected from H, $C_{1-6}$ alkyl, $C_{3-6}$ cycloalkyl, and $(CH_2)_r$phenyl substituted with 0–3 $R^{14e}$;

$R^{14b}$, at each occurrence, is selected from H, $C_{1-6}$ alkyl, $C_{3-6}$ cycloalkyl, and $(CH_2)_r$phenyl substituted with 0–3 $R^{14e}$;

$R^{14d}$, at each occurrence, is selected from $C_{1-6}$ alkyl and phenyl;

$R^{14e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl;

$R^{14f}$, at each occurrence, is selected from H, and $C_{1-5}$ alkyl; and r is celected from 0, 1, and 2.

27. The method of claim 26, wherein:

K is selected from $CH_2$ and $CHR^5$;

L is selected from $CH_2$ and $CHR^5$;

with the proviso that at least one of K or L is $CHR^5$;

$R^3$ is a $c_{3-10}$ carbocyclic residue substituted with 0–3 $R^{15}$, wherein the carbocyclic residue is selected from cyclopropyl, cyclopentyl, cyclohexyl, phenyl, naphthyl and adamantyl, and a $(CR^{3'}H)_r$-heterocyclic system substituted with 0–3 $R^{15}$, wherein the heterocyclic system is selected from pyridinyl, thiophenyl, furanyl, indazolyl, benzothiazolyl, benzimidazolyl, benzothiophenyl, benzofuranyl, benzoxazolyl, benzisoxazolyl, quinolinyl, isoquinolinyl, imidazolyl, indolyl, indolinyl, isoindolyl, isothiadiazolyl, isoxazolyl, piperidinyl, pyrrazolyl, 1,2,4-triazolyl, 1,2,3-triazolyl, tetrazolyl, thiadiazolyl, thiazolyl, oxazolyl, pyrazinyl, and pyrimidinyl; and $R^{15}$, at each occurrence, is selected from $C_{1-8}$ alkyl, $(CH_2)_rC_{3-6}$ cycloalkyl, $CF_3$, Cl, Br, I, F, $(CH_2)_r$ $NR^{15a}R^{15a'}$, $NO_2$, CN, OH, $(CH_2)_rOR^{15d}$, $(CH_2)_rC(O)R^{15b}$, $(CH_2)_rC(O)NR^{15a}R^{15a'}$, $(CH_2)_rNR^{15f}C(O)R^{15b}$, $(CH_2)_rS(O)_pR^{15b}$, $(CH_2)_rS(O)_2NR^{15a}R^{15a'}$, $(CH_2)_rNR^{15f}S(O)_2R^{15b}$, and $(CH_2)_r$phenyl substituted with 0–3 $R^{15e}$, and a $(CH_2)_r$-5–6 membered heterocyclic system containing 1–4 heteroatoms selected from N, O, and S, substituted with 0–2 $R^{15e}$;

$R^{15a}$ and $R^{15a'}$, at each occurrence, are selected from H, $C_{1-6}$ alkyl, $C_{3-6}$ cycloalkyl, and $(CH_2)_r$phenyl substituted with 0–3 $R^{15e}$;

$R^{15b}$, at each occurrence, is selected from H, $C_{1-6}$ alkyl, $C_{3-6}$ cycloalkyl, and $(CH_2)_r$phenyl substituted with 0–3 $R^{15e}$;

$R^{15d}$, at each occurrence, is selected from $C_{1-6}$ alkyl and phenyl;

$R^{15e}$, at each occurrence, is selected from $C_{1-6}$ alkyl, Cl, F, Br, I, CN, $NO_2$, $(CF_2)_rCF_3$, OH, and $(CH_2)_rOC_{1-5}$ alkyl; and $R^{15f}$, at each occurrence, is selected from H and $C_{1-5}$ alkyl.

\* \* \* \* \*